US006762318B2

(12) United States Patent
Kodra et al.

(10) Patent No.: US 6,762,318 B2
(45) Date of Patent: Jul. 13, 2004

(54) GLUCAGON ANTAGONISTS

(75) Inventors: Janos Tibor Kodra, Copenhagen (DK); Peter Madsen, Bagsvaerd (DK); Jesper Lau, Farum (DK); Anker Steen Jorgensen, Copenhagen (DK); Inge Thoger Christensen, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/308,528

(22) Filed: Dec. 3, 2002

(65) Prior Publication Data

US 2003/0236292 A1 Dec. 25, 2003

Related U.S. Application Data

(60) Provisional application No. 60/336,876, filed on Dec. 5, 2001, and provisional application No. 60/397,809, filed on Jul. 19, 2002.

(30) Foreign Application Priority Data

Dec. 3, 2001 (DK) .......................................... 2001 01789
Jul. 18, 2002 (DK) .......................................... 2002 01117

(51) Int. Cl.[7] .................... C07C 229/00; C07D 319/14; C07D 332/22; C07D 211/08; A61K 31/195
(52) U.S. Cl. .................... 562/445; 562/444; 549/366; 549/441; 549/77; 546/192; 514/563; 514/466; 514/452; 514/438
(58) Field of Search .......................... 562/445, 444; 549/366, 441, 77; 546/192; 514/563, 466, 452, 438

(56) References Cited

U.S. PATENT DOCUMENTS

| | | | | |
|---|---|---|---|---|
| 4,359,474 A | | 11/1982 | Anderson et al. | ........... 424/273 |
| 4,374,130 A | | 2/1983 | Barcza | ........................ 424/184 |
| 5,670,618 A | * | 9/1997 | McKenzie | .................. 530/303 |
| 5,763,437 A | * | 6/1998 | Sato et al. | .................... 514/221 |
| 5,776,954 A | | 7/1998 | DeLaszlo et al. | ........... 514/340 |
| 5,837,719 A | | 11/1998 | DeLaszlo et al. | ........... 514/343 |
| 5,880,139 A | | 3/1999 | Chang | ........................ 514/326 |
| 5,885,577 A | * | 3/1999 | Alvarez | ................... 424/155.1 |
| 6,093,730 A | * | 7/2000 | Weidmann et al. | ......... 514/309 |
| 6,130,231 A | * | 10/2000 | Wityak et al. | ............... 514/312 |
| 6,204,293 B1 | * | 3/2001 | Sebti et al. | .................. 514/570 |
| 6,358,976 B1 | * | 3/2002 | Wityak et al. | .............. 514/312 |
| 6,562,807 B2 | * | 5/2003 | Jorgensen et al. | .......... 514/186 |

FOREIGN PATENT DOCUMENTS

| | | |
|---|---|---|
| WO | WO 94/14426 | 7/1994 |
| WO | WO 97/16642 | 5/1997 |
| WO | WO 98/04582 | 2/1998 |
| WO | WO 98/21957 | 5/1998 |
| WO | WO 98/22108 | 5/1998 |
| WO | WO 98/22109 | 5/1998 |
| WO | WO 98/24780 | 6/1998 |
| WO | WO 98/24782 | 6/1998 |
| WO | WO 99/01423 | 1/1999 |
| WO | WO 99/24404 | 5/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 02/40445 | 5/2002 |
| WO | WO 02/40446 | 5/2002 |

OTHER PUBLICATIONS

Madsen et al., J. Med. Chem, 1998, vol. 41, pp. 5150–5157.
Collins et al., Bioorganic & Medicinal Chemistry Letters, 1992, vol. 2, No. 9, pp. 915–918.
Unson et al., The Journal of Biological Chemistry, 1994, vol. 269, No. 17, pp. 12548–12551.
Azizeh et al., Bioorganic & Medicinal Chemistry Letters, 1995, vol. 5, No. 16, pp. 1849–1852.
Post et al., Proceedings of the National Academy of Sciences of the 1993, vol. 90, pp. 1662–1666.
Unson et al., Peptides, 1989, vol. 10, pp. 1171–1177.

* cited by examiner

*Primary Examiner*—Deborah C. Lambkin
(74) *Attorney, Agent, or Firm*—Rosemarie R. Wilk-Orescan; Reza Green

(57) ABSTRACT

Novel compounds that act to antagonize the action of the glucagon peptide hormone on the glucagon receptor. More particularly, it relates to glucagon antagonists or inverse agonists.

59 Claims, No Drawings

GLUCAGON ANTAGONISTS

CROSS-REFERENCE TO RELATED APPLICATIONS

This application claims priority under 35 U.S.C. §119 of Danish Application No. PA 2001 01789, filed Dec. 3, 2001, Danish Application No. PA 2002 01117, filed Jul. 18, 2002, this application is a nonprovisional of Application No. 60/336,876, filed Dec. 5, 2001, and U.S. Application No. 60/397,809, filed Jul. 19, 2002, the contents of which are fully incorporated herein by reference.

FIELD OF THE INVENTION

The present invention relates to agents that act to antagonize the action of the glucagon peptide hormone on the glucagon receptor. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones.

Glucagon is produced in the alpha islet cells of the pancreas and insulin in the beta islet cells. Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, ie substances that inhibit or prevent glucagon-induced responses. The antagonist can be peptidic or non-peptidic in nature.

Native glucagon is a 29 amino acid peptide having the sequence: His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH Glucagon exerts its action by binding to and activating its receptor, which is part of the Glucagon-Secretin branch of the 7-transmembrane G-protein coupled receptor family. The receptor functions by activating the adenylyl cyclase second messenger system and the result is an increase in cAMP levels.

Several publications disclose peptides that are stated to act as glucagon antagonists. Probably, the most thoroughly characterized antagonist is DesHis[1][Glu[9]]-glucagon amide (Unson et al., Peptides 10, 1171 (1989); Post et al., Proc. Natl. Acad. Sci. USA 90, 1662 (1993)). Other antagonists are DesHis[1], Phe[6][Glu[9]]-glucagon amide (Azizh et al., Bioorganic & Medicinal Chem. Lett. 16, 1849 (1995)) and NLeu[9], Ala[11:16]-glucagon amide (Unson et al., J. Biol. Chem. 269 (17), 12548 (1994)).

Peptide antagonists of peptide hormones are often quite potent. However, they are generally known not to be orally available because of degradation by physiological enzymes, and poor distribution in vivo. Therefore, orally available non-peptide antagonists of peptide hormones are generally preferred. Among the non-peptide glucagon antagonists, a quinoxaline derivative, (2-styryl-3-[3-(dimethylamino) propylmethylamino]-6,7-dichloroquinoxaline was found to displace glucagon from the rat liver receptor (Collins, J. L. et al., Bioorganic and Medicinal Chem. Lett. 2(9):915–918 (1992)). WO 94/14426 (The Wellcome Foundation Limited) discloses use of skyrin, a natural product comprising a pair of linked 9,10-anthracenedione groups, and its synthetic analogues, as glucagon antagonists. U.S. Pat. No. 4,359,474 (Sandoz) discloses the glucagon inhibiting properties of 1-phenyl pyrazole derivatives. U.S. Pat. No. 4,374,130 (Sandoz) discloses substituted disilacyclohexanes as glucagon inhibiting agents. WO 98/04528 (Bayer Corporation) discloses substituted pyridines and biphenyls as glucagon antagonists. U.S. Pat. No. 5,776,954 (Merck & Co., Inc.) discloses substituted pyridyl pyrroles as glucagon antagonists and WO 98/21957, WO 98/22108, WO 98/22109 and U.S. Pat. No. 5,880,139 (Merck & Co., Inc.) disclose 2,4-diaryl-5-pyridylimidazoles as glucagon antagonists. Furthermore, WO 97/16442 and U.S. Pat. No. 5,837,719 (Merck & Co., Inc.) disclose 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to possess glucagon antagonistic activity. Madsen et al. (J. Med. Chem. 1998 (41) 5151–7) discloses a series of 2-(benzimidazol-2-ylthio)-1-(3,4-dihydroxyphenyl)-1-ethanones as competitive human glucagon receptor antagonists. WO 99/01423 and WO 00/39088 (Novo Nordisk A/S) disclose different series of alkylidene hydrazides as glucagon antagonists/inverse agonists. WO 00/69810, WO 02/00612, WO 02/40444, WO 02/40445 and WO 02/40446 (Novo Nordisk A/S) disclose further classes of glucagon antagonists.

These known glucagon antagonists differ structurally from the present compounds.

Definitions

The following is a detailed definition of the terms used to describe the compounds of the invention:

"Halogen" designates an atom selected from the group consisting of F, Cl, Br and I.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl and the like.

The term "$C_{1-6}$-alkoxy" as used herein refers to the radical —O—$C_{1-6}$-alkyl wherein $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{3-8}$-cycloalkyl" as used herein represents a saturated, carbocyclic group having from 3 to 8 carbon atoms. Representative examples are cyclopropyl, cyclobutyl, cyclopentyl, cyclohexyl, cycloheptyl, cyclooctyl and the like.

The term "$C_{4-8}$-cycloalkenyl" as used herein represents a non-aromatic, carbocyclic group having from 4 to 8 carbon atoms containing one or two double bonds. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a non-aromatic 3 to 10 membered ring containing one or more heteroatoms selected from nitrogen, oxygen and sulfur and optionally containing one or two double bonds. Representative examples are pyrrolidinyl, piperidyl, piperazinyl, morpholinyl, thiomorpholinyl, aziridinyl, tetrahydrofuranyl and the like.

The term "aryl" as used herein is intended to include carbocyclic, aromatic ring systems such as 6 membered monocyclic and 9 to 14 membered bi- and tricyclic, carbocyclic, aromatic ring systems. Representative examples are phenyl, biphenyl, naphthyl, anthracenyl, phenanthrenyl, fluorenyl, indenyl, azulenyl and the like. Aryl is also intended to include the partially hydrogenated derivatives of the ring systems enumerated above. Non-limiting examples of such partially hydrogenated derivatives are 1,2,3,4-tetrahydronaphthyl, 1,4-dihydronaphthyl, indanyl and the like.

The term "arylene" as used herein is intended to include divalent, carbocyclic, aromatic ring systems such as 6 membered monocyclic and 9 to 14 membered bi- and tricyclic, divalent, carbocyclic, aromatic ring systems. Representative examples are phenylene, biphenylene, naphthylene, anthracenylene, phenanthrenylene, fluorenylene, indenylene, azulenylene and the like. Arylene is also intended to include the partially hydrogenated derivatives of the ring systems enumerated above. Non-limiting examples of such partially hydrogenated derivatives are 1,2,3,4-tetrahydronaphthylene, 1,4-dihydronaphthylene and the like.

The term "aryloxy" as used herein denotes a group —O-aryl, wherein aryl is as defined above.

The term "aroyl" as used herein denotes a group —C(O)-aryl, wherein aryl is as defined above.

The term $C_{1-6}$-alkanoyl as used herein denotes a group —C(O)—$C_{1-6}$-alkyl, wherein $C_{1-6}$-alkyl is as defined above.

The term "heteroaryl" as used herein is intended to include aromatic, heterocyclic ring systems containing one or more heteroatoms selected from nitrogen, oxygen and sulfur such as 5 to 7 membered monocyclic and 8 to 14 membered bi- and tricyclic aromatic, heterocyclic ring systems containing one or more heteroatoms selected from nitrogen, oxygen and sulfur. Representative examples are furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the ring systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

The term "heteroarylene" as used herein is intended to include divalent, aromatic, heterocyclic ring systems containing one or more heteroatoms selected from nitrogen, oxygen and sulfur such as 5 to 7 membered monocyclic and 8 to 14 membered bi- and tricyclic aromatic, heterocyclic ring systems containing one or more heteroatoms selected from nitrogen, oxygen and sulfur. Representative examples are furylene, thienylene, pyrrolylene, oxazolylene, thiazolylene, imidazolylene, isoxazolylene, isothiazolylene, 1,2,3-triazolylene, 1,2,4-triazolylene, pyranylene, pyridylene, pyridazinylene, pyrimidinylene, pyrazinylene, 1,2,3-triazinylene, 1,2,4-triazinylene, 1,3,5-triazinylene, 1,2,3-oxadiazolylene, 1,2,4-oxadiazolylene, 1,2,5-oxadiazolylene, 1,3,4-oxadiazolylene, 1,2,3-thiadiazolylene, 1,2,4-thiadiazolylene, 1,2,5-thiadiazolylene, 1,3,4-thiadiazolylene, tetrazolylene, thiadiazinylene, indolylene, isoindolylene, benzofurylene, benzothienylene, indazolylene, benzimidazolylene, benzthiazolylene, benzisothiazolylene, benzoxazolylene, benzisoxazolylene, purinylene, quinazolinylene, quinolizinylene, quinolinylene, isoquinolinylene, quinoxalinylene, naphthyridinylene, pteridinylene, carbazolylene, azepinylene, diazepinylene, acridinylene and the like. Heteroaryl is also intended to include the partially hydrogenated derivatives of the ring systems enumerated above. Non-limiting examples of such partially hydrogenated derivatives are 2,3-dihydrobenzofuranylene, pyrrolinylene, pyrazolinylene, indolinylene, oxazolidinylene, oxazolinylene, oxazepinylene and the like.

"Aryl-$C_{1-6}$-alkyl", "heteroaryl-$C_{1-6}$-alkyl", "aryl-$C_{2-6}$-alkenyl" etc. mean $C_{1-6}$-alkyl or $C_{2-6}$-alkenyl as defined above, substituted by an aryl or heteroaryl as defined above, for example:

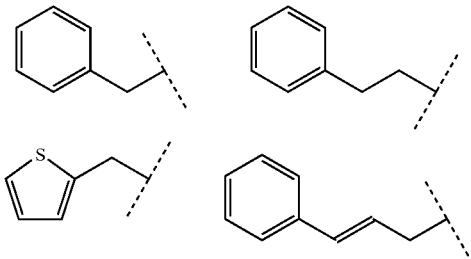

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DESCRIPTION OF THE INVENTION

The present invention relates to a compound of the general formula (I):

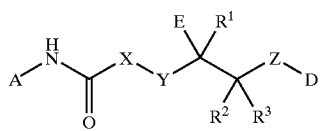

(I)

wherein

A is

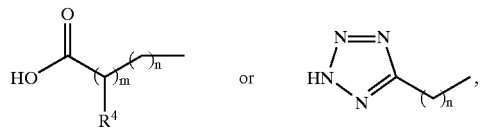

m is 0 or 1, n is 0, 1, 2 or 3, with the proviso that m and n must not both be 0, $R^4$ is hydrogen, halogen or —$(CH_2)_o$—$OR^5$, o is 0 or 1, $R^5$ is $C_{1-6}$-alkyl, $C_{1-6}$-alkanoyl, aryl or aryl-$C_{1-6}$-alkyl, $R^1$ and $R^2$ independently are hydrogen, halogen or $C_{1-6}$-alkyl, or $R^1$ and $R^2$ are combined to form a double bond, $R^3$ is hydrogen, $C_{1-6}$-alkyl or halogen, or $R^3$ and $R^2$ are combined to form a double bond to oxygen, X is arylene or heteroarylene, which may optionally be substituted with one or two groups $R^6$ and $R^7$ selected from halogen, —CN, —$CF_3$, —$OCF_3$, —$OCHF_2$, —$NO_2$, —$OR^8$, —$NR^8R^9$ and $C_{1-6}$-alkyl, $R^8$ and $R^9$ independently are hydrogen or $C_{1-6}$-alkyl, Y is —C(O)—, —O—, —$NR^{10}$—, —S—, —S(O)—, —$S(O)_2$— or —$CR^{11}R^{12}$—, $R^{10}$ is hydrogen or $C_{1-6}$-alkyl, $R^{11}$ and $R^{12}$ independently are hydrogen, $C_{1-6}$-alkyl or hydroxy, or $R^{11}$ is combined with $R^1$ to form a double bond, and $R^{12}$ is hydrogen, $C_{1-6}$-alkyl or hydroxy, Z is —C(O)—$(CR^{13}R^{14})_p$—, —O—$(CR^{13}R^{14})_p$—, —S—$(CR^{13}R^{14})_p$—, —S(O)—$(CR^{13}R^{14})_p$—, —$S(O)_2$—$(CR^{13}R^{14})_p$—, —$NR^{15}$—$(CR^{13}R^{14})_p$— or —$(CR^{13}R^{14})_p$—, p is 0, 1 or 2, $R^{13}$ and $R^{14}$ independently are selected from hydrogen, —$CF_3$, —$OCF_3$, —$OCHF_2$ and $C_{1-6}$-alkyl, $R^{15}$ is hydrogen or $C_{1-6}$-alkyl, D is aryl or heteroaryl, which may optionally be substituted with one or more substituents $R^{16}$, $R^{17}$, $R^{18}$, $R^{19}$, $R^{20}$ and $R^{21}$, wherein $R^{16}$, $R^{17}$, $R^{18}$ and $R^{19}$ independently are hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$SCF_3$, —$NO_2$, —$OR^{22}$, —$NR^{22}R^{23}$, —$SR^{22}$, —$NR^{22}S(O)_2R^{23}$, —$S(O)_2NR^{22}R^{23}$, —$S(O)NR^{22}R^{23}$, —$S(O)R^{22}$, —$S(O)_2R^{22}$, —$C(O)NR^{22}R^{23}$, —$OC(O)NR^{22}R^{23}$, —$NR^{22}C(O)R^{23}$, —$CH_2C(O)NR^{22}R^{23}$, —$OCH_2C(O)NR^{22}R^{23}$, —$CH_2OR^{22}$, —$CH_2NR^{22}R^{23}$, —$OC(O)R^{22}$, —$C(O)R^{22}$ or —$C(O)OR^{22}$, $C_{1-6}$-alkyl, $C_{2-6}$-alkenyl or $C_{2-6}$-alkynyl, which may optionally be substituted with one or more substituents selected from halogen, —CN, —$CF_3$, —$OCHF_2$, —$OCF_3$, —$NO_2$, —$OR^{22}$, —$NR^{22}R^{23}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the aromatic and non-aromatic ring systems optionally may be substituted with one or more substituents selected from halogen, —$C(O)OR^{22}$, —CN, —$CF_3$, —$OCF_3$, —$OCHF_2$, —$NO_2$, —$OR^{22}$, —$NR^{22}R^{23}$ and $C_{1-6}$-alkyl, $R^{22}$ and $R^{23}$ independently are hydrogen, $C_{1-6}$-alkyl, aryl-$C_{1-6}$-alkyl or aryl, or $R^{22}$ and $R^{23}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{16}$ to $R^{19}$ when placed in adjacent positions together may form a bridge —$(CR^{24}R^{25})_a$—O—$(CR^{26}R^{27})_c$—O—, a is 0, 1 or 2, c is 1 or 2, $R^{24}$, $R^{25}$, $R^{26}$ and $R^{27}$ independently are hydrogen, $C_{1-6}$-alkyl or fluoro, $R^{20}$ and $R^{21}$ independently are hydrogen, $C_{1-6}$-alkyl, $C_{3-8}$-cycloalkyl or $C_{3-8}$-cycloalkyl-$C_{1-6}$-alkyl, E is $C_{3-8}$-cycloalkyl or $C_{4-8}$-cycloalkenyl, which may optionally be substituted with one or two substituents $R^{28}$ and $R^{29}$, which are independently selected from hydrogen, halogen, —CN, —$CF_3$, —$OCF_3$, —$OCHF_2$, —$OR^{33}$, —$NR^{33}R^{34}$, $C_{1-6}$-alkyl, $C_{3-8}$-cycloalkyl, $C_{4-8}$-cycloalkenyl, heteroaryl and aryl, wherein the heteroaryl and aryl groups optionally may be substituted with one or more substituents selected from halogen, —CN, —$CF_3$, —$OCF_3$, —$OCHF_2$, —$NO_2$, —$OR^{33}$, —$NR^{33}R^{34}$ and $C_{1-6}$-alkyl, $R^{33}$ and $R^{34}$ independently are hydrogen or $C_{1-6}$-alkyl, or $R^{33}$ and $R^{34}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, aryl, heteroaryl, aryl-$C_{2-6}$-alkenyl or aryl-$C_{2-6}$-alkynyl, of which the aryl and heteroaryl moieties may optionally be substituted with one or more substitutents $R^{28}$, $R^{29}$, $R^{30}$, $R^{31}$ and $R^{32}$, wherein $R^{28}$ and $R^{29}$ are as defined above, and $R^{30}$, $R^{31}$ and $R^{32}$ are independently selected from hydrogen, halogen, —$CHF_2$, —$CF_3$, —$OCF_3$, —$OCHF_2$, —$OCH_2CF_3$, —$OCF_2CHF_2$, —$SCF_3$, —$OR^{35}$, —$NR^{35}R^{36}$, —$SR^{35}$, —$S(O)R^{35}$, —$S(O)_2R^{35}$, —$C(O)NR^{35}R^{36}$, —$OC(O)NR^{35}R^{36}$, —$NR^{35}C(O)R^{36}$, —$OCH_2C(O)NR^{35}R^{36}$, —$C(O)R^{35}$ and —$C(O)OR^{35}$, $C_{1-6}$-alkyl, $C_{2-6}$-alkenyl and $C_{2-6}$-alkynyl, which may optionally be substituted with one or more substituents selected from halogen, —CN, —$CF_3$, —$OCF_3$, —$OCHF_2$, —$NO_2$, —$OR^{35}$, —$NR^{35}R^{36}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl and heteroaryl-$C_{2-6}$-alkynyl, of which the aromatic and non-aromatic ring systems optionally may be substituted with one or more substituents selected from halogen, —CN, —$CF_3$, —$OCF_3$, —$OCHF_2$, —$NO_2$, —$OR^{35}$, —$NR^{35}R^{36}$ and $C_{1-6}$-alkyl, wherein $R^{35}$ and $R^{36}$ independently are hydrogen, $C_{1-6}$-alkyl or aryl, or $R^{35}$ and $R^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the substituents $R^{30}$, $R^{31}$ and $R^{32}$ when attached to the same ring carbon atom or adjacent ring carbon atoms together may form a bridge —O—$(CH_2)_t$—$CR^{37}R^{38}$—$(CH_2)_l$—O—, —$(CH_2)_t$—$CR^{37}R^{38}$—$(CH_2)_l$— or —S—$(CH_2)_t$—$CR^{37}R^{38}$—$(CH_2)_l$—S—, t and l independently are 0, 1, 2, 3, 4 or 5, $R^{37}$ and $R^{38}$ independently are hydrogen or $C_{1-6}$-alkyl, as well as any diastereomer or enantiomer or tautomeric form thereof including mixtures of these or a pharmaceutically acceptable salt thereof.

In another embodiment, A is

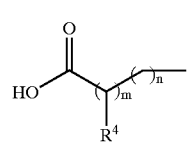

wherein m, n and $R^4$ are as defined for formula (I).

In another embodiment, A is

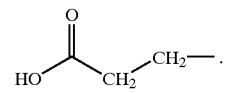

In another embodiment, A is

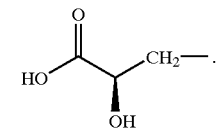

In another embodiment, A is

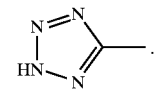

In another embodiment, X is monocyclic arylene or heteroarylene, which may optionally be substituted as defined for formula (I).

In another embodiment, X is

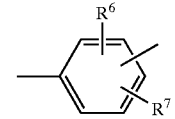

wherein $R^6$ and $R^7$ are as defined for formula (I).

In another embodiment, X is

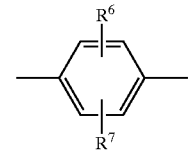

wherein $R^6$ and $R^7$ are as defined for formula (I).

In another embodiment, $R^6$ and $R^7$ are both hydrogen.

In another embodiment, E is

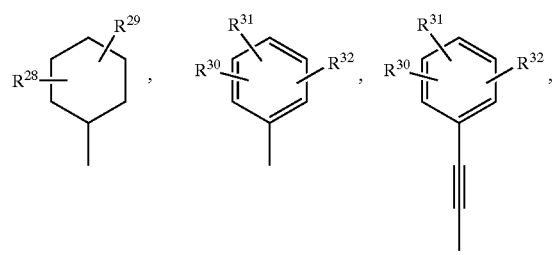

-continued

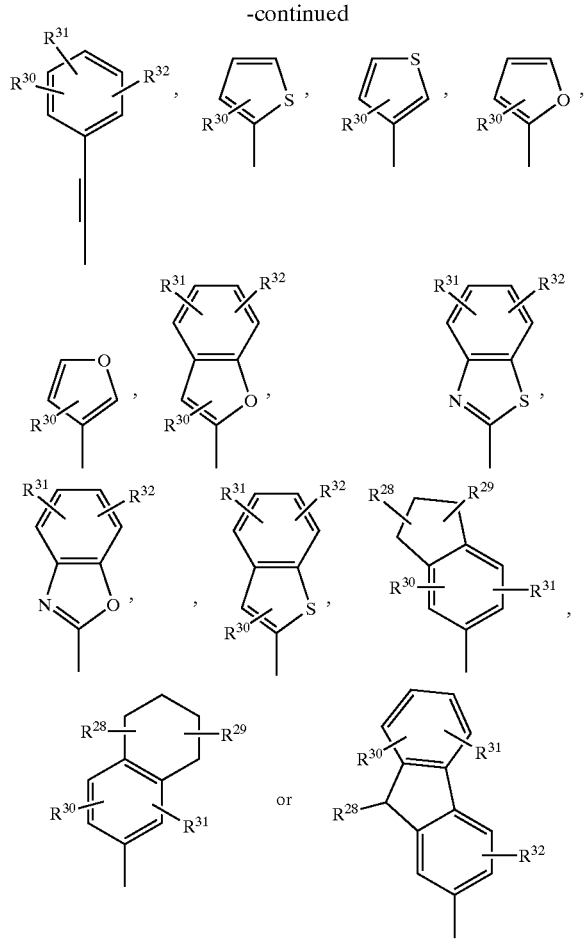

wherein $R^{28}$, $R^{29}$, $R^{30}$, $R^{31}$ and $R^{32}$ are as defined for formula (I).

In another embodiment, E is

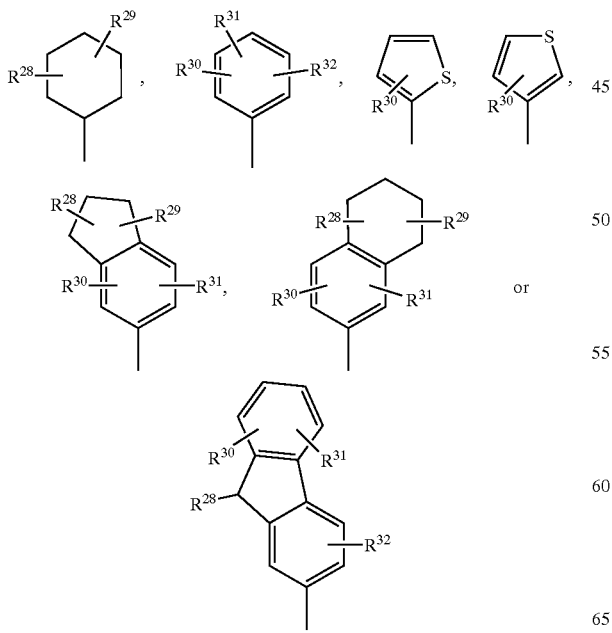

wherein $R^{28}$, $R^{29}$, $R^{30}$, $R^{31}$ and $R^{32}$ are as defined for formula (I).

In another embodiment, E is

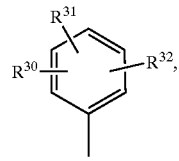

wherein $R^{30}$, $R^{31}$ and $R^{32}$ are as defined for formula (I).

In another embodiment, E is

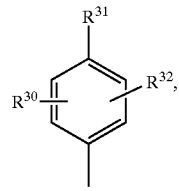

wherein $R^{30}$, $R^{31}$ and $R^{32}$ are as defined for formula (I).

In another embodiment E is

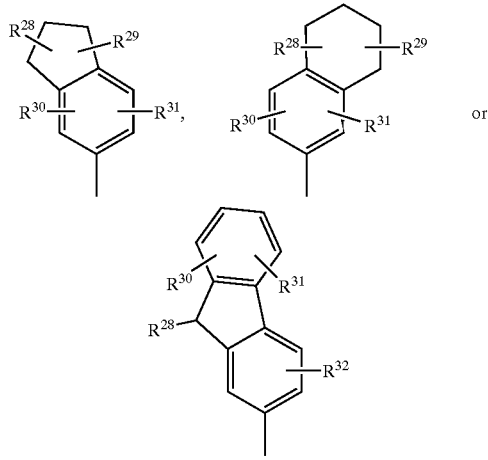

wherein $R^{28}$, $R^{29}$, $R^{30}$, $R^{31}$ and $R^{32}$ are as defined for formula (I).

In another embodiment, $R^{30}$, $R^{31}$ and $R^{32}$ are independently hydrogen, halogen, —$OCF_3$, —$SCF_3$ or —$CF_3$, $C_{1-6}$-alkyl, which may optionally be substituted with one or more substituents selected from fluoro, —CN, —$CF_3$, —$OCF_3$, —$OR^{35}$ and —$NR^{35}R^{36}$, $C_{3-8}$-cycloalkyl or $C_{4-8}$-cycloalkenyl, which may optionally be substituted with one or more substituents selected from fluoro, —CN, —$CF_3$, —$OCF_3$, —$OR^{35}$, —$NR^{35}R^{36}$ and $C_{1-6}$-alkyl, aryl, aryloxy or aryl-$C_{1-6}$-alkoxy, of which the aryl moieties may optionally be substituted with one or more substituents' selected from halogen, —CN, —$CF_3$, —$OCF_3$, —$NO_2$, —$R^{35}$, —$NR^{35}R^{36}$ and $C_{1-6}$-alkyl, $R^{35}$ and $R^{36}$ independently are hydrogen, $C_{1-6}$-alkyl or aryl, or $R^{35}$ and $R^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment, $R^{30}$, $R^{31}$ and $R^{32}$ are independently hydrogen, halogen, $OCF_3$, or —$SCF_3$, $C_{1-6}$-alkyl, which may optionally be substituted with one or more substituents selected from fluoro, —CN, —$CF_3$, —$OCF_3$, —$OR^{35}$ and —$NR^{35}R^{36}$, cyclohexyl or cyclohex-1-enyl, which may optionally be substituted with one or more substituents selected from fluoro, —CN, —$CF_3$, —$OCF_3$, —$OR^{35}$, —$NR^{35}R^{36}$ and $C_{1-6}$-alkyl, phenyl which may optionally be substituted with one or more substitutents selected from halogen, —CN, —$CF_3$, —$OCF_3$, —$NO_2$, —$OR^{35}$, —$NR^{35}R^{36}$ and $C_{1-6}$-alkyl, phenoxy or benzyloxy, of which the phenyl moieties may optionally be substituted with one or more substituents selected from halogen, —CN, —$CF_3$, —$OCF_3$, —$NO_2$, —$OR^{35}$, —$NR^{35}R^{36}$ and $C_{1-6}$-alkyl, $R^{35}$ and $R^{36}$ independently are hydrogen or $C_{1-6}$-alkyl.

In another embodiment, $R^{30}$ and $R^{32}$ are both hydrogen, and $R^{31}$ is different from hydrogen.

In another embodiment, E is

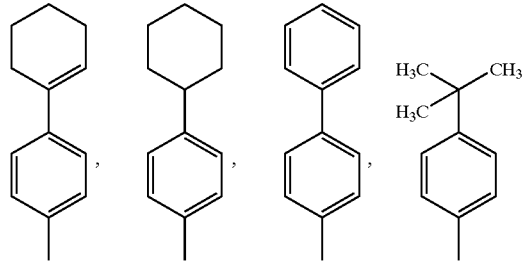

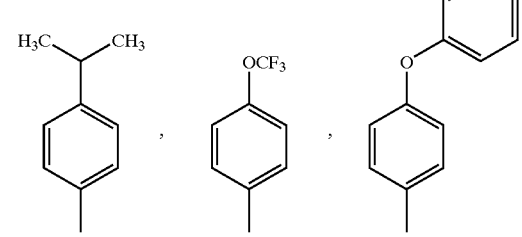

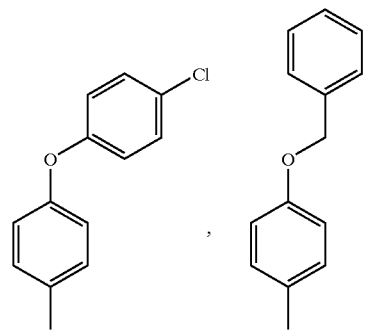

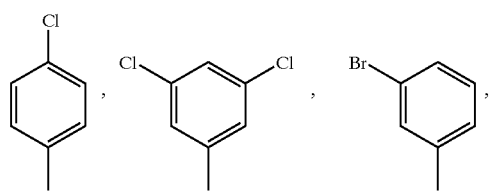

In another embodiment, E is

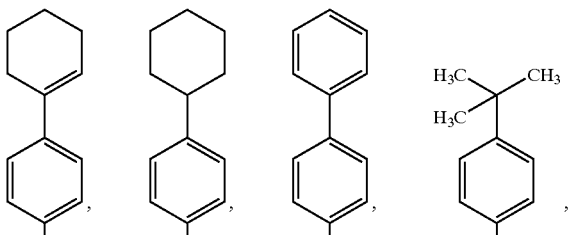

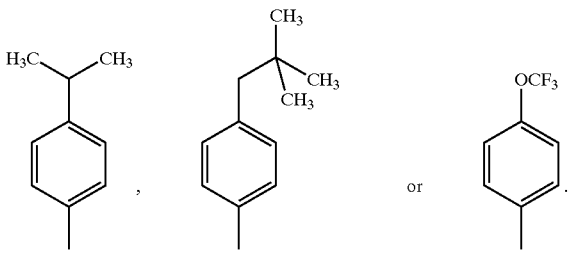

In another embodiment E is

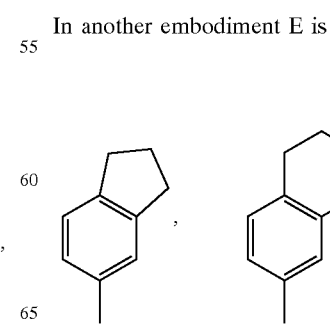 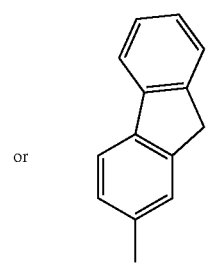

In another embodiment, E is

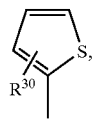

wherein $R^{30}$ is as defined for formula (I).

In another embodiment, $R^{30}$ is halogen or heteroaryl, which may optionally be substituted with one or more substituents selected from halogen, —CN, —CF$_3$, —NO$_2$, —OR$^{35}$, —NR$^{35}$R$^{36}$ and C$_{1-6}$alkyl, R$^{35}$ and R$^{36}$ independently are hydrogen or C$_{1-6}$-alkyl, or R$^{35}$ and R$^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment, $R^{30}$ is halogen or thienyl, which may optionally be substituted with one or more substituents selected from halogen, —CN, —CF$_3$, —NO$_2$, —OR$^{35}$, —NR$^{35}$R$^{36}$ and C$_{1-6}$-alkyl, R$^{35}$ and R$^{36}$ independently are hydrogen or C$_{1-6}$-alkyl, or R$^{35}$ and R$^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment, E is

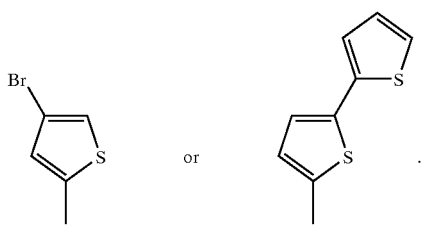

In another embodiment, Y is —C(O)—, —O—, —S(O)$_2$—, —NH— or —CH$_2$—.

In another embodiment, Y is —CHR$^{11}$—, wherein R$^{11}$ is combined with R$^1$ to form a double bond.

In another embodiment, Y is —C(O)—.

In another embodiment, R$^1$ and R$^2$ are both hydrogen.

In another embodiment, R$^1$ and R$^2$ are combined to form a double bond.

In another embodiment, R$^3$ is hydrogen.

In another embodiment Z is —C(O)—(CR$^{13}$R$^{14}$)$_p$—, —O—(CR$^{13}$R$^{14}$)$_p$—, —NR$^{15}$—(CR$^{13}$R$^{14}$)$_p$— or —S(O)$_2$—(CR$^{13}$R$^{14}$)$_p$—, wherein p, R$^{13}$, R$^{14}$ and R$^{15}$ are as defined for formula (I).

In another embodiment, Z is —NR$^{15}$—(CR$^{13}$R$^{14}$)$_p$ or —C(O)—(CR$^{13}$R$^{14}$)$_p$—, wherein p is as defined for formula (I), and R$^{13}$ and R$^{14}$ independently are selected from hydrogen, —CF$_3$, —OCF$_3$ and C$_{1-6}$-alkyl and R$^{15}$ is hydrogen.

In another embodiment, Z is —NH(CH$_2$)$_p$ or —C(O)—(CH$_2$)$_p$—, wherein p is as defined for formula (I).

In another embodiment, Z is NH or —C(O)—.
In another embodiment Z is —C(O)—.
In another embodiment, D is

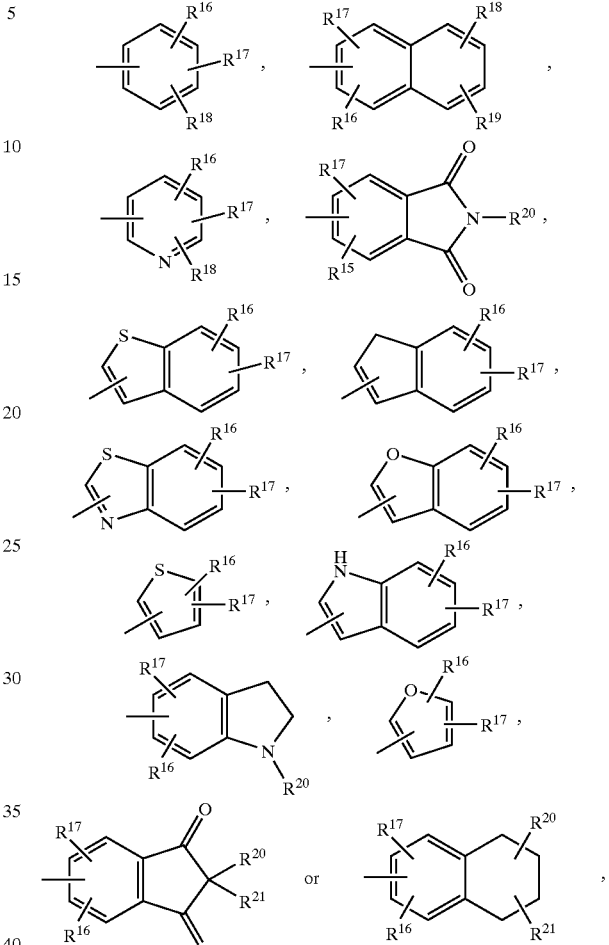

wherein $R^{16}$, $R^{17}$, $R^{18}$, $R^{19}$, $R^{20}$ and $R^{21}$ are as defined for formula (I).

In another embodiment, D is

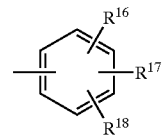

wherein $R^{16}$, $R^{17}$ and $R^{18}$ are as defined for formula (I).

In another embodiment, $R^{16}$, $R^{17}$ and $R^{18}$ are independently hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{22}$, —NR$^{22}$R$^{23}$, —SR$^{22}$, —NR$^{22}$S(O)$_2$R$^{23}$, —S(O)$_2$NR$^{22}$R$^{23}$, —S(O) NR$^{22}$R$^{23}$, —S(O)R$^{22}$, —S(O)$_2$R$^{22}$, —C(O)NR$^{22}$R$^{23}$, —OC(O)NR$^{22}$R$^{23}$, —NR$^{22}$C(O)R$^{23}$, —CH$_2$C(O) NR$^{22}$R$^{23}$, —OCH$_2$C(O)NR$^{22}$R$^{23}$, —CH$_2$OR$^{22}$, —CH$_2$NR$^{22}$R$^{23}$, —OC(O)R$^{22}$, —C(O)R$^{22}$ or —C(O) OR$^{22}$, C$_{1-6}$-alkyl, which may optionally be substituted with one or more substituents selected from fluoro, —CN, —CF$_3$, —OCF$_3$, —OR$^{22}$ and —NR$^{22}$R$^{23}$, C$_{3-8}$-cycloalkyl, which may optionally be substituted with one or more substituents selected from fluoro, —C(O)

$OR^{24}$, —CN, —$CF_3$, —$OCF_3$, —$OR^{22}$, —$NR^{22}R^{23}$ and $C_{1-6}$alkyl, aryl or aryloxy, which may optionally be substituted with one or more substituents selected from halogen, —C(O)$OR^{22}$, —CN, —$CF_3$, —$OCF_3$, —$NO_2$, —OR, —$NR^{22}R^{23}$ and $C_{1-6}$-alkyl, $R^{22}$ and $R^{23}$ independently are hydrogen, $C_{1-6}$-alkyl, aryl-$C_{1-6}$-alkyl or aryl, or $R^{22}$ and $R^{23}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{16}$ to $R^{18}$ when placed in adjacent positions together may form a bridge —$(CR^{24}R^{25})_a$—O—$(CR^{26}R^{27})_c$—O—, a is 0, 1 or 2, c is 1 or 2, $R^{24}$, $R^{25}$, $R^{26}$ and $R^{27}$ independently are hydrogen, $C_{1-6}$-alkyl or fluoro.

In another embodiment, $R^{16}$, $R^{17}$ and $R^{18}$ are independently, hydrogen, halogen, —$CF_3$, —$OCF_3$, —$SCF_3$, $C_{1-6}$-alkyl, $C_{1-6}$-alkoxy, phenyl, cyclopentyl, cyclohexyl or phenoxy, or two of the groups $R^{16}$ to $R^{18}$ when placed in adjacent positions together may form a bridge —O—$(CF_2)_2$—O—, —$CF_2$—O—$CF_2$—O— or —O—$CH_2$—O—.

In another embodiment, $R^{16}$ is hydrogen, and $R^{17}$ and $R^{18}$ are different from hydrogen.

In another embodiment, $R^{16}$ and $R^{17}$ are hydrogen, and $R^{18}$ is different from hydrogen.

In another embodiment, the invention relates to a compound of the general formula ($I_4$):

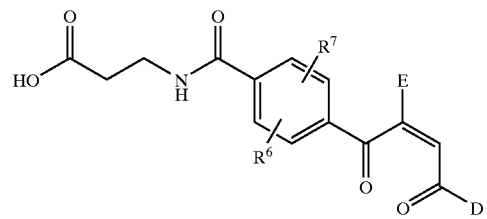

(I₄)

wherein $R^6$, $R^7$, E and D are as defined for formula (I) or in any one of the above embodiments, as well as any diastereomer or enantiomer or tautomeric form thereof including mixtures of these or a pharmaceutically acceptable salt thereof.

In another embodiment, the invention relates to a compound of the general formula ($I_5$):

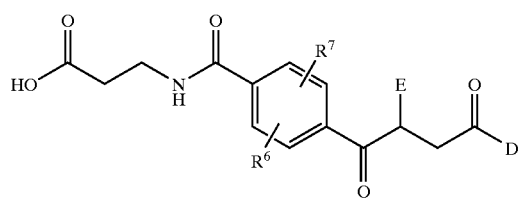

(I₅)

wherein $R^6$, $R^7$, E and D are as defined for formula (I) or in any one of the above embodiments, as well as any diastereomer or enantiomer or tautomeric form thereof including mixtures of these or a pharmaceutically acceptable salt thereof.

In another embodiment, the invention relates to a compound of the general formula ($I_5$a):

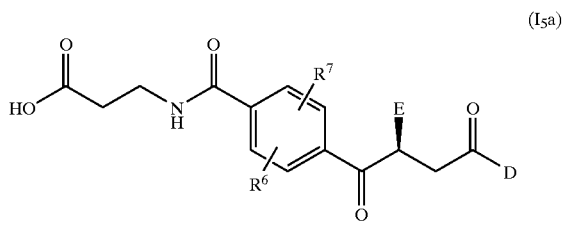

(I₅a)

wherein $R^6$, $R^7$, E and D are as defined for formula (I), as well as any diastereomer or enantiomer or tautomeric form thereof including mixtures of these or a pharmaceutically acceptable salt thereof.

In another embodiment, the invention relates to a compound of the general formula ($I_5$b):

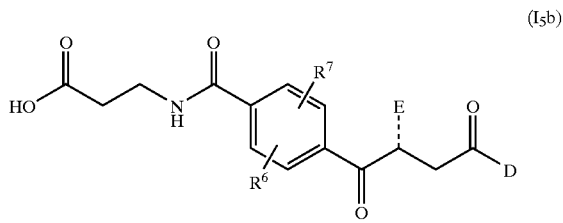

(I₅b)

wherein $R^6$, $R^7$, E and D are as defined for formula (I), as well as any diastereomer or enantiomer or tautomeric form thereof including mixtures of these or a pharmaceutically acceptable salt thereof.

In another embodiment, the invention relates to a compound of the general formula ($I_6$):

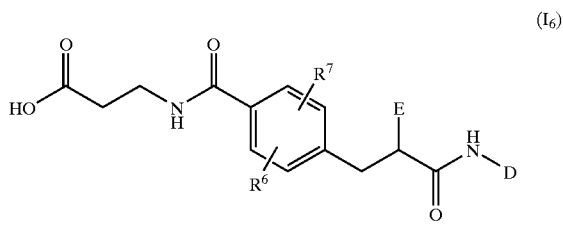

(I₆)

wherein $R^6$, $R^7$, E and D are as defined for formula (I) or in any one of the above embodiments, as well as any diastereomer or enantiomer or tautomeric form thereof including mixtures of these or a pharmaceutically acceptable salt thereof.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Also intended as pharmaceutically acceptable acid addition salts are the hydrates, which the present compounds, are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of then compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment of disorders and diseases in which such an antagonism is beneficial.

The compounds according to the present invention preferably have an $IC_{50}$ value of no greater than 5 $\mu$M, more preferably of less than 1 $\mu$M, even more preferred of less than 500 nM, such as of less than 100 nM as determined by the Glucagon Binding Assay (I) or Glucagon Binding Assay (II) disclosed herein.

Accordingly, the present compounds may be applicable for the treatment of hyperglycemia, IGT (impaired glucose tolerance), insulin resistance syndromes, syndrome X, type 1 diabetes, type 2 diabetes, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

Furthermore, they may be applicable as diagnostic agents for identifying patients having a defect in the glucagon receptor, as a therapy to increase gastric acid secretions and to reverse intestinal hypomobility due to glucagon administration.

They may also be useful as tool or reference molecules in labelled form eg radiolabelled in binding assays to identify new glucagon antagonists.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound according to the invention for the preparation of a pharmaceutical composition for the treatment of a disorder or disease, wherein a glucagon antagonistic action is beneficial.

The invention also relates to a method for the treatment of disorders or diseases, wherein a glucagon antagonistic action is beneficial the method comprising administering to a subject in need thereof an effective amount of a compound according to the invention.

In one embodiment, the present compounds are used for the preparation of a medicament for the treatment of any glucagon-mediated conditions and diseases.

In another embodiment, the present compounds are used for the preparation of a medicament for the treatment of hyperglycemia.

In yet another embodiment, the present compounds are used for the preparation of a medicament for lowering blood glucose in a mammal. The present compounds are effective in lowering the blood glucose, both in the fasting and the postprandial stage.

In yet another embodiment, the present compounds are used for the preparation of a pharmaceutical composition for the treatment of IGT.

In still another embodiment, the present compounds are used for the preparation of a pharmaceutical composition for the treatment of type 2 diabetes.

In yet another embodiment, the present compounds are used for the preparation of a pharmaceutical composition for the delaying or prevention of the progression from IGT to type 2 diabetes.

In yet another embodiment, the present compounds are used for the preparation of a pharmaceutical composition for the delaying or prevention of the progression from non-insulin requiring type 2 diabetes to insulin requiring type 2 diabetes.

In a further embodiment, the present compounds are used for the preparation of a pharmaceutical composition for the treatment of type 1 diabetes. Such treatment is normally accompanied by insulin therapy.

In still a further embodiment, the present compounds are used for the preparation of a pharmaceutical composition for the treatment of obesity.

In yet a further embodiment, the present compounds are used for the preparation of a pharmaceutical composition for the treatment of disorders of the lipid metabolism, such as dyslipidemia.

In still a further embodiment, the present compounds are used for the preparation of a pharmaceutical composition for the treatment of an appetite regulation or energy expenditure disorder.

In a further aspect of the invention, treatment of a patient with the present compounds is combined with diet and/or exercise.

In yet a further aspect of the invention, the present compounds are administered in combination with one or more further active substances in any suitable ratio(s). Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, insulin analogues and derivatives such as those disclosed in EP 792 290 (Novo Nordisk A/S), eg $N^{\epsilon B29}$-tetradecanoyl des (B30) human insulin, EP 214 826 and EP 705 275 (Novo Nordisk A/S), eg Asp$^{B28}$ human insulin, U.S. Pat. No. 5,504,188 (Eli Lilly), eg Lys$^{B28}$ Pro$^{B29}$ human insulin, EP 368 187 (Aventis), eg Lantus®, all of which are incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents include imidazolines, sulphonylureas, biguamides, meglitinides, oxadiazolidinediones, thiazolidinediones, α-glucosidase inhibitors, glucagon antagonists, GLP-1 agonists, agents acting on the ATP-dependent potassium channel of the β-cells, eg potassium channel openers such as those disclosed in WO 97/26265, WO 99/03861 and WO 00/37474 (Novo Nordisk A/S), all of which are incorporated herein by reference, or nateglinide or potassium channel blockers such as BTS-67582, insulin sensitizers, insulin secretagogues, DPP-IV (dipeptidyl peptidase-IV) inhibitors, PTPase inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707 and WO 02/08209 (Hoffman-La Roche), which are incorporated herein by reference, GSK-3 (glycogen synthase kinase-3) inhibitors, compounds modifying the lipid metabolism such as antihyperlipidemic agents and antilipidemic agents, compounds lowering food intake, PPAR (peroxisome proliferator-activated receptor) and RXR (retinoid X receptor) agonists such as ALRT-268, LG-1268 or LG-1069.

In one embodiment, the present compounds are administered in combination with insulin or an insulin analogue or derivative, such as $N^{\epsilon B29}$-tetradecanoyl des (B30) human insulin, Asp$^{B28}$ human insulin, Lys$^{B28}$ Pro$^{B29}$ human insulin, Lys$^{B29}$-(N$^\epsilon$(γ-glutamyl-N$^\alpha$litocholyl) des (B30) human insulin, Lantus, or a mix-preparation comprising one or more of these.

In a further embodiment, the present compounds are administered in combination with a sulphonylurea, eg tolbutamide, chlorpropamide, tolazamide, glibenclamide, glyburide, glipizide, glimepride or glicazide.

In another embodiment, the present compounds are administered in combination with a biguamide, eg metformin.

In yet another embodiment, the present compounds are administered in combination with a meglitinide, eg repaglinide or nateglinide.

In still another embodiment, the present compounds are administered in combination with a thiazolidinedione insulin sensitizer, eg troglitazone, ciglitazone, pioglitazone, rosiglitazone, isaglitazone, darglitazone, englitazone, CS-011/CI-1037 or T174 or the compounds disclosed in WO 97/41097, WO 97/41119, WO 97/41120, WO 00/41121 and WO 98/45292 (Dr. Reddy's Research Foundation).

In still another embodiment, the present compounds may be administered in combination with an insulin sensitizer such as GI 262570, YM-440, MCC-555, JTT-501, AR-H039242, KRP-297, GW-409544, CRE-16336, AR-H049020, LY510929, LY465608, MBX-102, CLX-0940, GW-501516, tesaglitazar (AZ 242) or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S).

In a further embodiment, the present compounds are administered in combination with an α-glucosidase inhibitor, eg voglibose, emiglitate, miglitol or acarbose.

In another embodiment, the present compounds are administered in combination with an agent acting on the ATP-dependent potassium channel of the β-cells, eg tolbutamide, chlorpropamide, tolazamide, glibenclamide, glyburide, glipizide, glicazide, BTS-67582, repaglinide or nateglinide.

In still another embodiment, the present compounds are administered in combination with an antihyperlipidemic agent or antilipidemic agent, eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds, eg in combination with metformin and a sulphonylurea such as glibenclamide or glyburide; a sulphonylurea and acarbose; metformin and a meglitinide such as repaglinide; acarbose and metformin; a sulfonylurea, metformin and troglitazone; a sulfonylurea, metformin and pioglitazone; a sulfonylurea, metformin and an insulin sensitizer such as disclosed in WO 00/63189 or WO 97/41097; a meglitinide such as repaglinide, metformin and troglitazone; a meglitinide such as repaglinide, metformin and pioglitazone; a meglitinide such as repaglinide, metformin and an insulin sensitizer such as disclosed in WO 00/63189 or WO 97/41097; insulin and a sulfonylurea; insulin and a meglitinide such as repaglinide; insulin and metformin; insulin, metformin and a meglitinide such as repaglinide; insulin, metformin and a sulfonylurea; insulin and troglitazone; insulin and pioglitazone; insulin and an insulin sensitizer such as such as disclosed in WO 00/63189 or WO 97/41097; insulin and lovastatin; an insulin analogue or derivative, metformin and a meglitinide such as repaglinide; an insulin analogue or derivative, metformin and a sulfonylurea; an insulin analogue or derivative and troglitazone; an insulin analogue or derivative and pioglitazone; an insulin analogue or derivative and an insulin sensitizer such as disclosed in WO 00/63189 or WO 97/41097; an insulin analogue or derivative and lovastatin; etc.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, H3 histamine antagonists, TNF (tumor necrosis factor) modulators, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators or TR β agonists.

In another embodiment, the antiobesity agent is dexamphetamine or amphetamine.

In another embodiment, the antiobesity agent is fenfluramine or dexfenfluramine.

In still another embodiment, the antiobesity agent is sibutramine.

In a further embodiment, the antiobesity agent is orlistat.

In another embodiment, the antiobesity agent is mazindol or phentermine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is a base addition salt of a compound having the utility of a free acid. When a compound of the formula (I) contains a free acid such salts are prepared in a conventional manner by treating a solution or suspension of a free acid of the formula (I) with a chemical equivalent of a pharmaceutically acceptable base. Representative examples are mentioned above.

For parenteral administration, solutions of the novel compounds of the formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | | |
|---|---|---|
| Active compound (as free compound or salt thereof) | | 5.0 mg |
| Lactosum Ph. Eur. | | 67.8 mg |
| Cellulose, microcryst. (Avicel) | | 31.4 mg |
| Amberlite ® IRP88* | | 1.0 mg |
| Magnesii stearas Ph. Eur. | | q.s. |
| Coating: | | |
| Hydroxypropyl methylcellulose | approx. | 9 mg |
| Mywacett 9-40 T** | approx. | 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of the glucagon antagonists of the invention. In general the compounds of the invention can be prepared by different methods of which only one representative example was disclosed below. As illustrative examples of this, some compounds were prepared by several methods. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Some of the NMR data shown in the following examples are only selected data.

In the examples the following terms are intended to have the following, general meanings:

DBU: 1,8-diazabicyclo[5.4.0]undec-5-ene
DCM: dichloromethane, methylenechloride
DIPEA: N,N-diisopropylethylamine
DMF: N,N-dimethyl formamide
DMSO: dimethyl sulfoxide, methyl sulfoxide
EDAC: 1-ethyl-3-(3-dimethylaminopropyl)carbodiimide hydrochloride
Fmoc: 9-fluorenylmethyloxycarbonyl
NMP: N-methyl-2-pyrrolidinone
TFA: trifluoroacetic acid
THF: tetrahydrofuran
HOBt: 1-hydroxybenzotriazole

HPLC-MS (Method A)

The following instrumentation is used:

Hewlett Packard series 1100 G1312A Bin Pump
Hewlett Packard series 1100 Column compartment
Hewlett Packard series 1100 G13 15A DAD diode array detector
Hewlett Packard series 1100 MSD The instrument is controlled by HP Chemstation software.
The HPLC pump is connected to two eluent reservoirs containing:

A: 0.01% TFA in water
B: 0.01% TFA in acetonitrile

The analysis is performed at 40° C. by injecting an appropriate volume of the sample (preferably 1 mL) onto the column, which is eluted with a gradient of acetonitrile.

The HPLC conditions, detector settings and mass spectrometer settings used are given in the following table.

| | |
|---|---|
| Column | Waters Xterra 100A MS C-18 3.5 μm, 3.0 mm × 50 mm |
| Gradient | 10%–100% acetonitrile lineary during 7.5 min at 1.0 mL/min |
| Detection | UV: 210 nm (diode array) |
| MS | Ionisation mode: API-ES |
| | Scan 100–1000 amu step 0.1 amu |

HPLC-MS (Method B)

The following instrumentation is used:

Hewlett Packard series 1100 MSD G1946A Single quadropole mass spectrometer
Hewlett Packard series 1100 MSD G1312A Bin pump
Hewlett Packard series 1100 MSD G1313A ALS autosampler
Hewlett Packard series 1100 MSD G1315A diode array detector (DAD)

The HP LC/MSD ChemStation control software running on a HP Vectra computer is used for the instrument control and data acquisition.

The HPLC pump is connected to two eluent reservoirs containing:

A: 0.01% TFA in water
B: 0.01% TFA in acetonitrile

The analysis is performed at room temperature by injecting 1 mL of the sample solution on the column which is eluted with a gradient of acetonitrile in 0.01% TFA.

The HPLC conditions, detector settings and mass spectrometer settings used are given in the following table.

| | |
|---|---|
| Column | Waters Xterra 100A MS C-18 3.5 $\mu$m, 3.0 mm × 50 mm |
| Gradient | 10%–100% acetonitrile in 0.05% TEA linearly during 4.5 min at 1.5 mL/min |
| Detection | UV: 210 nm (diode array) |
| MS | Ionisation mode: API-ES |
| | Experiment: Start: 100 amu Stop: 1000 amu Step: 0.1 amu |

HPLC-MS (Method C)

The following instrumentation is used:
Sciex API 100 Single quadropole mass spectrometer
Perkin Elmer Series 200 Quard pump
Perkin Elmer Series 200 autosampler
Applied Biosystems 785A UV detector
Sedex 55 evaporative light scattering detector
A Valco column switch with a Valco actuator controlled by timed events from the pump.

The Sciex Sample control software running on a Macintosh PowerPC 7200 computer is used for the instrument control and data acquisition.

The HPLC pump is connected to four eluent reservoirs containing:

A: Acetonitrile
B: Water
C: 0.5% TFA in water
D: 0.02 M ammonium acetate

The requirements for the samples are that they contain approximately 500 $\mu$g/mL of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis is performed at room temperature by injecting 20 $\mu$l of the sample solution on the column, which is eluted with a gradient of acetonitrile in either 0.05% TFA or 0.002 M ammonium acetate. Depending on the analysis method varying elution conditions are used.

The eluate from the column is passed through a flow splitting T-connector, which passed approximately 20 $\mu$l/min through approx. 1 m 75 $\mu$l fused silica capillary to the API interface of API 100 spectrometer.

The remaining 1.48 mL/min is passed through the UV detector and to the ELS detector.

During the LC-analysis the detection data are acquired concurrently from the mass spectrometer, the UV detector and the ELS detector.

The LC conditions, detector settings and mass spectrometer settings used for the different methods are given in the following table.

| | | |
|---|---|---|
| Column | YMC ODS-A 120Ås - 5$\mu$ 3 mm × 50 mm id | |
| Gradient | 5%–90% acetonitrile in 0.05% TFA linearly during 7.5 min at 1.5 mL/min | |
| Detection | UV: 214 nm | ELS: 40° C. |
| MS | Experiment: | Start: 100 amu Stop: 800 amu Step: 0.2 amu |
| | Dwell: | 0.571 msec |
| | Method: | Scan 284 times = 9.5 min |

HPLC-MS (Method D)

The following instrumentation is used:

Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector
The instrument is controlled by HP Chemstation software.
The HPLC pump is connected to two eluent reservoirs containing:

A: 0.01% TFA in water
B: 0.01% TFA in acetonitrile

The analysis is performed at 40° C. by injecting an appropriate volume of the sample (preferably 1 $\mu$l) onto the column which is eluted with a gradient of acetonitrile.

The HPLC conditions, detector settings and mass spectrometer settings used are given in the following table.

| | |
|---|---|
| Column | Waters Xterra MS C-18 × 3 mm id 5 $\mu$m |
| Gradient | 5%–100% acetonitrile linear during 7.5 min at 1.5 mL/min |
| Detection | 210 nm (analogue output from DAD) |
| | ELS (analogue output from ELS) |
| MS | ionisation mode API-ES |
| | Scan 100–1000 amu step 0.1 amu |

After the DAD the flow is divided yielding approximately 1 mL/min to the ELS and 0.5 mL/min to the MS.

Building Blocks

The following section refers to building blocks used to prepare intermediates of formula (II):

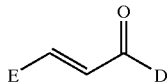

formula (II)

wherein E and D are as defined above.
Starting Material for Building Block Used to Prepare Intermediates of Formula (II)

4-Cyclohexylbenzaldehyde

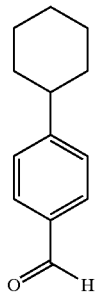

This compound was synthesized according to a modified literature procedure (*J. Org. Chem.*, 37, No.24, (1972), 3972–3973).

Cyclohexylbenzene (112.5 g, 0.702 mol) and hexamethylenetetramine (99.3 g, 0.708 mol) were mixed in TFA (375 mL). The mixture was stirred under nitrogen at 90° C. for 3 days. After cooling to room temperature the mixture was poured into ice-water (3600 mL) and stirred for 1 hour. The solution was neutralized with $Na_2CO_3$ (2 M solution in water) and extracted with DCM (2.5 l). The organic phase was dried ($Na_2SO_4$) and the solvent was removed in vacuo. The remaining oil was purified by fractional distillation to yield the title compound (51 g, 39%).

$^1$H NMR (CDCl$_3$): δ9.96 (s, 1H), 7.80 (d, 2H), 7.35 (d, 2H), 2.58 (m, 1H), 1.94–1.70 (m, 5H), 1.51–1.17 (m, 5H)
Starting Material for Building Block Used to Prepare Intermediates of Formula (II)

4-(2,2-Dimethylpropyl)benzaldehyde

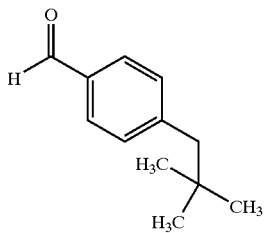

This compound was synthesized in analogy with a modified literature procedure (*J. Med. Chem.*, 36, 23, (1993), 3700–3704).

(2,2-Dimethylpropyl)benzene (9.33 g, 63 mmol) was dissolved in dichloromethane (50 mL) and cooled to 0° C. on an ice bath. With vigorous stirring, SnCl$_4$ (28.66 g, 110 mmol) was added all at once via syringe, followed by dropwise addition of dichloromethyl methyl ether (7.24 g, 63 mmol) over 10 min. After 20 min, the ice bath was removed, and the mixture was quenched by the addition of ice-water (100 mL). The aqueous layer was discarded and the organic phase was washed with water (3×25 mL), 3 N hydrochloric acid (3×25 mL), and aqueous saturated sodium chloride (2×25 mL). The organic phase was then treated with activated carbon, dried (magnesium sulphate), filtered and concentrated in vacuo. This afforded the title compound. Yield 7.49 g (62%).

$^1$H NMR (CDCl$_3$): δ0.94 (s, 9H), 2.57 (s, 2H), 7.28 (d, 2H), 7.80 (d, 2H), 9.98 (s, 1H).
Starting Material for Building Block Used to Prepare Intermediates of Formula (II)

Indan-5-carbaldehyde

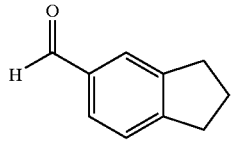

The title compound was prepared from indane and dichloromethyl methyl ether, using the same procedure as described above, providing a 1:2 mixture of indane-4-carbaldehyde and indane-5-carbaldehyde. The mixture was used for subsequent conversion to the chalcone (building block 7) without any further purification. Data only given for the title compound, (the major isomer)

$^1$H NMR (DMSO-d$_6$): δ2.05 (q, 2H), 2.90 (m, 4H), 7.41 (d, 1H), 7.67 (d, 1H), 7.70 (s, 1H). 9.95 (s, 1H). HPLC-MS (Method D): m/z=147 (M+1); R$_t$=3.53 min.
Starting Material for Building Block Used to Prepare Intermediates of Formula (II)

4-Cyclohex-1-enyl-benzaldehyde

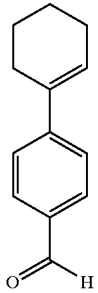

Magnesium turnings (14.6 g, 600 mmol) was placed in a dry 4-necked flask. Dry THF (50 mL) and a crystal of iodine were added. A mixture of 2-(4-bromophenyl)-[1,3]-dioxolane (*Tetrahedron*, 57, No.28, (2001), 5991–6002) (135 g, 589 mmol) in dry THF (200 mL) was slowly added to initiate the reaction. After the reaction had started, the addition of 2-(4-bromophenyl)-[1,3]-dioxolane was continued at such a rate that the temperature was maintained between 35 and 40° C. After the addition was complete the mixture was stirred for 2 hours and then cooled to 5° C. on an ice bath. Cyclohexanone (57.8 g, 580 mmol) was added dropwise while maintaining the temperature below 10° C. The mixture was stirred for 18 hours at room temperature and two third of the THF was removed in vacuo. The residue was poured into a mixture of ammonium chloride (65 g) in ice water (1 liter) and extracted with ethyl acetate. The organic phase was washed with water, dried (magnesium sulphate), filtered and evaporated in vacuo. The residual oil was slurred in petroleum ether to afford 48 g of 1-(4-[1,3]dioxolan-2yl-phenyl)cyclohexanol as a solid.

HPLC-MS (Method A): m/z=231 (M+1); $R_t$=3.27 min.

1-(4-[1,3]Dioxolan-2-yl-phenyl)cyclohexanol (45 g) and p-toluenesulfonic acid (3.4 g) in 300 mL of toluene were refluxed for 3 hours under Dean-Stark conditions. After cooling, ethyl acetate and a saturated sodium hydrogen carbonate solution were added. The organic layer was washed twice with water, dried (magnesium sulphate), filtered and concentrated in vacuo. The residual oil was dissolved in glacial acetic acid (250 mL) and 1 M hydrochloric acid (25 mL) was added and the mixture was stirred at 50° C. for 2 hours. After cooling, the mixture was concentrated in vacuo. The residual oil was partitioned between ethyl acetate and water. The organic phase was washed three times with water, dried (magnesium sulphate), filtered and concentrated in vacuo. The residual oil was distilled in vacuo and the fraction boiling at 120–130° C. (0.2 mmHg) was collected to afford 4.7 g of the title compound.

$^1$H NMR (CDCl$_3$): δ1.72 (m, 4H), 2.25 (m, 2H), 2.43 (m, 2H), 6.30 (m, 1H), 7.53 (d, 2H), 7.82 (d, 2H), 9.98 (s, 1 H).

Starting Material for Building Block Used to Prepare Intermediates of Formula (II)

1-(3,5-Dichlorophenyl)ethanone

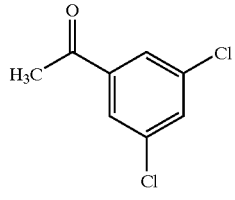

3,5-Dichlorobenzoic acid (19,10 g, 100 mmol) was dissolved in dry THF (165 mL) and cooled to 0° C. in an ice bath. With vigorous stirring, 138 mL (210 mmol) of methyl lithium (1.6 M in diethyl ether) was added dropwise over a period of 30 min via syringe. After 1 hour the mixture was poured into ice-water (500 mL). The aqueous phase was extracted with diethyl ether (4×50 mL). The combined organic phases were washed with saturated aqueous sodium hydrogen carbonate (2×50 mL) and saturated aqueous sodium chloride (2×50 mL). The organic phase was dried (magnesium sulphate), filtered and the solvent was removed in vacuo. This afforded 17.06 g of the title compound containing 18% by weight of 2-(3,5-dichlorophenyl)propan-2-ol. This compound was used in the next step without further purification.

$^1$H NMR (CDCl$_3$): δ2.62 (s, 3H), 7.92 (s, 2H), 7.94 (s, 1H).

Starting Material for Building Block Used to Prepare Intermediates of Formula (II)

1-(2,2,3,3-Tetrafluoro-2,3-dihydrobenzo[1,4]dioxin-6-yl)ethanone

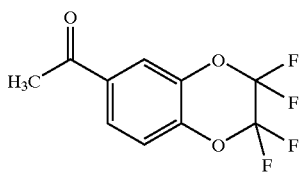

All equipment was dried at 120° C. for some hours in an oven.

Under an atmosphere of nitrogen in a dried three-necked 500 mL round bottom flask equipped with a separatory funnel and a condenser was added magnesium chips (7.31 g, 0.30 mol) and diethyl ether (20 mL). With magnetic stirring, iodomethane (4.7 mL, 75 mmol) was added dropwise to the Mg and the reaction was commenced. Iodomethane (14 mL, 0.22 mol) in diethyl ether (30 mL) was added slowly while maintaining reflux. After finished addition the mixture was stirred for 1½ hour. 6-Cyano-2,2,3,3-tetrafluoro-1.4-benzodioxene (35 g, 0.15 mol) was dissolved in toluene (60 mL) and added to the reaction mixture. The mixture was heated to 80° C. for 1 hour without condenser to remove the diethyl ether. Additional 6-cyano-2,2,3,3-tetrafluoro-1.4-benzodioxene (25 g, 0.11 mol) was added and the mixture was heated at reflux temperature for 16 hours. The mixture was cooled with an ice bath and hydrochloric acid (6 M, 150 mL) was added carefully and the mixture was then heated to reflux for 1.5 hour. After cooling, the mixture was partitioned between ethyl acetate and water, and washed with aqueous sodium hydrogen carbonate. The combined organic phases were dried (magnesium sulphate) and concentrated in vacuo. The residual oil was purified by chromatography on silica gel eluting with a mixture of ethyl acetate and heptane (2:8). This afforded the title compound (22 g, 34%).

$^1$H NMR (CDCl$_3$): δ7.80 (dd, 1H), 7.77 (d, 1H), 7.23 (d, 1H), 2.69 (s, 3H); HPLC-MS (Method A): m/z=251 (M+1); $R_t$=4.27 min.

General Procedure (A)

General procedure (A) for solution phase synthesis of building block compounds of the general formula (II):

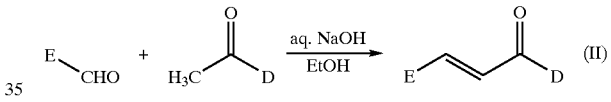

This procedure is illustrated under building block 1.

Building Block 1 (General Procedure (A))

3-(4-Cyclohexylphenyl)-1-(4-trifluoromethylsulfanylphenyl)propenone

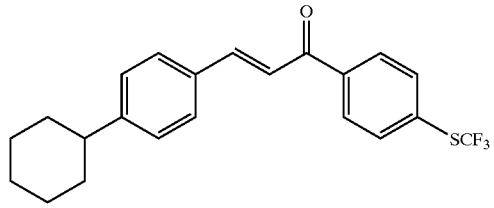

4-(Trifluoromethylsulfanyl)acetophenone (2.34 g, 10.6 mmol) and 4-cyclohexylbenzaldehyde (2 g, 10.6 mmol) were mixed in ethanol (3 mL). NaOH (0.425 g, 10.6 mmol) was dissolved in water (2 mL) and added to the mixture. The mixture was stirred at room temperature and after 10 min a precipitate was observed and additional ethanol (5 mL) was added while maintaining stirring for another 30 min. The mixture was poured into water (100 mL). The precipitate was filtered and dried. This crude product was pure enough for subsequent use without further purification (2.64 g, 64%). Alternatively, it can be recrystallized from heptane to give the pure product.

HPLC-MS (Method A): m/z=391 (M+1); $R_t$=6.68 min.

Building Block 2 (General Procedure (A))

3-(4-Cyclohex-1-enylphenyl)-1-(4-trifluoromethoxyphenyl)propenone

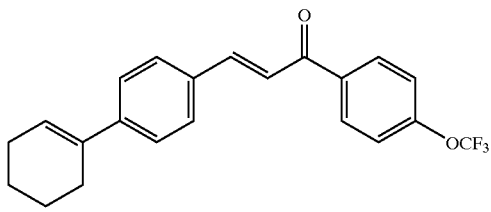

4-(Trifluoromethyloxy)acetophenone (5.18 g, 24.9 mmol) and 4-Cyclohex-1-enylbenzaldehyde (4.63 g, 24.9 mmol) were mixed in ethanol (7 mL). NaOH (1.0 g, 25 mmol) was dissolved in water (5 mL) and added to the mixture. The mixture was stirred at, room temperature and after 10 min a precipitate was observed and additional ethanol (10 mL) was added and the mixture was stirred for another 30 min. The mixture was poured into water (100 mL). The precipitate was filtered and dried. This crude product was pure enough for subsequent use without further purification (9.18 g, 99%). Alternatively, it can be recrystallized from heptane to give the pure product.

$^1$H NMR (DMSO-$d_6$): δ1.60–1.68 (m, 2H), 1.72–1.80 (m, 2H), 2.23 (m, 2H), 2.40 (m, 2H), 6.35 (t, 1H); 7.50 (d, 2H), 7.58 (d, 2H), 7.77 (d, 1H), 7.86 (d, 2H), 7.93 (d, 1H), 8.30 (d, 2H); HPLC-MS (Method C): m/z=373 (M+1); R$_t$=8.90 min.

Building Block 3 (General Procedure (A))

3-(4-Cyclohexylphenyl)-1-(3,5-dichlorophenyl)propenone

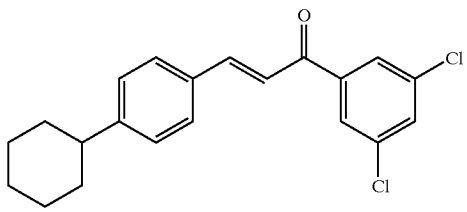

$^1$H NMR (DMSO-$d_6$): δ1.21–1.51 (m, 5H), 1.72–1.97 (m, 5H), 2.55 (m, 1H), 7.27 (d, 2H), 7.35 (d, 1H), 7.55 (s, 1H), 7.59 (d, 2H), 7.84 (d, 1H), 7.86 (s, 2H).

Building Block 4 (General Procedure (A))

3-Biphenyl-4-yl-1-(4-chlorophenyl)propenone

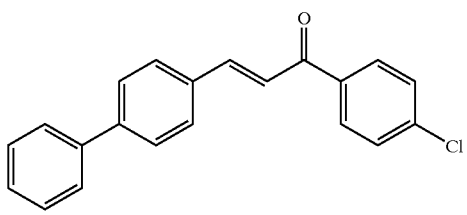

$^1$H NMR (DMSO-$d_6$): δ7.43–7.56 (m, 6H), 7.60–7.69 (m, 4H), 7.74 (d, 2H), 7.86 (d, 1H), 7.98 (d, 2H). HPLC-MS (Method C): m/z=(319); R$_t$=6.86 min.

Building Block 5 (General Procedure (A))

3-Biphenyl-4-yl-1-naphthalen-2-ylpropenone

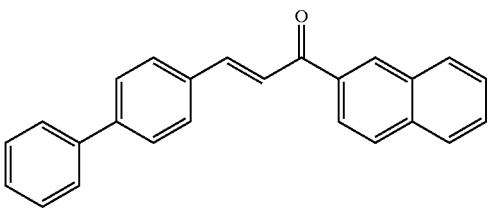

$^1$H NMR (DMSO-$d_6$): δ7.47 (m, 2H), 7.54–7.74 (m, 6H), 7.76 (m, 3H), 7.90 (d, 2H), 7.95 (d, 2H), 8.00 (d, 1H), 8.41 (d, 1H), 8.55 (s, 1H). HPLC-MS (Method C): m/z=335 (M+1); R$_t$=6.83 min.

Building Block 6 (General Procedure (A))

1-(4-Cyclohexylphenyl)-3-(4-isopropylphenyl)propenone

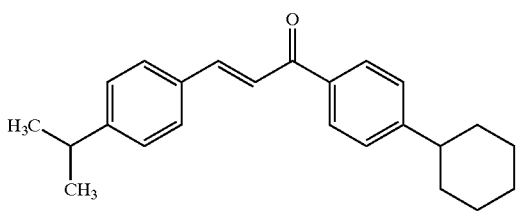

$^1$H NMR (DMSO-$d_6$): δ1.27 (d, 6H), 1.35–1.53 (m, 5H), 1.78 (m, 1H), 1.89 (m, 4H), 2.57 (m, 1H), 2.94 (m, 1H), 7.27 (d, 2H), 7.34 (d, 2H), 7.50 (d, 1H), 7.58 (d, 2H), 7.90 (d, 1H), 7.95 (d, 2H). HPLC-MS (Method C): m/z=333 (M+1); R$_t$=7.93 min.

Building Block 7 (General Procedure (A))

3-Indan-5-yl-1-(4-trifluoromethoxyphenyl)propenone

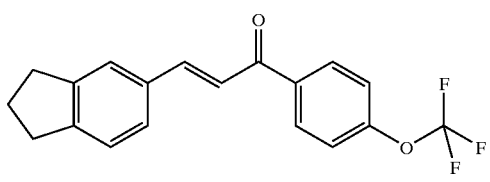

$^1$H NMR (DMSO-$d_6$): δ2.11 (p, 2H), 2.94 (t, 4H), 7.26 (d, 1H), 7.27 (d, 1H), 7.34 (s, 1H), 7.45 (d, 1H), 7.49 (d, 2H), 7.84 (d, 1H), 8.06 (d, 2H); HPLC-MS (Method A): m/z=333 (M+1); R$_t$=5.98 min.

Building Block 8 (General Procedure (A))

3-[4-(2,2-Dimethylpropyl)phenyl]-1-(4-trifluoromethoxyphenyl)propenone

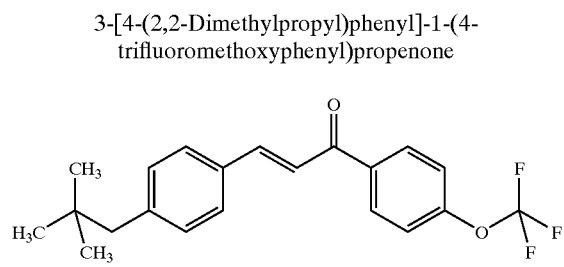

$^1$H NMR (DMSO-$d_6$): δ 0.92 (s, 9H), 2.54 (s, 2H), 7.17 (d, 2H), 7.33 (d, 2H), 7.45 (d, 1H), 7.55 (d, 2H), 7.84 (d, 1H), 8.07 (d, 2H); HPLC-MS (Method A): m/z=363 (M+1); R$_t$=6.56 min.

Building Block 9 (General Procedure (A))

1-Benzo[1,3]dioxol-5-yl-3-(4-cyclohexylphenyl)propenone

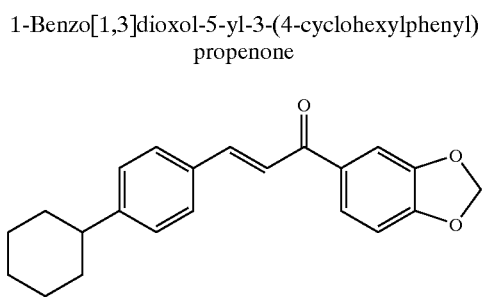

$^1$H NMR (DMSO-$d_6$): δ1.17–1.50 (m, 5H), 1.69–1.95 (m, 5H), 2.52 (m, 1H), 6.07 (s, 2H), 6.88 (d, 1H), 7.24 (d, 2H), 7.44 (d, 1H), 7.51 (d, 1H), 7.55 (d, 2H), 7.64 (dd, 1H), 7.88 (d, 1H).

Building Block 10 (General Procedure (A))

3-(4-Cyclohexylphenyl)-1-(4-isopropylphenyl)propenone

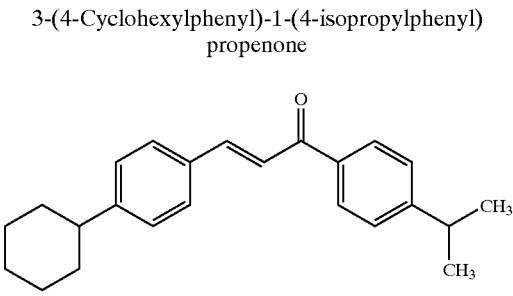

$^1$H NMR (DMSO-$d_6$): δ1.19–1.49 (m, 5H), 1.30 (d, 6H), 1.68–1.95 (m, 5H), 2.54 (m, 1H), 2.99 (m, 1H), 7.26 (d, 2H), 7.35 (d, 2H), 7.47 (d, 1H), 7.57 (d, 2H), 7.78 (d, 1H), 7.95 (d, 2H).

Building Block 11 (General Procedure (A))

1,3-Bis-(4-cyclohexylphenyl)propenone

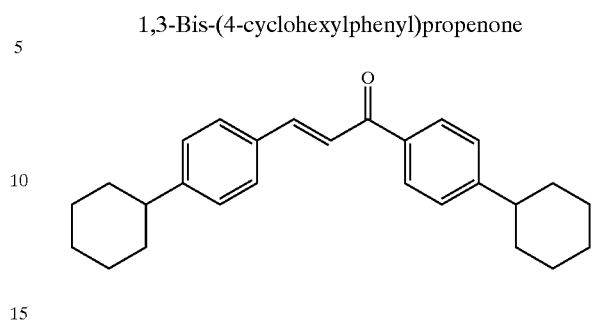

$^1$H NMR (DMSO-$d_6$): δ1.21–1.56 (m, 10H), 1.70–1.98 (m, 10H), 2.45–2.66 (m, 2H), 7.25 (d, 2H), 7.33 (d, 2H), 7.51 (d, 1H), 7.58 (d, 2H), 7.80 (d, 1H), 7.95 (d, 2H).

Building Block 12 (General Procedure (A))

1-(4-Isobutylphenyl)-3-(4-trifluoromethoxyphenyl)propenone

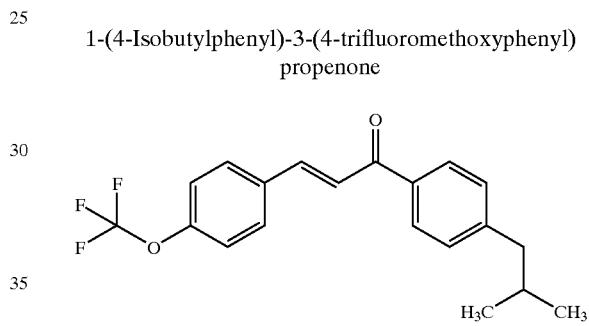

$^1$H NMR (DMSO-$d_6$): δ0.93 (d, 6H), 1.93 (m, 1H), 2.55 (d, 2H), 7.24 (d, 2H), 7.29 (d, 2H), 7.51 (d, 1H), 7.67 (d, 2H), 7.77 (d, 1H), 7.95 (d, 2H); HPLC-MS (Method D): m/z=349 (M+1); R$_t$=5.97 min.

Building Block 13 (General Procedure (A))

1-(4-Cyclopentylphenyl)-3-(4-trifluoromethoxyphenyl)propenone

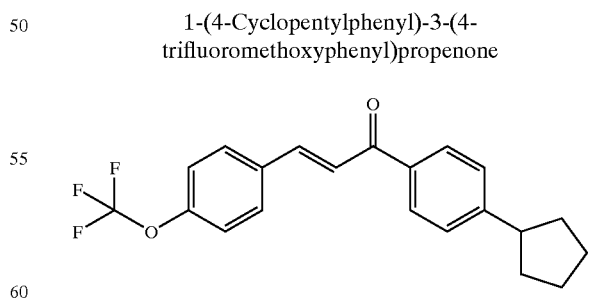

$^1$H NMR (DMSO-$d_6$): δ1.57–1.87 (m, 6H), 2.02–2.18 (m, 2H), 3.07 (p, 1H), 7.25 (d, 2H), 7.38 (d, 2H), 7.51 (d, 1H), 7.66 (d, 2H), 7.78 (d, 1H), 7.95 (d, 2H); HPLC-MS (Method D): m/z=361 (M+1); R$_t$=6.06 min.

Building Block 14 (General Procedure (A))

1-Phenyl-3-(4-trifluoromethoxyphenyl)propenone

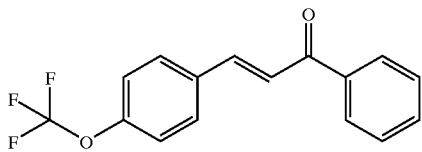

¹H NMR (DMSO-d₆): δ7.27 (d, 2H), 7.45–7.63 (m, 4H), 7.67 (d, 2H), 7.77 (d, 1H), 8.00 (d, 2H); HPLC-MS (Method D): m/z=293 (M+1); $R_t$=4.97 min.

Building Block 15 (General Procedure (A))

1-p-Tolyl-3-(4-trifluoromethoxyphenyl)propenone

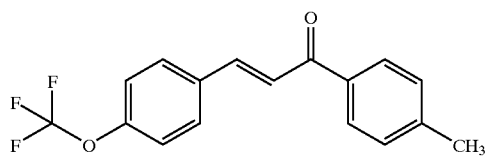

¹H NMR (DMSO-d₆): δ2.45 (s, 3H), 7.25 (d, 2H), 7.31 (d, 2H), 7.49 (d, 1H), 7.67 (d, 2H), 7.77 (d, 1H), 7.92 (d, 2H); HPLC-MS (Method D): m/z=307 (M+1); $R_t$=5.22 min.

Building Block 16 (General Procedure (A))

1-(4-Methoxyphenyl)-3-(4-trifluoromethoxyphenyl)propenone

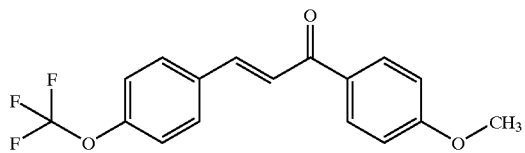

¹H NMR (DMSO-d₆): δ3.90 (s, 3H), 6.99 (d, 2H), 7.25 (d, 2H), 7.50 (d, 1H), 7.67 (d, 2H), 7.77 (d, 1H), 8.04 (d, 2H); HPLC-MS (Method D): m/z=323 (M+1); $R_t$=4.93 min.

Building Block 17 (General Procedure (A))

3-(4-Cyclohexylphenyl)-1-(4-trifluoromethoxyphenyl)propenone

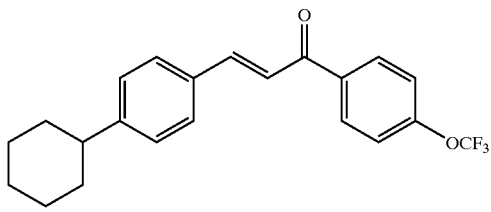

¹H NMR (CDCl₃): δ8.08 (d, 2H), 7.83 (d, 1H), 7.58 (d, 2H), 7.45 (d, 1H), 7.32 (d, 2H); 7.28 (2, 1H), 2.54 (m, 1H), 1.95–1.73 (m, 5H), 1.50–1.20 (m, 5H); HPLC-MS (Method A): m/z=375 (M+1); $R_t$=6.70 min.

Building Block 18 (General Procedure (A))

3-Biphenyl-4-yl-1-(4-trifluoromethoxyphenyl)propenone

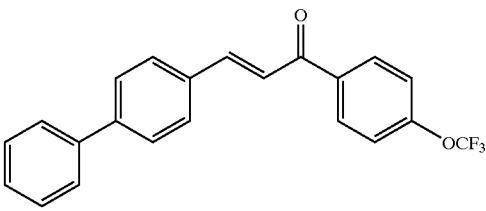

¹H NMR (CDCl₃): δ8.09 (d, 2H), 7.87 (d, 1H), 7.75–7.60 (m, 6H), 7.52 (d, 1H), 7.49–7.29 (m, 5H); HPLC-MS (Method A): m/z=369 (M+1); $R_t$=6.00 min.

Building Block 19 (General Procedure (A))

3-Biphenyl-4-yl-1-(4-trifluoromethylsulfanylphenyl)propenone

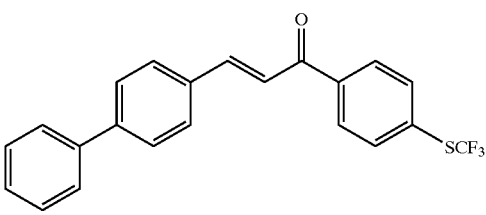

HPLC-MS (Method A): m/z=385 (M+1); $R_t$=6.18 min.

Building Block 20 (General Procedure (A))

3-Biphenyl-4-yl-1-(2,2,3,3-tetrafluoro-2,3-dihydrobenzo[1,4]dioxin-6-yl)propenone

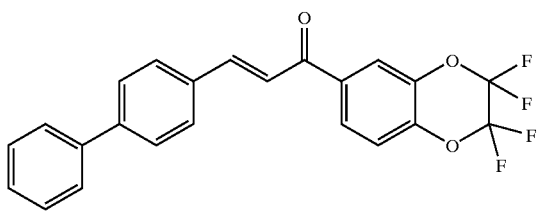

HPLC-MS (Method A): m/z=415 (M+1); $R_t$=6.22 min.

Building Block 21 (General Procedure (A))

3-(4-Cyclohexylphenyl)-1-(2,2,3,3-tetrafluoro-2,3-dihydrobenzo[1,4]dioxin-6-yl)propenone

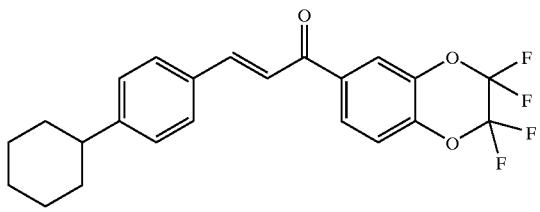

HPLC-MS (Method A): m/z=421 (M+1); $R_t$=6.76 min.

Building Block 22 (General Procedure (A))

3-(4-Cyclohexylphenyl)-1-(3-trifluoromethoxyphenyl)propenone

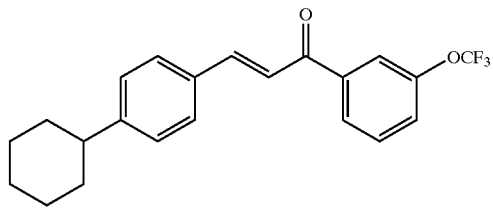

HPLC-MS (Method A): m/z=375 (M+1); $R_t$=6.54 min.

Building Block 23 (General Procedure (A))

3-(4-tert-Butylphenyl)-1-(4-trifluoromethylsulfanylphenyl)propenone

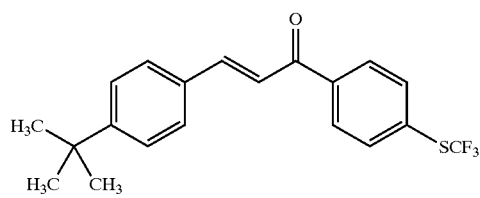

HPLC-MS (Method A): m/z=365 (M+1); $R_t$=6.32 min.

Building Block 24 (General Procedure (A))

3-Biphenyl-4-yl-1-(3-bromophenyl)propenone

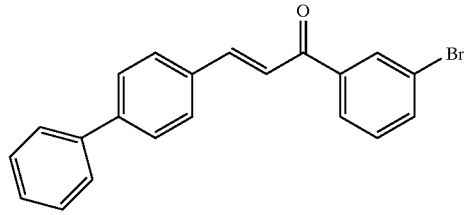

HPLC-MS (Method A): m/z=363 (M+1); $R_t$=5.91 min.

Building Block 25 (General Procedure (A))

3-Biphenyl-4-yl-1-(3-trifluoromethylphenyl)propenone

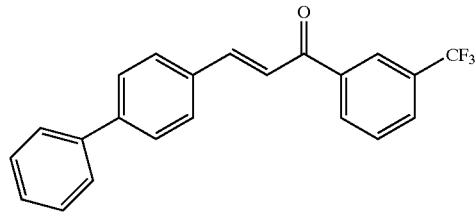

Building Block 26 (General Procedure (A))

3-(4-Bromothiophen-2-yl)-1-(4-trifluoromethoxyphenyl)propenone

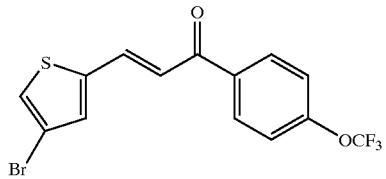

HPLC-MS (Method A): m/z=377 (M+1); $R_t$=5.50 min.

Building Block 27 (General Procedure (A))

1,3-Bis-(4-trifluoromethoxyphenyl)propenone

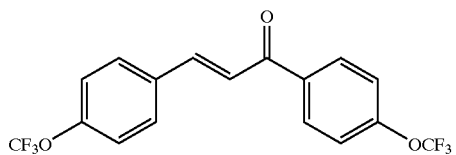

$^1$H NMR (CDCl$_3$): δ8.31 (d, 2H), 8.05 (d, 2H), 7.99 (d, 1H), 7.80 (d, 1H), 7.56 (d, 2H), 7.47 (d, 2H); HPLC-MS (Method A): m/z=377 (M+1); $R_t$=5.83 min.

Building Block 28 (General Procedure (A))

3-(4-tert-Butylphenyl)-1-(4-trifluoromethoxyphenyl)propenone

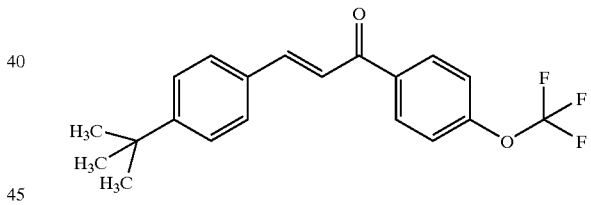

$^1$H NMR (CDCl$_3$): δ8.07 (d, 2H), 7.82 (d, 1H), 7.60 (d, 2H), 7.46 (m, 3H), 7.34 (d, 2H), 1.36 (s, 9H); HPLC-MS (Method A): m/z=349 (M+1); $R_t$=6.35 min.

Building Block 29 (General Procedure (A))

3-(4-Phenoxyphenyl)-1-(4-trifluoromethoxyphenyl)propenone

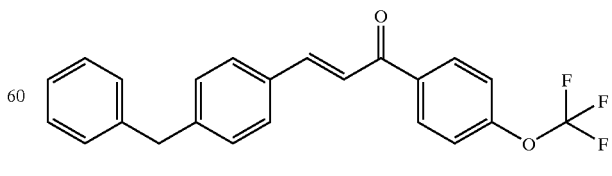

$^1$H NMR (CDCl$_3$): δ8.07 (d, 2H), 7.79 (d, 1H), 7.61 (d, 2H), 7.4–7.3 (m, 5H), 7.18 (t, 1H), 7.1–7.0 (m, 4H); HPLC-MS (Method A): m/z=385 (M+1); $R_t$=6.12 min.

Building Block 30 (General Procedure (A))

3-(3-Phenoxyphenyl)-1-(4-trifluoromethoxyphenyl)propenone

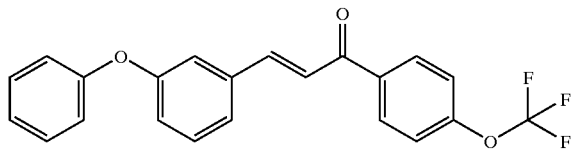

$^1$H NMR (DMSO-d$_6$): δ8.31 (d, 2H), 7.97 (d, 1H), 7.76 (d, 1H), 7.7 (m, 2H), 7.55–7.35 (m, 5H), 7.15 (t, 1H), 7.1–7.0 (m, 3H); HPLC-MS (Method A): m/z=385 (M+1); R$_t$=6.09 min.

Building Block 31 (General Procedure (A))

3-(4-Benzyloxyphenyl)-1-(4-trifluoromethoxyphenyl)propenone

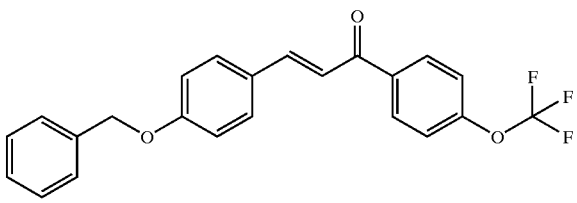

$^1$H NMR (CDCl$_3$): δ8.05 (d, 2H), 7.78 (d, 1H), 7.60 (d, 2H), 7.45–7.30 (m, 8H), 7.00 (d, 2H), 5.13 (s, 2H); HPLC-MS (Method A): m/z=399 (M+1); R$_t$=6.04 min.

Building Block 32 (General Procedure (A))

3-(4-Cyclohexylphenyl)-1-(3,4-difluorophenyl)propenone

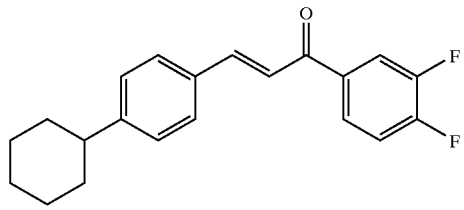

$^1$H NMR (CDCl$_3$): δ7.90–7.80 (m, 3H), 7.60 (d, 2H), 7.43 (d, 1H), 7.3 (m, H), 2.55 (m, 1H), 1.9–1.75 (m, 5H), 1.5 (m, 5H); HPLC-MS (Method A): m/z=327 (M+1); R$_t$=6.20 min.

Building Block 33 (General Procedure (A))

1-(4-sec-Butylphenyl)-3-(3-phenoxyphenyl)propenone

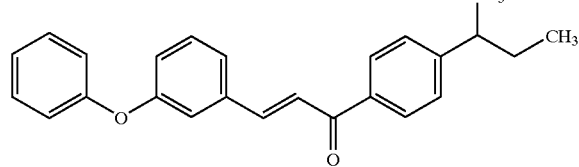

HPLC-MS (Method A): m/z=357 (M); R$_t$=7.16 min.

Building Block 34 (General Procedure (A))

3-[3-(4-Chlorophenoxy)phenyl]-1-(5,6,7,8-tetrahydronaphthalen-2-yl)propenone

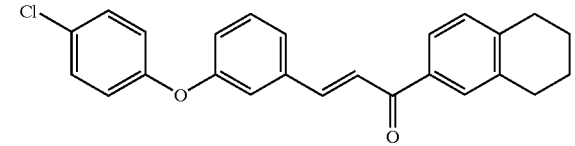

HPLC-MS (Method A): m/z=389 (M+1); R$_t$=7.68 min.

Building Block 35 (General Procedure (A))

3-(4-Benzyloxyphenyl)-1-(3-bromophenyl)propenone

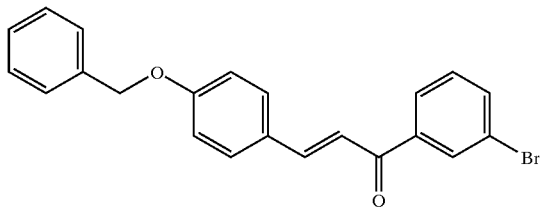

HPLC-MS (Method A): m/z=393 (M+1); R$_t$=6.82 min.

Building Block 36 (General Procedure (A))

1-Biphenyl-4-yl-3-(4-cyclohexylphenyl)propenone

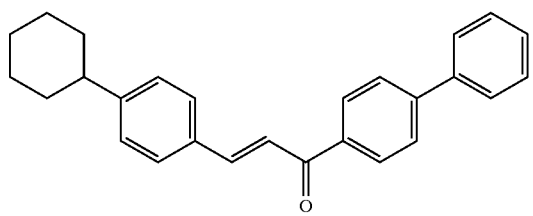

$^1$H NMR (DMSO-d$_6$): δ1.20–1.50 (5H, m), 1.65–1.85 (5H, m), 7.33 (2H, d), 7.45 (2H, d), 7.53 (2H, dd), 7.53–7.92 (6H, m), 8.25 (1H, d); HPLC-MS (Method C): m/z=367 (M+1); R$_t$=9.18 min.

Building Block 37 (General Procedure (A))

1-(2-Chlorophenyl)-3-(4-cyclohexylphenyl)propenone

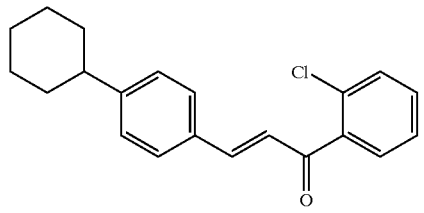

$^1$H NMR (DMSO-$d_6$): δ1.15–1.48 (5H, m), 1.62–1.85 (5H, m), 7.17–7.30 (5H, m), 7.37 (1H, d), 7.49 (1H, d), 7.56 (2H, dd), 7.67 (1H, d), 8.21 (1H, s), 8.53 (1H, t); HPLC-MS (Method C): m/z=325 (M+1); $R_t$=8.47 min.

Building Block 38 (General Procedure (A))

3-(4-Cyclohexylphenyl)-1-(2-trifluoromethylphenyl)propenone

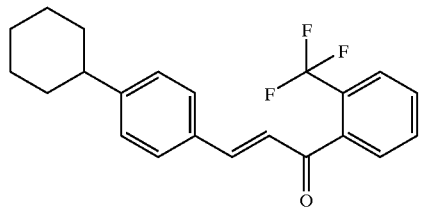

$^1$H NMR (DMSO-$d_6$): δ1.15–1.48 (5H, m), 1.65–1.88 (5H, m), 7.22 (1H, s), 7.30 (3H, d), 7.66 (3H, d), 7.72–7.82 (2H, m), 7.89 (1H, d); HPLC-MS (Method C): m/z=359 (M+1); $R_t$=8.47 min.

Building Block 39 (General Procedure (A))

1-(4-tert-Butylphenyl)-3-(4-cyclohexylphenyl)propenone

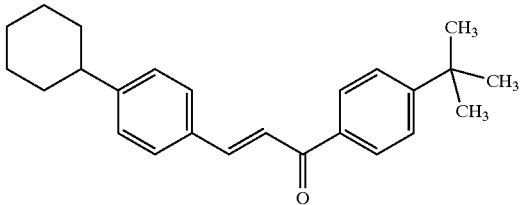

$^1$H NMR (DMSO-$d_6$): δ1.25–1.47 (14H, m), 1.65–1.85 (5H, m), 7.31 (2H, d), 7.58 (2H, d), 7.65–7.90 (4H, m), 8.07 (2H, d); HPLC-MS (Method C): m/z=347 (M+1); $R_t$=9.22 min.

Building Block 40 (General Procedure (A))

3-(4-Cyclohexylphenyl)-1-(4-phenoxyphenyl)propenone

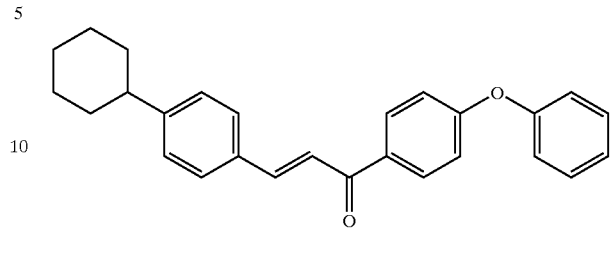

$^1$H NMR (DMSO-$d_6$): δ1.2–1.5 (5H, m), 1.7–1.85 (5H, m), 7.08 (2H, d), 7.14 (2H, d), 7.31 (3H, m), 7.47 (2H, dd), 7.67–7.90 (4H, m), 7.20 (2H, d); HPLC-MS (Method C): m/z=383 (M+1); $R_t$=9.13 min.

Building Block 41 (General Procedure (A))

3-(4-Cyclohexylphenyl)-1-(4-piperidin-1-ylphenyl)propenone

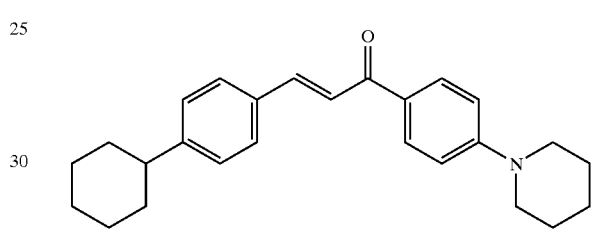

$^1$H NMR (DMSO-$d_6$): δ1.20–1.50 (5H, m), 1.59 (6H, s), 1.62–1.83 (5H, m), 3.40 (4H, s), 6.98 (2H, d), 7.29 (2H, d), 7.62 (1H, d), 7.76 (2H, d), 7.84 (1H, d), 8.02 (2H, d); HPLC-MS (Method C): m/z=374 (M+1); $R_t$=8.30 min.

Building Block 42 (General Procedure (A))

3-(4-Trifluoromethoxyphenyl)-1-(4-trifluoromethylsulfanylphenyl)propenone

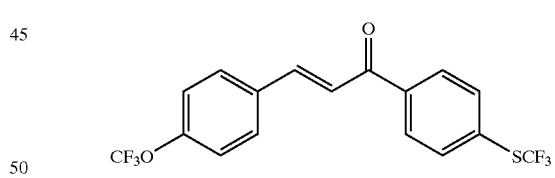

HPLC-MS (Method A): m/z=393 (M+1); $R_t$=6.05 min.

Building Block 43 (General Procedure (A))

1-(3-Trifluoromethoxyphenyl)-3-(4-trifluoromethoxyphenyl)propenone

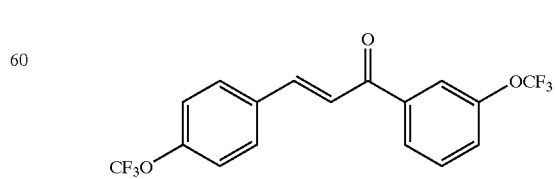

HPLC-MS (Method A): m/z=377 (M+1); $R_t$=5.87 min.

Building Block 44 (General Procedure (A))

1-3-(Biphenyl-4-yl)-1-(4-cyclohexylphenyl)propenone

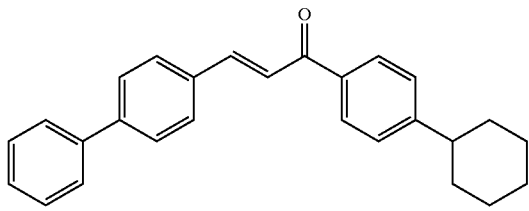

HPLC-MS (Method A): m/z=367 (M+1); $R_t$=6.82 min.

Building Block 45 (General Procedure (A))

1-(4-tert-butylphenyl)-3-(4-trifluoromethoxyphenyl)propenone

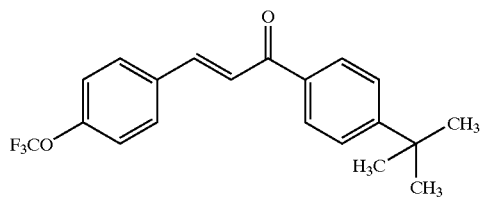

$^1$H NMR (DMSO-d$_6$): δ1.33 (s, 9H), 7.43–7.50 (d, 2H), 7.58–7.7.63 (d, 2H), 7.72–7.79 (d, 2H), 7.94 (s, 1H); 7.97–8.14 (m, 4H); HPLC-MS (Method C): m/z=349 (M+1); $R_t$=6.70 min.

Building Block 46 (General Procedure (A))

1-(2,2,3,3-Tetrafluoro-2,3-dihydrobenzo[1,4]dioxin-6-yl)-3-(4-triluoromethoxyphenyl)-propenone

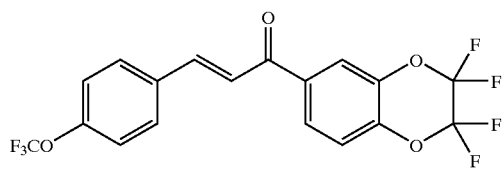

$^1$H NMR (DMSO-d$_6$) selected: δ7.42–7.50 (d, 2H), 7.67–7.73 (d, 1H), 7.78–7.76 (d, 1H), 7.99 (s, 1H); 8.03–8.11 (d, 2H); 8.13–8.18 (d, 1H), 8.33 (s, 1H); HPLC-MS (Method D): m/z=423 (M+1); $R_t$=5.97 min.

Building Block 47 (General Procedure (A))

1-(4-Chlorophenyl)-3-(4-cyclohexylphenyl)propenone

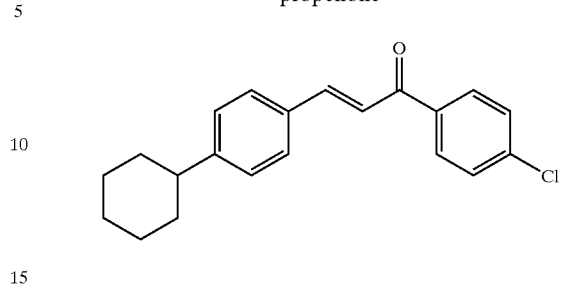

$^1$H NMR (DMSO-d$_6$): δ1.18–1.53 (m, 5H), 1.66–1.89 (m, 5H), 2.51–2.62 (m, 1H), 7.27–7.36 (d, 2H), 7.60–7.69 (d, 2H); 7.70–7.93 (m, 4H), 8.13–8.23 (d, 2H); HPLC-MS (Method C): m/z=325 (M+1); $R_t$=7.33 min. Microanalysis: Calculated for $C_{21}H_{21}ClO$, $0.25H_2O$: C, 76.58%; H, 6.58%; Found: C, 76.24%; H, 6.53%.

Building Block 48 (General Procedure (A))

3-(4-Cyclohexylphenyl)-1-(5,6,7,8-tetrahydronaphthalen-2-yl)propenone

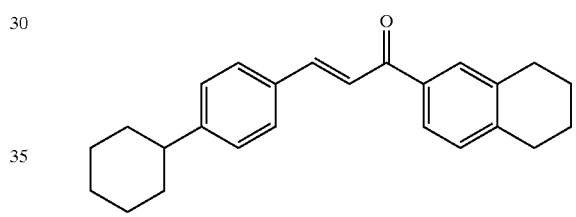

$^1$H NMR (DMSO-d$_6$): δ1.20–1.52 (m, 5H), 1.68–1.86 (m, 9H), 2.52–2.61 (m, 1H), 2.77–2.87 (m, 4H), 7.21–7.26 (d, 1H); 7.28–7.34 (d, 2H), 7.64–7.73 (d, 1H), 7.78–7.90 (m, 5H); HPLC-MS (Method A): m/z=345 (M+1); $R_t$=7.04 min. Microanalysis: Calculated for $C_{25}H_{28}O$, $0.25H_2O$: C, 86.04%; H, 8.23%; Found: C, 86.60%; H, 8.35%.

Building Block 49 (General Procedure (A))

1-(5,6,7,8-Tetrahydronaphthalen-2-yl)-3-(4-trifluoromethoxyphenyl)propenone

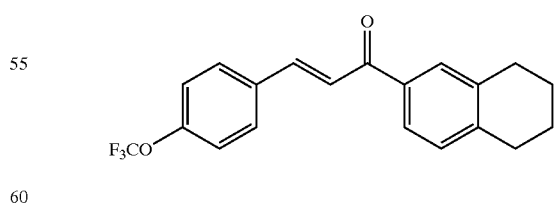

$^1$H NMR (DMSO-d$_6$): δ1.72–1.83 (m, 4H), 2.74–2.89 (m, 4H), 7.21–7.29 (d, 1H), 7.41–7.49 (d, 2H), 7.70–7.80 (d, 1H); 7.80–7.99 (m, 4H), 8.00–8.08 (d, 1H); HPLC-MS (Method C): m/z=347 (M+1); $R_t$=7.07 min. Microanalysis: Calculated for $C_{20}H_{17}F_3O_2$: C, 69.36%; H, 4.95%; Found: C, 69.13%; H, 4.96%.

Building Block 50 (General Procedure (A))

3-(4-Chlorophenyl)-1-(4-cyclohexylphenyl)propenone

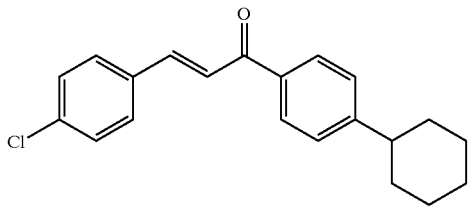

¹H NMR (DMSO-d₆): δ1.18–1.55 (m, 5H), 1.68–1.91 (m, 5H), 2.56–2.69 (m, 1H), 7.37–7.47 (d, 2H), 7.48–7.57 (d, 2H); 7.66–7.78 (d, 1H), 7.88–8.02 (m, 3H), 8.04–8.14 (d, 2H); HPLC-MS (Method C): m/z=325 (M+1); $R_t$=7.40 min. Microanalysis: Calculated for $C_{21}H_{21}ClO$, $0.25H_2O$: C, 76.58%; H, 6.58%; Found: C, 76.54%; H, 6.43%.

Building Block 51 (General Procedure (A))

1-Biphenyl-4-yl-3-(4-cyclohexylphenyl)propenone

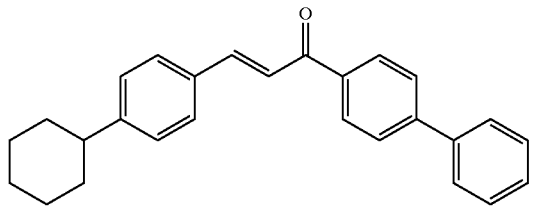

¹H NMR (CDCl₃): δ1.20–1.52 (m, 5H), 1.71–1.95 (m, 5H), 2.49–2.61 (m, 1H), 7.30 (d, 1H), 7.37–7.52 (m, 5H); 7.56–7.68 (m, 4H), 7.69–7.76 (d, 2H), 7.79–7.87 (d, 1H), 8.05–8.13 (d, 2H); HPLC-MS (Method C): m/z=367 (M+1); $R_t$=8.00 min.

Building Block 52 (General Procedure (A))

1-(4-Cyclohexylphenyl)-3-(4-trifluoromethoxyphenyl)propenone

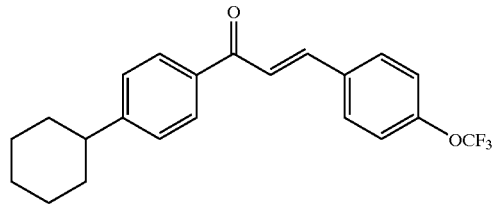

HPLC-MS (Method A): m/z=375 (M+1); $R_t$=6.60 min.

Building Block 53 (General Procedure (A))

1-Biphenyl-4-yl-3-(4-trifluoromethoxyphenyl)propenone

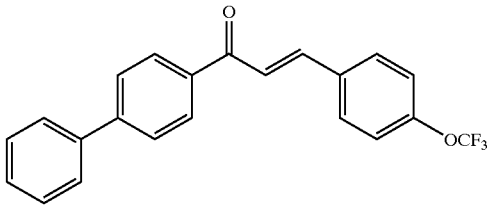

HPLC-MS (Method A): m/z=369 (M+1); $R_t$=5.86 min.

Building Block 54 (General Procedure (A))

1-(4-Cyclohexylphenyl)-3-(3,5-dichlorophenyl)propenone

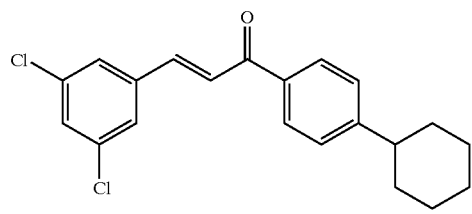

HPLC-MS (Method A): m/z=360 (M+1); $R_t$=6.52 min.

Building Block 55 (General Procedure (A))

3-(3-Bromophenyl)-1-(4-cyclohexylphenyl)propenone

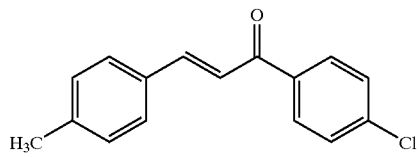

HPLC-MS (Method A): m/z=369 (M+1); $R_t$=6.39 min.

Building Block 56 (General Procedure (A))

3-(4-Methylphenyl)-1-(4-chlorophenyl)propenone

HPLC-MS (Method A): m/z=257 (M+1); $R_t$=5.05 min.
This compound is known (*Tet. Lett.* 39(16), 2235, (1998))

Building Block 57 (General Procedure (A))

1,3-Bis-(4-chlorophenyl)propenone

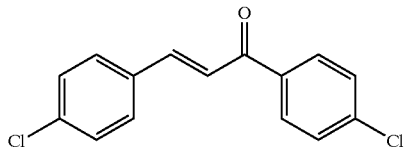

This compound is known (*Chem. Ber.* 42, 1813, (1909))

Building Block 58 (General Procedure (A))

3-(4-Cyclohexylphenyl)-1-indan-5-ylpropenone

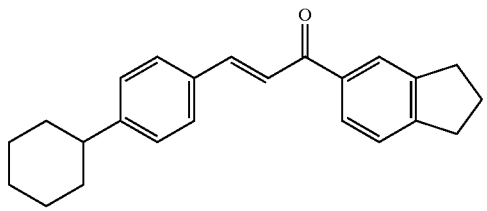

$^1$H NMR (DMSO-d$_6$): δ1.20–1.51 (m, 5H), 1.70–1.97 (m, 5H), 2.15 (p, 2H), 2.54 (m, 1H), 2.97 (t, 4H), 7.25 (d, 2H), 7.32 (d, 1H), 7.48 (d, 1H), 7.55 (d, 2H), 7.78 (d, 1H), 7.82 (d, 1H), 7.86 (s, 1H).

HPLC-MS (Method C): m/z=331 (M+1); R$_t$=6.46 min.

Building Block 59 (General Procedure (A))

3-(4-Cyclohexylphenyl)-1-(4-isobutylphenyl)propenone

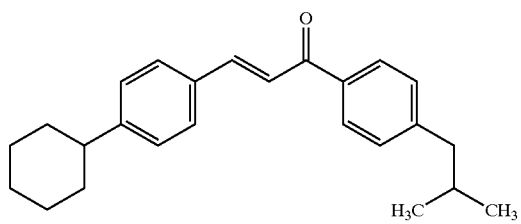

$^1$H NMR (DMSO-d$_6$): δ0.95 (d, 6H), 1.21–1.50 (m, 5H), 1.75 (m, 1H), 1.78–2.20 (m, 5H), 2.49 (m, 1H), 2.57 (d, 2H), 7.25 (d, 2H), 7.27 (d, 2H), 7.49 (d, 1H), 7.56 (d, 2H), 7.79 (d, 1H), 7.94 (d, 2H). HPLC-MS (Method C): m/z=347 (M+1); R$_t$=6.69 min.

Building Block 60 (General Procedure (A))

3-(4-Cyclohexylphenyl)-1-(4-cyclopentylphenyl)propenone

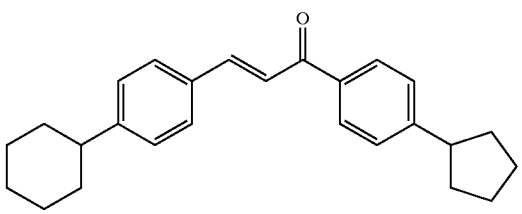

$^1$H NMR (DMSO-d$_6$): δ1.22–1.50 (m, 5H), 1.62–1.96 (m, 11H), 2.04–2.20 (m, 2H), 2.54 (m, 1H), 3.07 (p, 1H), 7.25 (d, 2H), 7.38 (d, 2H), 7.50 (d, 1H), 7.56 (d, 2H), 7.80 (d, 1H), 7.95 (d, 2H). HPLC-MS (Method C): m/z=359 (M+1); R$_t$=6.77 min.

Building Block 4 (General Procedure (A))

3-(4-Cyclohexylphenyl)-1-phenylpropenone

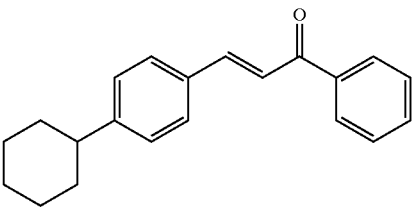

$^1$H NMR (DMSO-d$_6$): δ1.22–1.54 (m, 5H), 1.71–1.96 (m, 5H), 2.46–2.63 (m, 1H), 7.25 (d, 2H), 7.44–7.62 (m, 6H), 7.80 (d, 1H), 8.02 (d, 2H). HPLC-MS (Method C): m/z=291 (M+1); R$_t$=5.91 min.

Building Block 5 (General Procedure (A))

3-(4-Cyclohexylphenyl)-1-(4-methylphenyl)propenone

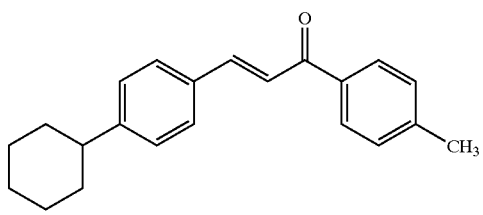

$^1$H NMR (DMSO-d$_6$): δ1.21–1.55 (m, 5H), 1.69–1.96 (m, 5H), 2.43 (s, 3H), 2.46–2.64 (m, 1H), 7.25 (d, 2H), 7.30 (d, 2H), 7.49 (d, 1H), 7.57 (d, 2H), 7.80 (d, 1H), 7.93 (d, 2H). HPLC-MS (Method A): m/z=305 (M+1); R$_t$=6.15 min.

Building Block 6 (General Procedure (A))

3-(4-Cyclohexylphenyl)-1-(4-methoxyphenyl)propenone

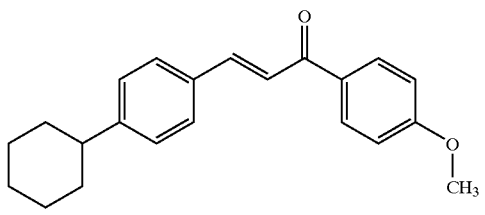

$^1$H NMR (DMSO-d$_6$): δ 1.19–1.54 (m, 5H), 1.68–1.95 (m, 5H), 2.45–2.62 (m, 1H), 3.90 (s, 3H), 6.96 (d, 2H), 7.25 (d, 2H), 7.50 (d, 1H), 7.56 (d, 2H), 7.79 (d, 1H), 8.04 (d, 2H). HPLC-MS (Method A): m/z=321 (M+1); R$_t$=5.85 min.

Building Block 61 (General Procedure (A))

1-(4-tert-Butylphenyl)-3-(4-trifluoromethoxyphenyl)propenone

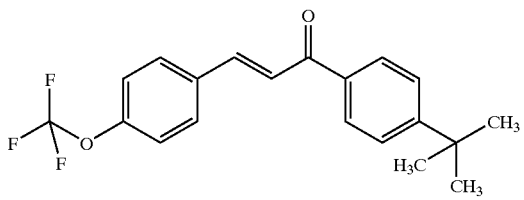

4-(Trifluoromethoxy)benzaldehyde (16,5 g, 87 mmol) and 4-tert-butylacetophenone (15.3 g, 87 mmol) were dissolved in ethanol 99% (25 mL). The solution was added sodium hydroxide (8N, 16.2 mL) The reaction mixture was stirred for 1½ hours, diluted with water (100 mL), filtered after 2½ hours, and washed with water. The product was dried in vacuo and then suspended in ethanol (80 mL) and stirred for 1½ h at 20° C. The mixture was placed in the refrigerator for 16 h and the precipitated product was filtered off and washed with ice-cooled 99% ethanol and dried to afford 11.5 g (38%) of 1-(4-tert-butylphenyl)-3-(4-trifluoromethoxyphenyl)propenone.

HPLC-MS (Method C): m/z=349 (M+1); R$_t$=7.10 min.

Building Block 62

1-(3,5-Bis-trifluoromethylphenyl)-3-(4-cyclohexylphenyl)propenone

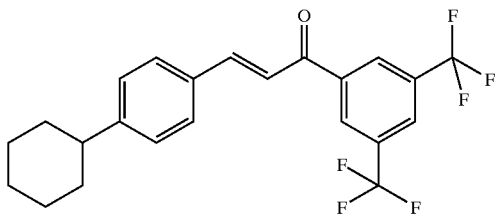

3',5'-Bis(trifluoromethyl)acetophenone (9.3 g, 36.3 mmol) and 4-cyclohexylbenzaldehyde (6.83 g, 36.3 mmol) was dissolved in NMP (18 mL). Zinc(II)acetate (398 mg, 1.8 mmol) and 2,2'-bipyridine (283 mg, 1.81 mmol) were added and the mixture was heated at 100° C. under nitrogen for 16 hours. After cooling the mixture was partitioned between heptane (250 mL) and water (250 mL). The organic phase was dried (NaSO$_4$) and evaporated to dryenes to give the crude material that could be recrystalized from heptane to give the pure title compound as a solid. Yield: 5.8 g (38%).

HPLC-MS (Method D): m/z 427 (M+1); R$_t$=6.71 min.

General Procedure (B)

General procedure (B) for solid phase synthesis of compounds of the general formula (I$_5$):

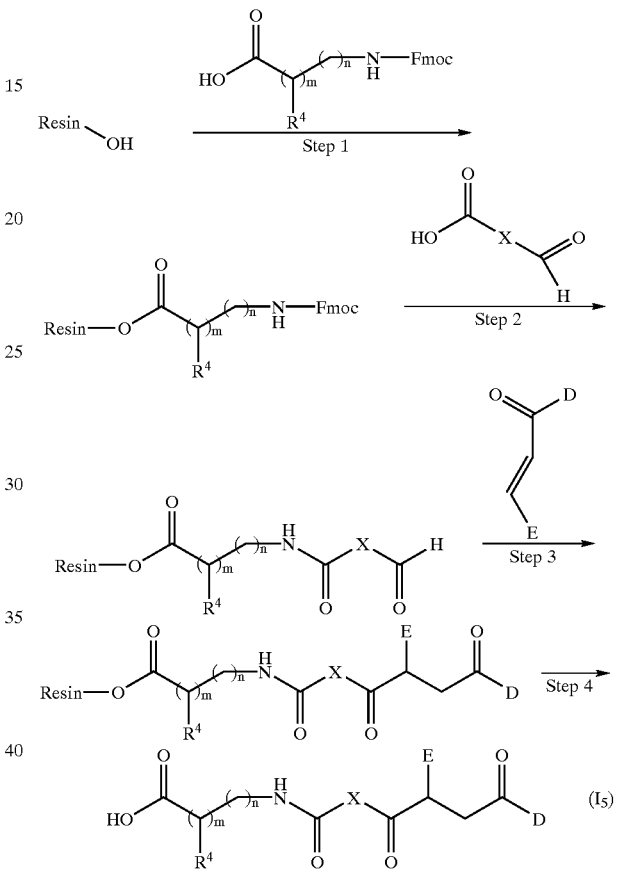

wherein X, D, E, m, n and R$^4$ are as defined for formula (I), and Resin is a polystyrene resin loaded with a Wang-linker.

Step 1:

This reaction is known (Wang S. J., *J. Am. Chem. Soc.* 95, 1328, 1973) and is generally performed by stirring polystyrene resin loaded with a linker such as the Wang linker with a 4–10 molar excess of Fmoc-protected amino acid activated with a 2–5 molar excess of diisopropylcarbodiimide, dicyclohexylcarbodiimide or 1-[3-(dimethylamino)propyl]-3-ethylcarbodiimide hydrochloride in the presence of a catalyst such as N,N-4-dimethylaminopyridine. The esterification is carried out in solvent such as THF, dioxane, toluene, DCM, DMF, NMP or a mixture of two or more of these. The reactions are performed between 0° C. and 80° C., preferably between 20° C. to 40° C. When the esterification is complete excess of reagent is removed by filtration. The resin is successively washed with the solvent used in the reaction, followed by washing with methanol. The resin bound product can be further dried and analyzed.

Step 2:

N-Fluorenylmethylcarbonyl protecting group is removed by treating the resin bound derivative with a 20%–50% solution of a secondary amine such as piperidine in a polar solvent such as DMF or NMP (Carpino L., Han G., *J. Org. Chem.* 37, 3404, 1972). The reaction is performed between 20° C. to 180° C., preferably between 20° C. to 40° C. When the reaction is complete excess of reagent is removed by filtration. The resin is successively washed with solvent used in the reaction. The resulting resin bound intermediate is acylated with acid. The acylation is known (The combinatorial index, Ed. Bunin B. A., 1998, Acedemic press, p. 78) and is generally performed by stirring the resin bound intermediate with a 2–5 molar excess of acid activated with a 2–5 molar excess of of diisopropyl-carbodiimide, dicyclohexylcarbodiimide or 1-[3-(dimethylamino)propyl]-3-ethylcarbodiimide hydrochloride in the presence of a side reaction inhibitor such as N-hydroxybenzotriazole. The acylation is carried out in a solvent such as THF, dioxane, toluene, DCM, DMF, NMP or a mixture of two or more of these. The reactions are performed between 0° C. to 80° C., preferably between 20° C. to 40° C. When the esterification is complete excess of reagent is removed by filtration. The resin is successively washed with the solvent used in the reaction, followed by washing with methanol. The resin bound product can be further dried and analyzed.

Step 3:

This reaction has not previously been reported on solid support but is a modification of a solution based procedure (Stetter H., Krasselt J. *J. Heterocyclic. Chem.* 14, 573, 1977). The addition of aldehydes to activated double bonds is generally carried out by stirring the aldehyde with a compound that contains an activated dobbelt bond such as a substituted propenone in the presence of a catalyst such as sodium or potassium cyanide or thiazolium salts such as 3,4-dimethyl-5-(2-hydroxyethyl)thiazolium iodide, 3-benzyl-5-(2-hydroxyethyl)-4-methyl-1,3-thiazolium chloride, 3-ethyl-5-(2-hydroxyethyl)-4-methyl-1,3-thiazolium bromide or vitamin $B_1$. When thiazolium salts are used as catalyst, a non-nucleophilic amine base such as triethyl amine, N,N-diisopropylethylamine or DBU is added. The addition is carried out in a solvent such as dioxane, DMSO, NMP or DMF or a mixture of two or more of these. The reactions are performed between 50° C. to 120° C., preferably between 50° C. to 80° C. When the reaction is complete, excess of reagent is removed by filtration. The resin is successively washed with the solvent used in the reaction, followed by washing with methanol. The resin bound product can be further dried and analyzed.

Step 4:

The reaction is known (The combinatorial index, Ed. Bunin B. A., 1998, Acedemic press, p. 21) and is generally performed by stirring the resin bound intermediate obtained in step 3 with a 50–95% solution of TFA. The final cleavage is carried out in a solvent such as THF, DCM, 1,2 dichloroethane, 1,3-dichloropropane, toluene or a mixture or more of these. The reactions are performed between 0° C. to 80° C., preferably between 20° C. to 40° C. When the reaction is complete the product is removed by filtration. The resin is successively washed with DCM. The product and washings are collected. The solvent is removed and the product is dried in vacuo.

The procedure is illustrated in the following example.

Example 1

General Procedure (B)

3-{4-[2-Biphenyl-4-yl-4-oxo-4-(4-trifluoromethoxyphenyl)butyryl]benzoylamino}propionic acid

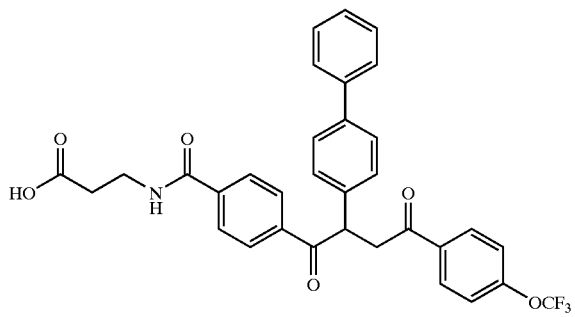

Step 1 and Step 2: Resin bound 3-(4-formylbenzoylamino)propionic acid 3-(4-Formylbenzoylamino)propionic acid resin bound to a Wang resin (loading approximately 0.2–0.8 mmol/g) was synthesized according to the procedure described in WO 00/69810.

Step 3 and Step 4: Preparation of 3-{4-[2-biphenyl-4-yl-4-oxo-4-(4-trifluoromethoxyphenyl)butyryl]benzoylamino}propionic acid The above resin bound 3-(4-formylbenzoylamino)propionic acid (496 mg resin) was suspended in NMP (10 mL). 3,4-Dimethyl-5-(2-hydroxyethyl)thiazolium iodide (432 mg, 1.5 mmol), 3-biphenyl-4-yl-1-(4-trifluoromethoxyphenyl)propenone (1.05 g, 2.7 mmol) and DBU (225 µL, 1.50 mmol) were added and the suspension was shaken at 70° C. for 16 hours. The resin was isolated by filtration and washed with DMF (3×10 mL), ethanol.(2×10 mL), DCM (10×10 mL). The resin bound 3-{4-[2-biphenyl-4-yl-4-oxo-4-(4-trifluoromethoxyphenyl)butyryl]benzoylamino}propionic acid was treated with 50% TFA in DCM (10 mL) for 0.5 hour at 25° C. The mixture was filtered and the resin was washed with DCM (10 mL). The combined filtrates were concentrated in vacuo to afford an oil which was purified on silica gel column eluted with DCM/methanol/acetic acid (95:4:1) to afford the title compound.

$^1$H NMR (CDCl$_3$): δ8.07 (d, 2H), 8.02 (d, 2H), 7.79 (d, 2H), 7.55–7.48 (m, 4H), 7.42–7.24 (m, 7H); 7.05 (t, 1H), 5.32 (dd, 1H), 4.20 (dd, 1H), 3.68 (q, 2H), 3.30 (dd, 1H), 2.64 (t, 2H); HPLC-MS (Method A): m/z=590 (M+1); $R_t$=5.15 min.

The following examples were made as described above.

Example 2

General Procedure (B)

3-{4-[2-Biphenyl-4-yl-4-oxo-4-(3-trifluoromethylphenyl)butyryl]benzoylamino}propionic acid

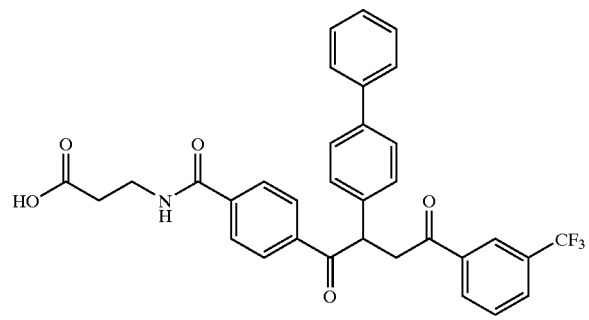

$^1$H NMR (CDCl$_3$): δ8.24 (s, 1H), 8.17 (d, 1H), 8.09 (d, 2H), 7.85–7.75 (m, 3H), 7.64–7.49 (m, 5H); 7.44–7.30 (m, 5H), 6.82 (t, 1H), 5.35 (dd, 1H), 4.26 (dd, 1H), 3.71 (q, 2H), 3.36 (dd, 1H), 2.70 (t, 2H); HPLC-MS (Method A): m/z=574 (M+1); R$_t$=5.04 min.

Example 3

General Procedure (B)

3-{4-[2-(4-Cyclohexylphenyl)-4-oxo-4-(4-trifluoromethylsulfanylphenyl)butyryl]benzoylamino}propionic acid

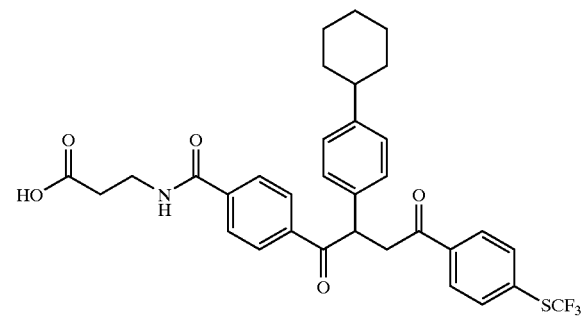

$^1$H NMR (CDCl$_3$): δ8.04 (d, 2H), 7.97 (d, 2H), 7.76 (d, 2H), 7.72 (d, 2H), 7.20 (d, 2H); 7.14 (d, 2H), 6.88 (t, 1H), 5.24 (dd, 1H), 4.17 (dd, 1H), 3.70 (q, 2H), 3.25 (dd, 1H), 2.68 (t, 2H), 2.42 (m, 1H), 1.85–1.68 (m, 5H), 1.45–1.15 (m, 5H); HPLC-MS (Method A): m/z=612 (M+1); R$_t$=5.78 min.

Example 4

General Procedure (B)

3-{4-[4-(3,5-Bistrifluoromethylphenyl)-2-(4-cyclohexylphenyl)-4-oxobutyryl]benzoylamino}propionic acid

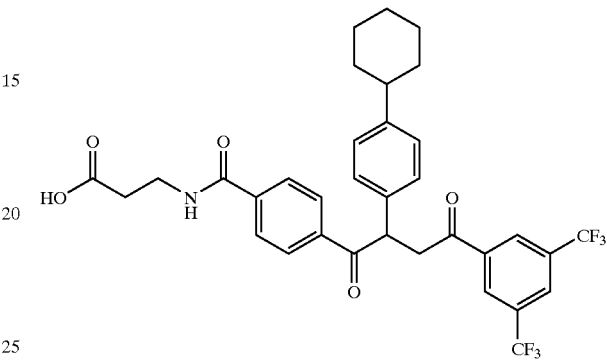

$^1$H NMR (DMSO-d$_6$): δ8.69 (t, 1H), 8.61 (s, 2H), 8.43 (s, 1H), 8.14 (d, 2H), 7.90 (d, 2H); 7.34 (d, 2H), 7.17 (d, 2H), 5.42 (dd, 1H), 4.29 (dd, 1H), 3.64 (dd, 1H), 1.78–1.64 (m, 5H), 1.38–1.25 (m, 5H); HPLC-MS (Method A): m/z=648 (M+1); R$_t$=5.77 min.

Example 5

General Procedure (B)

3-{4-[2-biphenyl-4-yl-4-(3-bromophenyl)-4-oxobutyryl]benzoylamino}propionic acid

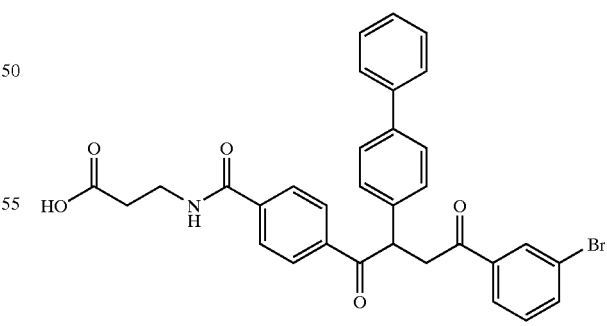

$^1$H NMR (DMSO-d$_6$): δ8.65 (t, 1H), 8.19 (m, 3H), 8.06 (d, 1H), 7.93–7.83 (m, 3H), 7.60 (m, 4H); 7.50 (m, 3H), 7.43 (m, 2H), 7.34 (m, 1H), 5.50 (dd, 1H), 4.20 (dd, 1H); HPLC-MS (Method A): m/z=586 (M+1); R$_t$=4.99 min.

Example 6

General Procedure (B)

3-{4-[2-Biphenyl-4-yl-4-oxo-4-(2,2,3,3-tetrafluoro-2,3-dihydrobenzo[1,4]dioxin-6-yl)butyryl]benzoylamino}propionic acid

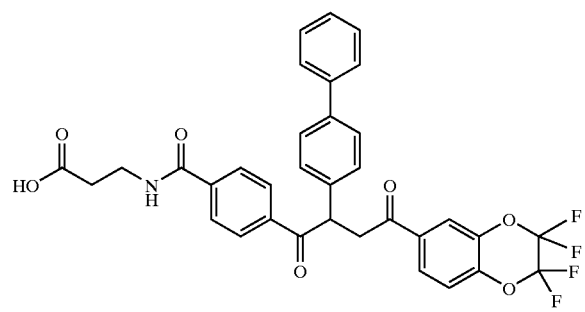

$^1$H NMR (CDCl$_3$): δ8.09 (d, 2H), 7.86–7.75 (m, 4H), 7.55–7.50 (m, 4H), 7.45–7.30 (m, 5H), 7.23 (d, 2H); 6.78 (t, 1H), 5.83 (dd, 1H), 4.18 (dd, 1H), 3.72 (q, 2H), 3.28 (dd, 1H), 2.71(t, 2H); HPLC-MS (Method A): m/z=636 (M+1); R$_t$=5.30 min. Microanalysis: Calculated for C$_{34}$H$_{25}$F$_4$NO$_7$, 0.75H$_2$O: C, 62.92%; H, 4.11%; N, 2.16%. Found: C, 62.94%; H, 3.99%; N, 2.25%.

Example 7

General Procedure (B)

3-{4-[2-(4-Cyclohexylphenyl)-4-oxo-4-(2,2,3,3-tetrafluoro-2,3-dihydrobenzo[1,4]dioxin-6-yl)butyryl]benzoylamino}propionic acid

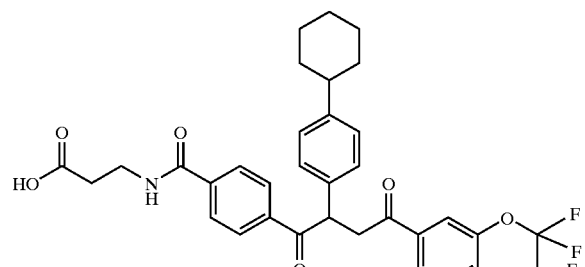

$^1$H NMR (CDCl$_3$): δ8.04 (d, 2H), 7.82–7.70 (m, 4H), 7.23–7.10 (m, 5H), 6.82 (t, 1H), 5.23 (dd, 1H); 4.13 (dd, 1H), 3.72 (br q, 2H), 3.20 (dd, 1H), 2.70 (br t, 2H), 2.44 (m, 1H), 1.85–1.70 (m, 5H), 1.46–1.15 (m, 5H)

Example 8

General Procedure (B)

3-{4-[2-Biphenyl-4-yl-4-(3,5-bis-trifluoromethylphenyl)-4-oxobutyryl]benzoylamino}propionic acid

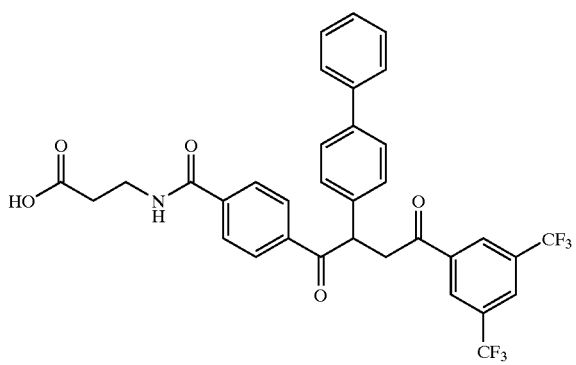

$^1$H NMR (DMSO-d$_6$): δ8.64 (m, 3H), 8.42 (s, 1H), 8.20 (d, 2H), 7.92 (d, 2H), 7.62 (m, 4H); 7.54 (m, 2H), 7.42 (m, 2H), 7.31 (m, 1H), 5.52 (dd, 1H), 4.34 (dd, 1H); HPLC-MS (Method A): m/z=642 (M+1); R$_t$=5.31 min.

Example 9

General Procedure (B)

3-{4-[2-(4-tert-Butylphenyl)-4-oxo-4-(4-trifluoromethylsulfanylphenyl)butyryl]benzoylamino}propionic acid

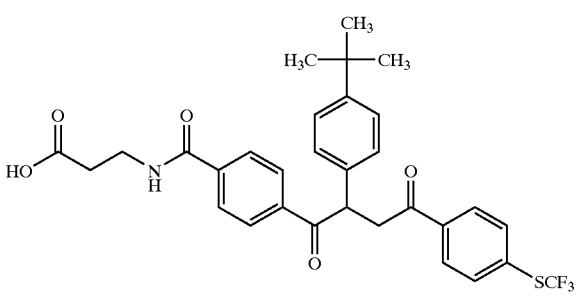

$^1$H NMR (DMSO-d$_6$): δ8.64 (t, 1H), 8.13 (m, 4H), 7.90 (m, 4H), 7.33 (s, 4H), 7.62 (m, 4H), 5.43 (dd, 1H), 4.12 (dd, 1H); HPLC-MS (Method A): m/z=586 (M+1); R$_t$=5.43 min.

Example 10

General Procedure (B)

3-{4-[2-(4-Bromothiophen-2-yl)-4-(3,4-dichlorophenyl)-4-oxobutyryl]benzoylamino}propionic acid

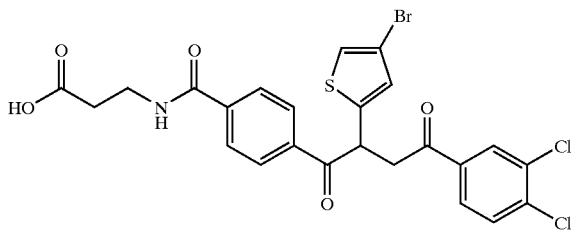

$^1$H NMR (DMSO-d$_6$): δ8.71 (t, 1H), 8.27 (s, 1H), 8.20 (d, 2H), 7.96 (m, 3H), 7.81 (d, 1H), 7.53 (s, 1H), 7.20 (s, 1H); HPLC-MS (Method A): m/z=583 (M+1); R$_t$=4.81 min.

Example 11

General Procedure (B)

3-{4-[2-(4-Bromothiophen-2-yl)-4-(4-chloro-3-methylphenyl)-4-oxobutyryl]benzoylamino}propionic acid

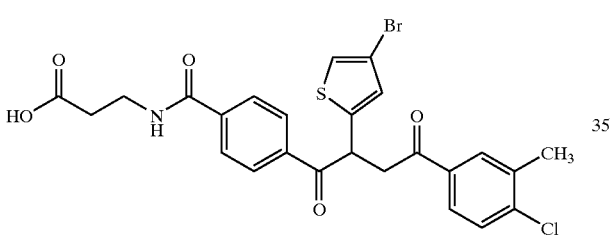

$^1$H NMR (DMSO-d$_6$): δ8.68 (t, 1H), 8.18 (d, 2H), 8.04 (d, 1H), 7.95 (d, 2H), 7.87 (dd, 1H), 7.55 (m, 2H), 7.17 (s, 1H), 5.75, (dd, 1H), 4.10 (dd, 1H); HPLC-MS (Method A): m/z=563 (M+1); R$_t$=4.81 min.

Example 12

General Procedure (B)

3-{4-[2-(4-tert-Butylphenyl)-4-oxo-4-(3-trifluoromethylphenyl)butyryl]benzoylamino}propionic acid

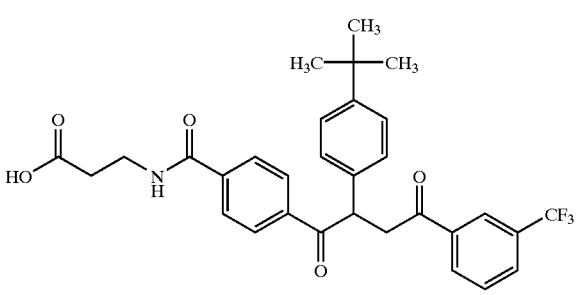

HPLC-MS (Method A): m/z=554 (M+1); R$_t$=5.14 min.

Example 13

General Procedure (B)

3-{4-[2-Biphenyl-4-yl-4-oxo-4-(4-trifluoromethylsulfanylphenyl)butyryl]benzoylamino}propionic acid

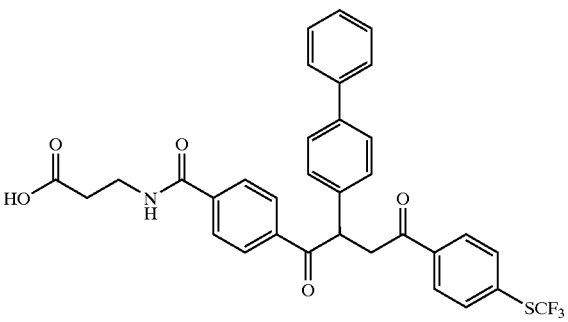

$^1$H NMR (CDCl$_3$): δ8.08 (d, 2H), 8.00 (d, 2H), 7.80–7.68 (m, 5H), 7.56–7.48 (m, 4H), 7.42–7.32 (m, 4H), 6.97 (t, 1H), 5.32 (dd, 1H); 4.22 (dd, 1H), 3.71 (q, 2H), 3.32 (dd, 1H), 2.70 (t, 2H); HPLC-MS (Method B): m/z=606 (M+1); R$_t$=5.34 min.

Example 14

General Procedure (B)

3-{4-[2-(4-Benzyloxyphenyl)-4-oxo-4-(4-trifluoromethoxyphenyl)butyryl]benzoylamino}propionic acid

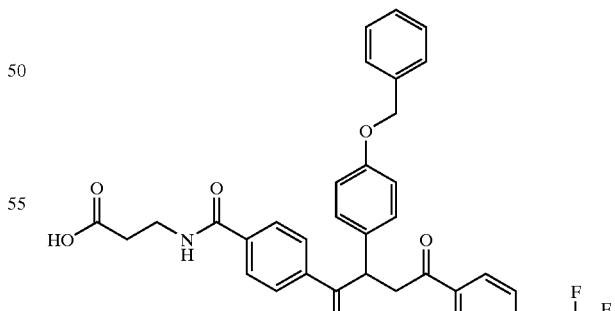

$^1$H NMR (CDCl$_3$): δ7.95 (m, 4H), 7.68 (d, 2H), 7.4–7.15 (m, 10H), 6.85 (m, 2H), 5.15 (d, 1H), 4.93 (s, 2H), 4.10 (m, 2H); HPLC-MS (Method A): m/z=620 (M+1); R$_t$=5.04 min.

Example 15

General Procedure (B)

3-{4-[4-Oxo-2-(4-phenoxyphenyl)-4-(4-trifluoromethoxyphenyl)butyryl]benzoylamino}propionic acid

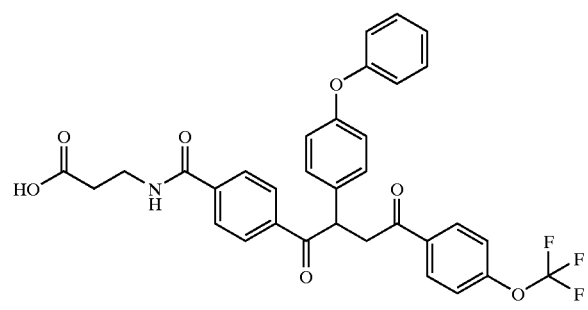

HPLC-MS (Method A): m/z=606 (M+1); $R_t$=5.29 min.

Example 16

General Procedure (B)

3-{4-[2-(4-tert-Butylphenyl)-4-oxo-4-(4-trifluoromethoxyphenyl)butyryl]benzoylamino}propionic acid

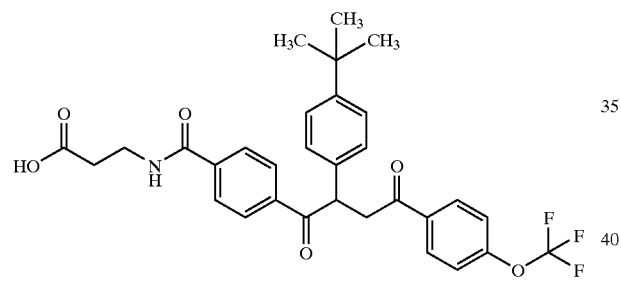

HPLC-MS (Method A): m/z=570 (M+1); $R_t$=5.42 min.

Example 17

General Procedure (B)

3-{4-[4-Oxo-2-(3-phenoxyphenyl)-4-(4-trifluoromethoxyphenyl)butyryl]benzoylamino}propionic acid

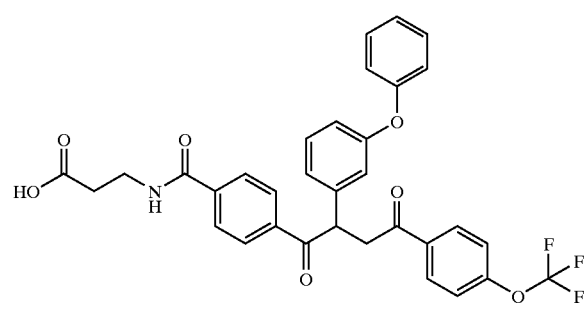

HPLC-MS (Method A): m/z 606 (M+1); $R_t$=5.20 min.

Example 18

General Procedure (B)

3-{4-[2-Biphenyl-4-yl-4-(4-chlorophenyl)-4-oxobutyryl]benzoylamino}propionic acid

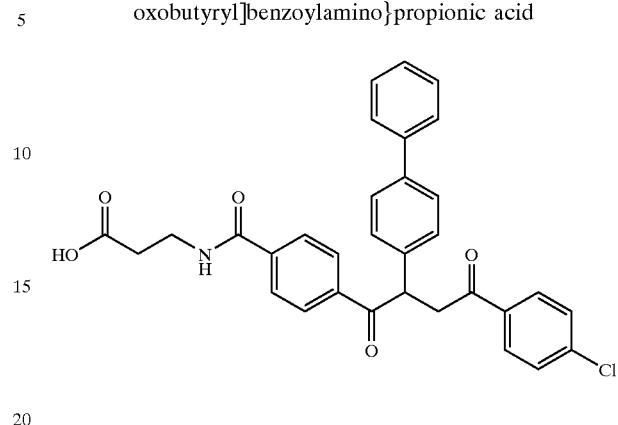

HPLC-MS (Method A): m/z=540 (M); $R_t$=4.85 min.

Example 19

General Procedure (B)

3-[4-(2-Biphenyl-4-yl-4-naphthalen-2-yl-4-oxobutyryl)benzoylamino]propionic acid

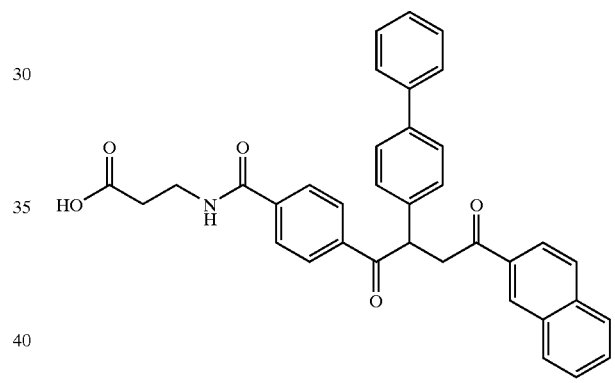

HPLC-MS (Method A): m/z=556 (M); $R_t$=4.97 min.

Example 20

General Procedure (B)

3-{4-[4-(4-sec-Butylphenyl)-4-oxo-2-(3-phenoxyphenyl)butyryl]benzoylamino}propionic acid

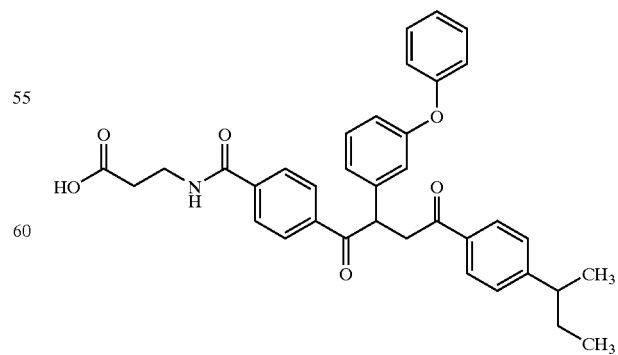

HPLC-MS (Method A): m/z=578 (M); $R_t$=5.62 min.

Example 21

General Procedure (B)

3-{4-[2-[3-(4-Chlorophenoxy)phenyl]-4-oxo-4-(5,6,7,8-tetrahydronaphthalen-2-yl)butyryl]benzoylamino}propionic acid

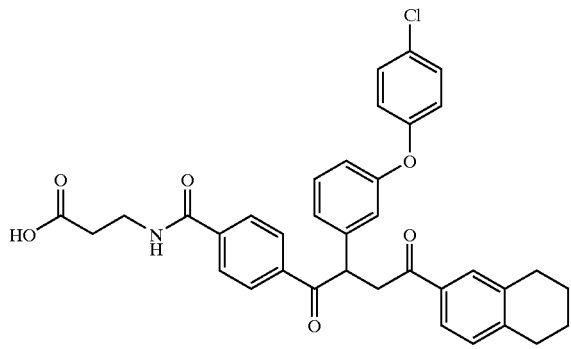

HPLC-MS (Method A): m/z=610 (M); $R_t$=5.56 min.

Example 22

General Procedure (B)

3-{4-[2-(4-Benzyloxyphenyl)-4-(3-bromophenyl)-4-oxobutyryl]benzoylamino}propionic acid

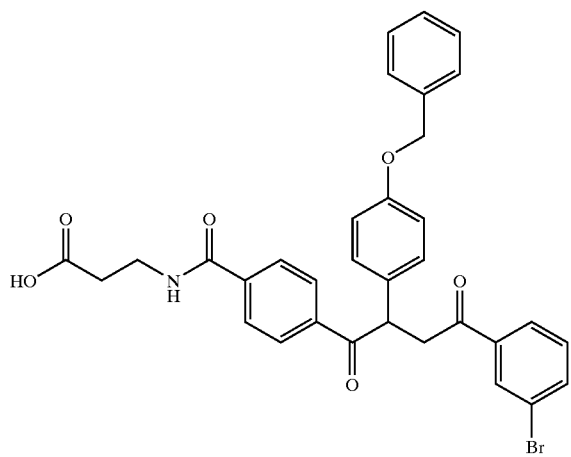

HPLC-MS (Method A): m/z=616 (M+1); $R_t$=5.07 min.

Example 23

General Procedure (B)

3-{4-[4-(4-Cyclohexylphenyl)-2-(4-isopropylphenyl)-4-oxobutyryl]benzoylamino}propionic acid

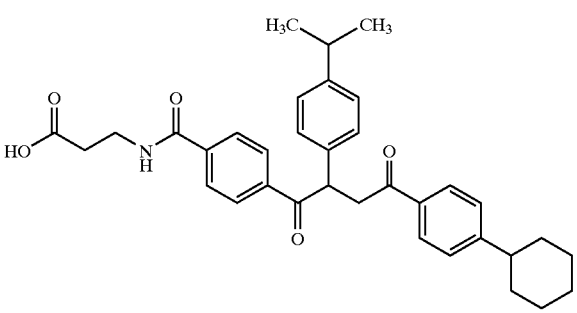

HPLC-MS (Method A): m/z=554 (M); $R_t$=6.04 min.

Example 24

General Procedure (B)

3-{4-[4-Biphenyl-4-yl-2-(4-cyclohexylphenyl)-4-oxobutyryl]benzoylamino}propionic acid

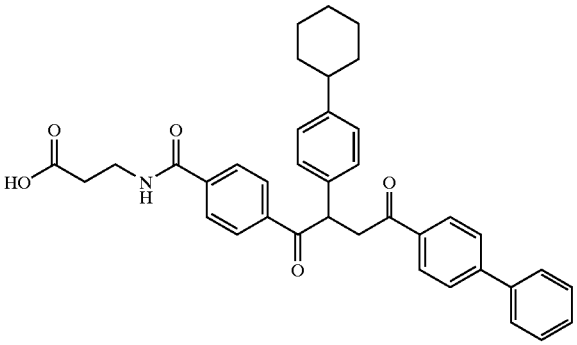

$^1$H NMR (CDCl$_3$): δ1.05–1.42 (5H, m), 1.55–1.89 (5H, m), 2.41 (1H, m), 2.62 (2H, m), 3.31 (1H, d, 3.63 (2H, m), 4.20 (1H, m), 5.23 (1H, m), 7.12 (2H, d), 7.21 (1H, d), 7.38 (1H, d), 7.42 (2H, d), 7.58–7.80 (6H, m), 7.99 (4H, dd); HPLC-MS (Method C): m/z=588 (M+1); $R_t$=7.97 min.

Example 25

General Procedure (B)

3-{4-[4-(2-Chlorophenyl)-2-(4-cyclohexylphenyl)-4-oxobutyryl]benzoylamino}propionic acid

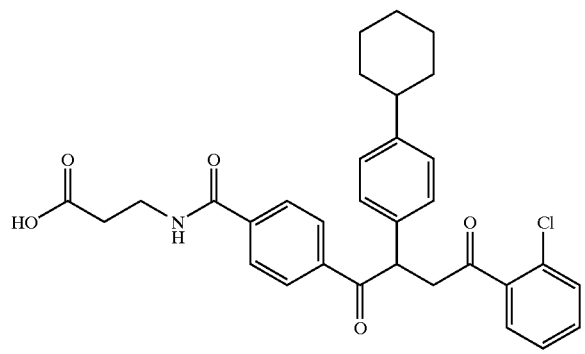

¹H NMR (DMSO-d$_6$): δ1.15–1.45 (6H, m), 1.63–1.80 (5H, m), 3.94 (1H, m), 5.40 (1H, m), 7.14 (1H, d), 7.30 (2H, dd), 7.47 (1H, d), 7.54 (3H, m), 7.90 (2H, dd), 7.97 (1H, d), 8.14 (1H, d), 8.68 (1H, t). 12.25 (1H, bs); HPLC-MS (Method C): m/z=546 (M+1); R$_t$=7.32+7.40 min.

Example 26

General Procedure (B)

3-{4-[2-(4-Cyclohexylphenyl)-4-oxo-4-(2-trifluoromethylphenyl)butyryl]benzoylamino}propionic acid

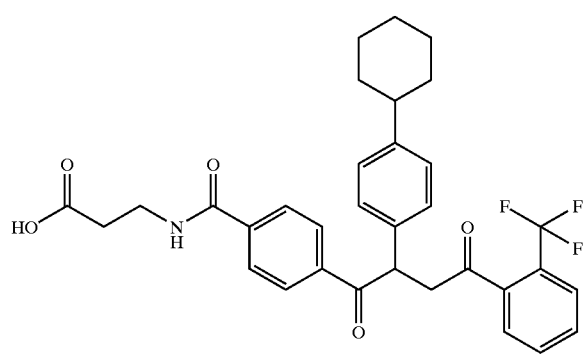

¹H NMR (DMSO-d$_6$): δ1.15–1.40 (5H, m), 1.65–1.87 (5H, m), 3.47 (2H, q), 3.99 (1H, m), 5.43 (1H, m), 7.14 (2H, d), 7.31 (2H, d), 7.65–8.00 (6H, m), 8.15 (2H, d), 8.68 (1H, t), 12.23 (1H, bs); HPLC-MS (Method C): m/z=580 (M+1); R$_t$=7.67 min.

Example 27

General Procedure (B)

3-{4-[4-(4-tert-Butylphenyl)-2-(4-cyclohexylphenyl)-4-oxobutyryl]benzoylamino}propionic acid

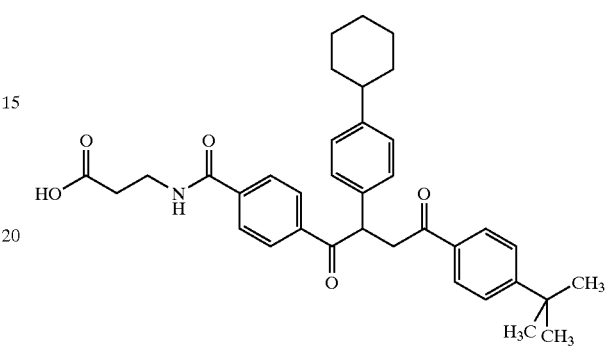

¹H NMR (DMSO-d$_6$): δ1.15–1.40 (14H, m), 1.65–1.80 (5H, m), 3.47 (2H, q), 4.08 (1H, m), 5.38 (1H, m), 7.15 (2H, d), 7.31 (2H, d), 7.53 (2H, d), 7.85–8.00 (4H, m), 8.13 (2H, d), 8.67 (1H, t); HPLC-MS (Method C): m/z=568 (M+1); R$_t$=8.47 min.

Example 28

General Procedure (B)

3-{4-[2-(4-Cyclohexylphenyl)-4-oxo-4-(4-piperidin-1-ylphenyl)butyryl]benzoylamino}propionic acid

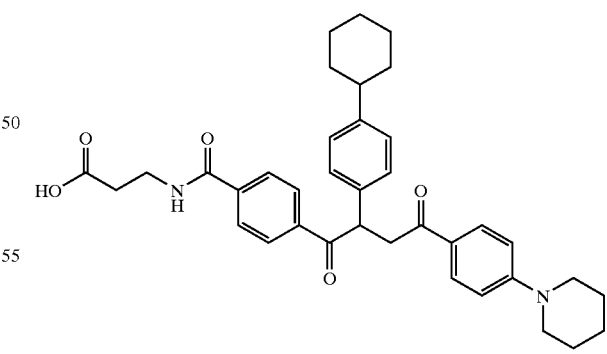

¹H NMR (DMSO-d$_6$): δ1.15–1.40 (8H, m), 1.50–1.80 (12H, m), 2.42 (1H, m), 3.46 (2H, m), 4.99 (1H, q), 5.34 (1H, m), 6.92 (2H, d), 7.15 (2H, d), 7.31 (2H, d), 7.82 (2H, d), 7.89 (2H, d), 8.12 (2H, d), 8.66 (1H, t); HPLC-MS (Method C): m/z=595 (M+1); R$_t$=6.70 min.

Example 29

General Procedure (B)

3-{4-[2-(4-Cyclohexylphenyl)-4-oxo-4-(4-phenoxyphenyl)butyryl]benzoylamino}propionic acid

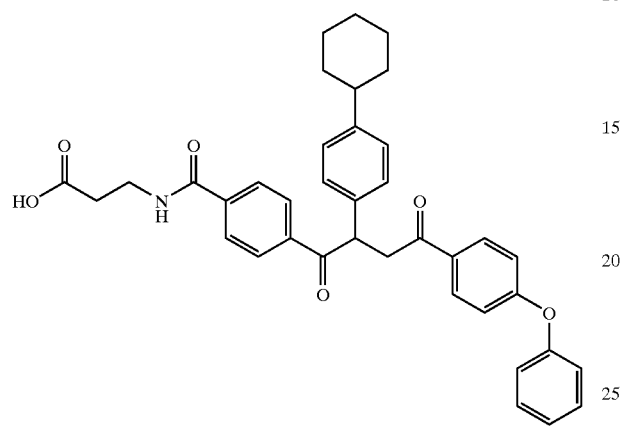

¹H NMR (DMSO-d₆): δ1.15–1.40 (5H, m), 1.60–1.80 (5H, m), 3.46 (2H, q), 4.06 (1H, m), 5.38 (1H, m), 7.02 (2H, d), 7.13 (4H, dd), 7.32 (3H, m), 7.48 (2H, dd), 7.88 (3H, dd), 8.02 (2H, d), 8.12 (2H, d), 8.66 (1H, t), 12.25 (1H, bs); HPLC-MS (Method C): m/z=604 (M+1); R$_t$=8.13 min.

Example 30

General Procedure (B)

3-{4-[4-(4-Cyclohexylphenyl)-4-oxo-2-(4-trifluoromethoxyphenyl)butyryl]benzoylamino}propionic acid

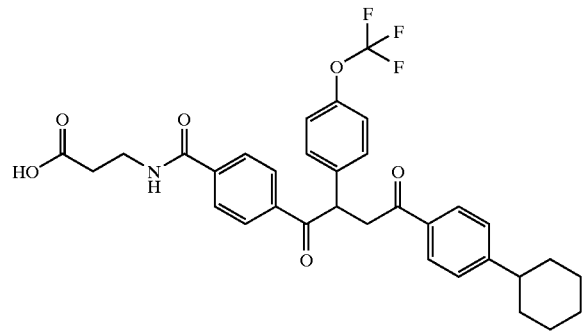

¹H NMR (CDCl₃): δ1.20–1.50 (5H, m), 1.70–1.90 (5H, m), 2.55 (1H, m), 2.70 (2H, t), 3.32 (1H, dd), 3.72 (2H, q), 4.15 (2H, dd), 5.30 (1H, dd), 6.83 (1H, t), 7.14 (2H, d), 7.28 (2H, d), 7.36 (2H, d), 7.79 (2H, d); 7.90 (2H, d), 8.06 (2H, d); HPLC-MS (Method A): m/z=596 (M+1); R$_t$=5.68 min.

Example 31

General Procedure (B)

3-{4-[4-Biphenyl-4-yl-4-oxo-2-(4-trifluoromethoxyphenyl)butyryl]benzoylamino}propionic acid

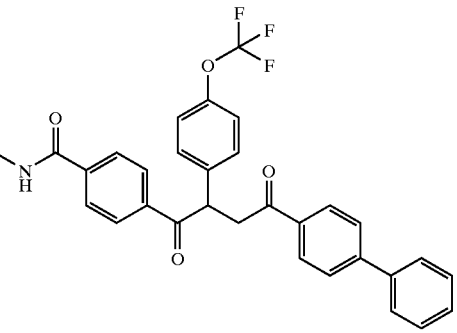

¹H NMR (CDCl₃): δ2.70 (2H, t), 3.38 (1H, dd), 3.73 (2H, q), 4.24 (2H, dd), 5.35 (1H, dd), 6.85 (1H, t), 7.16 (2H, d), 7.28 (2H, d), 7.35–7.50 (5H, m), 7.61 (2H, d); 7.67 (2H, d), 7.80 (2H, d), 8.03 (2H, d), 8.07, (2H, d); HPLC-MS (Method A): m/z=590 (M+1); R$_t$=5.03 min.

Example 32

General Procedure (B)

3-{4-[4-(4-Cyclohexylphenyl)-2-(3,5-dichlorophenyl)-4-oxobutyryl]benzoylamino}propionic acid

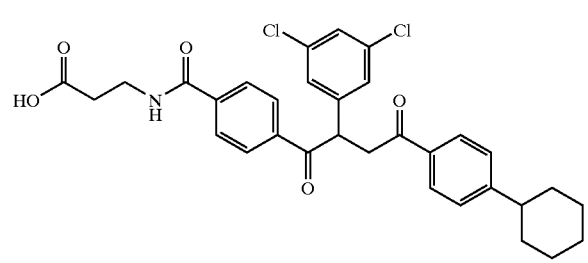

¹H NMR (CDCl₃): δ1.15–1.50 (5H, m), 1.70–1.95 (5H, m), 2.57 (1H, m), 2.70 (2H, t), 3.30 (1H, dd), 3.73 (1H, q), 4.13 (1H, dd), 5.23 (1H, dd), 6.90 (1H, t), 7.24 (3H, s); 7.29 (2H, d), 7.80 (2H, d), 7.88 (2H, d), 8.03, (2H, d).

Example 33

General Procedure (B)

3-{4-[2-(3-Bromophenyl)-4-(4-cyclohexylphenyl)-4-oxobutyryl]benzoylamino}propionic acid

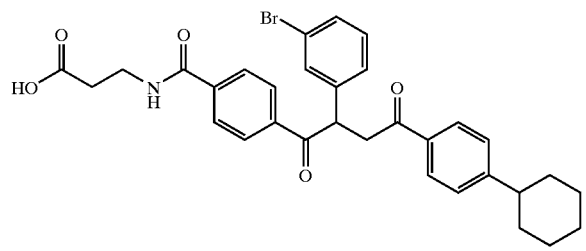

$^1$H NMR (CDCl$_3$): δ1.17–1.50 (5H, m), 1.70–1.92 (5H, m), 2.55 (1H, m), 2.69 (2H, t), 3.29 (1H, dd), 3.70 (1H, q), 4.15 (1H, dd), 5.24 (1H, dd), 6.97 (1H, t), 7.15 (1H, t), 7.20–7.30 (3H, m); 7.35 (1H, d), 7.49 (1H, s), 7.76 (2H, d), 7.88, (2H, d), 8.02 (2H, d).

Example 34

General Procedure (B)

3-{4-[4-Benzo[1,3]dioxol-5-yl-2-(4-cyclohexylphenyl)-4-oxobutyryl]benzoylamino}propionic acid

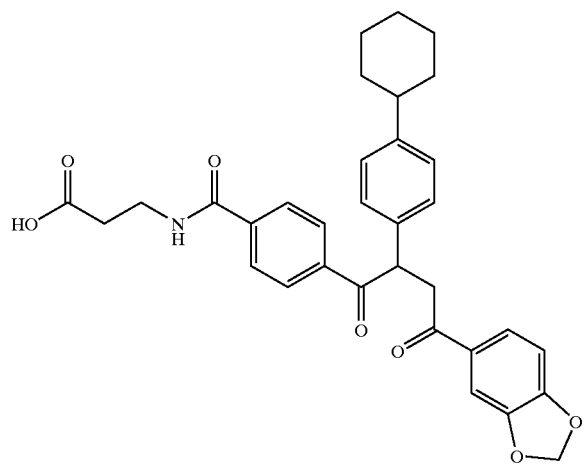

$^1$H NMR (CDCl$_3$): δ1.20–1.48 (m, 5H), 1.66–1.87 (m, 5H), 2.47 (m, 1H), 2.64 (t, 2H), 3.65 (q, 2H), 5.20 (dd, 2H), 6.02 (s, 2H), 6.81 (d, 1H), 6.99 (t, 1H), 7.12 (m, 1H), 7.23 (d, 2H), 7.38 (s, 1H), 7.46 (d, 2H), 7.62 (d, 1H), 7.73 (d, 2H), 8.02 (d, 2H); HPLC-MS (Method A): m/z=556 (M+1); R$_t$=5.11 min.

General Procedure (C)

General procedure (C) for solid phase synthesis of compounds of the general formula (I$_4$):

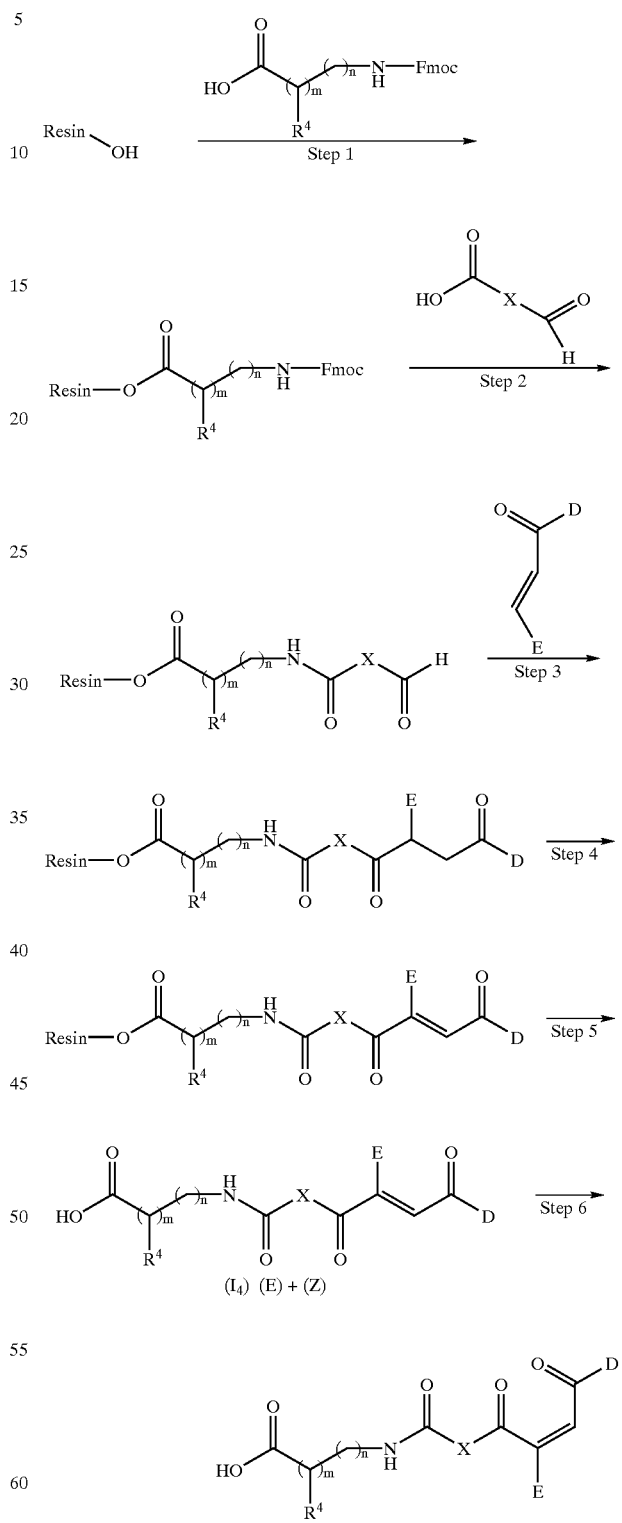

wherein X, D, E, m, n and R$^4$ are as defined for formula (I), and Resin is a polystyrene resin loaded with a Wang-linker.

The procedure is illustrated in the following example.

Example 35

General Procedure (C)

(Z)-3-{4-[2-(4-Cyclohexylphenyl)-4-oxo-4-(4-trifluoromethoxyphenyl)but-2-enoyl]benzoylamino}propionic acid

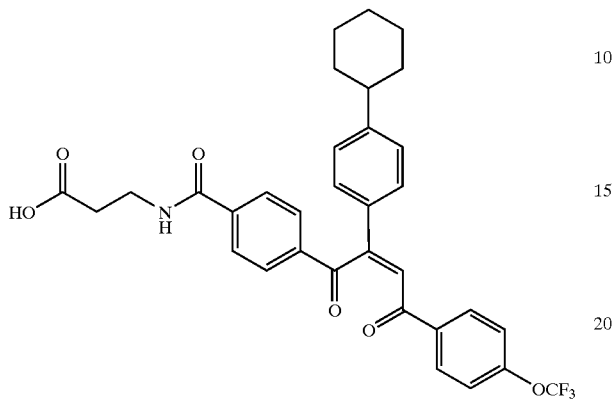

Step 1–Step 3: Preparation of resin bound 3-{4-[2-(4-cyclohexylphenyl)-4-oxo-4-(4-trifluoromethoxyphenyl)butyryl]benzoylamino}propionic acid The compound was synthesized according to general procedure (B).

Step 4 and Step 5: Preparation of 3-{4-[2-(4-cyclohexylphenyl)-4-oxo-4-(4-trifluoromethoxyphenyl)but-2-enoyl]benzoylamino}propionic acid The above resin bound 3-{4-[2-(4-cyclohexylphenyl)-4-oxo-4-(4-trifluoromethoxyphenyl)butyryl]benzoylamino}propionic acid (500 mg resin) was suspended in THF (10 mL), and iodine crystals (344 mg, 1.35 mmol) and DBU (225 μl) were added. The suspension was shaken at room temperature for 3.5 hours. The resin was isolated by filtration and washed with THF (1×10 mL), sodium pyrosulfite solution (2% in water) (1×10 mL), THF (2×10 mL), DCM (10×10 mL). The resin bound 3-{4-[2-(4-cyclohexylphenyl)-4-oxo-4-(4-trifluoromethoxyphenyl)but-2-enoyl]benzoylamino}propionic acid was treated with 50% TFA in DCM (10 mL) for 0.5 hour at 25° C. The mixture was filtered and the resin was washed with DCM (10 mL). The combined filtrates were concentrated in vacuo to afford an oil which was purified on silica/gel column eluted with DCM/methanol/acetic acid (95:4:1) to afford an E and Z mixture of 3-{4-[2-(4-cyclohexylphenyl)-4-oxo-4-(4-trifluoromethoxyphenyl)but-2-enoyl]benzoylamino}propionic acid.

$^1$H NMR (CDCl$_3$): δ8.03–7.92 (m, 3H), 7.88–7.77 (m, 3H), 7.58–7.47 (m, 1H), 7.15 (t, 3H), 7.01 (d, 1H); 6.90–6.80 (m, 2H), 3.73 (q, 2H), 2.72(t, 2H), 2.37 (m, 1H), 1.78–1.66 (m, 5H), 1.42–1.23 (m, 5H); HPLC-MS (Method A): m/z=594 (M+1); R$_t$=5.44 min.

Step 6: Preparation of (Z)-3-{4-[2-(4-cyclohexylphenyl)-4-oxo-4-(4-trifluoromethoxyphenyl)but-2-enoyl]benzoylamino}propionic acid The rearrangement of the End Z mixture to the Z-isomer was done by a modified literature procedure (*J. Am. Chem. Soc.*, 75, 5997–6002, 1953).

The E and Z mixture of 3-{4-[2-(4-cyclohexylphenyl)-4-oxo-4-(4-trifluoromethoxyphenyl)but-2-enoyl]benzoylamino}propionic acid (155 mg, 0.26 mmol) was dissolved in toluene (15 mL) and concentrated HCl (37%, 3 drops) was added and the mixture was heated to reflux for 1 hour. The solvent was removed by evaporation to give the pure Z isomer of 3-{4-[2-(4-cyclohexylphenyl)-4-oxo-4-(4-trifluoromethoxyphenyl)but-2-enoyl]benzoylamino}propionic acid.

$^1$H NMR (CDCl$_3$): δ8.03 (d, 4H), 7.79 (d, 2H), 7.57 (s, 1H), 7.48 (d, 2H), 7.30 (d, 2H); 7.24 (d, 2H), 6.84 (t, 1H), 3.71 (q, 2H), 2.70 (t, 2H), 2.52 (m, 1H), 1.90–1.70 (m, 5H), 1.45–1.17 (m, 5H); HPLC-MS (Method A): m/z=594 (M+1); R$_t$=5.37 min. Microanalysis: Calculated for C$_{33}$H$_{30}$F$_3$NO$_6$, 0.25H$_2$O: C, 66.27%; H, 5.14%; N, 2.34%. Found: C, 66.33%; H, 5.20%; N, 2.57%.

Example 36

General Procedure (C)

(Z)-3-{4-[2-(4-Cyclohexylphenyl)-4-oxo-4-(2,2,3,3-tetrafluoro-2,3-dihydrobenzo[1,4]dioxin-6-yl)but-2-enoyl]benzoylamino}propionic acid

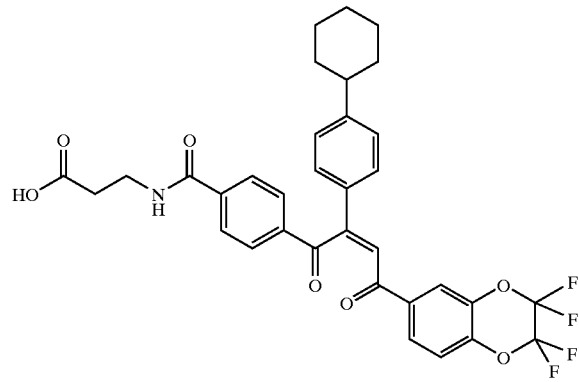

Data for the E and Z mixture resulting from Step 5 in general procedure (C):

$^1$H NMR (CDCl$_3$): δ8.01–7.92 (m, 2H), 7.83–7.45 (m, 6H), 7.26–7.00 (m, 3H), 6.84 (br t, 1H), 3.71 (q, 2H), 2.70 (q, 2H), 2.52 (m, 1H), 1.88–1.67 (m, 5H), 1.45–1.17 (m, 5H).

Data for title compound:

$^1$H NMR (CDCl$_3$): δ7.98 (br d, 2H), 7.88–7.70 (m, 4H), 7.50 (t, 3H), 7.18 (d, 1H), 6.84 (br s, 1H), 3.71 (br s, 2H), 2.70 (br s, 2H), 2.52 (m, 1H), 1.90–1.70 (m, 5H), 1.45–1.15 (m, 5H).

Example 37

General Procedure (C)

(Z)-3-{4-[4-(3,5-Bistrifluoromethylphenyl)-2-(4-cyclohexylphenyl)-4-oxobut-2-enoyl]benzoylamino}propionic acid

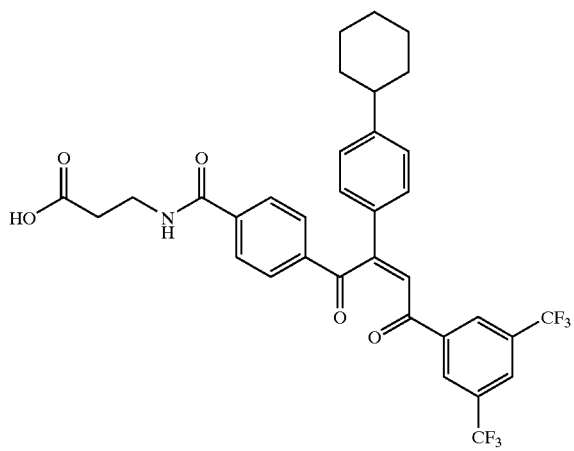

$^1$H NMR (CDCl$_3$): δ8.40 (s, 2H), 8.07, (s, 1H), 8.00 (d, 2H), 7.81 (d, 2H), 7.58 (s, 1H), 7.52 (d, 2H), 7.29 (d, 2H), 6.93 (br s, 1H), 3.72 (q, 2H), 2.69 (t, 2H), 2.52 (m, 1H), 1.90–1.72 (m, 5H), 1.48–1.25 (m, 5H).

Example 38

General Procedure (C)

(Z)-3-{4-[4-(3,5-Bis(trifluoromethyl)phenyl)-2-[2,2']bithiophenyl-5-yl-4-oxobut-2-enoyl]benzoylamino}propionic acid

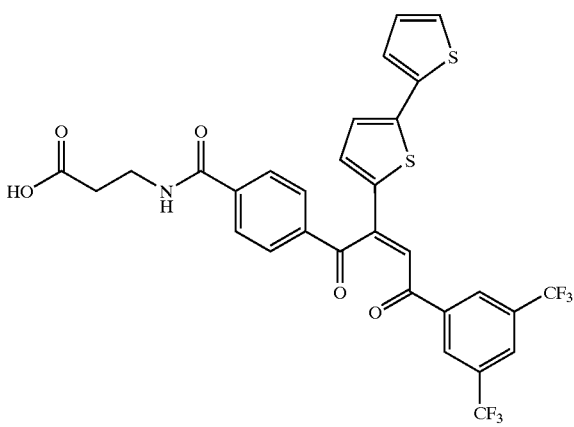

$^1$H NMR (CDCl$_3$): δ8.38 (s, 2H), 8.07, (s, 1H), 8.05 (d, 2H), 7.85 (d, 2H), 7.38–7.32 (m, 2H), 7.18 (d, 2H), 7.12–7.05 (m, 2H), 6.84 (br t, 1H), 3.74 (q, 2H), 2.70 (t, 2H).

Example 39

General Procedure (C)

(Z)-3-{4-[2-(4-Bromothiophen-2-yl)-4-oxo-4-(4-trifluoromethoxyphenyl)but-2-enoyl]benzoylamino}propionic acid

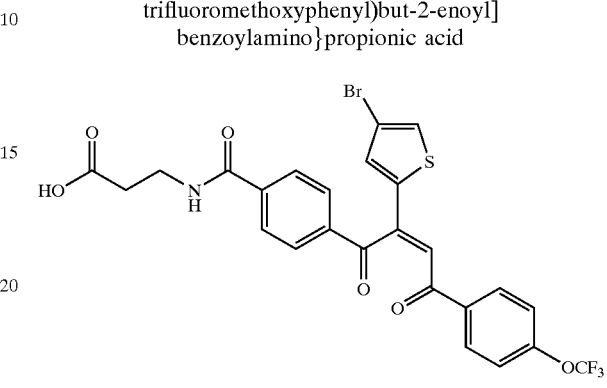

$^1$H NMR (CDCl$_3$): δ8.03 (d, 2H), 7.99, (d, 2H), 7.84 (d, 3H), 7.47 (s, 1H), 7.38 (s, 1H), 7.31 (s, 1H), 7.02 (s, 1H), 6.84 (m, 1H), 3.74 (q, 2H), 2.72 (t, 2H).

Example 40

General Procedure (C)

(Z)-3-{4-[2-(4-Cyclohexylphenyl)-4-oxo-4-(3-trifluoromethoxyphenyl)but-2-enoyl]benzoylamino}propionic acid

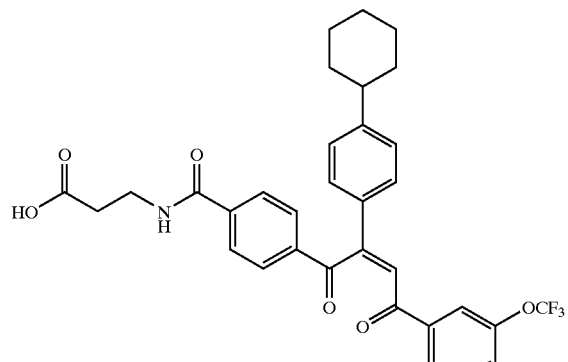

$^1$H NMR (CDCl$_3$): δ8.01 (d, 2H), 7.90, (d, 1H), 7.80 (d and s, 3H), 7.58–7.38 (m, 5H), 7.22 (s, 1H), 7.28 (d, 1H), 6.82 (br s, 1H), 3.74 (br s, 2H), 2.70 (br s, 2H), 2.53 (br m, 1H), 1.90–1.70 (m, 5H), 1.47–1.20 (m, 5H)

Example 41

General Procedure (C)

(Z)-3-{4-[2-(4-Cyclohexylphenyl)-4-oxo-4-(4-trifluoromethylsulfanylphenyl)but-2-enoyl]benzoylamino}propionic acid

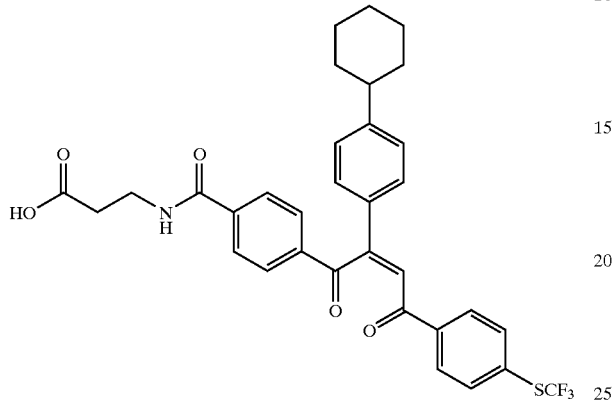

$^1$H NMR (CDCl$_3$): δ8.02 (d, 2H), 7.98, (d, 2H), 7.80 (d, 2H), 7.73 (d, 2H), 7.58 (s, 1H), 7.49 (d, 2H), 7.26 (d, 2H), 6.78 (br t, 1H), 3.73 (q, 2H), 2.72 (t, 2H), 2.53 (br m, 1H), 1.90–1.70 (m, 5H), 1.46–1.25 (m, 5H); HPLC-MS (Method B): m/z=610 (M+1); R$_t$=5.63 min.

Example 42

General Procedure (C)

(Z)-3-{4-[4-Biphenyl-4-yl-2-(4-cyclohexylphenyl)-4-oxobut-2-enoyl]benzoylamino}propionic acid

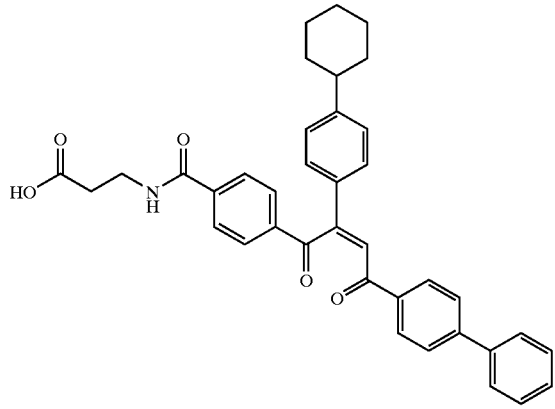

$^1$H NMR (DMSO-d$_6$): δ1.20–1.45 (5H, m), 1.65–1.85 (5H, m), 2.48 (below DMSO-signal), 3.45 (2H, q), 7.33 (2H, d), 7.45 (1H, d), 7.51 (2H, d), 7.61 (2H, d), 7.77 (2H, d), 7.87 (4H, dd), 7.95 (1H, d), 8.22 (2H, d), 8.66 (1H, t), 12.20 (1H, bs); HPLC-MS (Method C): m/z=586 (M+1); R$_t$=8.03 min.

Example 43

General Procedure (C)

(Z)-3-{4-[4-(2-Chlorophenyl)-2-(4-cyclohexylphenyl)-4-oxobut-2-enoyl]benzoylamino}propionic acid

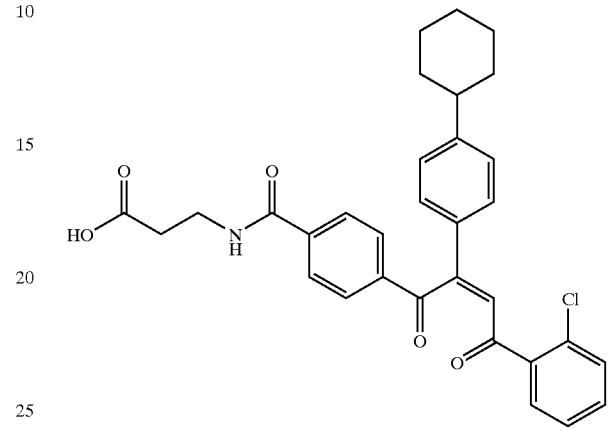

$^1$H NMR (DMSO-d$_6$): δ1.15–1.42 (5H, m), 1.65–1.80 (5H, m), 3.46 (2H, q), 7.31 (2H, d), 7.48 (1H, d), 7.52 (2H, d), 7.59 (2H, d), 7.68 (1H, d), 7.91 (2H, d), 7.98 (2H, d), 8.69 (1H, t), 12.23 (1H, bs); HPLC-MS (Method C): m/z=544 (M+1); R$_t$=7.33 min.

Example 44

General Procedure (C)

(Z)-3-{4-[2-(4-Cyclohexylphenyl)-4-oxo-4-(2-trifluoromethylphenyl)but-2-enoyl]benzoylamino}propionic acid

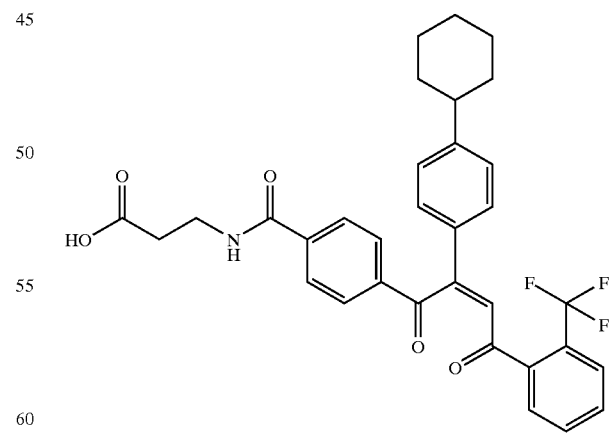

$^1$H NMR (DMSO-d$_6$): δ1.15–1.45 (5H, m), 1.60–1.85 (5H, m), 3.47 (2H, q), 7.31 (2H, d), 7.55 (3H, m), 7.74 (1H, d), 7.85 (2H, d), 7.90–8.05 (4H, dd), 8.70 (1H, t), 12.23 (1H, bs); HPLC-MS (Method C): m/z=578 (M+1); R$_t$=7.43 min.

Example 45

General Procedure (C)

(Z)-3-{4-[4-(4-tert-Butylphenyl)-2-(4-cyclohexylphenyl)-4-oxobut-2-enoyl]benzoylamino}propionic acid

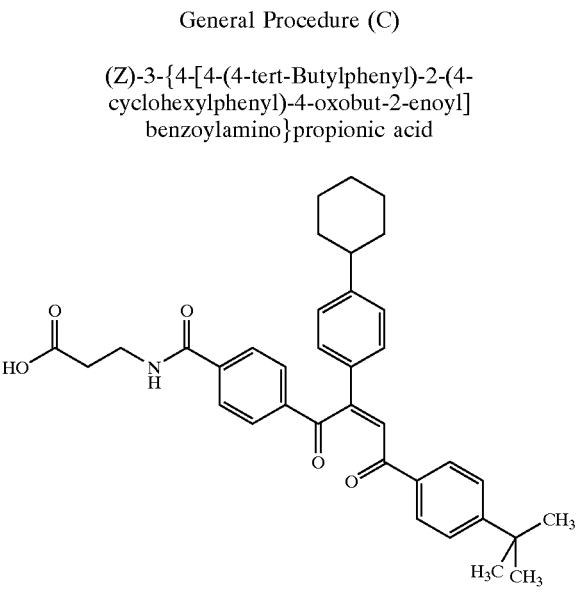

$^1$H NMR (DMSO-d$_6$): δ1.20–1.45 (5H, m), 1.31 (9H, s), 1.65–1.85 (5H, m), 3.46 (2H, q), 7.32 (2H, d), 7.57 (4H, m), 7.88 (2H, d), 7.92 (2H, d), 8.05 (2H, m), 8.65 (1H, t), 12.23 (1H, bs); HPLC-MS (Method C): m/z=566 (M+1); R$_t$=8.17 min.

Example 46

General Procedure (C)

(Z)-3-{4-[2-(4-Cyclohexylphenyl)-4-oxo-4-(4-phenoxyphenyl)but-2-enoyl]benzoylamino}propionic acid

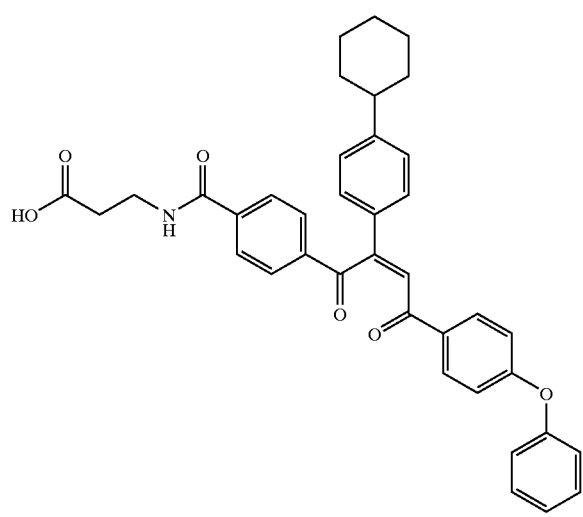

$^1$H NMR (DMSO-d$_6$): δ1.15–1.50 (5H, m), 1.65–1.90 (5H, m), 3.46 (2H, q), 7.05 (2H, d), 7.16 (2H, d), 7.31 (3H, m), 7.47 (2H, d), 7.59 (2H, d), 7.85–8.00 (4H, m), 8.17 (2H, d), 8.66 (1H, t), 12.25 (1H, bs); HPLC-MS (Method C): m/z=602 (M+1); R$_t$=7.90 min.

Example 47

General Procedure (C)

(Z)-3-{4-[2-(4-tert-Butyllphenyl)-4-oxo-4-(4-trifluoromethoxyphenyl)but-2-enoyl]benzoylamino}propionic acid

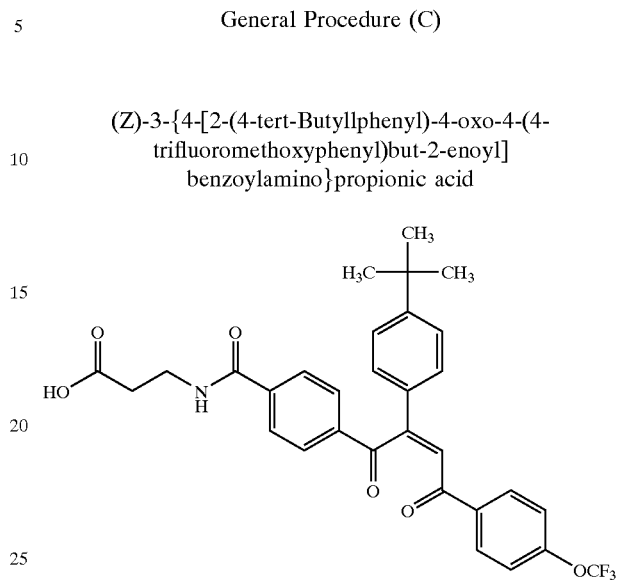

$^1$H NMR (DMSO-d$_6$,): δ8.70 (t, 1H), 8.26 (d, 2H), 8.0–7.9 (m, 5H), 7.61 (d, 2H), 7.5 (m, 3H), 1.28 (s, 9H); HPLC-MS (Method A): m/z=568 (M+1); R$_t$=5.21 min.

Example 48

General Procedure (C)

(Z)-3-{4-[4-Oxo-2-(4-phenoxyphenyl)-4-(4-trifluoromethoxyphenyl)but-2-enoyl]benzoylamino}propionic acid

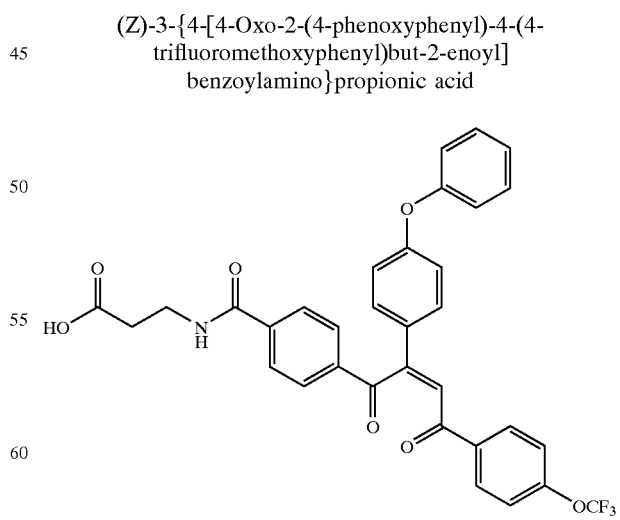

HPLC-MS (Method A): m/z=604 (M+1); R$_t$=5.07 min.

Example 49

General Procedure (C)

(Z)-3-{4-[4-Oxo-2-(3-phenoxyphenyl)-4-(4-trifluoromethoxyphenyl)but-2-enoyl]benzoylamino}propionic acid

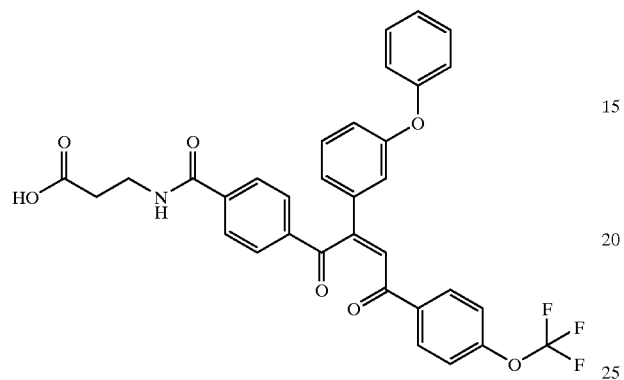

$^1$H NMR (CD$_3$OD): δ8.16 (d, 2H), 7.98 (d, 2H), 7.86 (m, 3H), 7.4 (m, 4H), 7.34 (m, 2H), 7.25 (s, 1H), 7.15–7.05 (m, 2H), 6.94 (d, 2H), 3.65 (m, 2H), 2.65 (m, 2H); HPLC-MS (Method A): m/z=604 (M+1); R$_t$=5.06 min.

Example 50

General Procedure (C)

(Z)-3-{4-[2-(4-Benzyloxyphenyl)-4-oxo-4-(4-trifluoromethoxyphenyl)but-2-enoyl]benzoylamino}propionic acid

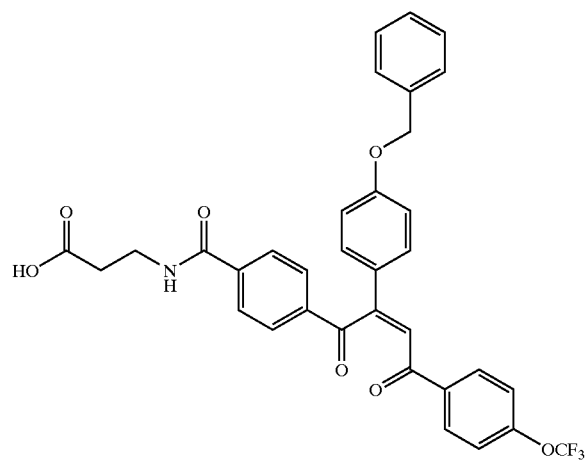

HPLC-MS (Method A): m/z=618 (M+1); R$_t$=5.00 min.

Example 51

General Procedure (C)

(Z)-3-{4-[4-Oxo-2,4-bis-(4-trifluoromethoxyphenyl)but-2-enoyl]benzoylamino}propionic acid $^1$H NMR (CD$_3$OD): δ8.18 (d, 2H), 8.00 (d, 2H), 7.93 (s, 1H), 7.85 (d, 2H), 7.79 (d, 2H), 7.42 (d, 2H), 7.36 (d, 2H), 3.62 (t, 2H), 2.63 (t, 2H); HPLC-MS (Method A): m/z=596 (M+1); R$_t$=4.90 min.

Example 52

General Procedure (C)

(Z)-3-{4-[2-(4-Cyclohexylphenyl)-4-(3,4-difluorophenyl)-4-oxobut-2-enoyl]benzoylamino}propionic acid HPLC-MS (Method A): m/z=546 (M+1); R$_t$=5.25 min.

Example 53

General Procedure (C)

(Z)-3-{4-[2-Biphenyl-4-yl-4-oxo-4-(4-trifluoromethoxyphenyl)but-2-enoyl]benzoylamino}propionic acid

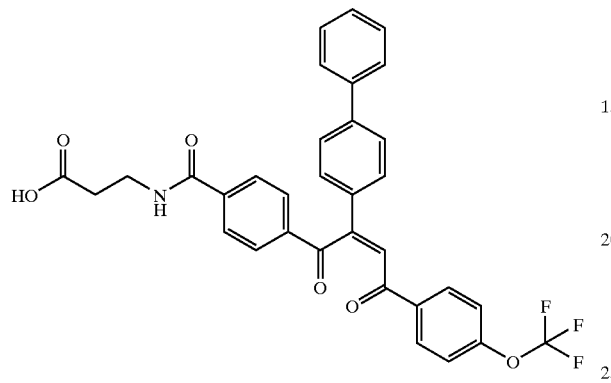

$^1$H NMR (DMSO-d$_6$): δ12.2 (bs, 1H), 8.69 (t, 1H), 8.30 (d, 2H), 8.15 (s, 1H), 7.99 (d, 2H), 7.90 (d, 2H), 7.73 (d, 2H), 7.4–7.55 (m, 8H), 3.46 (m, 2H); HPLC-MS (Method A): m/z=588 (M+1); R$_t$=5.08 min.

Example 54

General Procedure (C)

(Z)-3-{4-[2-Biphenyl-4-yl-4-oxo-4-(2,2,3,3-tetrafluoro-2,3-dihydrobenzo[1,4]dioxin-6-yl)but-2-enoyl]benzoylamino}propionic acid

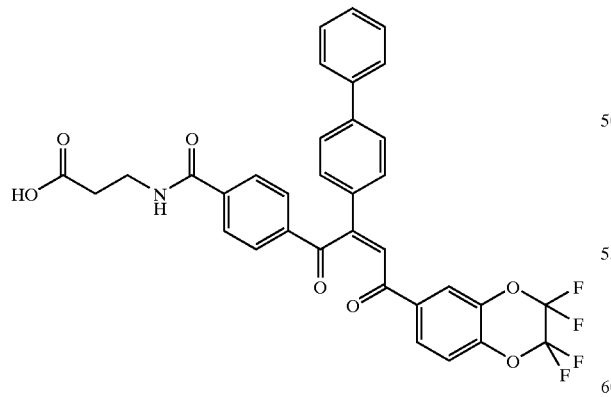

$^1$H NMR (CDCl$_3$): δ8.00 (d, 2H), 7.85–7.75 (m, 3H), 7.63–7.35 (m, 10H), 7.23 (d, 1H), 7.18 (d, 1H), 6.88 (t, 1H), 3.71 (q, 2H); 2.70 (t, 2H); HPLC-MS (Method A): m/z=634 (M+1); R$_t$=5.07 min.

Example 55

General Procedure (C)

(Z)-3-{4-[4-(4-Cyclohexylphenyl)-4-oxo-2-(4-trifluoromethoxyphenyl)but-2-enoyl]benzoylamino}propionic acid

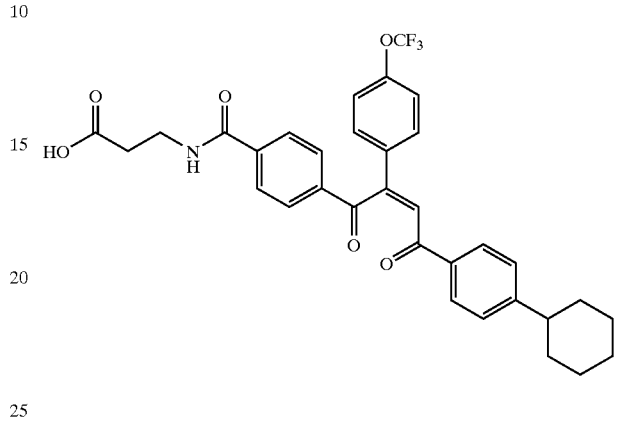

$^1$H NMR (CDCl$_3$): δ7.99 (d, 2H), 7.90 (d, 2H), 7.79 (d, 2H), 7.62 (d, 2H), 7.30 (d, 2H), 7.23 (d, 2H), 6.82 (br t, 1H), 3.71 (q, 2H); 2.70 (t, 2H), 2.57 (br m, 1H), 1.90–1.70 (m, 5H), 1.45–1.20 (m, 5H); HPLC-MS (Method A): m/z=594 (M+1); R$_t$=5.45 min.

Example 56

General Procedure (C)

(Z) 3-{4-[4-Benzo[1,3]dioxol-5-yl-2-(4-cyclohexylphenyl)-4-oxobut-2-enoyl]benzoylamino}propionic acid

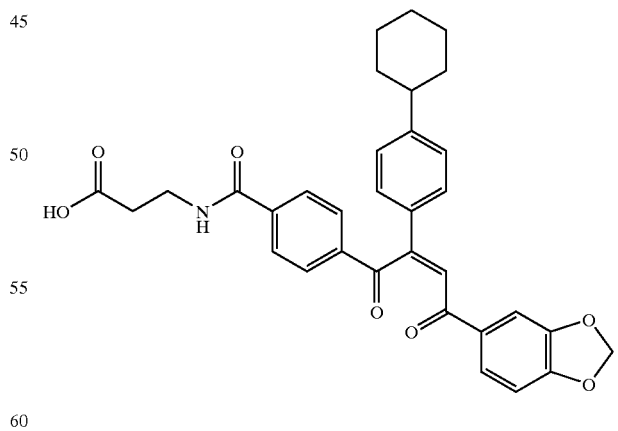

$^1$H NMR (CDCl$_3$): δ1.10–1.45 (m, 5H), 1.67–1.90 (m, 5H), 2.46 (m, 1H), 2.64 (t, 2H), 3.70 (q, 2H), 6.03 (s, 2H), 6.84 (br s, 1H), 7.08 (d, 2H), 7.19 (d, 2H), 7.40 (s, 1H), 7.47 (d, 1H), 7.56 (s, 1H), 7.69 (d, 1H), 7.74 (d, 2H), 8.03 (d, 2H); HPLC-MS (Method A): m/z=554 (M+1); R$_t$=4.95 min.

Example 57

General Procedure (C)

(Z)-3-{4-[2-(4-Cyclohexylphenyl)-4-(4-isopropylphenyl)-4-oxobut-2-enoyl]benzoylamino}propionic acid

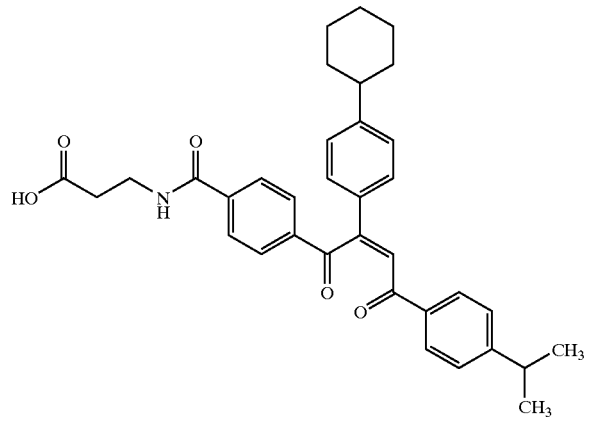

$^1$H NMR (CDCl$_3$): δ1.14–1.45 (m, 5H), 1.25 (d, 6H), 1.66–1.95 (m, 5H), 2.50 (m, 1H), 2.65 (t, 2H), 2.95 (m, 1H), 3.67 (q, 2H), 6.95 (br s, 1H), 7.13–7.34 (m, 4H), 7.47 (d, 2H), 7.62 (s, 1H), 7.74 (d, 2H), 7.89 (d, 2H), 7.97 (d, 2H); HPLC-MS (Method A): m/z=552 (M+1); R$_t$=5.82 min.

Example 58

General Procedure (C)

(Z)-3-{4-[2,4-Bis-(4-cyclohexylphenyl)-4-oxobut-2-enoyl]benzoylamino}propionic acid

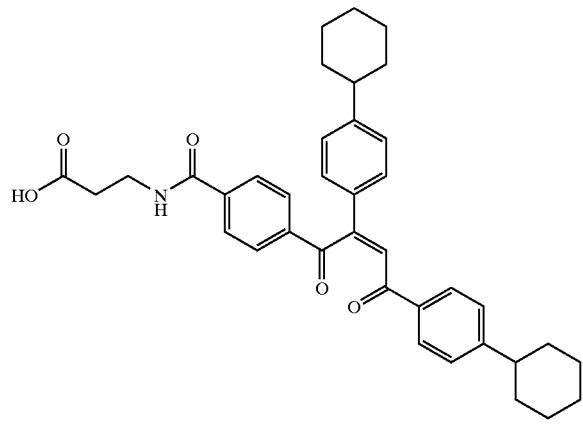

$^1$H NMR (CDCl$_3$): δ1.08–1.50 (m, 10H), 1.67–1.95 (m, 10H), 2.54 (m, 2H), 2.65 (t, 2H), 3.67 (q, 2H), 7.00 (br s, 1H), 7.12–7.34 (m, 4H), 7.47 (d, 2H), 7.63 (s, 1H), 7.75 (d, 2H), 7.89 (d, 2H), 7.98 (d, 2H); HPLC-MS (Method A): m/z=592 (M+1); R$_t$=6.13 min.

Example 59

General Procedure (C)

(Z)-3-{4-[2-(4-Cyclohexylphenyl)-4-(3,5-dichlorophenyl)-4-oxobut-2-enoyl]benzoylamino}propionic acid

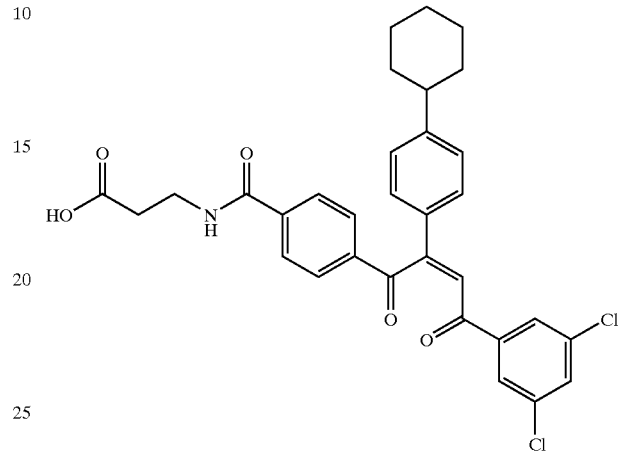

$^1$H NMR (CDCl$_3$): δ1.18–1.48 (m, 5H), 1.65–1.94 (m, 5H), 2.50 (m, 1H), 2.66 (t, 2H), 3.67 (q, 2H), 6.94 (br s, 1H), 7.15 (d, 2H), 7.22 (d, 2H), 7.49 (m, 3H), 7.86 (m, 3H), 7.94 (d, 2H); HPLC-MS (Method A): m/z=578 (M+1); R$_t$=5.60 min.

Example 60

General Procedure (C)

(Z)-3-{4-[4-(4-isobutylphenyl)-4-oxo-2-(4-trifluoromethoxyphenyl)but-2-enoyl]benzoylamino}propionic acid

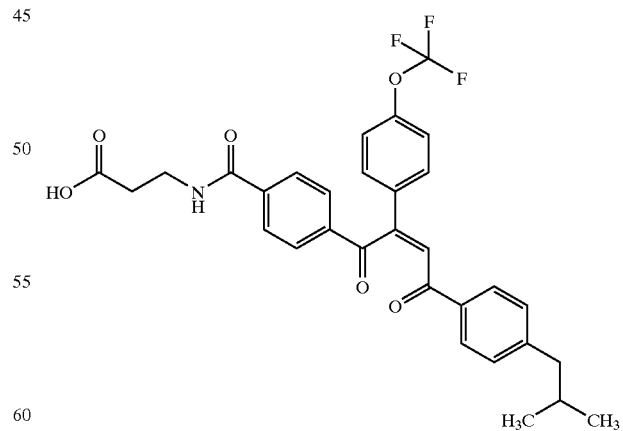

$^1$H NMR (CDCl$_3$): δ0.90 (d, 6H), 1.88 (m, 1H), 2.54 (d, 2H), 2.69 (t, 2H), 3.70 (q, 2H), 6.86 (br s, 1H), 7.24 (m, 4H), 7.62 (m, 3H), 7.78 (d, 2H), 7.87 (d, 2H), 7.99 (d, 2H); HPLC-MS (Method A): m/z=568 (M+1); R$_t$=6.03 min.

Example 61

General Procedure (C)

(Z)-3-{4-[4-(4-Cyclopentylphenyl)-4-oxo-2-(4-trifluoromethoxyphenyl)but-2-enoyl]benzoylamino}propionic acid

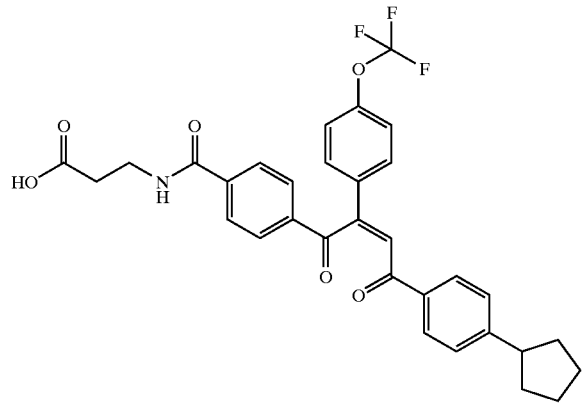

$^1$H NMR (CDCl$_3$): δ1.48–1.89 (m, 6H), 1.99–2.15 (m, 2H), 2.69 (t, 2H), 3.04 (m, 1H), 3.70 (q, 2H), 6.90 (br s, 1H), 7.20 (d, 2H), 7.32 (d, 2H), 7.62 (m, 3H), 7.79 (d, 2H), 7.88 (d, 2H), 7.99 (d, 2H); HPLC-MS (Method A): m/z=580 (M+1); R$_t$=5.08 min.

Example 62

General Procedure (C)

(Z)-3-{4-[4-Oxo-4-phenyl-2-(4-trifluoromethoxyphenyl)but-2-enoyl]benzoylamino}propionic acid

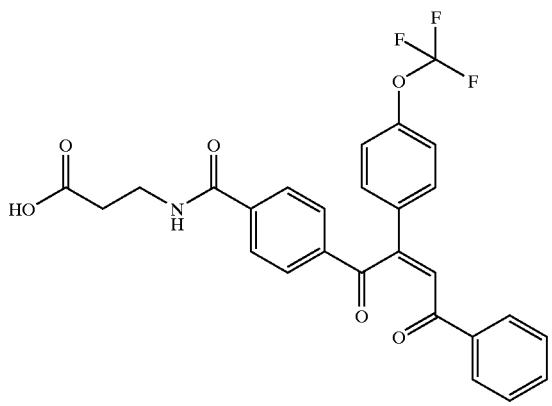

$^1$H NMR (CDCl$_3$): δ2.71 (t, 2H), 3.73 (q, 2H), 6.87 (br s, 1H), 7.15 (d, 2H), 7.23 (d, 2H), 7.47 (d, 2H), 7.64 (m, 3H), 7.83 (d, 2H), 8.00 (m, 3H); HPLC-MS (Method A): m/z=512 (M+1); R$_t$=5.09 min.

Example 63

General Procedure (C)

(Z)-3-{4-[4-Oxo-4-p-tolyl-2-(4-trifluoromethoxyphenyl)but-2-enoyl]benzoylamino}propionic acid

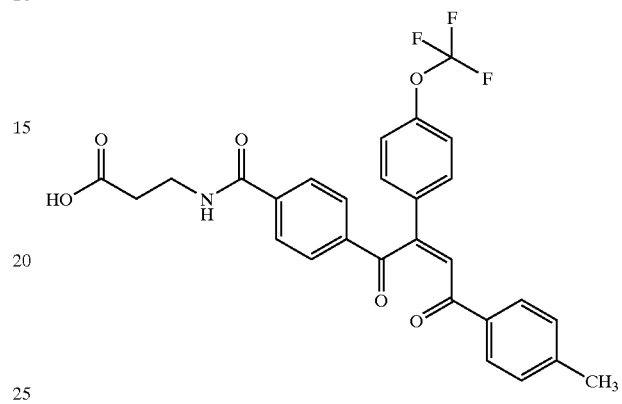

$^1$H NMR (CDCl$_3$): δ2.44 (s, 3H), 2.69 (t, 2H), 3.74 (q, 2H), 6.96 (br s, 1H), 7.16 (d, 2H), 7.25 (d, 2H), 7.63 (m, 3H), 7.79 (d, 2H), 7.88 (d, 2H), 8.00 (d, 2H); HPLC-MS (Method A): m/z=526 (M+1); R$_t$=5.26 min.

Example 64

General Procedure (C)

(Z)-3-{4-[4-(4-Methoxyphenyl)-4-oxo-2-(4-trifluoromethoxyphenyl)but-2-enoyl]benzoylamino}propionic acid

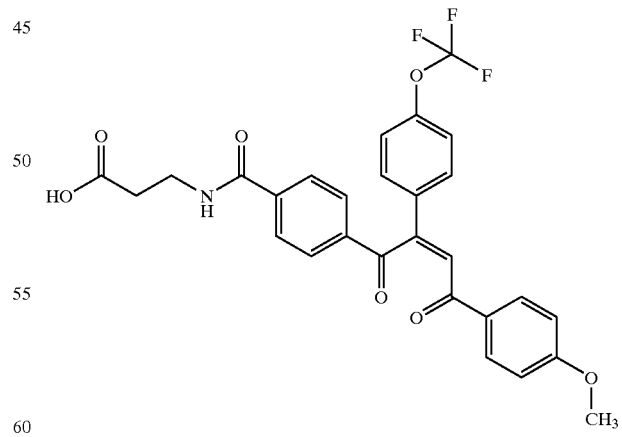

$^1$H NMR (CDCl$_3$): δ2.70 (t, 2H), 3.73 (q, 2H), 3.88 (s, 3H), 6.96 (br s, 1H), 7.16 (d, 2H), 7.24 (d, 2H), 7.65 (m, 3H), 7.80 (d, 2H), 8.00 (m, 4H); HPLC-MS (Method A): m/z=542 (M+1); R$_t$=5.09 min.

Example 65

General Procedure (C)

(Z)-3-{4-[2-[4-(2,2-Dimethylpropyl)phenyl]-4-oxo-4-(4-trifluoromethoxyphenyl)but-2-enoyl]benzoylamino}propionic acid

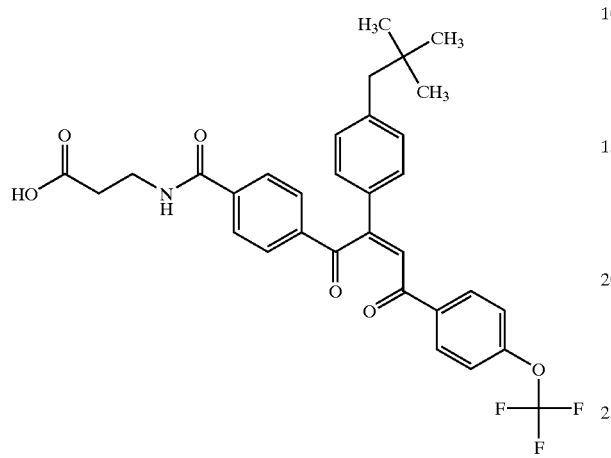

$^1$H NMR (CDCl$_3$): δ0.88 (s, 9H), 2.51 (s, 2H), 2.68 (t, 2H), 3.70 (q, 2H), 6.99 (br s, 1H), 7.15 (d, 2H), 7.27 (d, 2H), 7.47 (d, 2H), 7.60 (s, 1H), 7.78 (d, 2H), 8.00 (m, 4H); HPLC-MS (Method D): m/z=582 (M+1); R$_t$=5.21 min.

Example 66

General Procedure (C)

(Z)-3-{4-[2-Indan-5-yl-4-oxo-4-(4-trifluoromethoxyphenyl)but-2-enoyl]benzoylamino}propionic acid

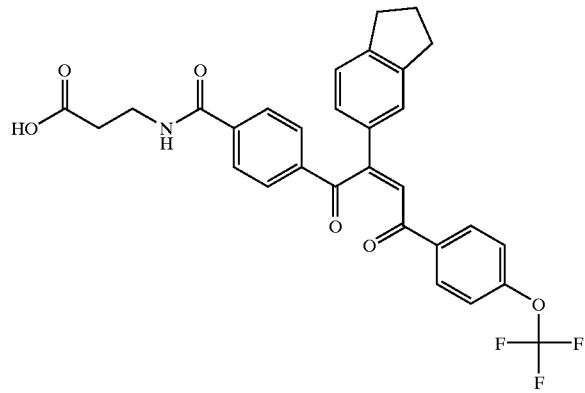

$^1$H NMR (CDCl$_3$): δ2.01 (m, 2H), 2.64 (t, 2H), 2.84 (m, 4H), 3.64 (q, 2H), 6.81 (br s, 1H), 7.14 (d, 1H), 7.22 (d, 2H), 7.27 (d, 1H), 7.35 (s, 1H), 7.53 (s, 1H), 7.71 (d, 2H), 7.94 (m, 4H); HPLC-MS (Method A): m/z=552 (M+1); R$_t$=4.75 min.

Example 67

General Procedure (C)

(Z)-3-{4-[2-Biphenyl-4-yl-4-(4-chlorophenyl)-4-oxobut-2-enoyl]benzoylamino}propionic acid

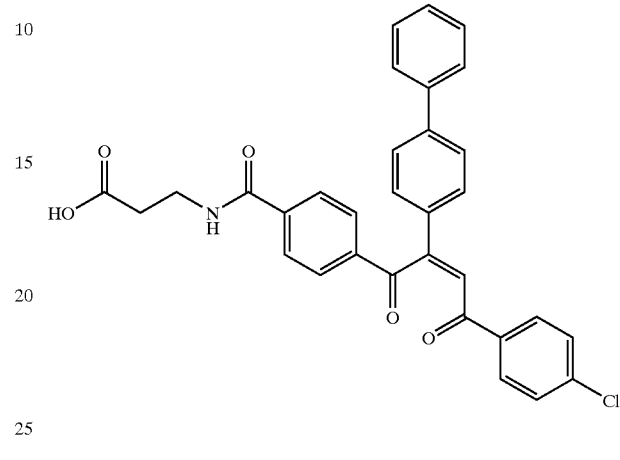

$^1$H NMR (CDCl$_3$): δ2.74 (t, 2H), 3.73 (q, 2H), 6.77 (br s, 1H), 7.44 (m, 6H), 7.54 (s, 1H), 7.61 (d, 2H), 7.65 (m, 3H), 7.84 (d, 2H), 7.95 (d, 2H), 8.05 (d, 2H); HPLC-MS (Method A): m/z=552 (M+1); R$_t$=4.75 min.

Example 68

General Procedure (C)

(Z)-3-[4-(2-Biphenyl-4-yl-4-naphthalen-2-yl-4-oxobut-2-enoyl)benzoylamino]propionic acid

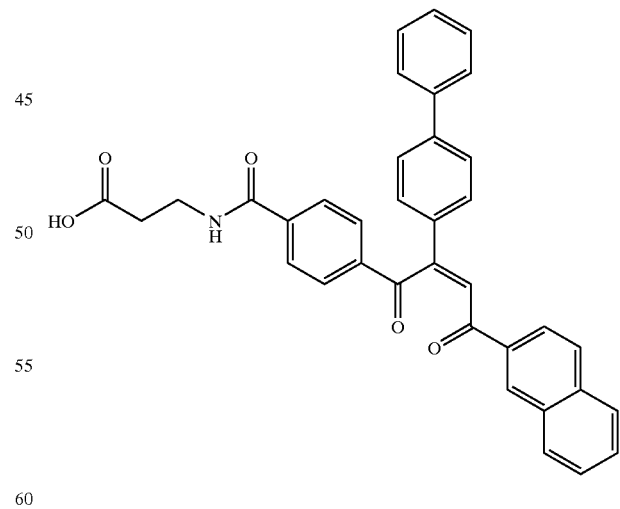

$^1$H NMR (CDCl$_3$): δ2.70 (t, 2H), 3.72 (q, 2H), 6.80 (br s, 1H), 7.38 (m, 1H), 7.45 (d, 2H), 7.57 (m, 2H), 7.62 (m, 2H), 7.67 (m, 3H), 7.74 (m, 1H), 7.83 (d, 2H), 7.91 (m, 1H), 7.92 (d, 2H), 7.99 (m, 2H), 8.10 (d, 2H), 8.56 (m, 1H); HPLC-MS (Method A): m/z=554 (M+1); R$_t$=4.71 min.

Example 69

General Procedure (C)

(Z)-3-{4-[4-(4-Cyclohexylphenyl)-2-(4-isopropylphenyl)-4-oxobut-2-enoyl]benzoylamino}propionic acid

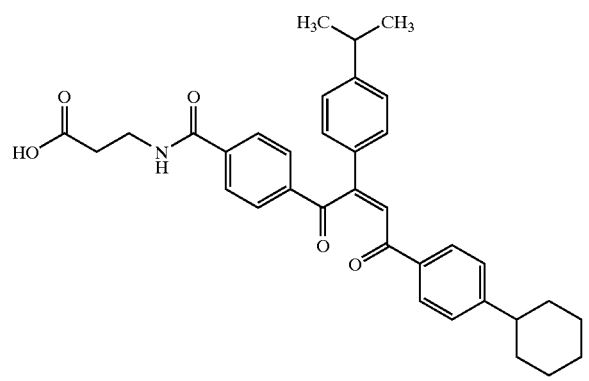

$^1$H NMR (CDCl$_3$): δ1.24 (d, 6H), 1.24–1.50 (m, 5H), 1.68–1.95 (m, 5H), 2.57 (m, 1H), 2.70 (t, 2H), 2.93 (m, 1H), 3.70 (q, 2H), 6.85 (br s, 1H), 7.20 (d, 2H), 7.29 (d, 2H), 7.50 (d, 2H), 7.64 (s, 1H), 7.77 (d, 2H), 7.90 (d, 2H), 8.01 (d, 2H); HPLC-MS (Method A): m/z=552 (M+1); R$_t$=5.84 min.

Example 70

General Procedure (C)

(Z)-3-{4-[4-Oxo-2-(4-trifluoromethoxyphenyl)-4-(4-trifluoromethylsulfanylphenyl)but-2-enoyl]benzoylamino}propionic acid

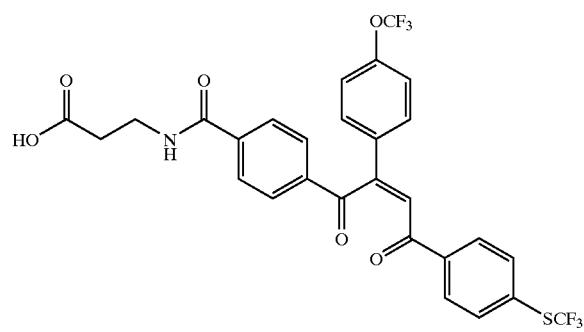

HPLC-MS (Method A): m/z=612 (M+1); R$_t$=4.94 min.

Example 71

General Procedure (C)

(Z)-3-{4-[4-Oxo-2,4-bis-(4-trifluoromethoxyphenyl)but-2-enoyl]benzoylamino}propionic acid

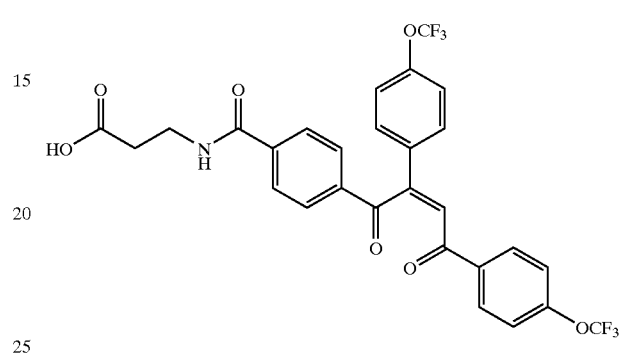

$^1$H NMR (DMSO-d$_6$): δ2.5 (2H, below DMSO-d$_6$), 3.47 (2H, q), 7.50 (2H, d), 7.54 (2H, d), 7.85 (2H, d), 7.89 (2H, d), 7.97 (2H, d), 8.10 (1H, s), 8.28 (2H, d), 8.68 (1H, t). HPLC-MS (Method A): m/z=596 (M+1); R$_t$=4.97 min.

Example 72

General Procedure (C)

(Z)-3-{4-[4-Oxo-4-(3-trifluoromethoxyphenyl)-2-(4-trifluoromethoxyphenyl)but-2-enoyl]benzoylamino}propionic acid HPLC-MS (Method A): m/z=596 (M+1); R$_t$=4.73 min.

Example 73

General Procedure (C)

(Z)-3-{4-[2-Biphenyl-4-yl-4-(4-cyclohexylphenyl)-4-oxobut-2-enoyl]benzoylamino}propionic acid

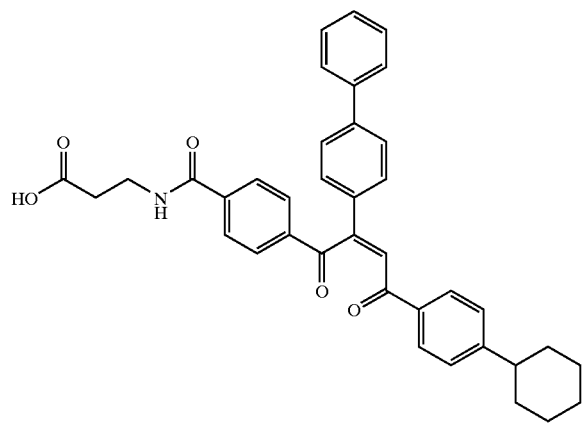

HPLC-MS (Method A): m/z=588 (M+1); R$_t$=5.83 min.

Example 74

General Procedure (C)

(Z)-3-{4-[2-Biphenyl-4-yl-4-oxo-4-(4-trifluoromethoxyphenyl)but-2-enoyl]benzoylamino}propionic acid

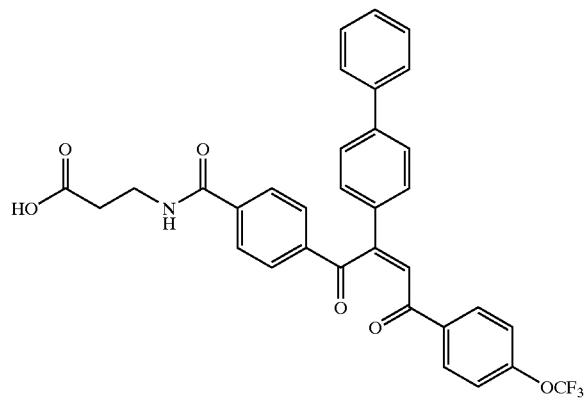

$^1$H NMR (DMSO-d$_6$): δ2.5 (2H, below DMSO-d$_6$), 3.46 (2H, q), 7.73 (2H, d), 7.90 (2H, d), 7.99 (2H, d), 8.16 (1H, s), 8.30 (2H, d), 8.70 (1H, t), 12.1 (1H, bs). HPLC-MS (Method A): m/z=588 (M+1); R$_t$=5.08 min.

Example 75

General Procedure (C)

(Z)-(3-{4-[4-Biphenyl-4-yl-4-oxo-2-(4-trifluoromethoxyphenyl)but-2-enoyl]benzoylamino}propionic acid

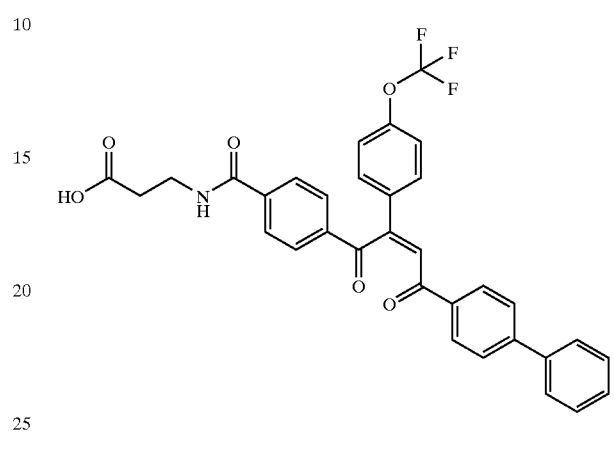

$^1$H NMR (CDCl$_3$): δ2.70 (2H, t), 3.72 (2H, q), 6.84 (1H, t), 7.40–7.50 (3H, m), 7.59–7.73 (8H, m), 7.81 (2H, d), 8.00–8.08 (4H, dd). HPLC-MS (Method A): m/z=588 (M+1); R$_t$=4.86 min.

Example 76

(Z)-3-{4-[2-(4-Cyclohex-1-enylphenyl)-4-oxo-4-(4-trifluoromethoxyphenyl)but-2-enoyl]benzoylamino}propionic acid

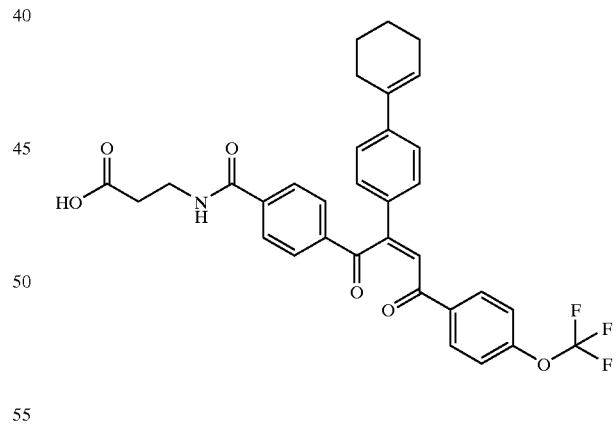

This compound was prepared according to general procedure (B), with the modification (step 3) that the resin was shaked for 3 days at 70° C. before cleavage. This afforded the oxidized product.

$^1$H NMR (CDCl$_3$): δ1.60–1.74 (m, 2H), 1.75–1.83 (m, 2H), 2.18–2.27 (m, 2H), 2.37–2.43 (m, 2H), 2.68–2.75 (t, 2H), 3.68–3.78 (q, 2H); 6.24 (t, 1H), 6.83 (t, 1H), 7.30 (d, 2H), 7.42 (d, 2H); 7.50 (d, 2H), 7.61 (s, 1H); 7.80 (d, 2H), 8.01 (dd, 4H); HPLC-MS (Method C): m/z=592 (M+1); R$_t$=7.60 min.

Example 77

General Procedure (C)

(Z)-3-{4-[4-(4-tert-Butylphenyl)-4-oxo-2-(4-trifluoromethoxyphenyl)but-2-enoyl]benzoylamino}propionic acid

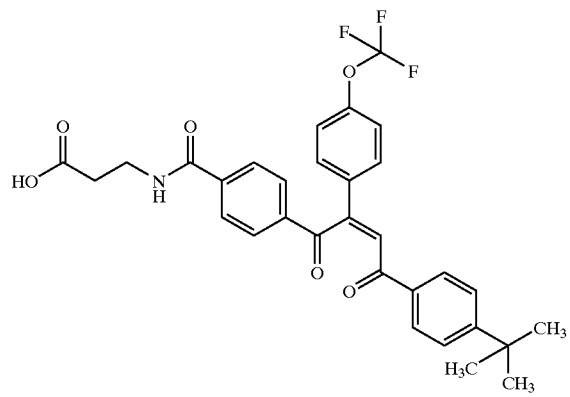

$^1$H NMR (CDCl$_3$) selected: δ1.33 (s, 9H), 2.62–2.78 (broad, 2H), 3.62–3.79 (broad, 2H), 7.23 (broad, 1H (below CDCl$_3$)), 7.44–7.52 (broad, 2H), 7.56–7.67 (broad, 4H); 7.72–7.87 (broad, 2H), 7.88–8.04 (broad, 4H); HPLC-MS (Method C): m/z=568 (M+1); R$_t$=5.53 min.

Example 78

General Procedure (C)

(Z)-3-{4-[4-Oxo-4-(2,2,3,3-tetrafluoro-2,3-dihydrobenzo[1,4]dioxin-6-yl)-2-(4-trifluoromethoxyphenyl)but-2-enoyl]benzoylamino}propionic acid

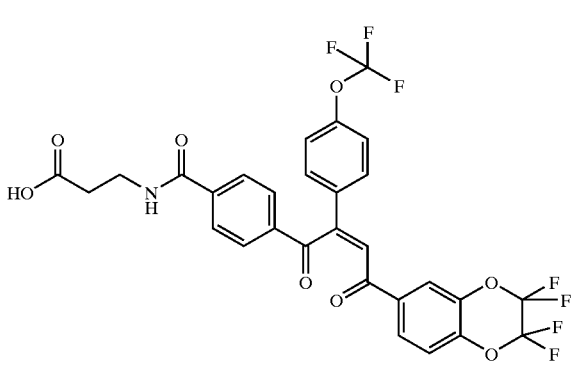

$^1$H NMR (CDCl$_3$) selected: δ2.62–2.77 (broad, 2H), 3.62–3.78 (broad, 2H), 7.86–7.98 (broad, 1H), 7.24 (broad, 2H (below CDCl$_3$)), 7.50–7.58 (broad, 1H), 7.58–7.68 (broad, 2H); 7.73–7.89 (broad, 4H), 7.94–8.04 (broad, 2H); HPLC-MS (Method C): m/z=642 (M+1); R$_t$=5.53 min.

Example 79

General Procedure (C)

(Z)-3-{4-[4-(4-Chlorophenyl)-2-(4-cyclohexylphenyl)-4-oxobut-2-enoyl]benzoylamino}propionic acid

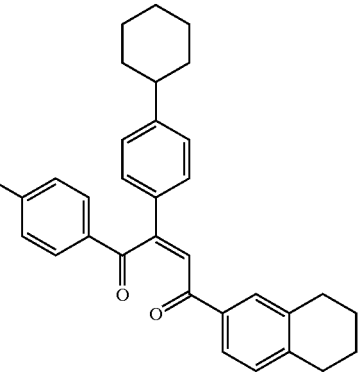

$^1$H NMR (DMSO-d$_6$): δ1.15–1.46 (m, 5H), 1.65–1.83 (m, 5H), 2.50 (m, 3H (below DMSO)), 3.42–3.50 (q, 2H); 7.30–7.35 (d, 2H), 7.55–7.72 (dd, 4H), 7.85–8.05 (m, 5H), 8.10–8.20 (d, 2H); 8.66 (t, 1H), 12.23 (s, 1H); HPLC-MS (Method C): m/z=544 (M+1); R$_t$=5.87 min.

Example 80

General Procedure (C)

(Z)-3-{4-[2-(4-Cyclohexyl phenyl)-4-oxo-4-(5,6,7,8-tetrahydronaphthalen-2-yl)but-2-enoyl]benzoylamino}propionic acid $^1$H NMR (CDCl$_3$): δ1.10–1.42 (m, 5H), 1.60–1.88 (m, 9H), 2.29–2.43 (m, 1H), 2.61–2.83 (m, 6H), 3.62–3.79 (q, 2H), 6.86 (s, 1H), 6.97–7.11 (m, 4H); 7.13–7.24 (d, 2H), 7.50–7.62 (m, 2H), 7.75–7.86 (d, 2H), 7.92–8.04 (d, 2H); HPLC-MS (Method C): m/z=564 (M+1); R$_t$=6.20 min.

Example 81

General Procedure (C)

(Z)-3-{4-[4-Oxo-4-(5,6,7,8-tetrahydronaphthalen-2-yl)-2-(4-trifluoromethoxyphenyl)but-2-enoyl]benzoylamino}propionic acid

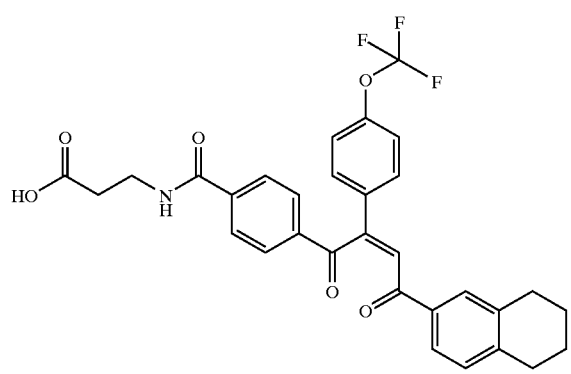

$^1$H NMR (DMSO-$d_6$): δ1.72–1.81 (m, 4H), 2.51 (m, 2H (below DMSO)), 2.74–2.84 (m, 4H), 3.42–3.50 (q, 2H), 7.20–7.26 (d, 1H), 7.45–7.52 (d, 2H), 7.78–7.98 (m, 8H), 8.05 (s, 1H); 8.66 (t, 1H), 12.22 (s, 1H); HPLC-MS (Method C): m/z=566 (M+1); R$_t$=5.47 min.

Example 82

General Procedure (C)

(Z)-3-{4-[2-(4-Chlorophenyl)-4-(4-cyclohexylphenyl)-4-oxobut-2-enoyl]benzoylamino}propionic acid

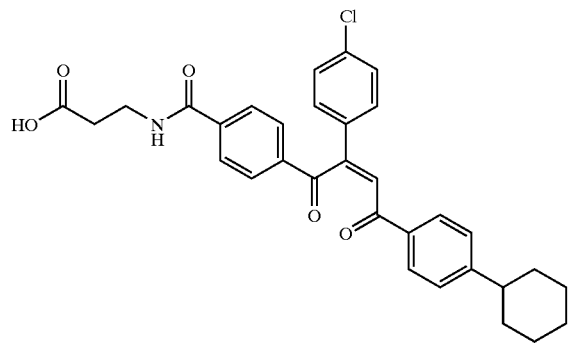

$^1$H NMR (DMSO-$d_6$): δ1.22–1.53 (m, 5H), 1.68–1.87 (m, 5H), 2.51 (t, 2H (below DMSO)), 3.41–3.52 (q, 2H), 7.36–7.43 (d, 2H), 7.52–7.58 (d, 2H); 7.68–7.75 (d, 2H), 7.85–7.97 (dd, 4H), 8.02–8.08 (m, 3H), 8.62–8.71 (t, 1H), 12.22 (s, 1H); HPLC-MS (Method C): m/z=544 (M+1); R$_t$=5.83 min.

Example 83

General Procedure (C)

(Z)-3-{4-[4-(4-Chlorophenyl)-4-oxo-2-p-tolylbut-2-enoyl]benzoylamino}propionic acid

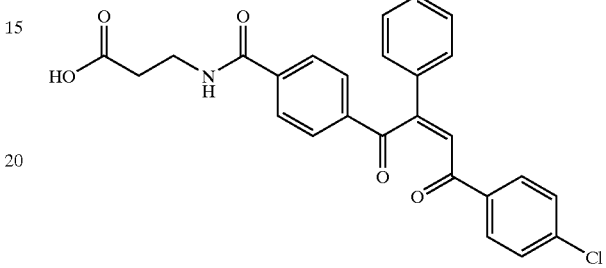

$^1$H NMR (DMSO-$d_6$): δ2.33 (3H, s), 2.5 (below DMSO), 3.44 (2H, q), 7.29 (2H, d), 7.61 (4H, m), 7.90 (4H, dd), 8.01 (1H, s), 8.15 (2H, d), 8.66 (1H, t), 12.2 (1H, bs). HPLC-MS (Method D): m/z=476 (M+1); R$_t$=4.11 min.

Example 84

General Procedure (C)

(Z)-3-{4-[2,4-Bis-(4-chlorophenyl)-4-oxobut-2-enoyl]benzoylamino}propionic acid $^1$H NMR (DMSO-$d_6$): δ2.5 (below DMSO), 3.44 (2H, q), 7.55 (2H, d), 7.63 (2H, d), 7.91 (4H, "q"), 8.07 (1H, s), 8.15 (2H, d), 8.65 (1H, t), 12.3 (1H, bs). HPLC-MS (Method D): m/z=496 (M+1); R$_t$=4.20 min.

Example 85

General Procedure (C)

(Z) 3-{4-[2-(4-Cyclohexylphenyl)-4-indan-5-yl-4-oxobut-2-enoyl]benzoylamino}propionic acid

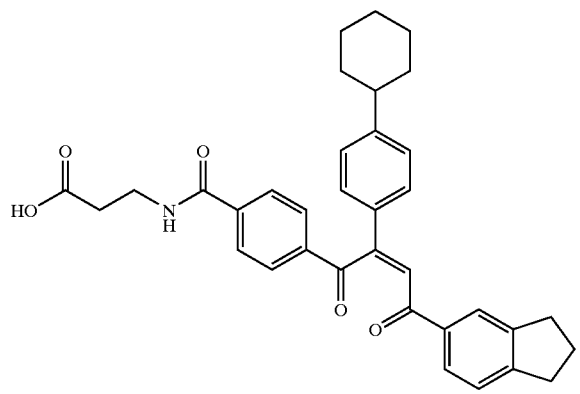

$^1$H NMR (CDCl$_3$): δ1.00–1.46 (m, 5H), 1.54–1.97 (m, 5H), 2.12 (p, 2H), 2.67 (t, 2H), 2.84 (m, 1H), 2.94 (t, 4H), 3.70 (q, 2H), 6.98 (m, 1H), 7.13–7.32 (m, 4H), 7.48 (d, 2H), 7.63 (s, 1H), 7.70–7.84 (m, 3H), 8.00 (d, 2H). HPLC-MS (Method D): m/z=550 (M+1); R$_t$=5.35 min.

Example 86

General Procedure (C)

(Z) 3-{4-[2-(4-Cyclohexylphenyl)-4-(4-isobutylphenyl)-4-oxobut-2-enoyl]benzoylamino}propionic acid

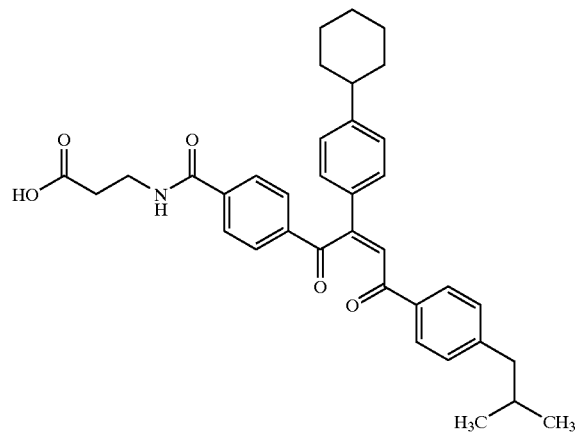

$^1$H NMR (CDCl$_3$): δ0.88 (d, 6H), 1.00–1.46 (m, 5H), 1.64–1.96 (m, 5H), 2.44 (m, 1H), 2.53 (d, 2H), 2.67 (t, 2H), 2.86 (m, 1H), 3.68 (q, 2H), 6.93 (m, 1H), 7.06–7.30 (m, 4H), 7.46 (d, 2H), 7.61 (s, 1H), 7.68 (d, 2H), 7.86 (d, 2H), 7.98 (d, 2H), 9.98 (br s, 1H). HPLC-MS (Method D): m/z=566 (M+1); R$_t$=5.73 min.

Example 87

General Procedure (C)

(Z) 3-{4-[2-(4-Cyclohexylphenyl)-4-(4-cyclopentylphenyl)-4-oxobut-2-enoyl]benzoylamino}propionic acid

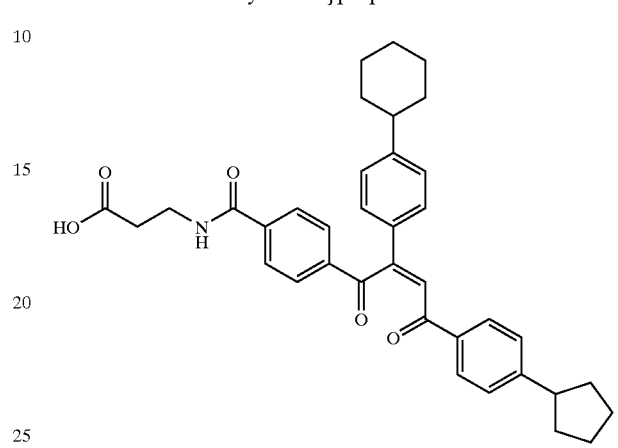

$^1$H NMR (CDCl$_3$): δ1.00–1.45 (m, 5H), 1.51–1.94 (m, 11H), 1.96–2.17 (m, 2H), 2.52 (m, 1H), 2.65 (t, 2H), 3.03 (p, 1H), 3.67 (q, 2H), 7.04 (m, 1H), 7.12–7.35 (m, 4H), 7.46 (d, 2H), 7.60 (s, 1H), 7.76 (d, 2H), 7.87 (d, 2H), 7.99 (d, 2H). HPLC-MS (Method D): m/z=578 (M+1); R$_t$=5.81 min.

Example 88

General Procedure (C)

(Z) 3-{4-[2-(4-Cyclohexylphenyl)-4-oxo-4-phenylbut-2-enoyl]benzoylamino}propionic acid

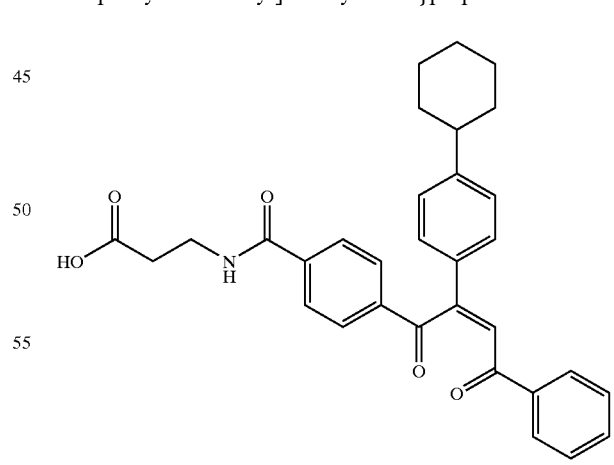

$^1$H NMR (CDCl$_3$): δ1.00–1.48 (m, 5H), 1.56–1.94 (m, 5H), 2.51 (m, 1H), 2.65 (t, 2H), 3.67 (q, 2H), 7.04 (m, 1H), 7.10–7.27 (m, 4H), 7.37–7.56 (m, 3H), 7.62 (s, 1H), 7.80 (d, 2H), 7.93 (d, 2H), 7.96 (d, 2H), 10.47 (br s, 1H). HPLC-MS (Method D): m/z=510 (M+1); R$_t$=4.84 min.

Example 89

General Procedure (C)

(Z) 3-{4-[2-(4-Cyclohexylphenyl)-4-oxo-4-p-tolylbut-2-enoyl]benzoylamino}propionic acid

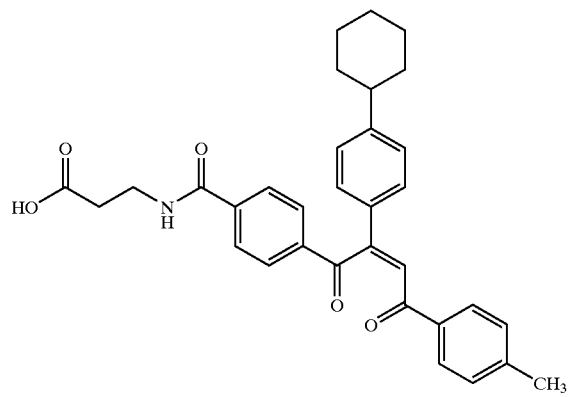

$^1$H NMR (CDCl$_3$): δ1.01–1.47 (m, 5H), 1.59–1.96 (m, 5H), 2.40 (s, 3H), 2.51 (m, 1H), 2.65 (t, 2H), 3.66 (q, 2H), 7.04 (m, 1H), 7.12–7.27 (m, 4H), 7.46 (d, 2H), 7.59 (s, 1H), 7.76 (d, 2H), 7.85 (d, 2H), 7.97 (d, 2H). HPLC-MS (Method D): m/z=524 (M+1); R$_t$=5.06 min.

Example 90

General Procedure (C)

(Z) 3-{4-[2-(4-Cyclohexylphenyl)-4-(4-methoxyphenyl)-4-oxobut-2-enoyl]benzoylamino}propionic acid

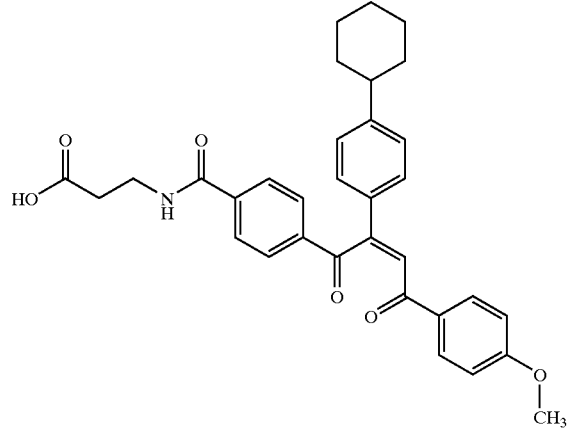

$^1$H NMR (CDCl$_3$): δ1.00–1.39 (m, 5H), 1.56–1.96 (m, 5H), 2.51 (m, 1H), 2.67 (t, 2H), 3.70 (q, 2H), 3.85 (s, 3H), 7.03 (m, 1H), 7.13–7.26 (m, 4H), 7.46 (d, 2H), 7.60 (s, 1H), 7.82 (d, 2H), 7.95 (d, 2H), 8.00 (d, 2H), 10.57 (br s, 1H). HPLC-MS (Method D): m/z 540 (M+1); R$_t$=4.87 min.

Example 91

(E)-3-{4-[2-(4-Cyclohexylphenyl)-4-oxo-4-(4-trifluoromethoxyphenyl)but-2-enoyl]benzoylamino}propionic acid

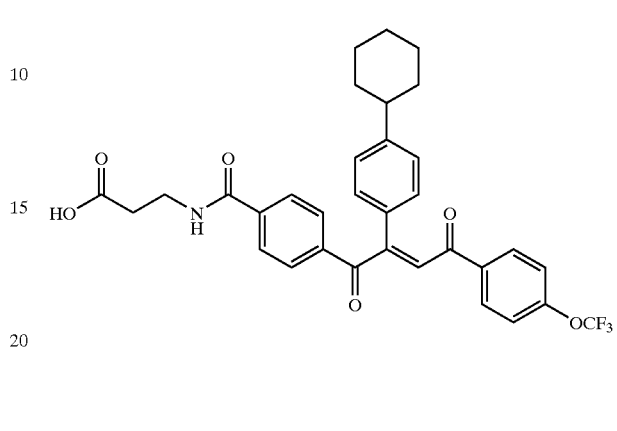

A mixture of E and Z of 3-{4-[2-(4-cyclohexylphenyl)-4-oxo-4-(4-trifluoromethoxyphenyl)but-2-enoyl]benzoylamino}propionic acid was prepared as described in step 1–5 in general procedure (C). The mixture was separated by HPLC (chiralcel OD, 25×2 cm, eluted with isopropanol:heptane:trifluoroacetic acid (20:80:0.1), 6 mL/min) to give the pure E-isomer.

$^1$H NMR (CDCl$_3$): δ1.66–2.05 (m, 5H), 2.41 (m, 1H), 2.51 (m, 2H), 3.47 (q, 2H), 7.12 (d, 4H), 7.44 (d, 2H), 7.96–8.01 (m, 6H), 8.72 (t, 1H).

General Procedure (D)

General procedure (D) for solution phase synthesis of compounds of the general formulae (I$_3$):

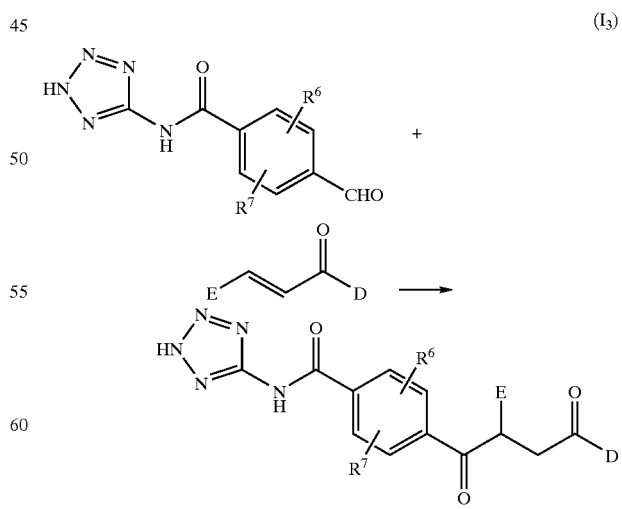

The procedure is illustrated in the following example:

Example 92

General Procedure (D)

4-[2-Biphenyl-4-yl-4-oxo-4-(3-trifluoromethylphenyl)butyryl]-N-(2H-tetrazol-5-yl)benzamide

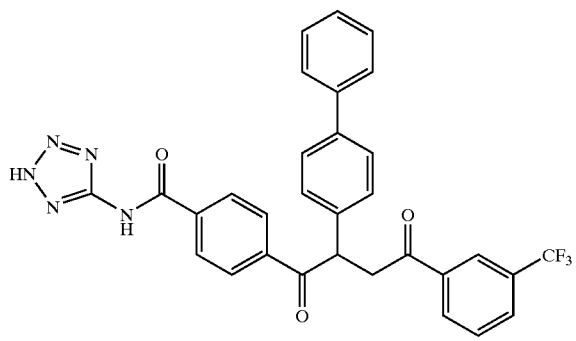

4-Formyl-N-(2H-tetrazol-5-yl)benzamide (128 mg) (synthesized according to the procedure described in WO 00/69810), 3-biphenyl-4-yl-1-(3-trifluoromethylphenyl)propenone (223 mg) and 3,4-dimethyl-5-(2-hydroxyethyl)thiazoliumiodide (89 mg) were dissolved in dry DMF (2.2 mL). Triethylamine (0.180 mL) was added and the mixture was stirred at 70° C. for 3 days under nitrogen. The reaction mixture was filtered through a silica gel column eluted with DCM/methanol/acetic acid (90:9:1), and the solvent was removed by evaporation to yield an oil. The oil was washed with boiling heptane (4 mL) to remove unreacted 3-biphenyl-4-yl-1-(3-trifluoromethylphenyl)propenone, and remaining material was purified on silica gel column eluted with DCM/methanol/acetic acid (95:4:1) to yield the title compound (30 mg, 9%).

$^1$H NMR (CDCl$_3$): δ12.8 (br s, 1H), 8.38 (d, 2H), 8.30 (s, 1H), 8.26 (d, 2H), 8.18 (d, 1H), 7.83 (d, 1H), 7.67–7.30 (m, 11H); 5.41 (dd, 1H), 4.30 (dd, 1H), 3.42 (dd, 1H); HPLC-MS (Method A): m/z=570 (M+1); R$_t$=5.12 min.

General Procedure (E)

General procedure (E) for solution phase synthesis of compounds of the general formula (I$_5$):

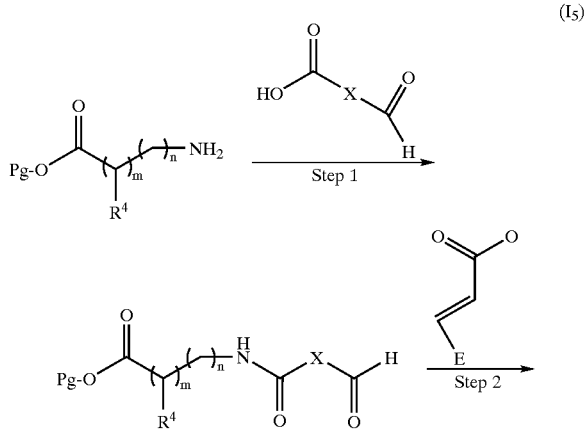

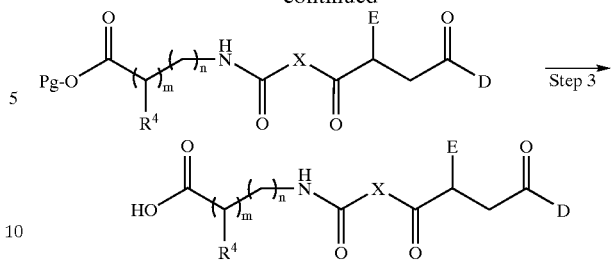

wherein X, D, E, m, n and R$^4$ are as defined for formula (I), and Pg is a standard acid protecting group like methyl, ethyl, propyl, isopropyl, tert-butyl or benzyl.

The procedure is illustrated in the following examples.

Step 1:

This reaction is known and has previously been described in WO 00/69810. The acylation of the amino group of of a protected amino acid is generally performed by activating the carboxylic acid with diisopropyl-carbodiimide, dicyclohexylcarbodiimide or 1-[3-(dimethylamino)propyl]-3-ethylcarbodiimide hydrochloride optionally in the presence of a side reaction inhibitor such as N-hydroxybenzotriazole. The protected amino acid (protected eg as methyl, ethyl, propyl, isopropyl, tert-butyl or benzyl ester) is then added to the activated carboxylic acid. When the protected amino acid is an ammonium salt, a non-nucleophilic base such as triethylamine or diisopropylethyl amine is added. The acylation is carried out in a solvent such as THF, dioxane, toluene, DCM, DMF, NMP or a mixture of two or more of these. The reaction is generally performed between 0° C. to 80° C., preferably between 20° C. to 40° C. The product can be obtained by work-up procedures known to those skilled in the art.

Step 2:

This reaction is known and (Stetter H., Krasselt J. *J. Heterocyclic. Chem.* 14, 573, 1977). The addition of aldehydes to activated double bonds is generally carried out by stirring the aldehyde with a compound that contains an activated dobbelt bond such as a substituted propenone in the presence of a catalyst such as cyanid or thiazoliums salts such as 3,4-dimethyl-5-(2-hydroxyethyl)thiazolium iodide, 3-benzyl-5-(2-hydroxyethyl)-4-methyl-1,3-thiazolium chloride, 3-ethyl-5-(2-hydroxyethyl)-4-methyl-1,3-thiazolium bromide or vitamin B$_1$. When thiaziliums salts are used as catalyst a non-nucleophilic amine base such as triethyl amine or DBU is added. The addition is carried out in a solvent such as ethanol, methanol, 1-propanol, 2-propanol, dioxane, DMSO, NMP or DMF or a mixture of two or more of these. The reactions are performed between 50° C. to 120° C., preferably between 50° C. to 80° C. The product can be obtained by work-up procedures known to those skilled in the art.

Step 3:

Removal of the standard acid protecting groups depends on the nature of the protecting groups but has in general been described. (*Protective Groups in Organic Chemistry.* Greene T. W., Wuts P. G. M. 1999, Wiley-Interscience, p. 377)

The procedure is illustrated in the following examples.

Example 93
General Procedure (E)
3-{4-[4-(4-tert-Butylphenyl)-(4-cyclohexylphenyl)-4-oxobutyryl]benzoylamino}-2R-hydroxypropionic acid

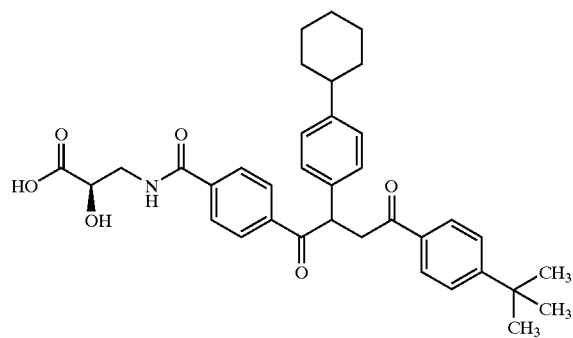

Step 1: 3-(4-Formylbenzoylamino)-2R-hydroxypropionic acid methyl ester

In a 500 mL round bottom flask 4-formylbenzoic acid (7.5 g, 50 mmol) was dissolved in DMF (80 mL). 1-Hydroxybenzotriazole, hydrate (8.11 g, 60 mmol, 1.2 eq) and N'-(3-dimethylaminopropyl)-N-ethylcarbodiimide hydrochloride (9.59 g, 50 mmol, 1 eq) were added. The solution was stirred under $N_2$ for ¾ hour and the R-isoserine methyl ester hydrochloride (prepared as described in WO 02/00612, 11.67 g, 75 mmol, 1.5 eq) and DIPEA (13.6 mL, 80 mmol, 1.6 eq.) were added and the mixture was stirred the overnight. The reaction mixture was evaporated to 80 mL and then partitioned between ethyl acetate (200 mL) and water (200 mL). The aqueous phase was extracted twice with ethyl acetate (100 mL and 80 mL). The combined organic phases were washed with 0.2 N HCl (3×100 mL) and saturated sodium chloride: water (1:1) (3×100 mL), dried over magnesium sulphate and evaporated to dryness. The compound was suspended in acetic acid ethyl ester (30 mL) and filtered. The solid was washed and the combined filtrates were evaporated in vacuo. The residue was purified by column chromatography. As eluent acetic acid ethyl ester:n-heptane (95:5) and acetic acid ethyl ester:methanol (95:5) were used. 3-(4-Formylbenzoylamino)-2R-hydroxypropionic acid methyl ester (2.24 g, 10%) was isolated.

$^1$H NMR (CDCl$_3$): δ3.82 (3H, s), 3.80–3.94 (1H, m), 4.42–4.49 (1H, m), 4.69 (1H, br s), 6.78 (1H, br s), 7.92 (4H, s).

Step 2: Preparation of 3-{4-[4-(4-tert-butylphenyl)-2-(4-cyclohexylphenyl)-4-oxobutyryl]benzoylamino}-2R-hydroxypropionic acid ethyl ester To a mixture of 1-(4-tert-butylphenyl)-3-(4-cyclohexylphenyl)propenone (1.00 g, 2.91 mmol) in absolute ethanol (99%, 10 mL) under nitrogen, 3,4-dimethyl-5-(2-hydroxyethyl)thiazolium iodide (165 mg, 0.58 mmol) and triethylamine (0.325 mL, 2.33 mmol) were added and the mixture was heated to reflux. (R)-3-(4-Formylbenzoylamino)-2-hydroxypropionic acid methyl ester (1.01 g, 3.78 mmol) was dissolved in absolute ethanol (99%, 10 mL) and was added dropwise to the refluxing mixture over an hour. The reaction mixture was refluxed for 7 days, allowed to cool to room temperature and partitioned between DCM (50 mL) and aqueous HCl (1 N, 50 mL). The aqueous phase was washed with DCM (50 mL). The combined organic phases were dried ($Na_2SO_4$) and evaporated in vacuo. The residual oil was purified by silica gel column chromatography using ethyl acetate and heptane (1:1) as eluent to give the pure 3-{4-[4-(4-tert-butylphenyl)-2-(4-cyclohexylphenyl)-4-oxobutyryl]benzoylamino}-2R-hydroxypropionic acid ethyl ester.

HPLC-MS (Method D): m/z=612 (M+1); $R_t$=6.07 min.

Step 3: Preparation of 3-{4-[4-(4-tert-butylphenyl)-2-(4-cyclohexylphenyl)-4-oxobutyryl]benzoylamino}-2R-hydroxypropionic acid To the above 3-{4-[4-(4-tert-butylphenyl)-2R-(4-cyclohexylphenyl)-4-oxobutyryl]benzoylamino}-2-hydroxypropionic acid ethyl ester was added ethanol (10 mL). NaOH (244 mg) was dissolved in water (1 mL) and added to the mixture. The mixture was stirred for 30 min, diluted with water (15 mL) and pH was adjusted to 2 with aqueous HCl (1 N). The precipitate was isolated by filtration to afford the title compound. Yield: 430 mg (25%).

$^1$H NMR (DMSO-d$_6$): δ1.08–1.42 (14H, m), 1.60–1.90 (5H, m), 2.42 (1H, m), 3.32–3.53 (3H, m), 3.95 (1H, t), 4.08 (1H, dd), 5.40 (1H, dd), 7.15 (2H, d), 7.32 (2H, d), 7.52 (2H), 7.90 (2H, d), 7.95 (2H, d), 8.14 (2H, d), 8.70 (1H, t); HPLC-MS (Method D): m/z=584 (M+1); $R_t$=5.68 min.

Example 94
General Procedure (E)
3-{4-[4-Biphenyl-4-yl-2-(4-cyclohexylphenyl)-4-oxobutyryl]benzoylamino}-2R-hydroxypropionic acid

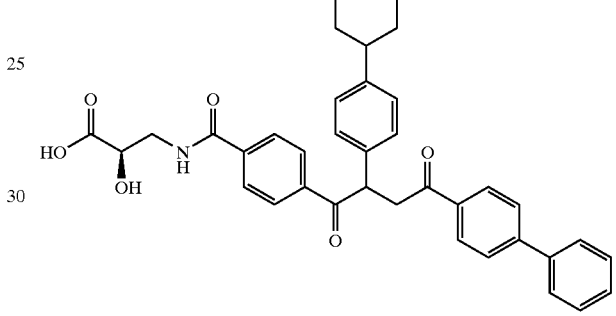

$^1$H NMR (DMSO-d$_6$) selected: δ1.15–1.39 (m, 5H), 1.62–1.79 (m, 5H), 2.38–2.47 (t, 1H), 3.40–3.51 (m, 2H), 3.84–3.93 (broad, 1H), 4.09–4.19 (dd, 1H), 5.38–5.45 (dd, 1H), 7.12–7.20 (d, 2H), 7.32–7.38 (d, 2H), 7.41–7.55 (m, 3H), 7.72–7.86 (dd, 4H), 7.89–7.97 (d, 2H), 8.08–8.18 (dd, 4H), 8.58–8.65 (t, 1H); HPLC-MS (Method C): m/z=604 (M+1); $R_t$=6.57 min.

Example 95
General Procedure (E)
3-{4-[2-Biphenyl-4-yl-4-oxo-4-(4-trifluoromethoxyphenyl)butyryl]benzoylamino}-2R-hydroxypropionic acid

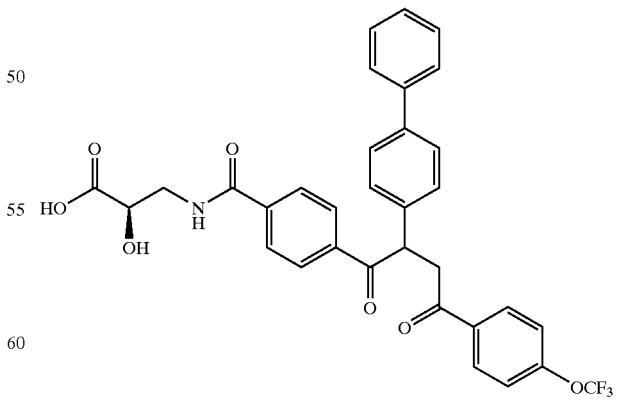

$^1$H NMR (CDCl$_3$): δ 3.32 (1H, d), 3.89 (2H, bd), 4.23 (1H, dd), 4.44 (1H, bs), 5.33 (1H, d), 7.06 (1H, bs), 7.3–7.7 (11H, m), 7.80 (2H, d), 8.05 (2H, d), 8.10 (2H, d). HPLC-MS (Method A): m/z=606 (M+1); $R_t$=5.08 min.

Example 96

General Procedure (E)

3-{4-[4-(4-Cyclohexylphenyl)-2-(4-isopropylphenyl)-4-oxo-butyryl]benzoylamino}-2-(R)-hydroxypropionic acid

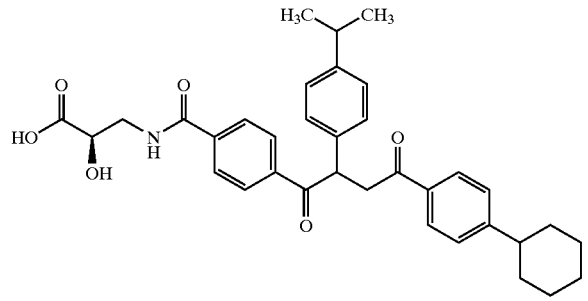

$^1$H NMR (DMSO-$d_6$) selected: δ1.13 (d, 6H), 1.10–1.50 (m, 5H) 1.65–1.90 (m, 5H), 2.57 (m, 1H), 2.80 (m, 1H), 4.02–4.15 (m, 3H), 5.39 (dd, 1H), 7.16 (d, 2H), 7.35 (dd, 4H), 7.93 (d, 4H), 8.13 (d, 2H), 8.63 (br m, 1H).

General Procedure (F)

General procedure (F) for solution phase synthesis of compounds of the general formula ($I_4$):

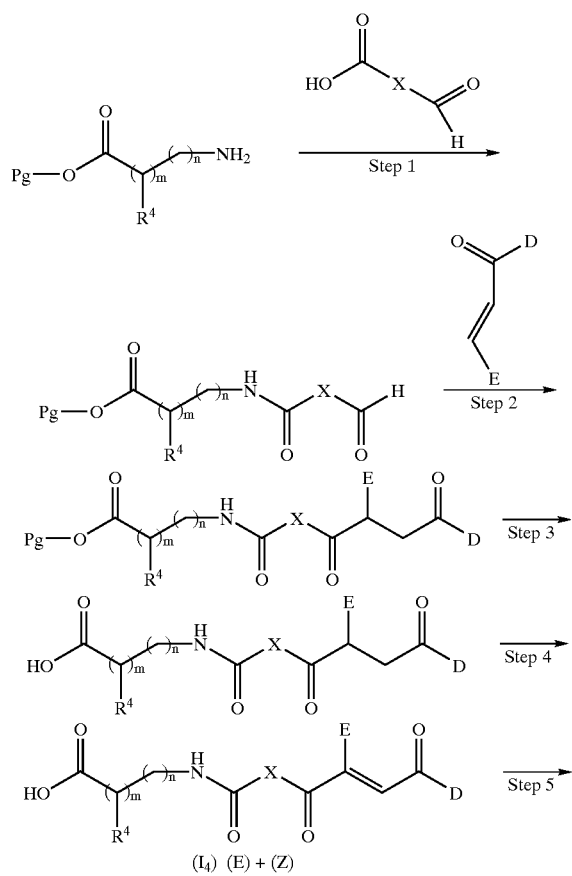

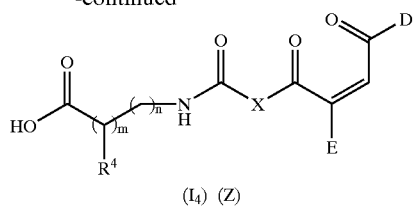

wherein X, D, E, m, n and $R^4$ are as defined for formula (I), and Pg is a standard carboxylic acid protecting group like methyl, ethyl, propyl, isopropyl, tert-butyl or benzyl.

The procedure is illustrated in the following example.

Example 97

General Procedure (F)

(Z)-3-{4-[4-(4-tert-Butylphenyl)-2-(4-cyclohexylphenyl)-4-oxobut-2-enoyl]benzoylamino}-2R-hydroxypropionic acid

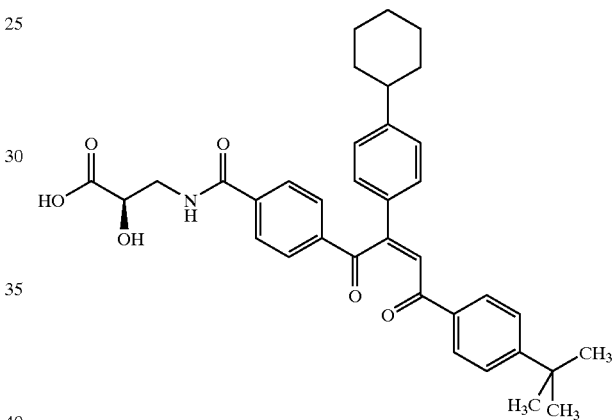

Step 1–Step 3: Preparation of 3-{4-[4-(4-tert-butylphenyl)-2-(4-cyclohexylphenyl)-4-oxobutyryl]benzoylamino}-2R-hydroxypropionic acid The compound was synthesized according to general procedure (E).

Step 4: Preparation of 3-{4-[4-(4-tert-Butylphenyl)-2-(4-cyclohexylphenyl)-4-oxobut-2-enoyl]-benzoylamino}-2R-hydroxypropionic acid 3-{4-[4-(4-tert-Butylphenyl)-2-(4-cyclohexylphenyl)-4-oxobutyryl]benzoylamino}-2R-hydroxypropionic acid (350 mg, 0.599 mmol) was dissolved in THF (5 mL). DBU (0.323 mL, 2.16 mmol) and crystalline iodine (183 mg, 0.719 mmol) were added. The mixture was stirred at room temperature for 30 min and poured into DCM (100 mL) and washed with aqueous sodium sulfite (2%, 50 mL). The organic phase was washed with aqueous HCl (1 N, 50 mL), dried (Na$_2$SO$_4$) and evaporated to dryness to afford an E and Z mixture of 3-{4-[4-(4-tert-butylphenyl)-2-(4-cyclohexylphenyl)-4-oxobut-2-enoyl]benzoylamino}-2R-hydroxypropionic acid.

$^1$H NMR (CDCl$_3$): δ1.28 and 1.32 (9H, s, two peaks), 1.15–1.40 (5H, m), 1.60–1.85 (5H, m), 2.36 and 2.50 (1H, m, two peaks), 4.38 (1H, q), 6.88 and 7.62 (1H, s, two peaks), 7.01 (1H, d), 7.13–7.25 (2H, dd), 7.30–7.40 (2H, m), 7.45 (2H, dd), 7.73–8.00 (6H, m).

Step 5: Preparation of (Z)-3-{4-[4-(4-tert-butylphenyl)-2R-(4-cyclohexylphenyl)-4-oxobut-2-enoyl]benzoylamino}-2R-hydroxypropionic acid The E and Z mixture of 3-{4-[4-(4-tert-butylphenyl)-2-(4-cyclohexylphenyl)-4-oxobut-2-enoyl]benzoylamino}-2R-hydroxypropionic acid was dissolved in toluene (25 mL). Concentrated HCl (37%, 900 μl) was added and the mixture was heated to reflux for 1 hour. The solvents were removed by evaporation to afford, after drying overnight in vacuo, (Z)-3-{4-[4-(4-tert-butylphenyl)-2-(4-cyclohexylphenyl)-4-oxobut-2-enoyl]benzoylamino}-2R-hydroxypropionic acid.

$^1$H NMR (CDCl$_3$): δ1.32 (9H, s), 1.15–1.42(5H, m), 1.60–1.90 (5H, m), 2.50 (1H, m), 3.78 (1H, m), 3.88 (1H, m), 4.38 (1H, m), 7.22 (2H, d), 7.46 (2H, d), 7.48 (2H, d), 7.61 (1H, s), 7.78 (2H, d), 7.88 (2H, d), 7.98 (2H, d). HPLC-MS (Method D): m/z=582 (M+1), R$_t$=5.40 min.

Example 98
General Procedure (F)
(Z)-3-{4-[4-(4-tert-Butylphenyl)-2-(4-cyclohexylphenyl)-4-oxobut-2-enoyl]benzoylamino}-2R-hydroxypropionic acid

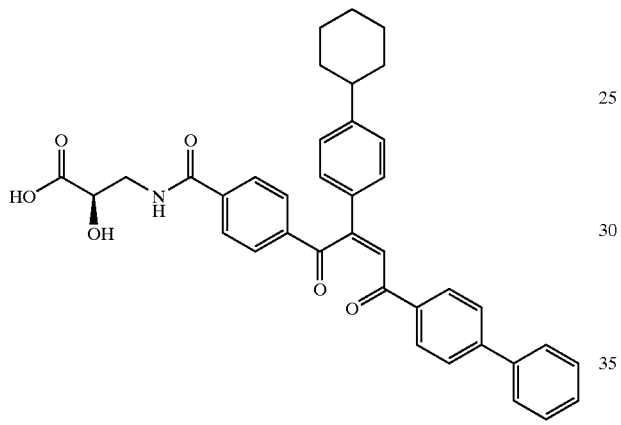

$^1$H NMR (CDCl$_3$): δ1.18–1.41 (5H, m), 1.60–1.90 (5H, m), 2.47 (1H, m), 3.75 (2H, m), 4.32 (1H, m), 7.19 (2H, d), 7.29–7.50 (6H, m), 7.52–7.67 (4H, m), 7.71 (2H, d), 7.92 (2H, d), 7.98 (2H, d).

Example 99
General Procedure (F)

The compound of example 42 was also prepared according to the general procedure (F) as illustrated below:
(Z)-3-{4-[2-Biphenyl-4-yl-4-oxo-4-(4-trifluoromethoxyphenyl)but-2-enoyl]benzoylamino}-2R-hydroxypropionic acid

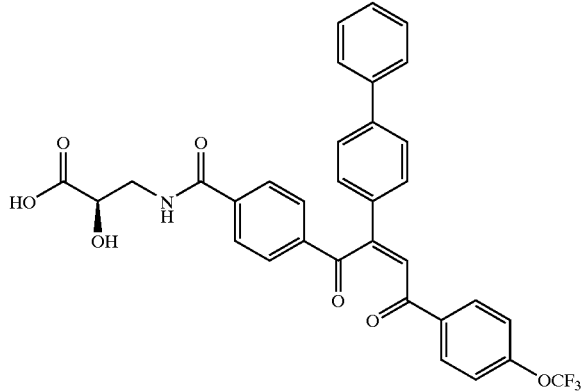

HPLC-MS (Method A): m/z=604 (M+1); R$_t$=4.98 min.

Example 100
General Procedure (F)
(Z)-3-{4-[4-(4-Cyclohexylphenyl)-2-(4-isopropylphenyl)-4-oxobut-2-enoyl]benzoylamino}-2R-hydroxypropionic acid

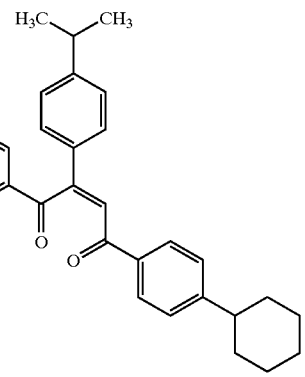

$^1$H NMR (CDCl$_3$): δ1.18 (d, 6H), 1.10–1.50 (m, 5H), 1.60–1.93 (m, 5H), 2.52 (m, 1H), 2.88 (m, 1H), 3.70 (m, 2H), 4.37 (br s, 1H), 7.23 (dd, 4H), 7.44 (d, 2H), 7.58 (s, 1H), 7.70–8.00 (m, 6H). HPLC-MS (Method D): m/z=568 (M+1); R$_t$=5.34 min

Example 101
General Procedure (F)
(Z)-3-{4-[2-(4-Cyclohexylphenyl)-4-(3,5-dichlorophenyl)-4-oxobut-2-enoyl]benzoylamino}propionic acid

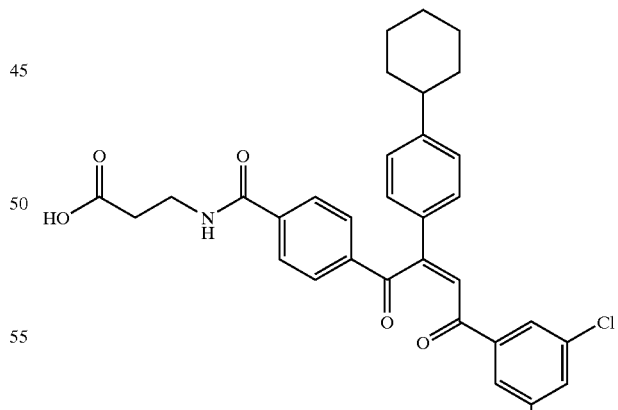

$^1$H NMR (CDCl$_3$): δ1.18–1.48 (m, 5H), 1.65–1.94 (m, 5H), 2.50 (m, 1H), 2.66 (t, 2H), 3.67 (q, 2H), 6.94 (br s, 1H), 7.15 (d, 2H), 7.22 (d, 2H), 7.49 (m, 3H), 7.86 (m, 3H), 7.94 (d, 2H); HPLC-MS (Method D): m/z=579 (M+1); R$_t$=5.60 min.

General Procedure (G)

General procedure (G) for solution phase synthesis of compounds of the general formula (I₄):

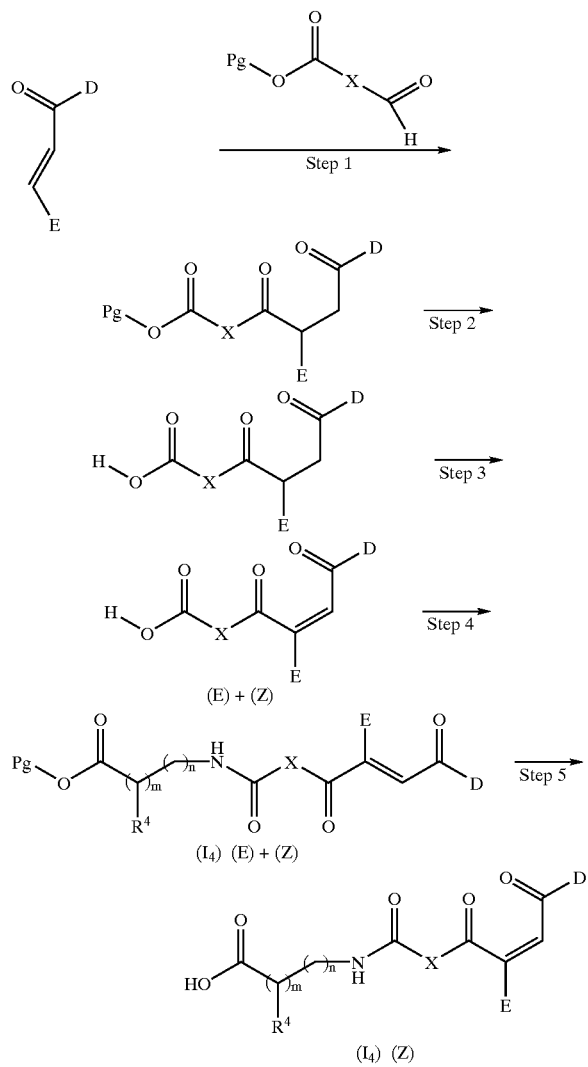

wherein X, D, E, m, n and R⁴ are as defined for formula (I), and Pg is a standard carboxylic acid protecting group like methyl, ethyl, propyl, isopropyl, tert-butyl or benzyl.

Example 102

General Procedure (G)

The compound of example 65 was also prepared according to the general procedure (G) as illustrated below:

3-{4-[2-[4-(2,2-Dimethyl-propyl)phenyl]-4-oxo-4-(4-trifluoromethoxyphenyl)but-2-enoyl] benzoylamino}propionic acid

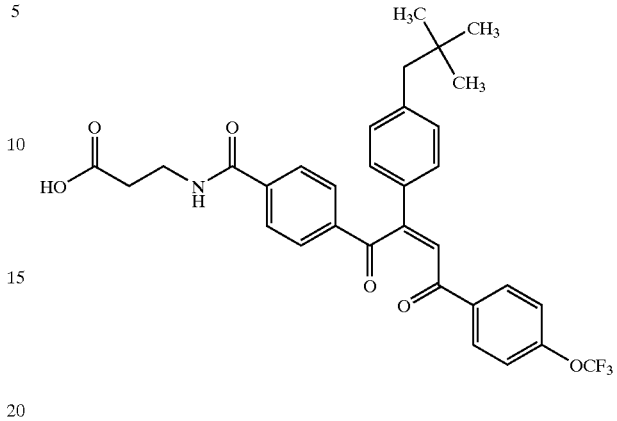

Step 1 and Step 2: 4-[2-[2,2-dimethylpropyl)phenyl]-4-oxo-4-(4-trifluoromethoxyphenyl)butyryl]acid A mixture of 3-[4-(2,2-Dimethylpropyl)phenyl]-1-(4-trifluoromethoxyphenyl)propenone (10.51 g; 29 mmol) (Building Block 8), 3,4-Dimethyl-5-(2-hydroxyethyl) thiazolium iodide (1.77 g, 6.2 mmol) and triethylamine (3.52 mL; 25.27 mmol) was stirred and refluxed in 100 mL of absolute ethanol. A solution of methyl 4-formylbenzoate (6.8 g, 41.4 mmol) in 50 mL of absolute ethanol was added drop wise to the mixture. Stirring and heating was continued for 16 hours. The mixture was cooled and partitioned between 1N HCl (150 mL) and DCM (200 mL). The, organic phase was separated and the aqueous phase was further extracted with DCM (200 mL). The combined DCM extrats was washed with water, dried ($Na_2SO_4$), clarified with Norite A, filtered and evaporated to afford 14 g (80%) of intermediary ester compound. This substance was dissolved in 80 mL of methanol and sodium hydroxide (2.68 g; 67.1 mmol) in 10 mL of water was added to the mixture. Stirring was continued till the disappearance of the ester starting material, and the pH was adjusted to 2 with dilute hydrochloric acid. The precipitate was filtered off and dried to afford 10.3 g of 4-[2-[4-(2,2-dimethylpropyl)phenyl]-4-oxo-4-(4-trifluoromethoxyphenyl)butyryl]benzoic acid.

$^1$H NMR ($CDCl_3$,): δ8.12 (d, 2H), 8.09 (d, 2H), 8.02 (d, 2H), 7.28 (d, 2H), 7.21 (d, 2H), 7.08 (d, 2H), 5.25 (dd, 1H) 4.20 (m, 1H), 3.30 (dd, 1H), 2.43 (s, 2H), 0.88 (s, 9H).

Step 3: Preparation of (E,Z)-4-[2-[4-(2,2-Dimethylpropyl)phenyl]-4-oxo-4-(4-trifluoromethoxyphenyl)but-2-enonyl] benzoic acid.

4-[2-[4-(2,2-dimethylpropyl)phenyl]-4-oxo-4-(4-trifluoromethoxyphenyl)butyryl]benzoic acid (9.3 g; 20.1 mmol) was dissolved in THF (700 mL). The mixture was stirred while iodine (6.34 g; 24.1 mmol) and DBU (11 g; 42.4 mmol) were added. The mixture was stirred for 2 hours and concentrated under reduced pressure to about 100 mL of volume. A 2% solution of sodium sulfite (150 mL) and 1N hydrochloric acid (150 mL) was added. The mixture was extracted with DCM (2×300 mL), washed with brine (400 mL). The organic phase was separated, dried ($Na_2SO_4$), clarified with Norite A, filtered and evaporated to afford 8.2 (88%) of (E,Z)-4-[2-[4-(2,2-Dimethylpropyl)phenyl]-4-oxo-4-(4-trifluoromethoxyphenyl)but-2-enonyl]benzoic acid HPLC-MS (Method A): m/z=511 (M+1); $R_t$=5.60 min.

Step 4 and Step 5: Preparation of (Z)-3-{4-[2-[4-(2,2-Dimethyl-propyl)phenyl]-4-oxo-4-(4-trifluoromethoxyphenyl)but-2-enoyl]-benzoylamino}propionic acid A solution of (E,Z)-4-[2-[4-(2,2-Dimethylpropyl)phenyl]-4-oxo-4-(4-trifluoromethoxyphenyl)but-2-enonyl]benzoic acid (7.2 g; 14.1 mmol) in 20 mL of DMF was stirred while 1-hydroxybenzotriazole hydrate (2.29 g; 19.9 mmol) was added. The mixture was stirred for 1 hour at room temperature follow by the addition of EDAC (3.24 g; 16.92 mmol), methyl 3-aminopropionate hydrochloride (2.95 g; 21.16 mmol) and DIPEA (7.37 mL; 42.31 mmol), respectively. The mixture was stirred at 40° C. for 2 hours. The mixture was evaporated under reduced pressure and the residue was partitioned between water and ethyl acetate. The organic phase was separated, washed with brine, dried ($Na_2SO_4$) and evaporated. The residue was dissolved in a mixture of methanol (80 mL) and THF (20 mL) and sodium hydroxide (1.69 g; 42.3 mmol) in 10 mL of water was added. The mixture was stirred for 1.5 hours at room temperature. The mixture was concentrated to about 30 mL under reduced pressure and 40 mL of water was added. The pH was adjusted to 1.5 by addition of 1 M hydrochloric acid. The precipitate was filtered off and dried to afford 7.9 g of crude substance. This substance was boiled for one hour in a mixture of toluene (100 mL) and concentrated hydrochloric acid (2.7 mL). The mixture was cooled to room temperature and the precipitate was isolated to afford 5.6 g (68%) of the title compound.

$^1$H NMR ($CDCl_3$): δ8.02 (m, 4H), 7.80 (d, 2H), 7.60 (s, 1H), 7.48 (d, 2H), 7.30 (d, 2H); 7.18 (d, 2H), 6.84 (t, 1H), 3.63 (q, 2H), 2.72 (t, 2H), 2.50 (s, 2H), 0.90 (s, 9H); HPLC-MS (Method A): m/z=583 (M+1); $R_t$=5.03 min.

Example 103

3-{4-[4-(4-tert-Butylphenyl)-4-oxo-2-(4-trifluoromethoxyphenyl)butyryl]benzoylamino}propionic acid

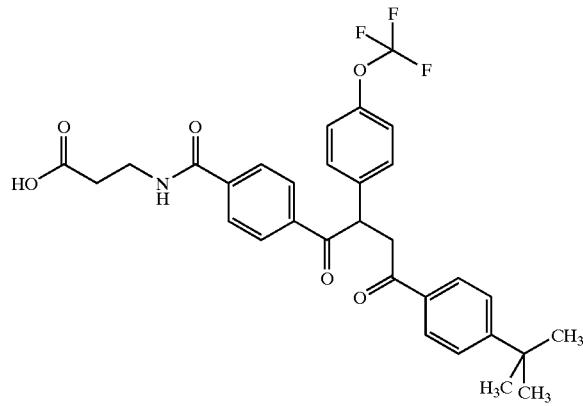

Step 1: 4-[4-(4-tert-Butylphenyl)-4-oxo-2-(4-trifluoromethoxyphenyl)butyryl]benzoic acid methyl ester In a dry three necked 50 mL round bottom flask was placed 1-(4-tert-butylphenyl)-3-(4-trifluoromethoxyphenyl)propenone (9.47 g, 27.18 mmol), 3,4-dimethyl-5-(2-hydroxyethyl)thiazolium iodide (7.75 g, 27.18 mmol) and triethylamine (13.26 mL, 95.13 mmol) under nitrogen. The mixture was dissolved in refluxing ethanol (45 mL, 99%). A solution of 3-(4-formylbenzoylamino)propionic acid methyl ester (6.97 g, 40.77 mmol) in ethanol (50 mL, 99%) was drop wise added over approximately 2 ½ h. The mixture was refluxed for 5 h under nitrogen where after the reaction was cooled and evaporated to dryness. The residual oil was dissolved in DCM (100 mL) and extracted with 1 N HCl (150 mL) and the water phase was extracted with DCM (50 mL) once more. The combined organic phases were dried with magnesium sulphate, filtered and evaporated to dryness to afford 4-[4-(4-tert-butylphenyl)-4-oxo-2-(4-trifluoromethoxyphenyl)butyryl]benzoic acid methyl ester (16.9 g).

HPLC-MS (Method C): m/z=513 (M+1); $R_t$=7.33 min.

Step 2: 4-[4-(4-tert-Butylphenyl)-4-oxo-2-(4-trifluoromethoxyphenyl)butyryl]benzoic acid 4-[4-(4-tert-Butylphenyl)-4-oxo-2-(4-trifluoromethoxyphenyl)butyryl]benzoic acid methyl ester (13.9 g, 27.2 mmol) was suspended in ethanol (120 mL, 96%) and added sodium hydroxide (4N, 27,2 mL). After 4½ h the reaction was evaporated to dryness. The residue was added water (200 mL) and hydrochloric acid (4N, 30 mL) to pH 1–2 causing precipitation. The mixture was stirred for ½ h. The precipitate was filtered, washed carefully with water, and dried the night over at 40° C. in vacuo. The residue was crystallised from methanol and water to afford 4-[4-(4-tert-butylphenyl)-4-oxo-2-(4-trifluoromethoxyphenyl)butyryl]benzoic acid (10.4 g).

HPLC-MS (Method D): m/z=499 (M+1); $R_t$=5.51 min.

3-{4-[4-(4-tert-Butylphenyl)-4-oxo-2-(4-trifluoromethoxyphenyl)butyryl]benzoylamino}propionic acid methyl ester 4-[4-(4-tert-Butylphenyl)-4-oxo-2-(4-trifluoromethoxyphenyl)butyryl]benzoic acid (10.4 g, 20.86 mmol) was dissolved in DMF (150 mL) and added EDAC (5.60 g, 29.20) and HOBt (4.23 g, 31.29 mmol). After ½ h a solution of beta-alanine methyl ester hydrochloride (4.37 g, 31.29 mmol) and DIPEA (5.36 mL, 31.29 mmol) in DMF (20 mL) was added to the above mixture and the reaction mixture was stirred night over. The reaction was concentrated to approximately 100 mL and diluted with water (200 mL) and extracted with ethyl acetate (200 mL). The water phase was extracted with additional ethyl acetate (75 mL). The combined organic phases were washed with hydrochloric acid (0.2 N, 3×150 mL), aqueous sodium chloride (50% saturation, 3×150 mL) and dried over magnesium sulphate. The dried organic phase was filtered and evaporated to dryness to afford 3-{4-[4-(4-tert-butylphenyl)-4-oxo-2-(4-trifluoromethoxyphenyl)butyryl]benzoylamino}propionic acid methyl ester (12.76 g).

HPLC-MS (Method D): m/z=584 (M+1); $R_t$=5.48 min.

Step 4: 3-{4-[4-(4-tert-Butylphenyl)-4-oxo-2-(4-trifluoromethoxyphenyl)butyryl]benzoylamino}propionic acid 3-{4-[4-(4-tert-Butylphenyl)-4-oxo-2-(4-trifluoromethoxyphenyl)butyryl]benzoylamino}propionic acid methyl ester (12 g, 21 mmol) was dissolved in ethanol 96% (250 mL), added 4N NaOH (31.2 mL, 125 mmol), and stirred for 2 h 45 min. The reaction mixture was concentrated in vacuo and the residue suspended in water (150 mL) and added hydrochloric acid (4N, 34 mL) to pH 1–2. After 1 h the precipitate was filtered and washed carefully with water and dried. The residue was purified by preparative HPLC using acetonitrile (gradient from 42% to 97.5%), water and TFA (2.5%) as eluent to afford 4.7 g of the title compound.

$^1$H NMR (DMSO-$d_6$) selected data: δ8.68 (t, 1H), 8.15 (d, 2H), 7.93 (m, 4H), 7.56 (m, 4H), 7.33 (d, 2H); 5.51 (m, 1H), 4.10 (m, 1H), 3.45 (m, 4H), 1.31 (s, 9H); HPLC-MS (Method A): m/z=570 (M+1); $R_t$=5.95 min.

Example 104

3-{4-[4-(4-tert-Butylphenyl)-4-oxo-2-(4-trifluoromethoxyphenyl)butyryl]benzoylamino}-2R-hydroxypropionic acid

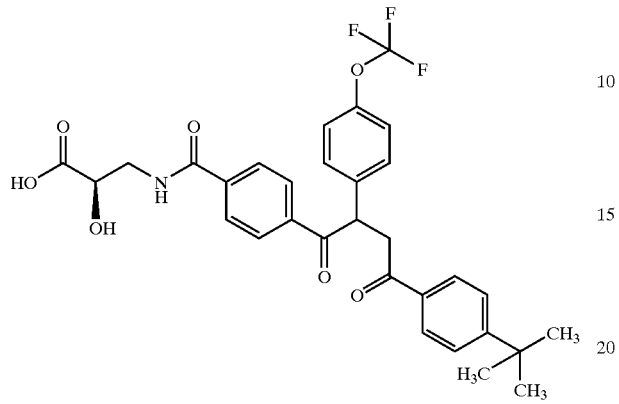

3-{4-[4-(4-tert-Butylphenyl)-4-oxo-2-(4-trifluoromethoxyphenyl)butyryl]benzoylamino}-2R-hydroxypropionic acid methyl ester 4-[4-(4-tert-Butylphenyl)-4-oxo-2-(4-trifluoromethoxyphenyl)butyryl]benzoic acid (0.64 g, 1.28 mmol) was dissolved in DMF (10 mL) and added EDAC (0.35 g, 1.8 mmol) and HOBt 0,26 9. After ½ h a solution of R-isoserine methyl ester hydrochloride (0.30 g, 1.92 mmol) and diisopropylethylamine (0.31 mL, 1.92 mmol) in DMF (6 mL) were added to the above mixture and stirred at room temperature for 16 hours. The mixture was diluted with water (30 mL) and extracted with ethyl acetate (30 mL). The aqueous phase was extracted once more with ethyl acetate (15 mL) and the combined organic phases were washed with hydrochloric acid (0.2N, 3×20 mL), an aqueous solution of 50% saturated sodium chloride (3×20 mL), dried over magnesium sulphate, filtered and evaporated to dryness to afford 0.79 g of 3-{4-[4-(4-tert-Butylphenyl)-4-oxo-2-(4-trifluoromethoxyphenyl)butyryl]benzoylamino}-2R-hydroxypropionic acid methyl ester.

HPLC-MS (Method D): m/z=600 (M+1); $R_t$=5.20 min.

3-{4-[4-(4-tert-Butylphenyl)-4-oxo-2-(4-trifluoromethoxyphenyl)butyryl]benzoylamino}-2R-hydroxypropionic acid methyl ester (0.77 g, 1.28 mmol) was dissolved in ethanol (96%, 30 mL), added sodium hydroxide (4N, 1.93 mL), and stirred for 2½ h. The reaction was concentrated in vacuo and the residue suspended in water (30 mL) and added hydrochloric acid (4N, 2 mL) to pH 1–2. After ½ h the precipitate was filtered, washed carefully with water, and dried in vacuo. The product was purified by preparative HPLC using acetonitrile (gradient from 55.5% to 97.5%), water and TFA (2.5%) as eluent to afford 0.16 g of the title compound.

$^1$H NMR (DMSO-d$_6$) selected data: δ8.66 (t, 1H), 8.15 (d, 2H), 7.93 (m, 4H), 7.56 (m, 4H), 7.33 (d, 2H); 5.53 (m, 1H), 4.07–4,20 (m, 2H), 3.48–3,63 (m, 2H), 1.31 (s, 9H); HPLC-MS (Method C): m/z=586 (M+1); $R_t$=5.42 min.

Example 105

3-{4-[4-(4-tert-Butylphenyl)-4-oxo-2-(4-trifluoromethoxyphenyl)but-2-enoyl]benzoylamino}-2R-hydroxypropionic acid

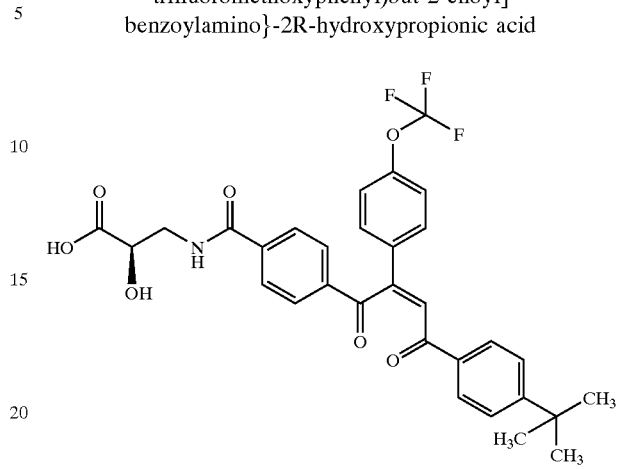

Step 3: 3-{4-[4-(4-tert-Butylphenyl)-4-oxo-2-(4-trifluoromethoxyphenyl)but-2-enoyl]benzoylamino}-2R-hydroxypropionic acid 3-{4-[4-(4-tert-Butylphenyl)-4-oxo-2-(4-trifluoromethoxyphenyl)butyryl]benzoylamino}-2R-hydroxypropionic acid (0.15 g, 0.24 mmol) from Example 104 was dissolved in THF (3 mL) and added DBU (0,13 mL, 0.86 mmol), iodine (0.11 g, 0.44 mmol) and stirred at RT. The solvent was evaporated off and the residue dissolved in DCM (25 mL) and washed with sodium sulphite (2%, 10 mL), hydrogen chloride (1 N, 10 mL), water and saturated sodium chloride (2×1:1, 10 mL), dried over magnesium sulphate, filtered and evaporated to dryness giving 0.11 g of a mixture of E and Z formation. The residue was dissolved in toluene (5 mL) and added concentrated hydrogen chloride and refluxed for 1 h at 130° C. in an oil bath. The reaction was cooled and evaporated to dryness and this was repeated twice with DCM (2×5 mL). The product was purified by preparative HPLC using acetonitrile (57.5% to 97.5%), water and TFA (2.5%) as eluent and evaporated to afford 0.04 g of the title compound.

$^1$H NMR (DMSO-d$_6$) selected data: δ8.63 (t, 1H), 8.05 (m, 3H), 7.95 (d, 2H), 7.91 (d, 2H), 7.80 (d, 2H); 7.58 (d, 2H), 7.48 (d, 2H), 5.48 (broad, 1H), 4,15 (m, 1H), 3.54 (m, 1H) 1.31 (s, 9H); HPLC-MS (Method C): m/z=585 (M+1); $R_t$=5.78 min.

General Procedure (H)

General procedure (H) for separation of eantiomers of compounds of the general formula (I$_1$):

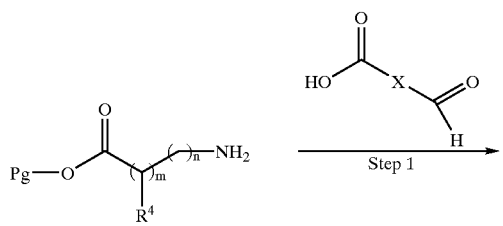

-continued

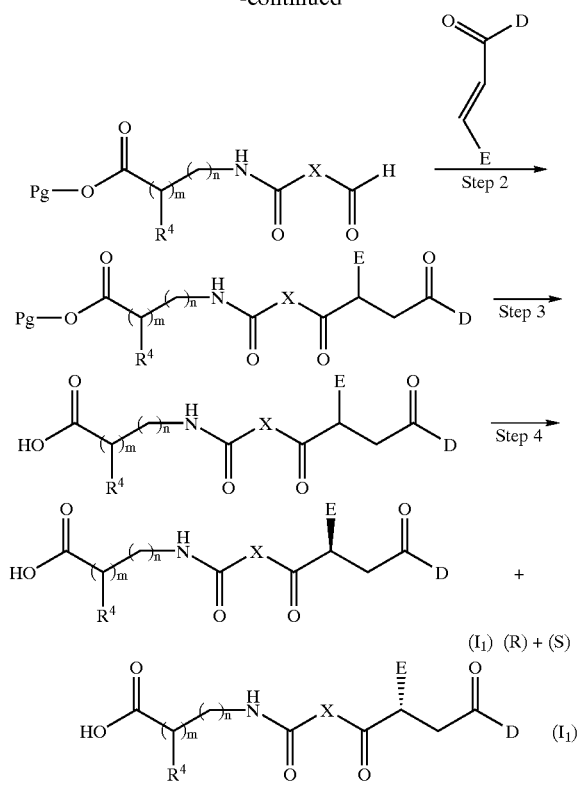

Example 106

General Procedure (H)

The compound of example 4 was also prepared and the enantiomers seperated according to general procedure (H) as illustrated below 3-{4-[4-(3,5-Bis-trifluoromethylphenyl)-2-(4-cyclohexylphenyl)-4-oxo-butyryl]benzoylamino}propionic acid

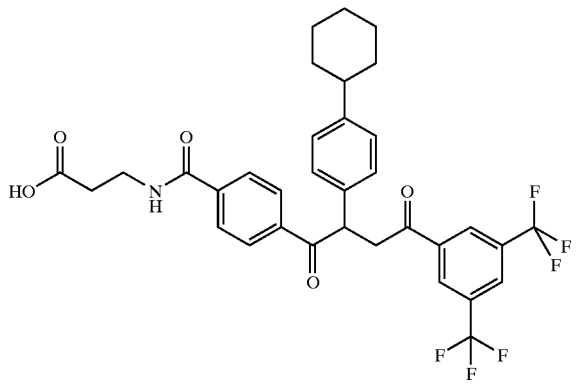

Step 1: 3-(4-Formylbenzoylamino)propionic acid methyl ester 3-(4-Formylbenzoylamino)propionic methyl ester was synthesized according to the procedure described in WO 00/69810

Step 2: 3-{4-[4-(3,5-Bis-trifluoromethylphenyl)-2-(4-cyclohexylphenyl)-4-oxo-butyryl]benzoylamino}propionic acid methyl ester To a mixture of 1-(3,5-Bis-trifluoromethylphenyl)-3-(4-cyclohexylphenyl)propenone (6.12 g, 14.35 mmol) in absolute ethanol (99%, 25 mL) under nitrogen, 3,4-dimethyl-5-(2-hydroxyethyl)thiazolium iodide (819 mg, 2.87 mmol) and triethylamine (1.60 mL, 11.5 mmol) were added and the mixture was heated to reflux. 3-(4-Formylbenzoylamino) propionic acid methyl ester (4.39 g, 18.7 mmol) was dissolved in absolute ethanol (99%, 15 mL) and was added dropwise to the refluxing mixture over 2 hours. The reaction mixture was refluxed for 30 min, allowed to cool to room temperature. 3-{4-[4-(3,5-Bis-trifluoromethyl-phenyl)-2-(4-cyclohexyl-phenyl)-4-oxo-butyryl]-benzoylamino}-propionic acid methyl ester could be isolated by filtration followed by washing with ethanol and drying in vacuo. Yield: 6.9 g (73%).

Step 3: 3-{4-[4-(3,5-Bis-trifluoromethylphenyl)-2-(4-cyclohexylphenyl)-4-oxobutyryl]-benzoylamino}propionic acid.

3-{4-[4-(3,5-Bis-trifluoromethylphenyl)-2-(4-cyclohexylphenyl)-4-oxobutyryl]benzoylamino}propionic acid methyl ester (6.20 g, 9.38 mmol) was dissolved in THF (75 mL), HCl (6 N, 25 mL) was added and the mixture was heated to reflux, after 2 hours the heat was turned of and the mixture was stirred at room temperature for 16 hours. The mixture was evaporated to dryness to give the title compound. Yield: quantitative.

$^1$H NMR (DMSO-$d_6$): δ8.72 (t, 1H), 8.60(s, 2H), 8.42 (s, 1H), 8.14 (d, 2H), 7.90 (d, 2H); 7.34 (d, 2H), 7.17 (d, 2H), 5.43 (dd, 1H), 4.29 (dd, 1H), 3.64 (dd, 1H and t 2H), 3.42 (t, 2H), 2.42 (m, 1H), 1.78–1.64 (m, 5H), 1.38–1.25 (m, 5H); HPLC-MS (Method D): m/z=648 (M+1); $R_t$=5.58 min.

Step 4: Resolution by chiral HPLC

3-{4-[4-(3,5-Bis-trifluoromethylphenyl)-2-(4-cyclohexylphenyl)-4-oxobutyryl]benzoylamino}propionic acid (500 mg, 0.77 mmol) was dissolved isopropanol:heptane 60:40 (20 mL). Trifluoro acetic acid (0.02 mL) was added. The racemic mixture was separated on an AD column 50×500 mm (from DAICEL), flow 100 mL/min. Eluted with isopropanol:heptane mixture 6:4 with 0.01% trifluoroacetic acid. Two fractions containing compound in eluent were collected. Each fraction was kept separate but otherwise treated identically. The volume of each fraction was reduced in vacuo to about ⅛ of iFnitial volume, separated between dichloromethane (1 L) and aqeous NaHCO$_3$ (10%, 500 mL). The organic phase was dried (NaSO$_4$) and evaporated to a white crystals. The crystals were reluxed in acetonitrile, followed by subsequent cooling to room temperature. The pure enantiomers could be isolated by filtration followed by drying in vacuo.

Example 107

3-{4-[4-(3,5-Bis-trifluoromethylphenyl)-2-(4-cyclohexylphenyl)-4-oxo-butyryl]benzoylamino}propionic acid Fastest eluting enatiomer: Chiralpak AD, 4.6×250 mm Heptane, isopropanol, trifluoroacetic acid 60:40:0.1, 0.6 mL/min flow. Retentiontime=8.2 min.

Example 108

3-{4-[4-(3,5-Bis-trifluoromethylphenyl)-2-(4-cyclohexylphenyl)-4-oxo-butyryl]benzoylamino}propionic acid Slowest eluting enantiomer: Chiralpak AD, 4.6×250 mm Heptane, isopananol, trifluoroacetic acid 60:40:0.1, 0.6 mL/min flow. Retention time=12.1 min.

Further preferred compounds of the invention include:
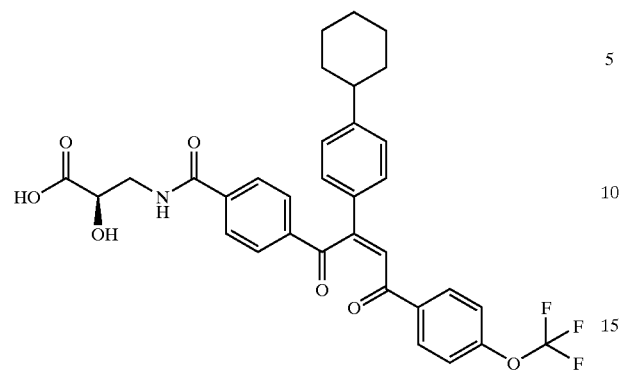
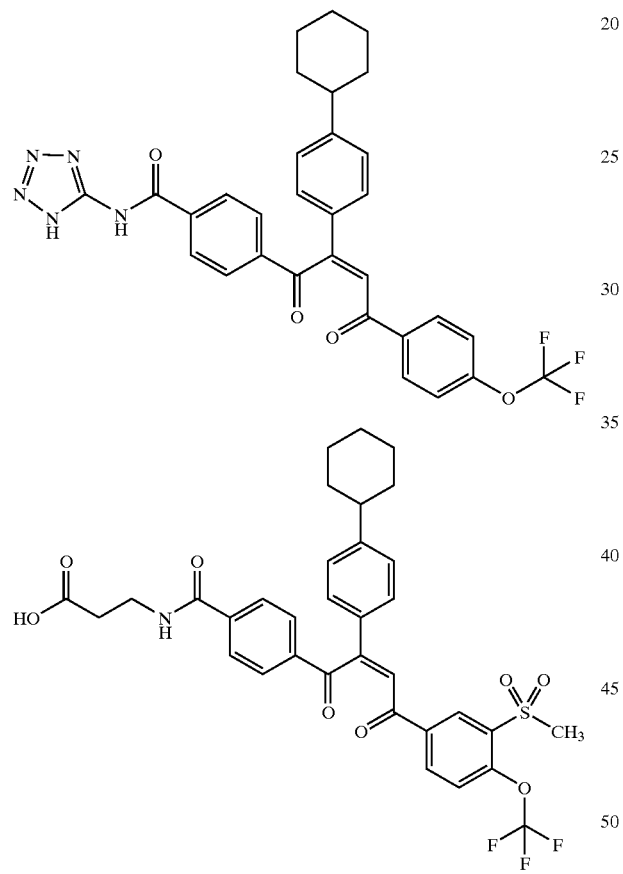
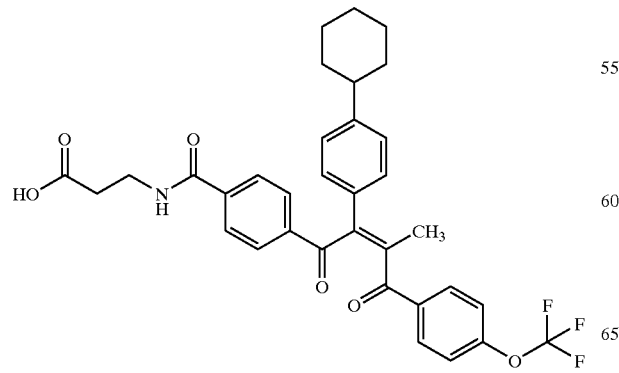
-continued
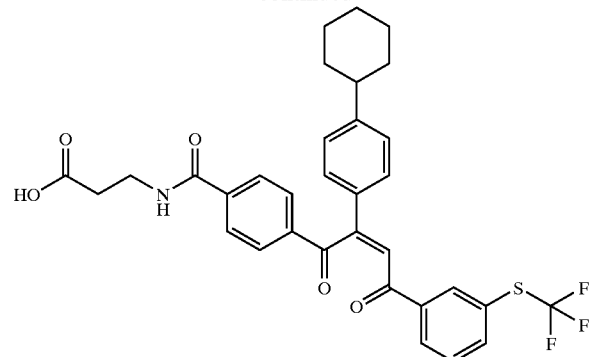
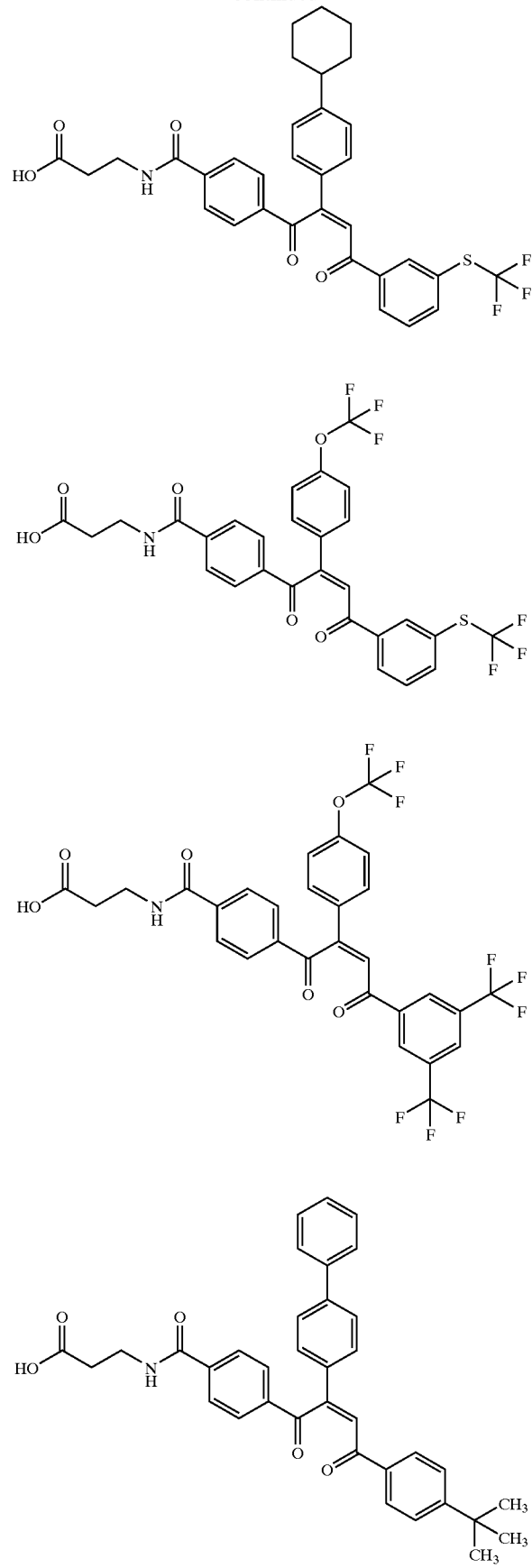

117
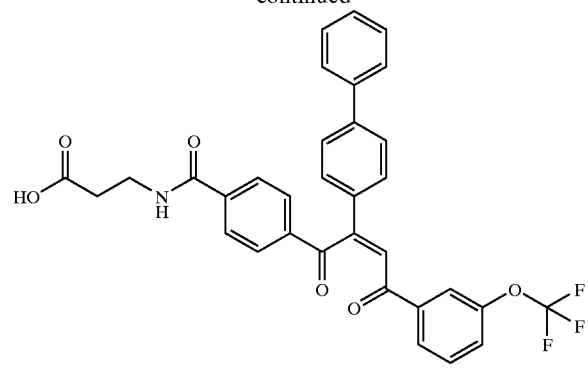
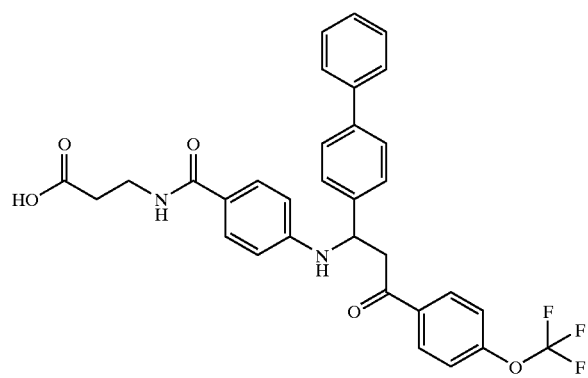
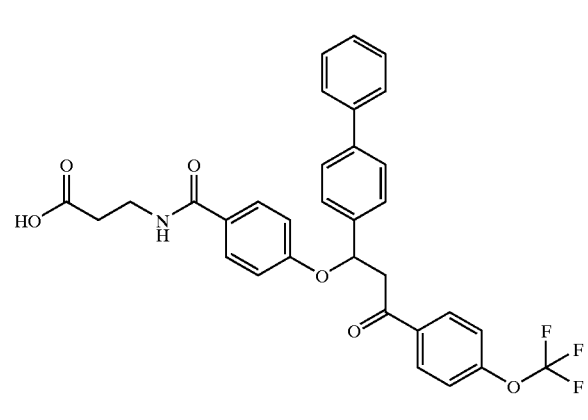
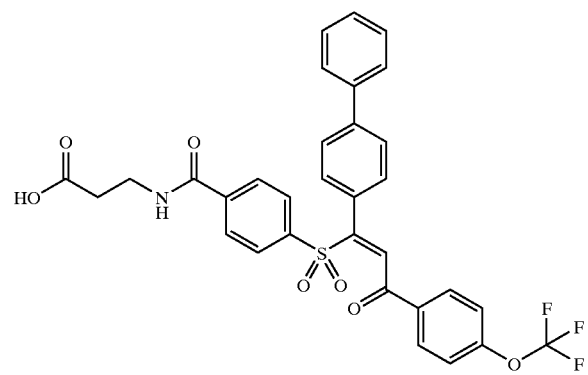
118
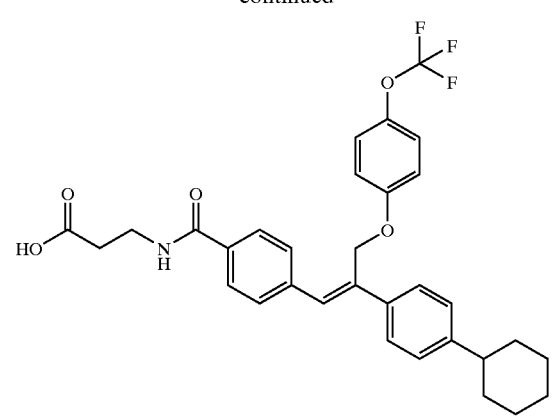
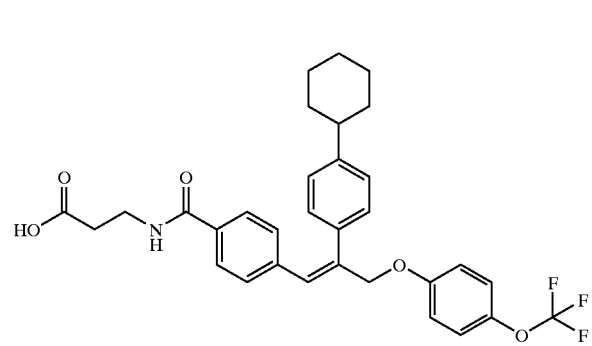
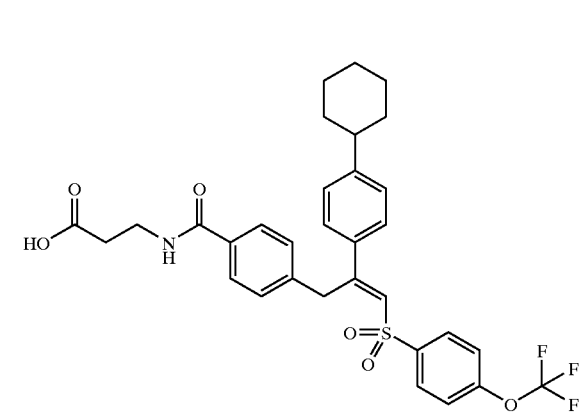
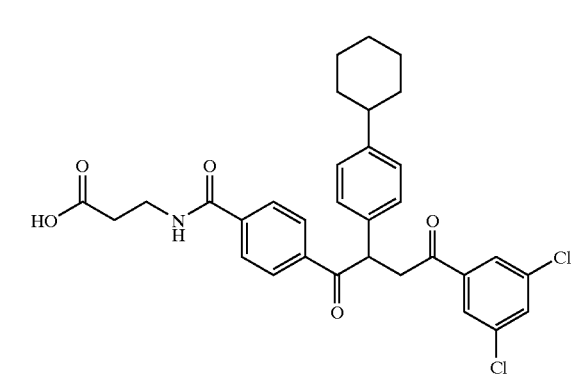

119
-continued
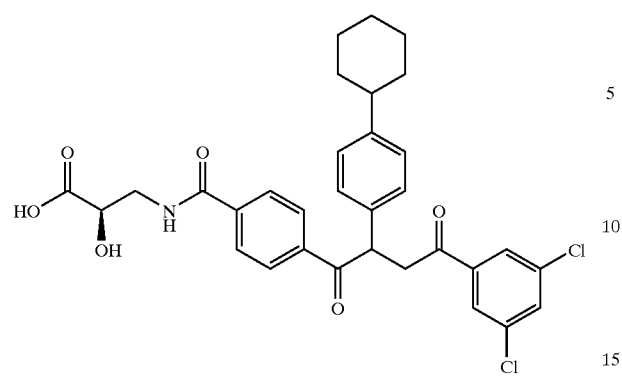
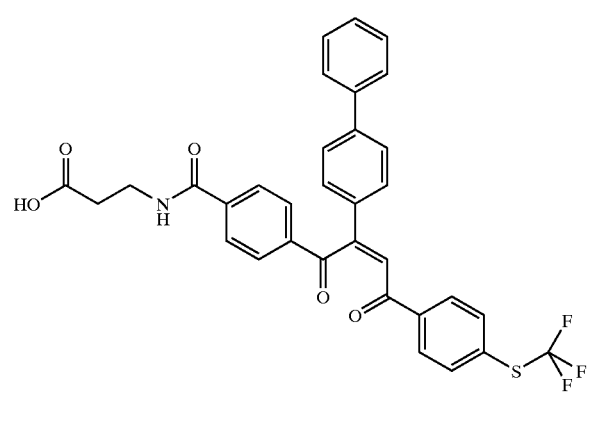
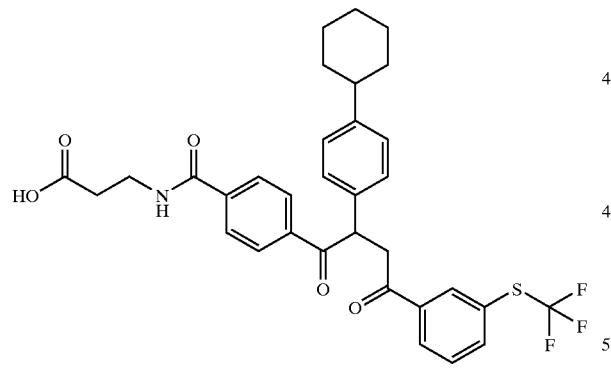
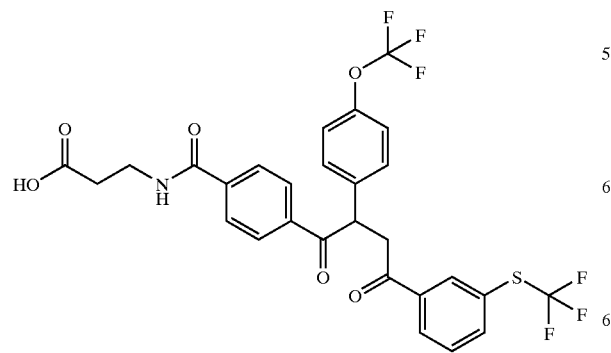
120
-continued
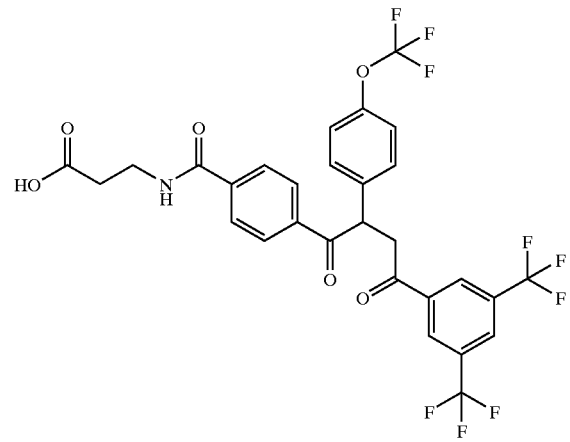
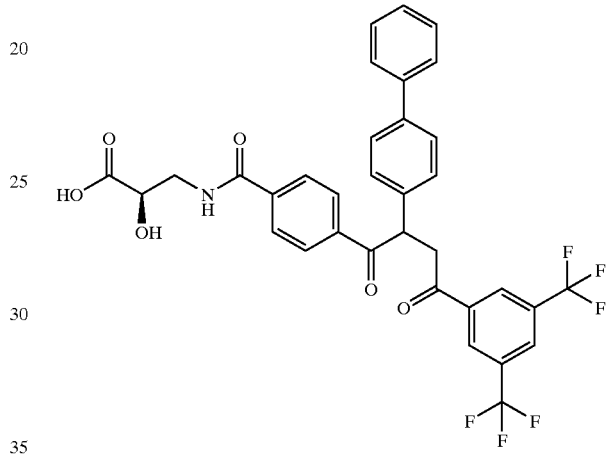
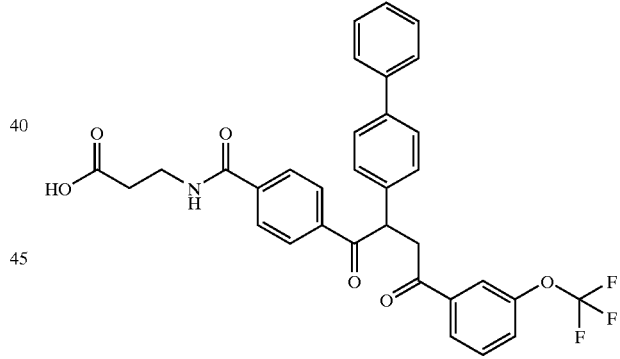
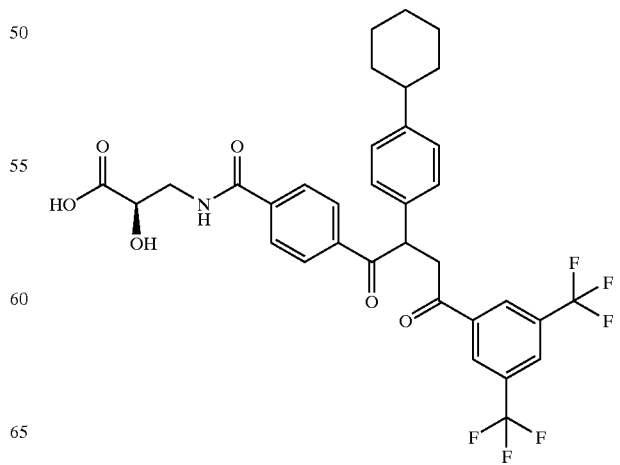

-continued
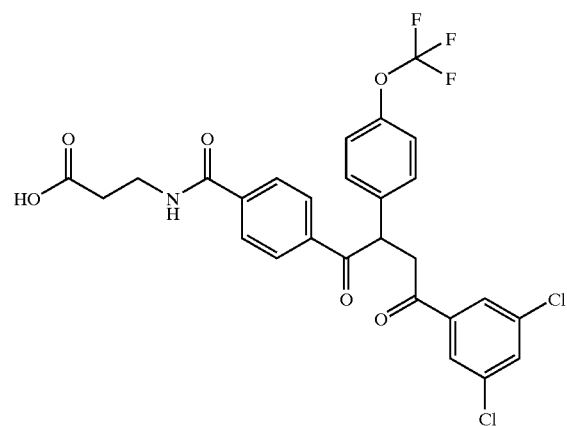
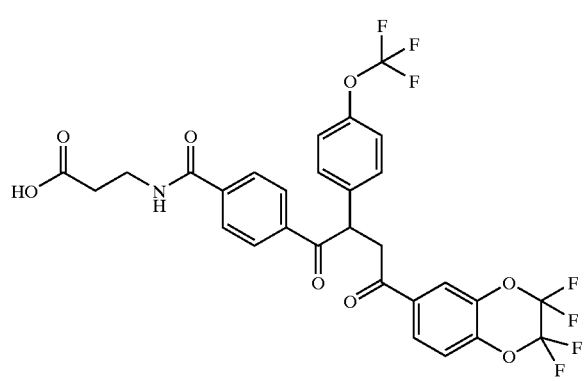
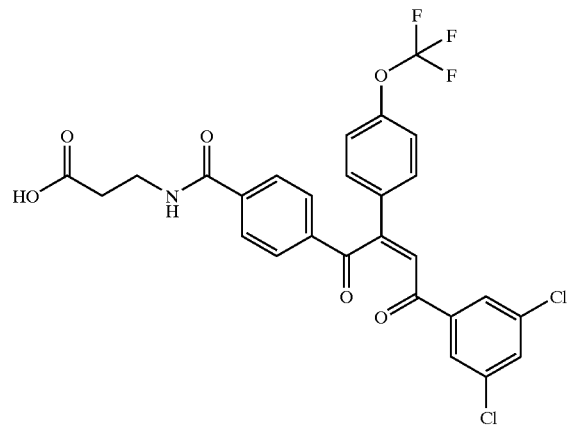
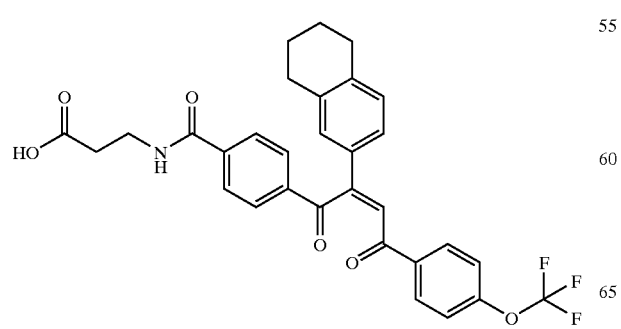
-continued
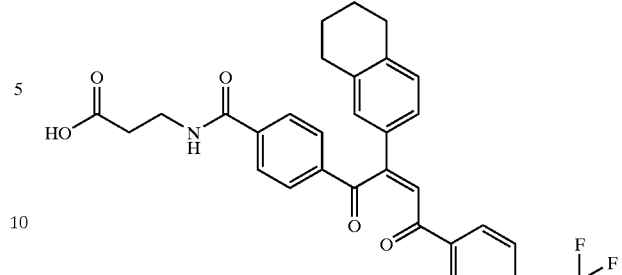
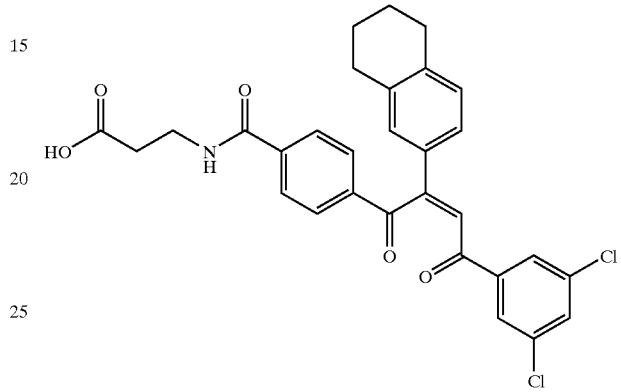
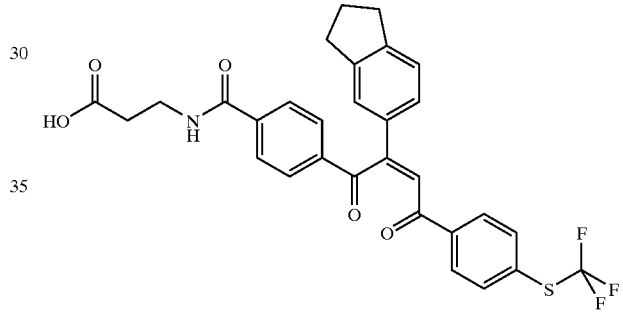
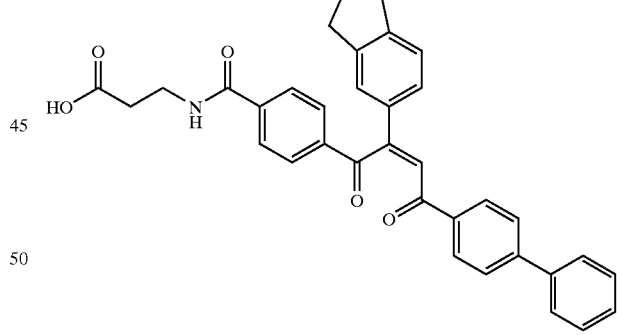
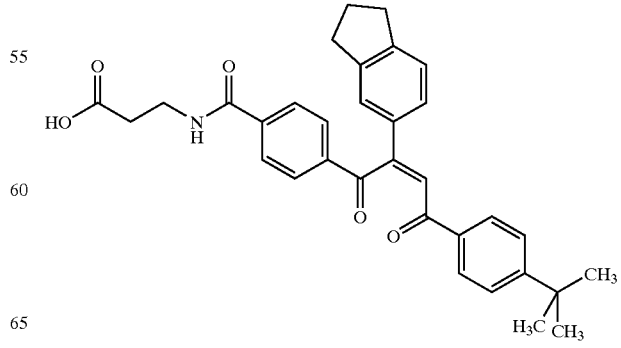

123
-continued
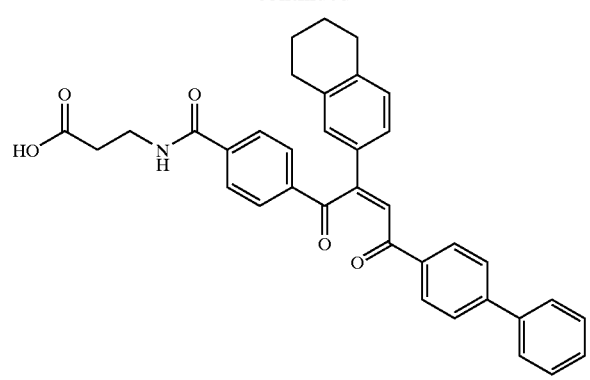
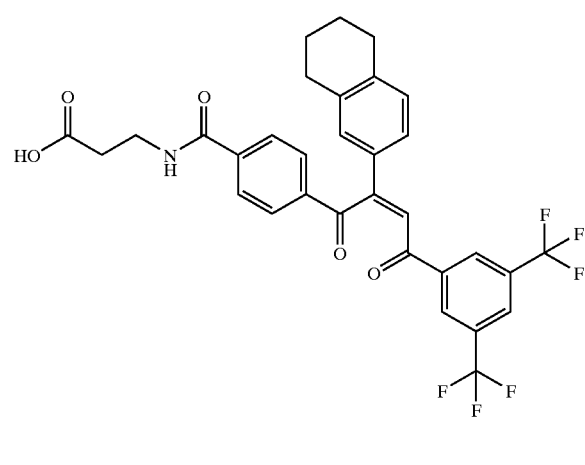
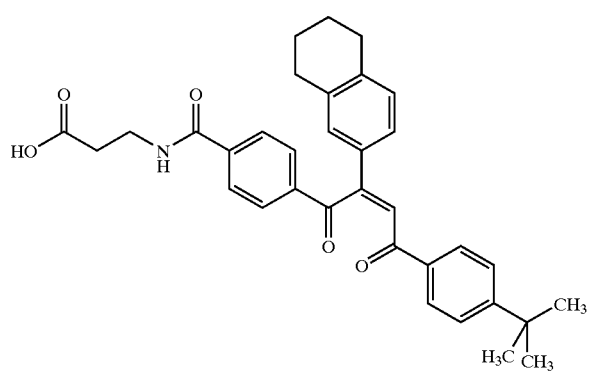
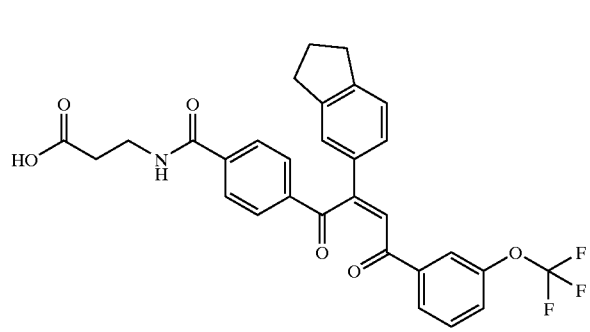
124
-continued
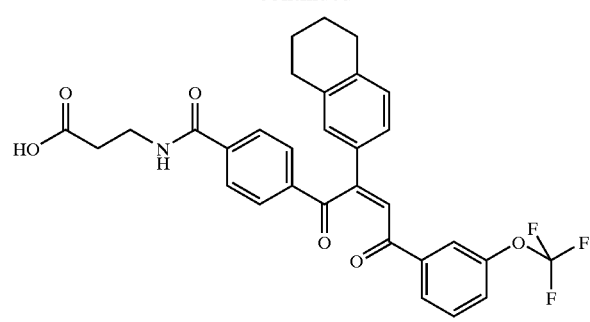
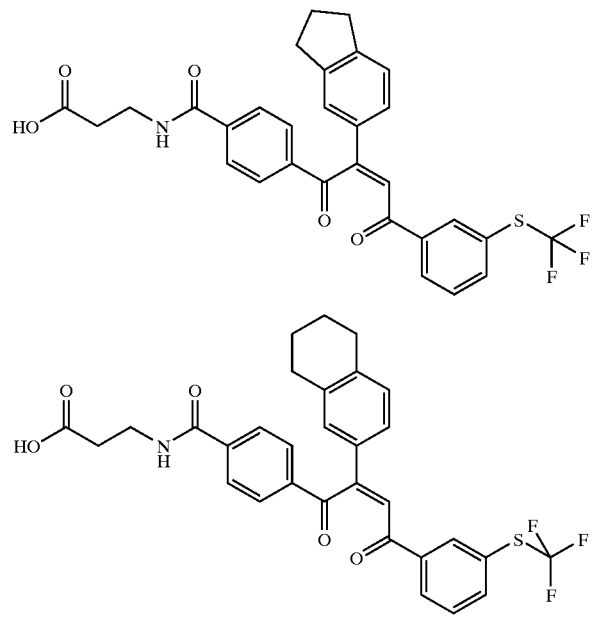
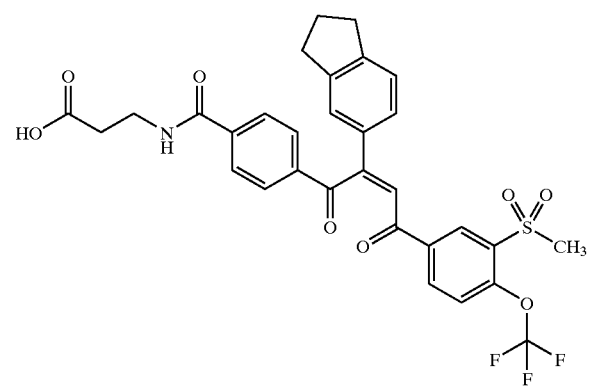
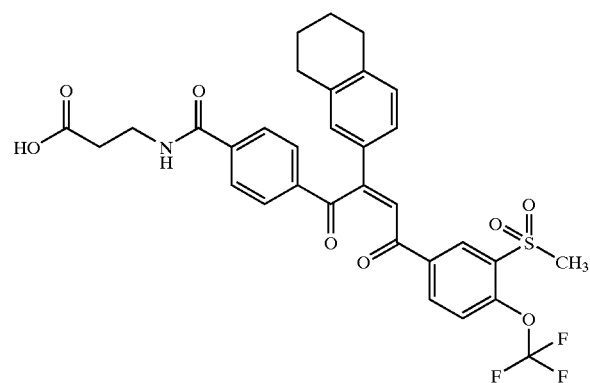

125
-continued
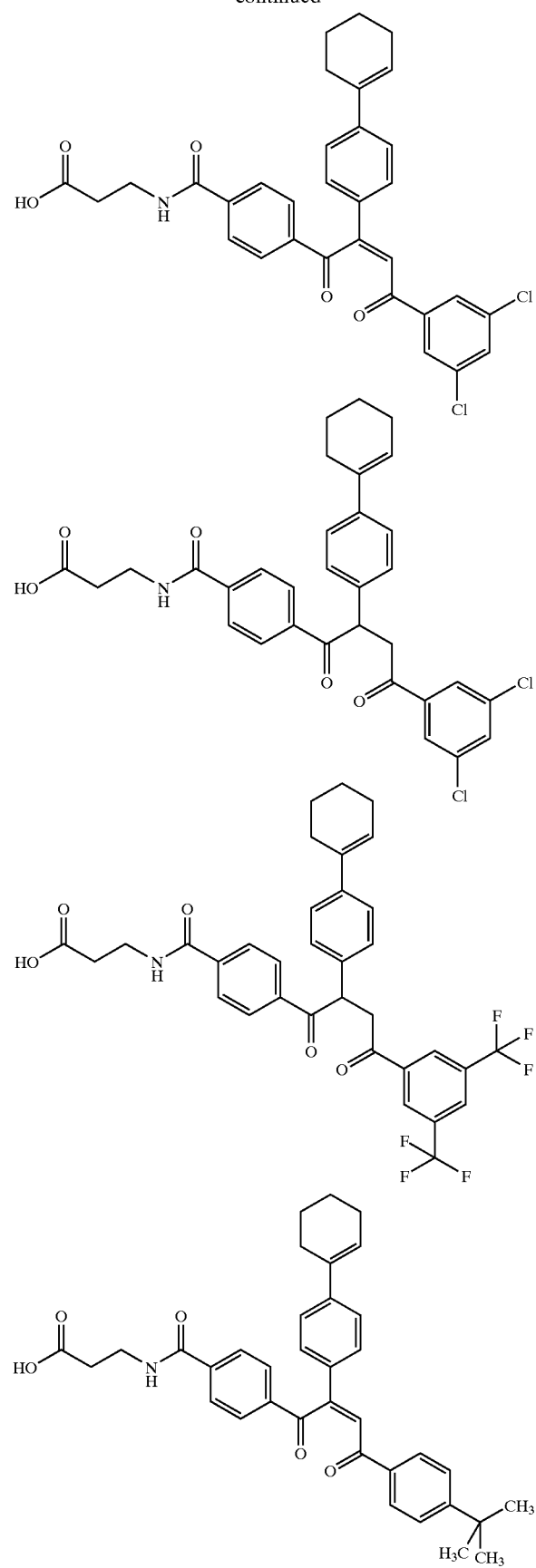
126
-continued
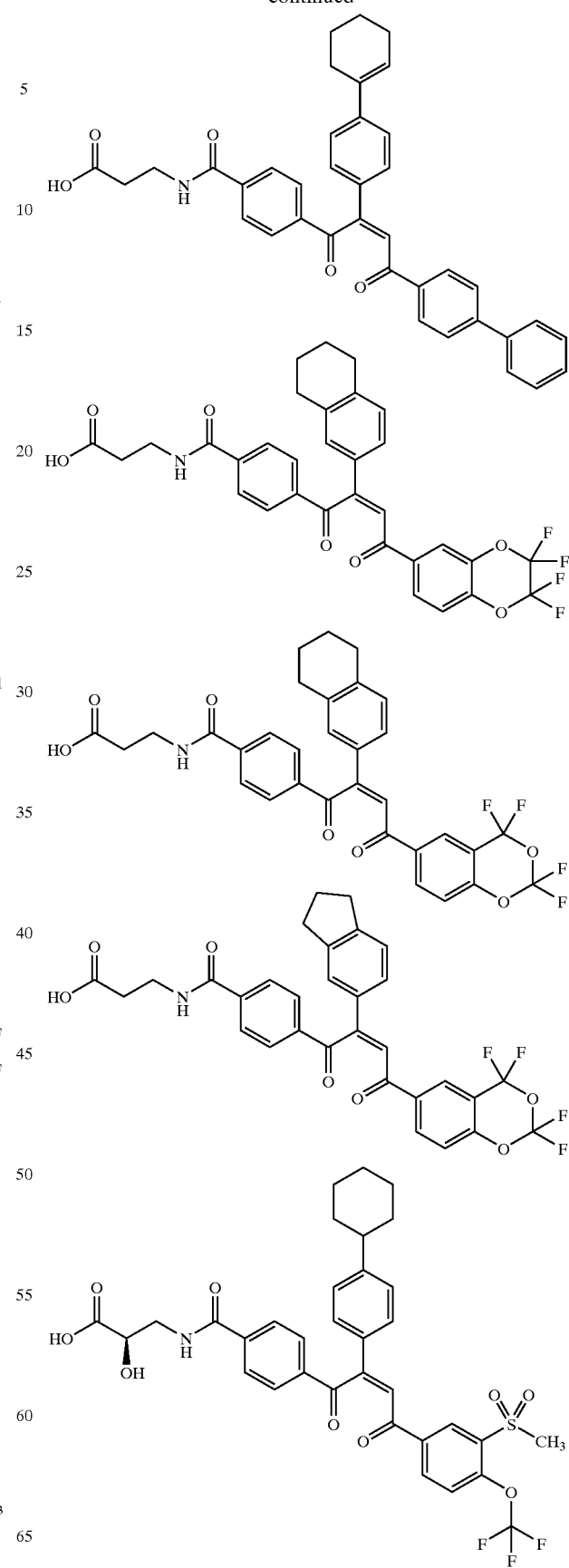

127
-continued
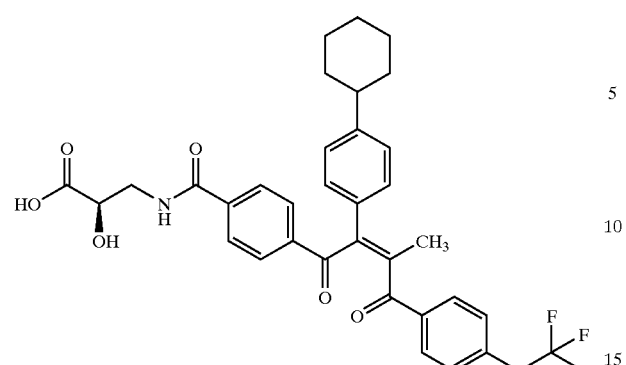
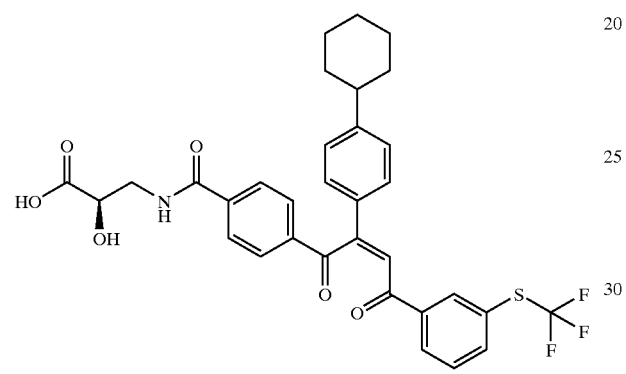
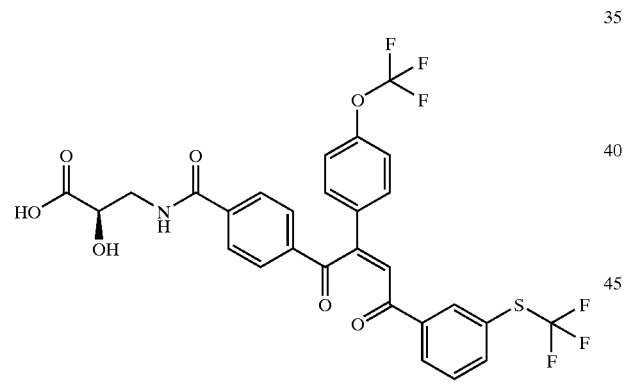
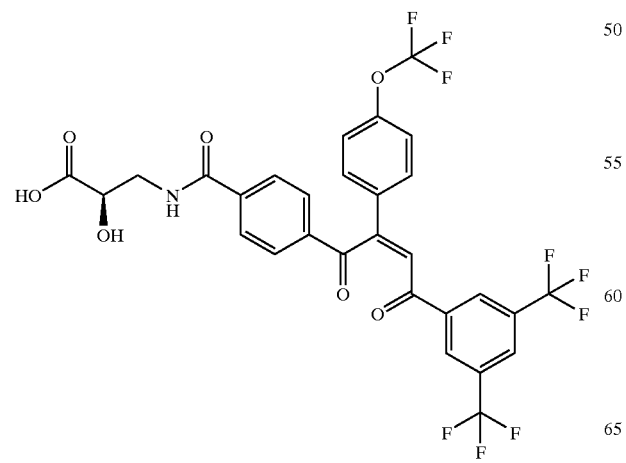
128
-continued
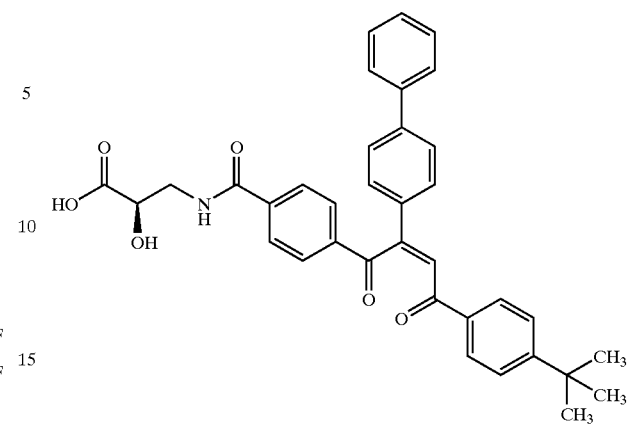
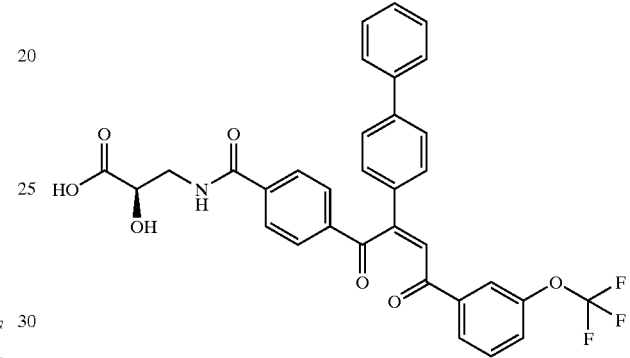
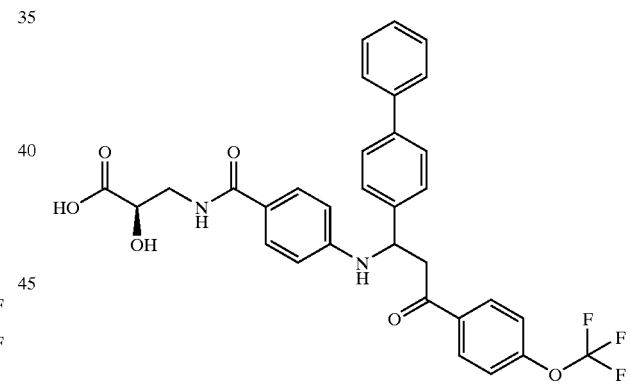
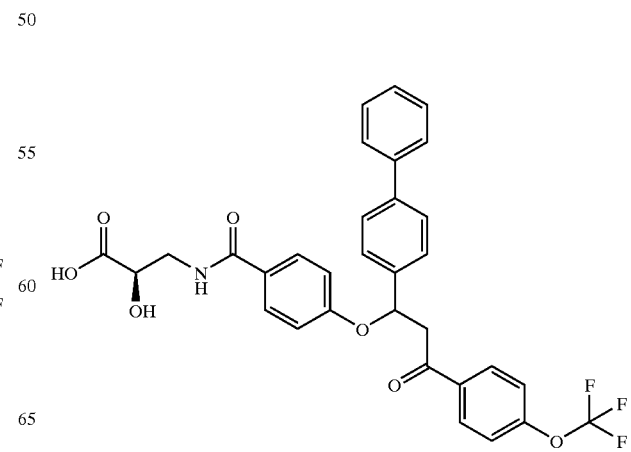

129
-continued
130
-continued
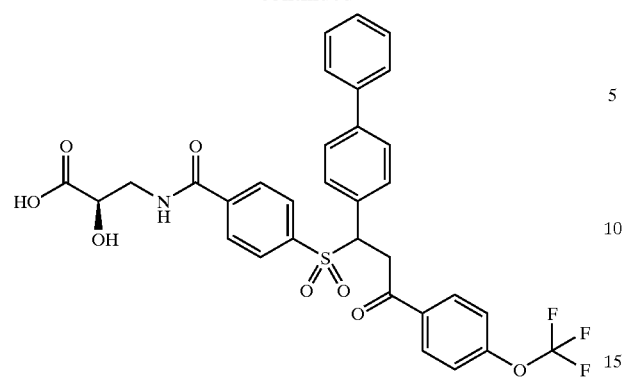
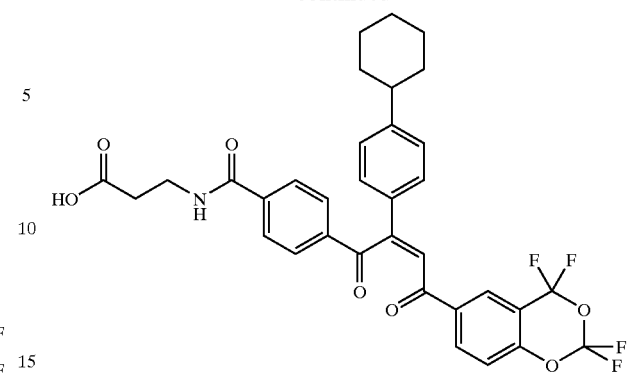
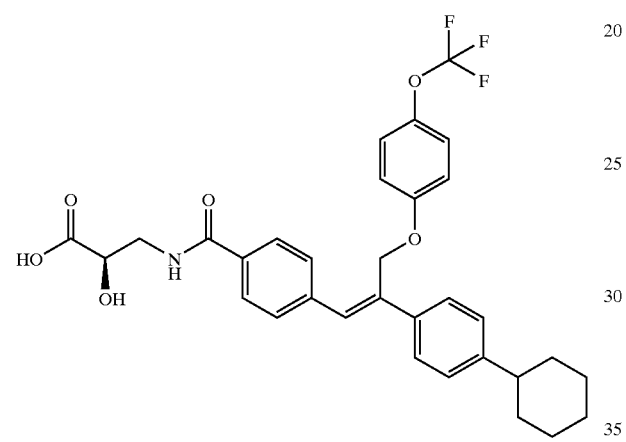
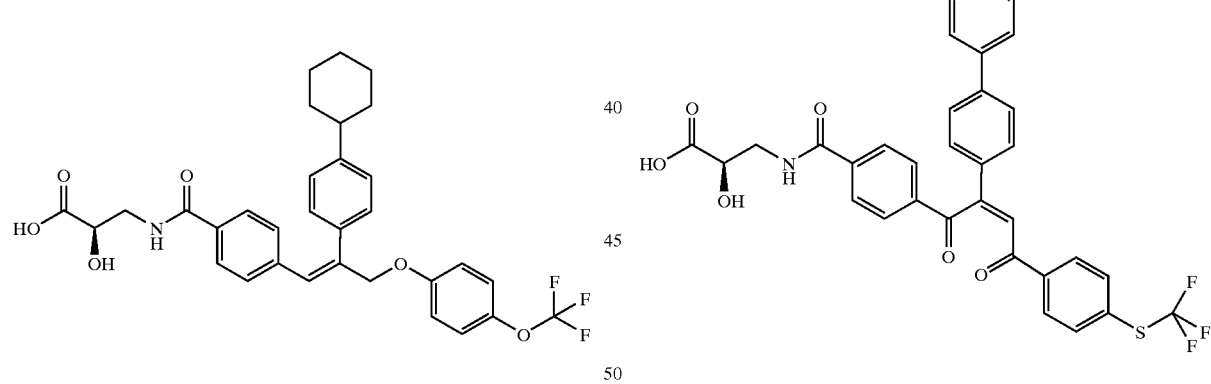
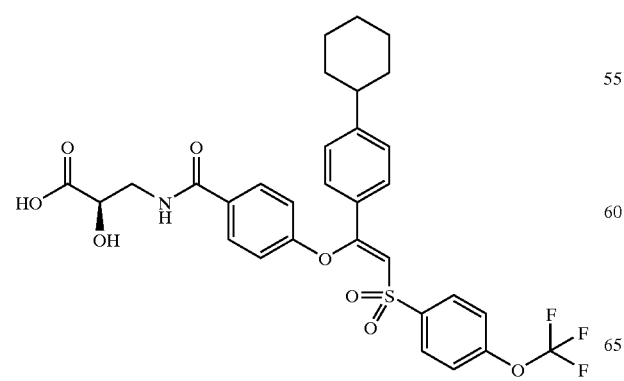

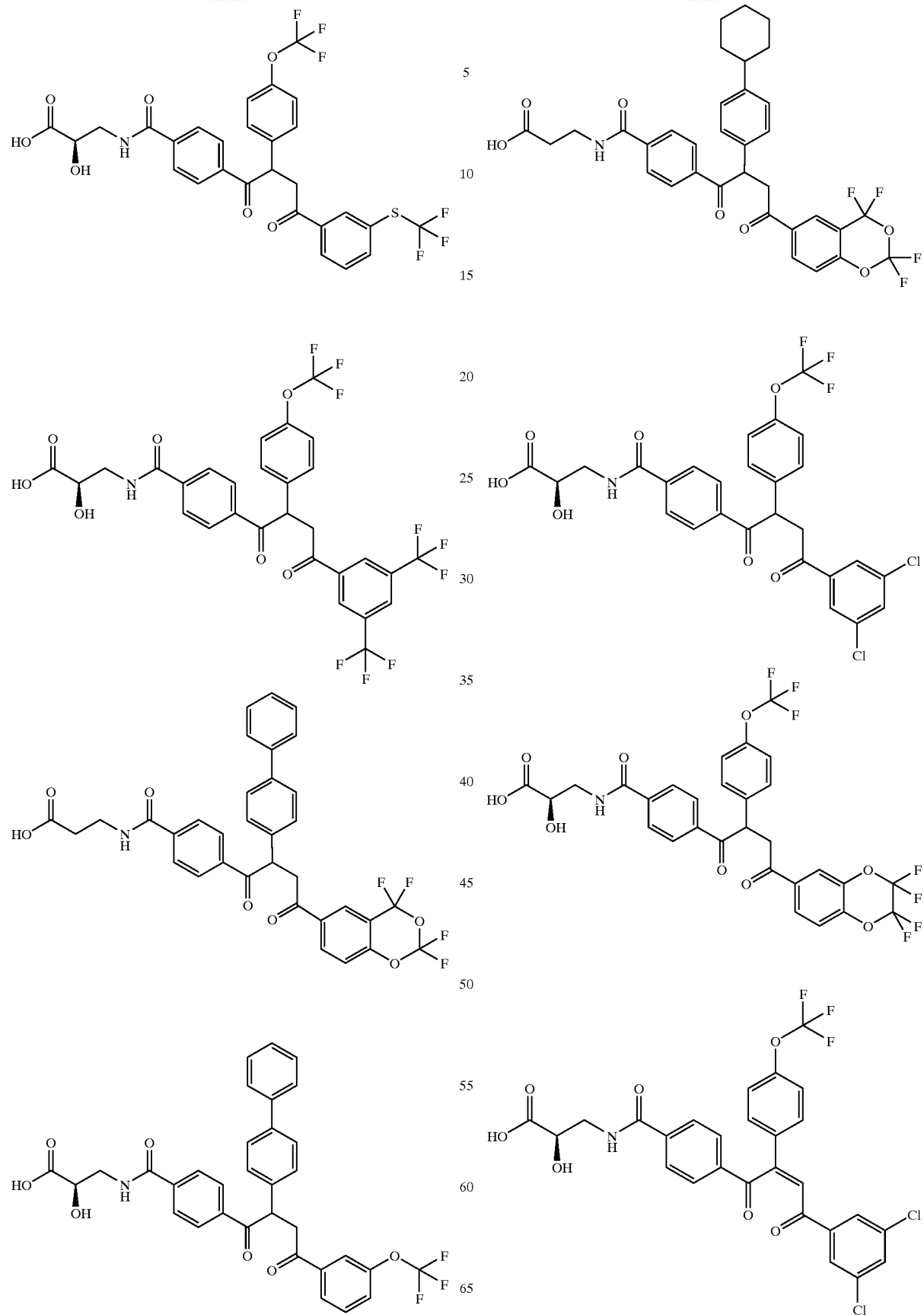

133
-continued
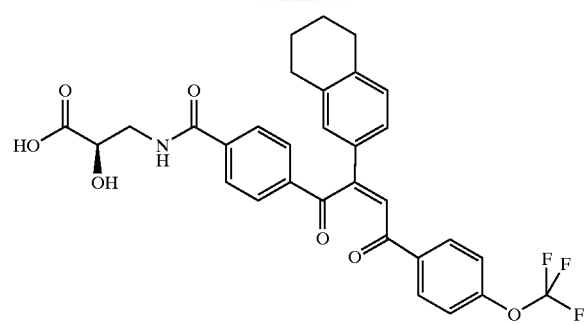
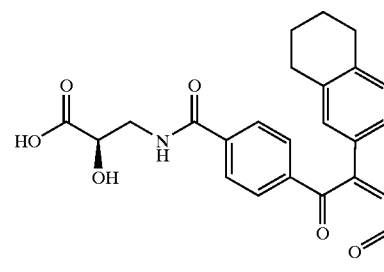
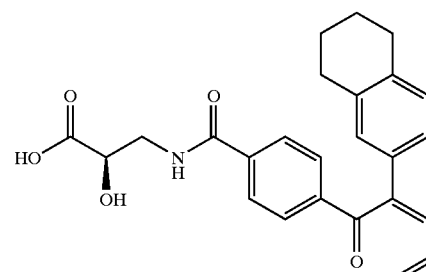
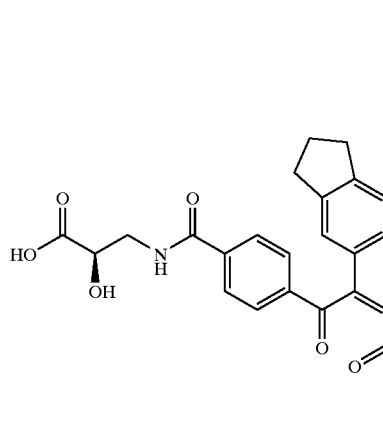
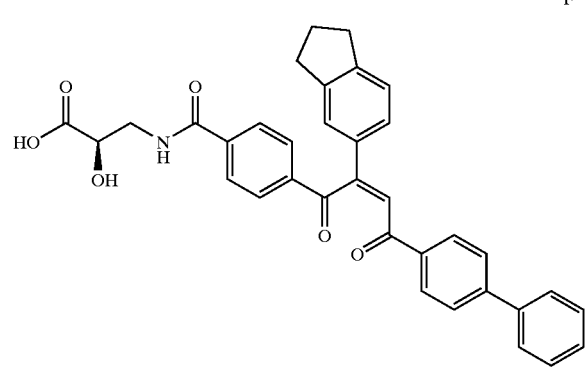
134
-continued
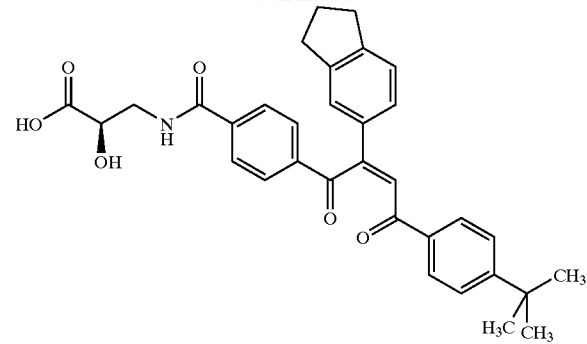
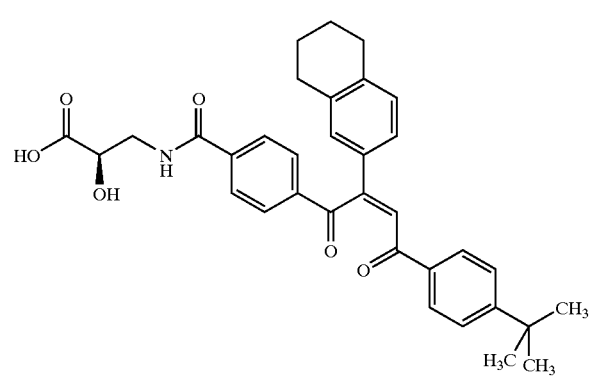

135
-continued
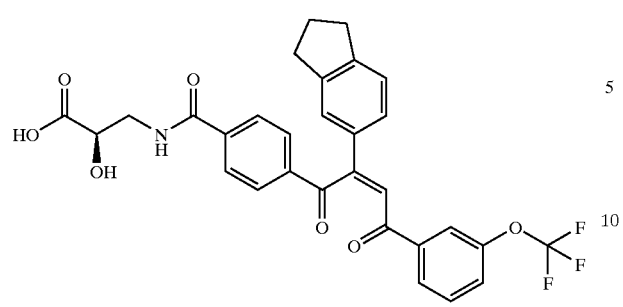
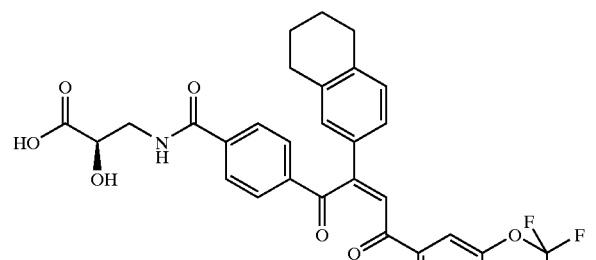
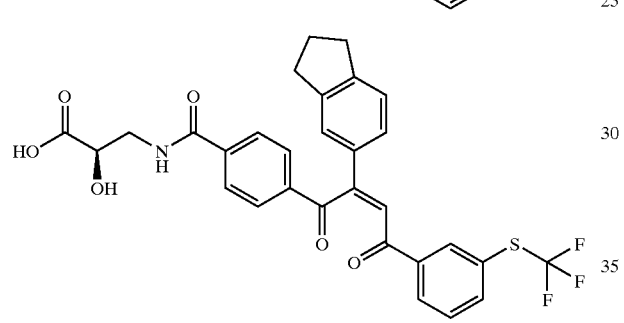
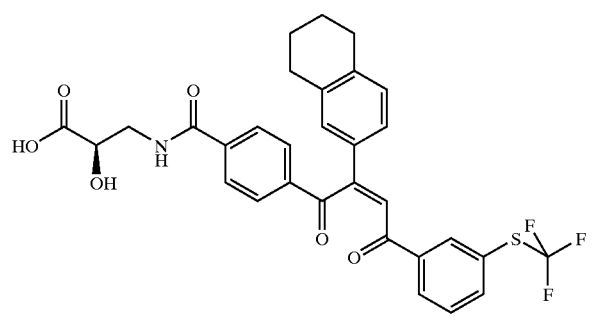
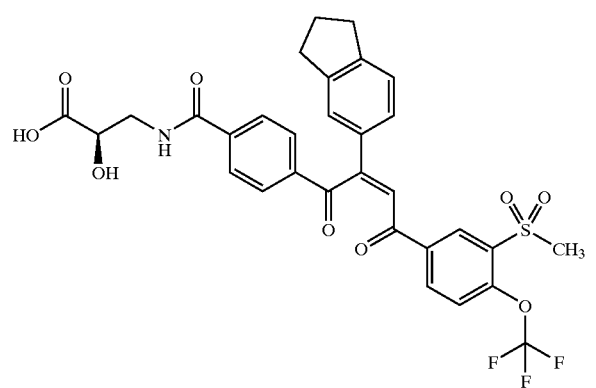
136
-continued
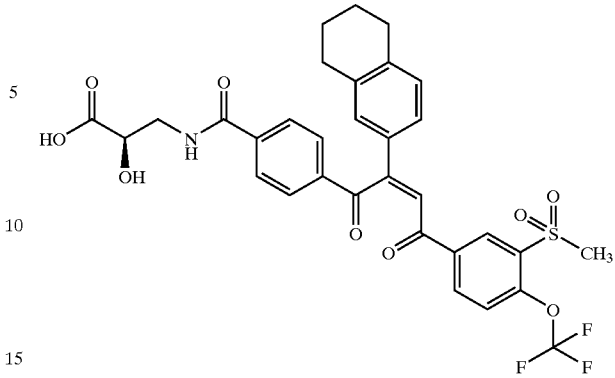
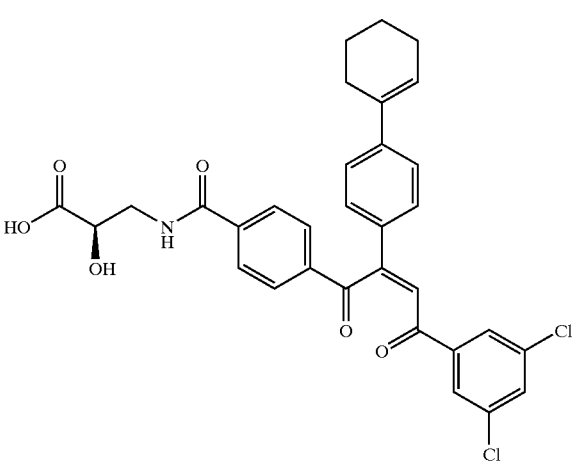
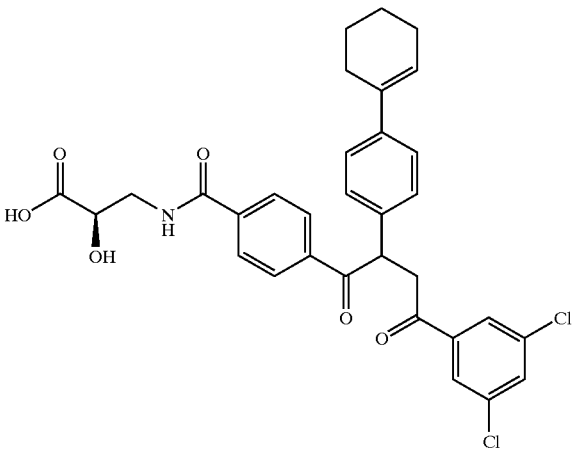
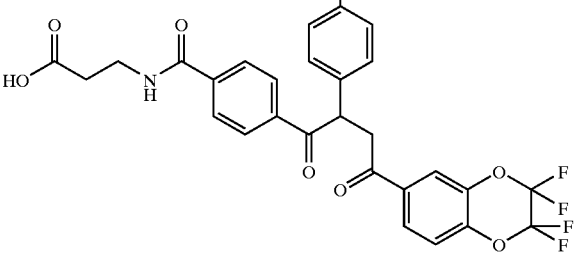

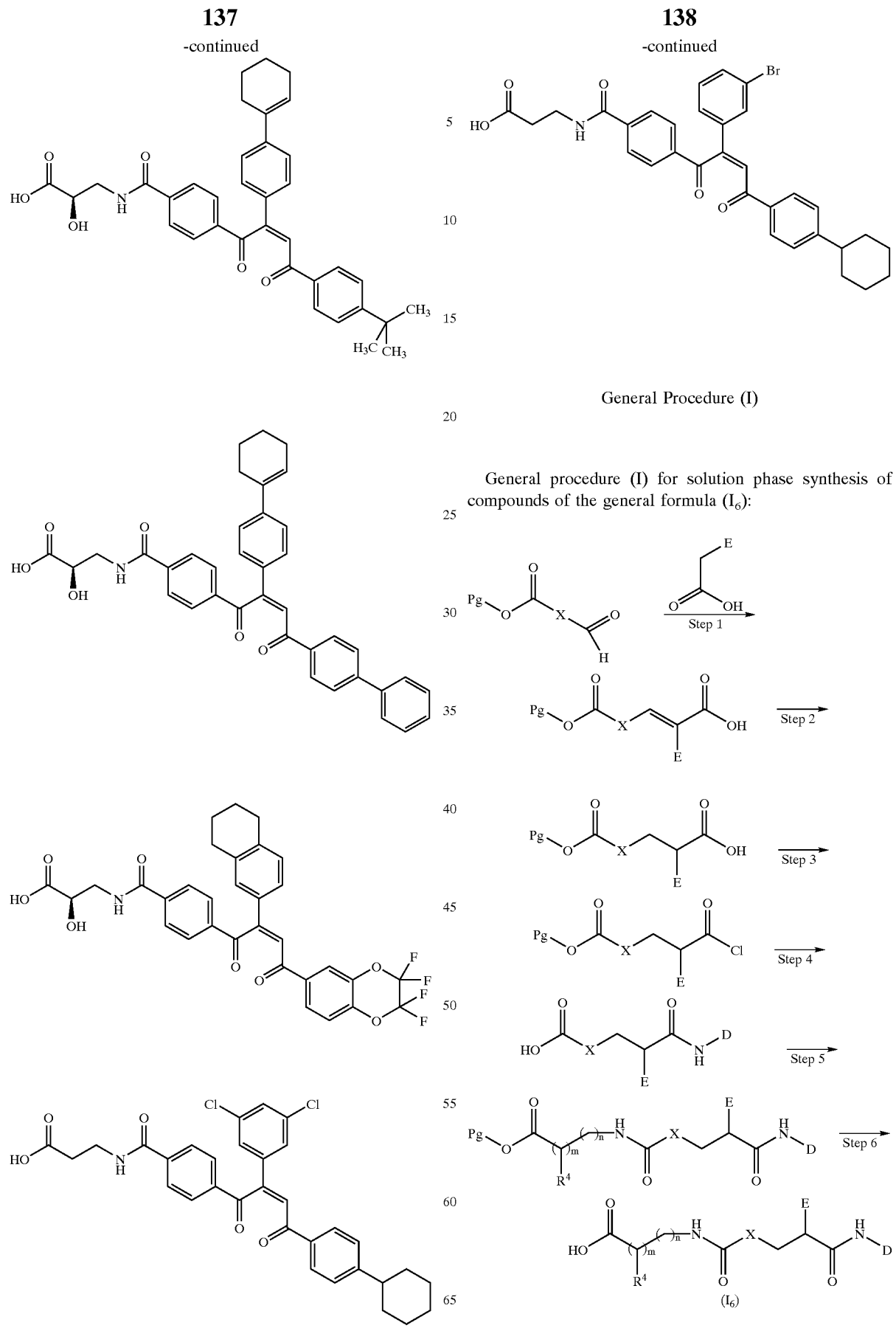
General Procedure (I)
General procedure (I) for solution phase synthesis of compounds of the general formula ($I_6$):

wherein Pg, E, X, D and R[4] are as defined above. The Pg added in step 5 may be different from the Pg of the previous steps.

Example 109

General Procedure (I)

3-{4-[2-(4-Cyclohexylphenyl)-2-(4-trifluoromethoxyphenylcarbamoyl)ethyl]-benzoylamino}propionic acid

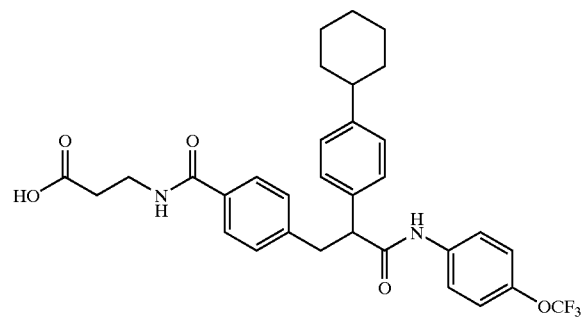

Step 1: E,Z-4-[2-Carboxy-2-(4-cyclohexylphenyl)vinyl] benzoic acid methyl ester

A mixture of methyl 4-formylbenzoate (5.75 g; 35 mmol), 4-cyclohexylphenylacetic acid (10.93 g, 50.05 mmol) (Chem. Ber., 76, (1943), 308), acetic anhydride (17.54 mL, 185.5 mmol) and triethylamine (4.87 mL; 35 mmol) was stirred and heated at 155° C. for 15 minutes. The mixture was cooled to 90° C. and water (18 mL) was added drop wise at such a rate that the temperature was maintained between 90° C. and 100° C. The mixture was cooled to room temperature and a 50% aqueous acetic acid solution (25 mL) was added. The precipitate was filtered off, washed with 25% aqueous acetic acid (100 mL) and finally water (125 mL). The crude product was dried and recrystallised from heptane to afford 10.89 g (85%) of a E/Z mixture of 4-[2-carboxy-2-(4-cyclohexylphenyl)vinyl]benzoic acid methyl ester.

$^1$H NMR (DMSO-$d_6$): δ12.88 (br s, 1H), 8.98–7.05 (m, 9H), 3.87 and 3.83 (s, 3H) 2.54 (m, 1H), 1.68–1.78 (m, 5H), 1.48–1.20 (m, 5H).

Step 2: 4-[2-Carboxy-2-(4-cyclohexylphenyl)ethyl]-benzoic acid methyl ester

A mixture of E,Z-4-[2-carboxy-2-(4-cyclohexylphenyl) vinyl]benzoic acid methyl ester (10.85 g, 28.77 mmol) and palladium on activated carbon (1.085 g, 10%) in 100 mL of methanol was hydrogenated at 56 psi for 7 hours. The catalyst was filtered off, and the filtrate was evaporated to dryness to afford 5.73 (53%) of 4-[2-carboxy-2-(4-cyclohexylphenyl)ethyl]benzoic acid methyl ester as a solid.

$^1$H NMR (CDCl$_3$): δ7.90 (d, 2H), 7.23–7.13 (m, 6H), 3.88 (s, 3H), 3.84 (t, 1H), 2.43 (dd, 1H), 3.07 (dd, 1H), 2.48 (m, 1H), 1.90–1.70 (m, 5H), 1.45–1.18 (m, 5H). HPLC-MS (Method D): m/z=367 (M+1); $R_t$=5.03 min.

Step 3: 4-[2-Chlorocarbonyl-2-(4-cyclohexylphenyl)ethyl] benzoic acid methyl ester A solution of 4-[2-carboxy-2-(4-cyclohexylphenyl)ethyl]-benzoic acid methyl ester (5.58 g, 15.2 mmol) in toluene was stirred and thionyl chloride (2.79 mL, 38.20 mmol) was added. The mixture was stirred and refluxed for 15 minutes and the toluene removed under reduced pressure. The residue was stripped twice with toluene to afford 5.75 g (98%) of 4-[2-chlorocarbonyl-2-(4-cyclohexylphenyl)ethyl] benzoic acid methyl ester.

$^1$H NMR (CDCl$_3$): δ7.79 (d, 2H), 7.40–7.08 (m, 6H), 4.11 (m, 1H), 3.85 (s, 3H), 3.30 (m, 1H), 3.03 (m, 1H), 2.45 (m, 1H), 1.83–1.65 (m, 5H), 1.42–1.15 (m, 5H).

Step 4: 4-[2-(4-Cyclohexylphenyl)-2-(4-trifluoromethoxyphenylcarbamoyl)ethyl]benzoic acid A solution of 4-trifluoromethoxyaniline (0.575 g, 3.25 mmol) in dry toluene (50 mL) was stirred under a nitrogen atmosphere. Triethylamine (0.448 mL, 3.25 mmol) was added followed by a solution of 4-[2-chlorocarbonyl-2-(4-cyclohexylphenyl)ethyl]-benzoic acid methyl ester (1.25 g, 3.25 mmol) in dry toluene (25 mL). The mixture was refluxed for 1 hour, cooled to room temperature, washed with water (2×100 mL) and a saturated sodium chloride solution (2×100 mL). The organic phase was collect evaporated to dryness under reduced pressure to afford 1.43 g of crude intermediary ester compound. The ester was dissolved in a mixture of methanol (12.5 mL) and THF (5 mL) and a 4M aqueous sodium hydroxide (2.43 mL, 9.75 mmol) was added. The mixture was stirred for 16 hours at room temperature. The mixture was filtered and the filtrate was made acidic (pH=2) with concentrated hydrochloric acid. The mixture was stirred for one hour and the precipitate was filtered off, washed with water and dried to afford 1.32 g (80%) of 4-[2-(4-cyclohexylphenyl)-2-(4-trifluoromethoxyphenylcarbamoyl)ethyl]benzoic acid as a solid.

$^1$H NMR (DMSO-$d_6$): δ10.38 (s, 1H), 7.78 (d, 2H), 7.65 (d, 2H); 7.28 (m, 2H), 7.30 (d, 2H), 7.18 (d, 2H), 4.03 (m, 1H), 3.45 (m, 1H), 2.42 (m, 1H), 1.85–1.13 (m, 10H).

Step 5 and Step 6: 3-{4-[2-(4-Cyclohexylphenyl)-2-(4-trifluoromethoxyphenylcarbamoyl)ethyl] benzoylamino}propionic acid A solution of 4-[2-(4-cyclohexylphenyl)-2-(4-trifluoromethoxyphenylcarbamoyl)ethyl]-benzoic acid (1.44 g; 2.82 mmol) in DMF (45 mL) was stirred while 1-hydroxy-benzotriazole hydrate (0.456 9; 3.38 mmol) was added. The mixture was stirred for 1 hour at room temperature followed by the addition of EDAC (0.648 9; 3.38 mmol), methyl 3-aminopropionate hydrochloride (0.589 g; 4.22 mmol) and DIPEA (1.47 mL; 8.45 mmol). The mixture was stirred at 40° C. for 2 hours. The mixture was evaporated under reduced pressure and the residue was partitioned between water and ethyl acetate. The organic phase was washed with brine, dried (MgSO$_4$) and evaporated to afford 2.11 g of intermediary ester. This substance (0.3 g, 0.5 mmol) was dissolved in a mixture of methanol (11 mL) and THF (4.4 mL) and a 4 M sodium hydroxide solution (0.37 mL; 1.50 mmol) was added. The mixture was stirred for 16 hours at room temperature. The mixture was concentrated to about 1 mL under reduced pressure and water (15 mL) was added. The pH was adjusted to 1.5 by addition of 1 M hydrochloric acid. The precipitate was filtered off, washed with water and dried to afford 0.25 g (85%) of the title compound.

$^1$H NMR (DMSO-$d_6$): δ12.20 (br s, 1H), 10.25 (s, 1H), 8.43 (t, 1H), 7.70 (d, 2H), 7.62 (d, 2H), 7.35 (d, 2H), 7.30 (d, 2H), 7.26 (d, 2H), 7.18 (d, 2H), 3.99 (m, 1H), 3.40 (m, 1H), 3.00 (dd, 1H), 2.48 (m, 3H), 1.85–1.13 (m, 10H).

The following compounds (examples 110–110) were prepared in analogy with the above method.

Example 110

General Procedure (I)

3-{4-[2-(3,5-Dichlorophenylcarbamoyl)-2-(4-trifluoromethoxyphenyl)ethyl]benzoylamino}propionic acid

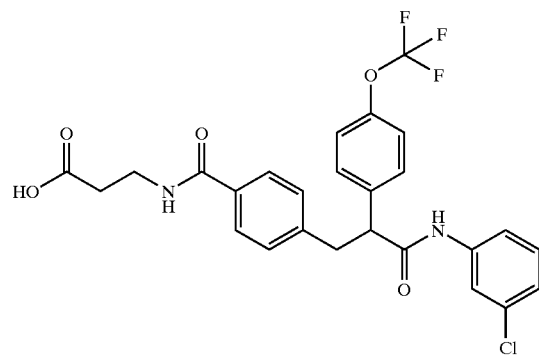

$^1$H NMR (DMSO-d$_6$): δ12.30 (br s, 1H), 10.50 (s, 1H), 8.45 (t, 1H), 7.88–7.20 (m, 11H), 4.08 (m, 1H), 3.42 (m, 3H), 3.05 (dd, 1H), 2.48 (m, 2H). HPLC-MS (Method D): m/z=569 (M+1); R$_t$=4.83 min.

Example 111

General Procedure (I)

3-{4-[2-(3,5-Dichlorophenylcarbamoyl)-2-(4-trifluoromethoxyphenyl)ethyl]benzoylamino}-2R-hydroxyproprionic acid

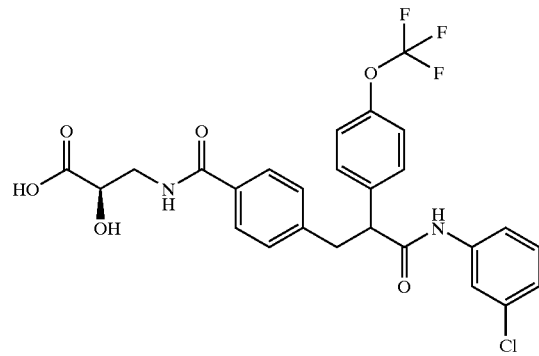

$^1$H NMR (DMSO-d$_6$): δ12.55 (br s, 1H), 10.53 (s, 1H), 8.43 (t, 1H), 7.75 (d, 2H), 7.62 (s, 2H); 7.55 (d, 2H), 7.35 (d, 2H), 7.30 (d, 2H), 7.28 (s, 1H), 4.12 (m, 1H), 3.08 (dd, 1H). HPLC-MS (Method D): m/z=585 (M+1); R$_t$=4.65 min.

Example 112

General Procedure (I)

2R-Hydroxy-3-{4-2-(4-trifluoromethoxyphenyl)-2-(4-trifluoromethoxyphenylcarbamoyl)ethyl]benzoylamino}propionic acid

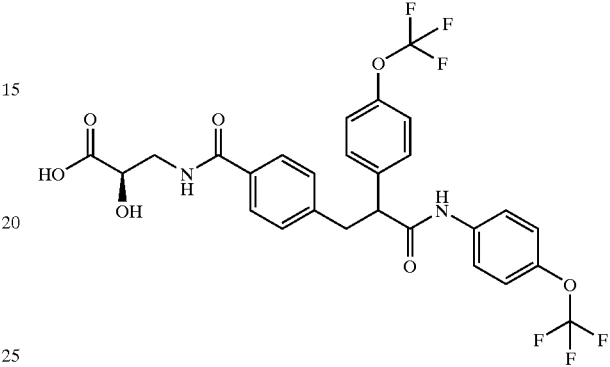

$^1$H NMR (DMSO-d$_6$): δ8.40 (t, 1H), 7.75 (d, 2H), 7.62 (s, 2H); 7.55 (d, 2H), 7.30 (m, 6H), 4.10 (m, 2H), 3.08 (dd, 1H). HPLC-MS (Method D): m/z=601 (M+1); R$_t$=4.42 min.

Example 113

General Procedure (I)

3-{4-[2-(4-Trifluoromethoxyphenyl)-2-(4-trifluoromethoxyphenylcarbamoyl)ethyl]benzoylamino}propionic acid

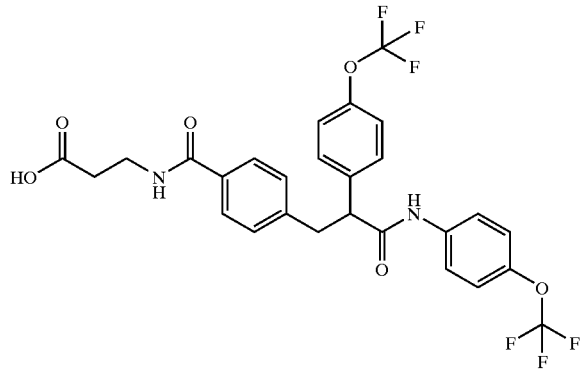

$^1$H NMR (DMSO-d$_6$): δ10.40 (s, 1H), 8.47 (t, 1H), 7.70 (d, 2H), 7.65 (d, 2H); 7.55 (d, 2H), 7.30 (m, 6H), 4.10 (m, 1H), 3.05 (dd, 1H), 2.47 (t, 2H). HPLC-MS (Method D): m/z=585 (M+1); R$_t$=4.58 min.

Example 114

General Procedure (I)

3-{4-[2-(4-Cyclohexylphenyl)-2-(3,5-dichlorophenylcarbamoyl)ethyl]-benzoylamino}-propionic acid

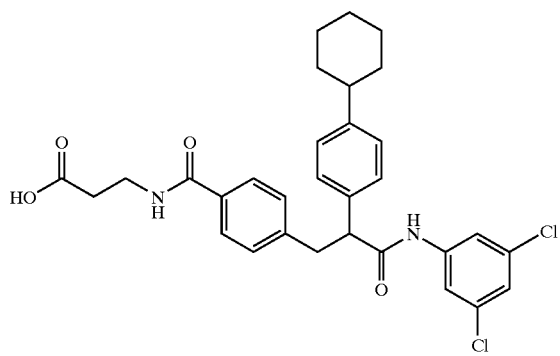

$^1$H NMR (DMSO-d$_6$): δ12.22 (br s, 1H), 10.40 (s, 1H), 8.42 (t, 1H), 7.70 (d, 2H), 7.60 (s, 2H), 7.35–7.10 (m, 7H), 3.95 (m, 1H), 3.42 (m, 2H), 3.00 (dd, 1H), 2.48 (m, 3H), 1.85–1.13 (m, 10H).

Example 115

General Procedure (I)

3-{4-[2-(4-Cyclohexylphenyl)-2-(4-trifluoromethylphenylcarbamoyl)ethyl]benzoylamino}propionic acid

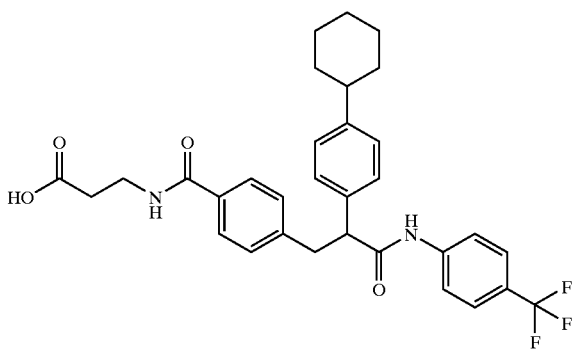

$^1$H NMR (DMSO-d$_6$): δ12.32 (br s, 1H), 10.40 (s, 1H), 8.43 (t, 1H), 7.72 (d, 2H), 7.69 (d, 2H), 7.35 (d, 2H), 7.30 (d, 2H), 7.28 (d, 2H), 7.18 (d, 2H), 4.02 (m, 1H), 3.40 (m, 2H), 3.00 (dd, 1H), 2.46 (m, 3H), 1.85–1.13 (m, 10H).

The following two compounds (examples 116 and 117) were prepared according to general procedure (I) except that the hydrogenation step (step 2) was omitted.

Example 116

3-{4-[2-(4-tert-Butylphenylcarbamoyl)-2-(4-trifluoromethoxyphenyl)vinyl]benzoylamino}propionic acid

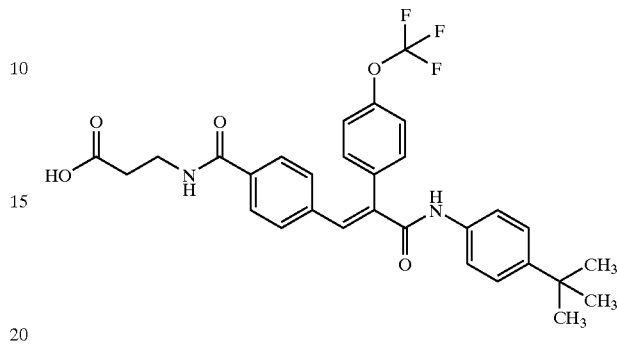

$^1$H NMR (DMSO-d$_6$): δ12.22 (br s, 1H), 10.10 (s, 1H), 8.50 (t, 1H), 7.69–7.10 (m, 13H), 3.43 (q, 2H), 2.47 (t, 2H), 1.29 (s, 9H).

Example 117

3-{4-[2-(4-tert-Butylphenylcarbamoyl)-2-(4-trifluoromethoxypheny)vinyl]benzoylamino}2R-hydroxy-propionic acid

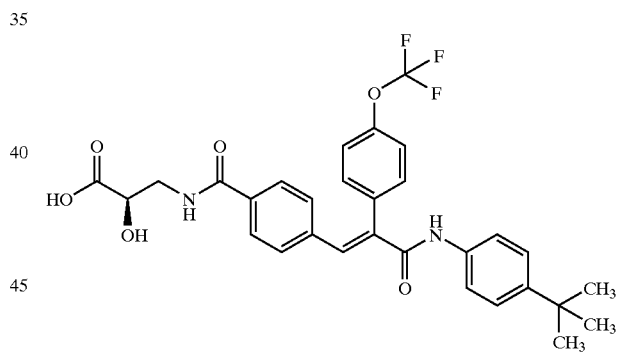

$^1$H NMR (DMSO-d$_6$): δ10.10 (s, 1H), 8.50 (t, 1H), 7.72–7.12 (m, 13H), 4.12 (t, 1H), 3.55 (m, 1H), 1.28 (s, 9H).

The following preferred compounds are within the scope of the invention and may be prepared according to the procedures disclosed herein.

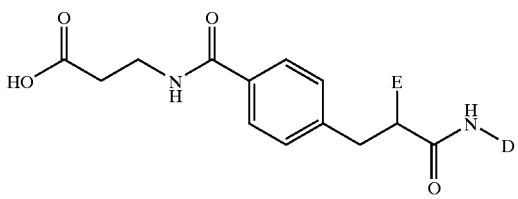

wherein
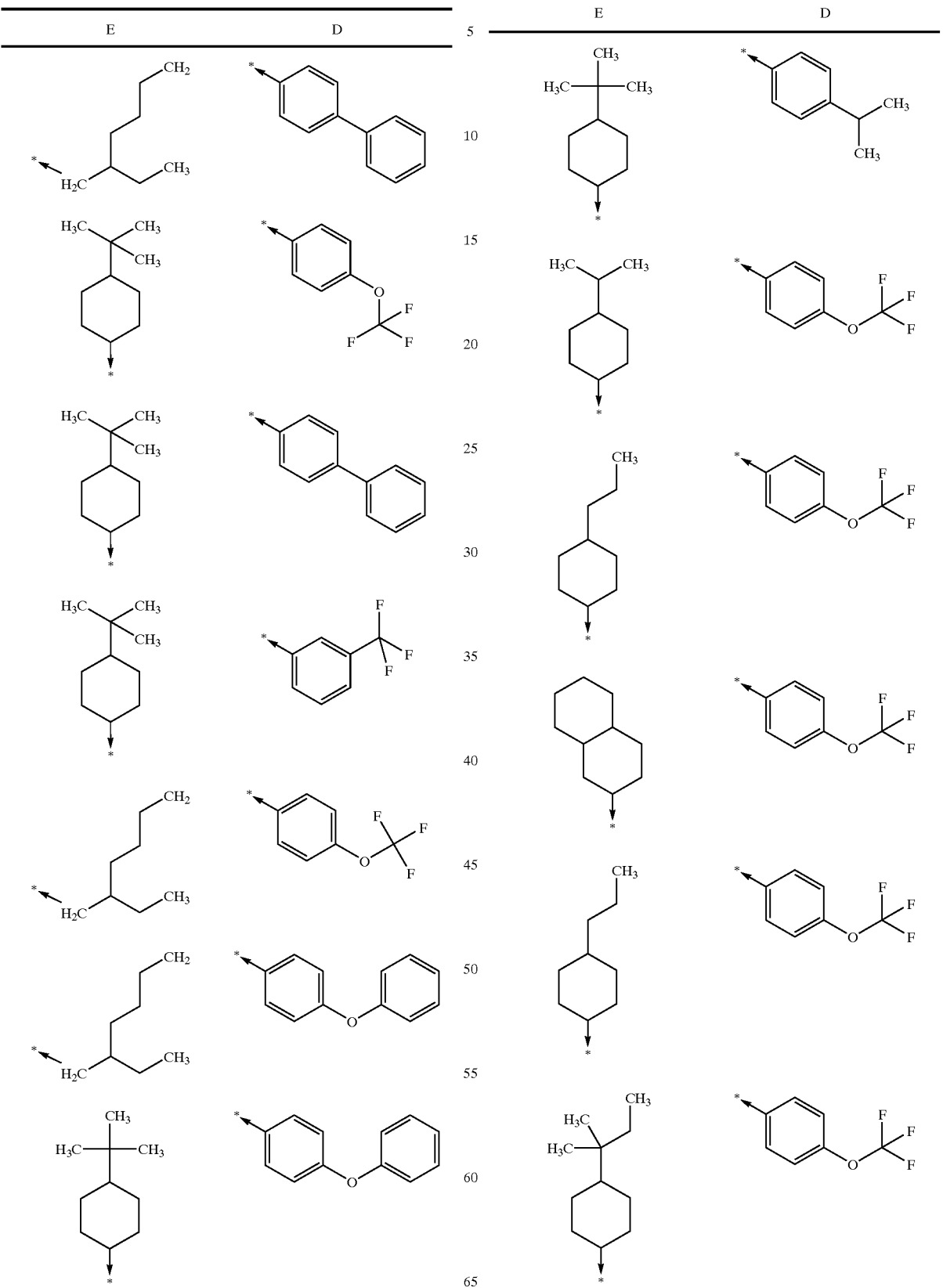

-continued
| E | D |
|---|---|
| 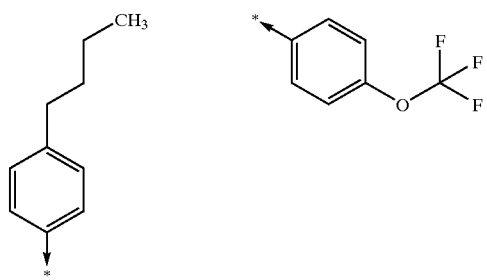 | |
| 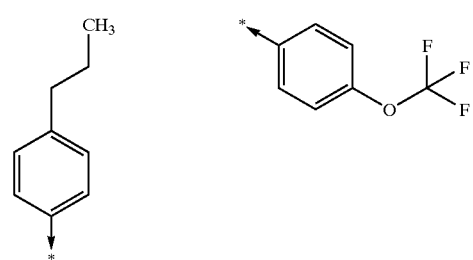 | |
| 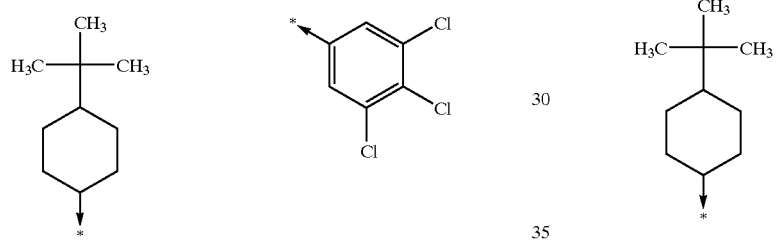 | |
| 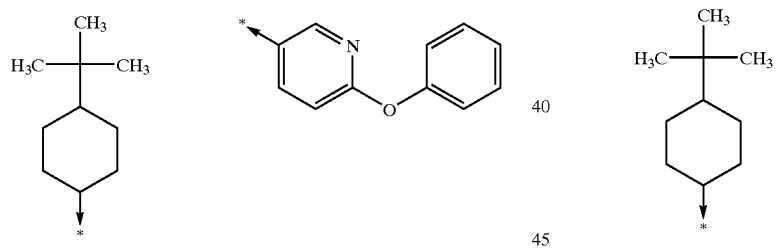 | |
| 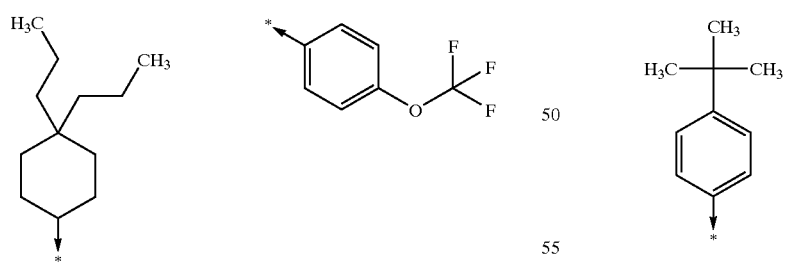 | |
| 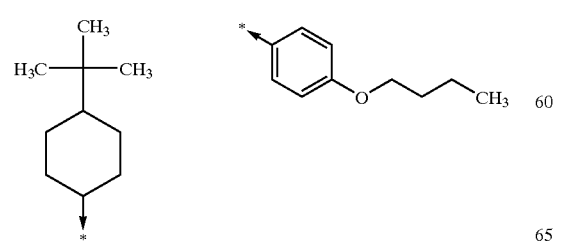 | |
-continued
| E | D |
|---|---|
| 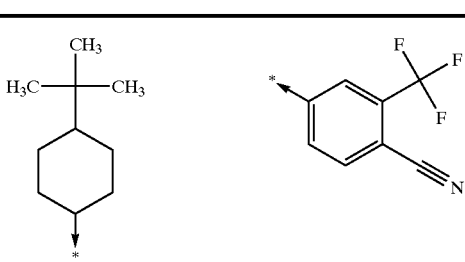 | |
| 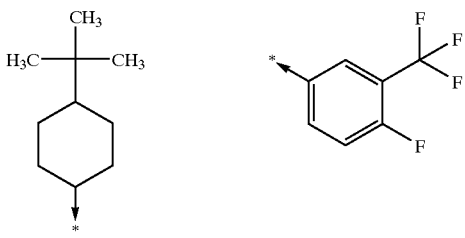 | |
| 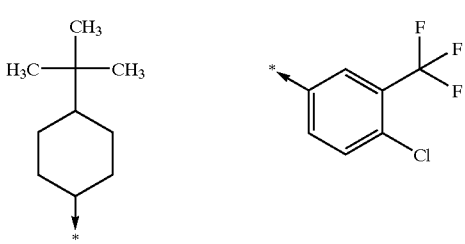 | |
| 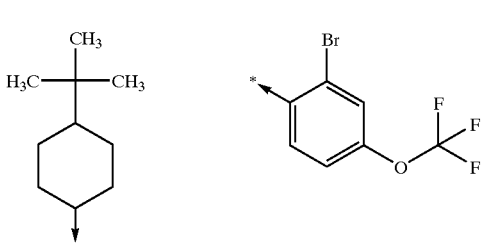 | |
| 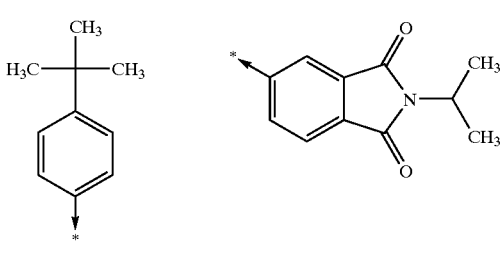 | |
| 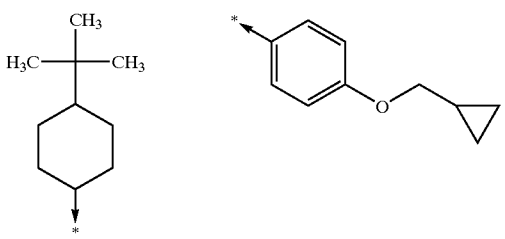 | |

-continued
| E | D |
|---|---|
| 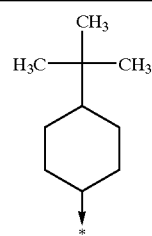 | 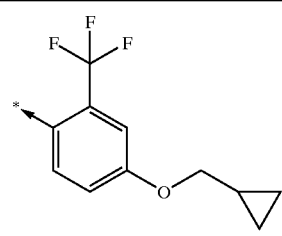 |
| 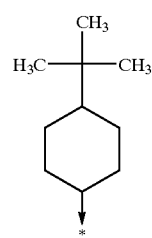 | 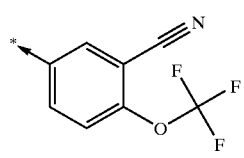 |
| 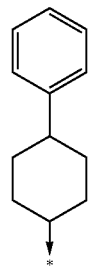 | 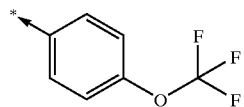 |
| 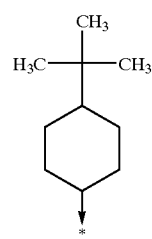 | 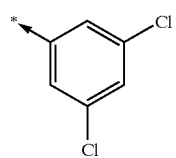 |
| 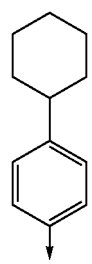 | 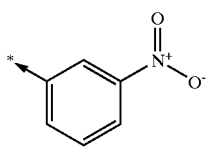 |
| 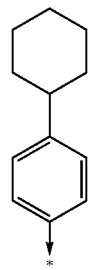 | 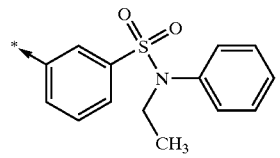 |
-continued
| E | D |
|---|---|
| 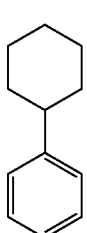 | 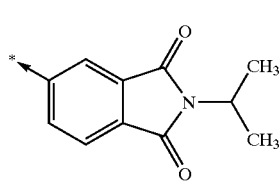 |
| 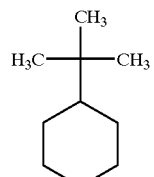 | 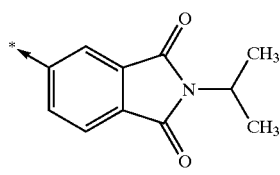 |
| 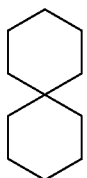 | 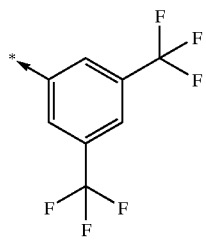 |
| 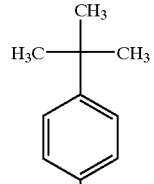 | 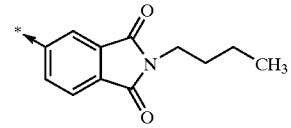 |
| 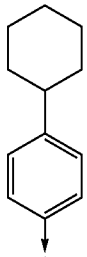 | 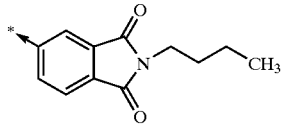 |
| 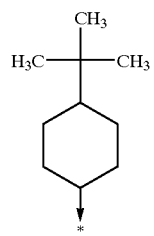 | 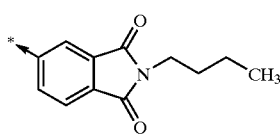 |

-continued
| E | D |
|---|---|
| 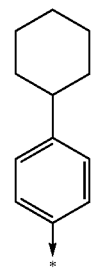 | 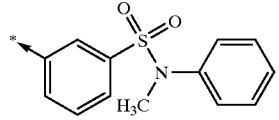 |
| 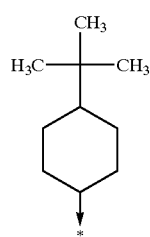 | 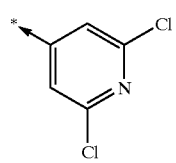 |
| 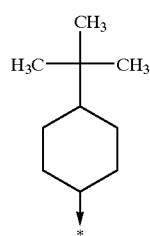 | 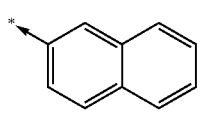 |
| 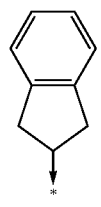 | 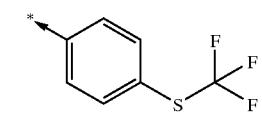 |
| 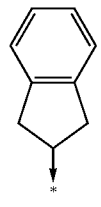 | 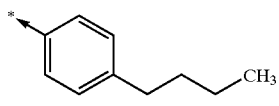 |
| 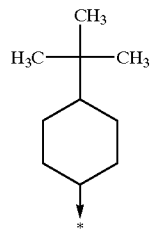 | 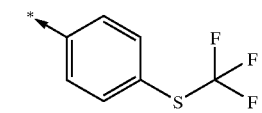 |
-continued
| E | D |
|---|---|
| 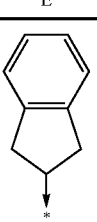 | 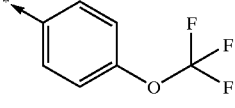 |
| 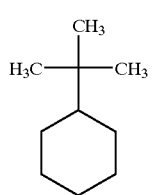 | 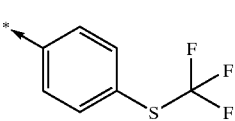 |
| 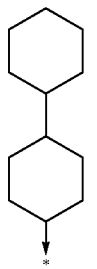 | 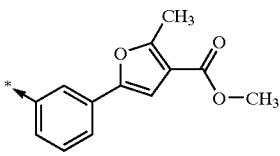 |
| 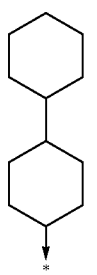 | 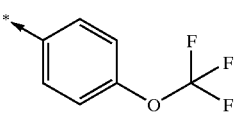 |
| 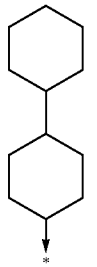 | 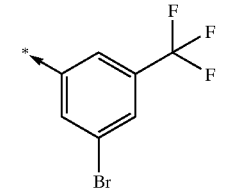 |
| 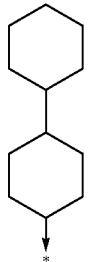 | 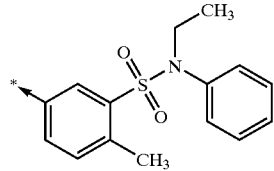 |

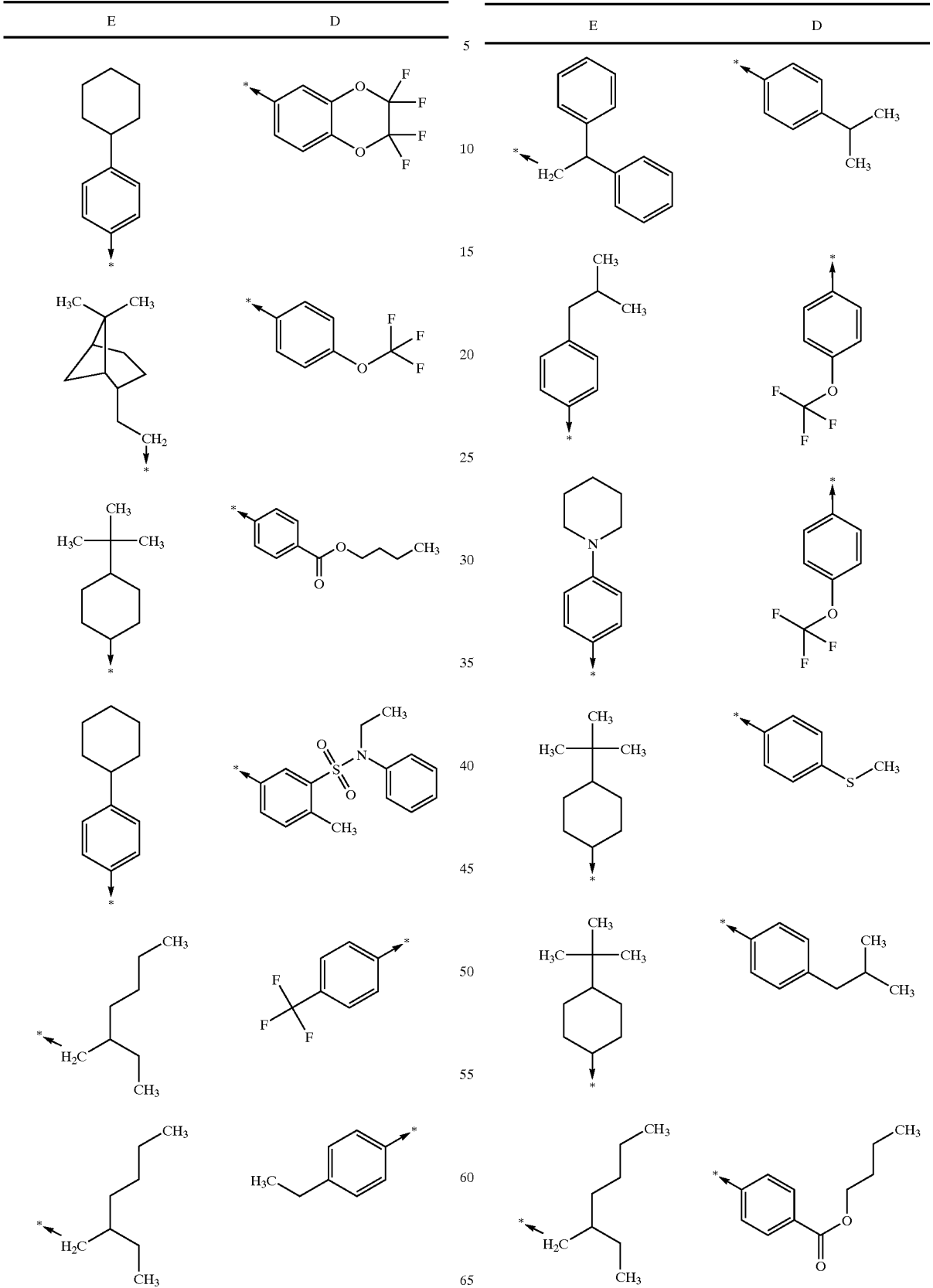

| E | D |
|---|---|
| 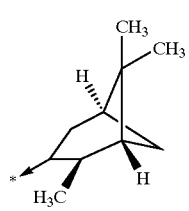 | 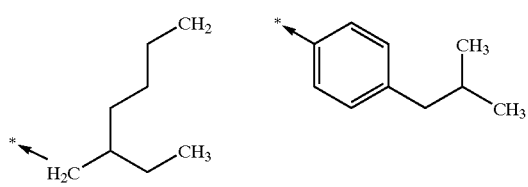 |
| 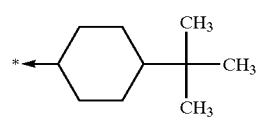 | 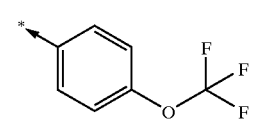 |
| 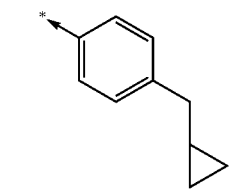 | 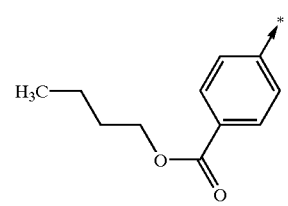 |
| 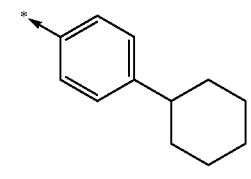 | 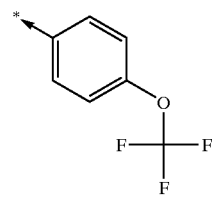 |
| 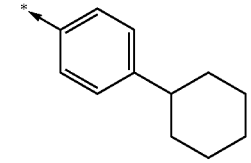 | 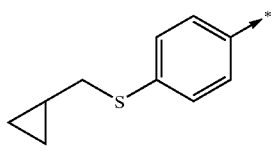 |
| 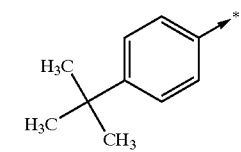 | 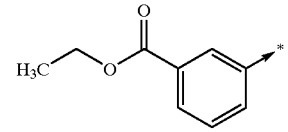 |
| | 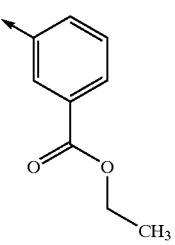 |
-continued
| E | D |
|---|---|
| 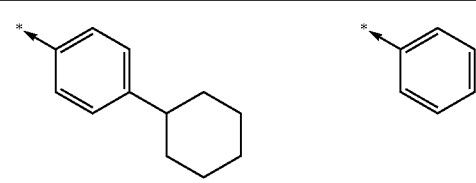 | |
| 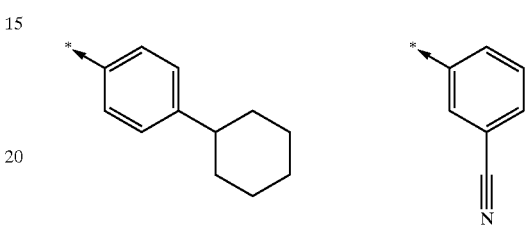 | |
| 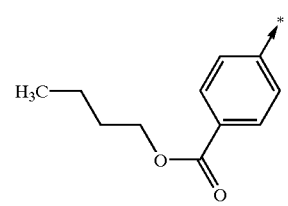 | 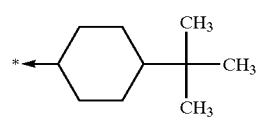 |
| 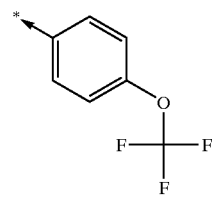 | 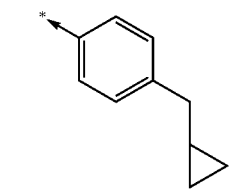 |
| 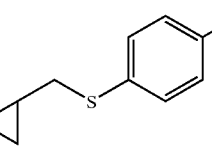 | 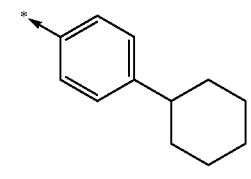 |
| 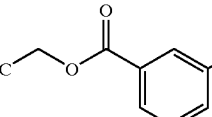 | 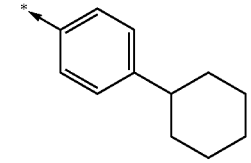 |
| 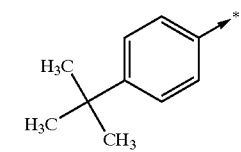 | 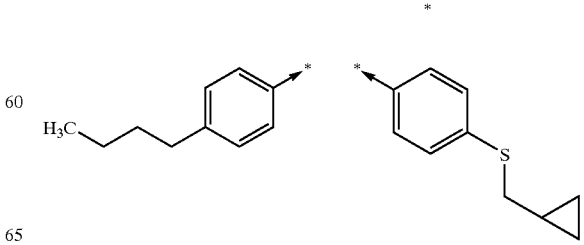 |

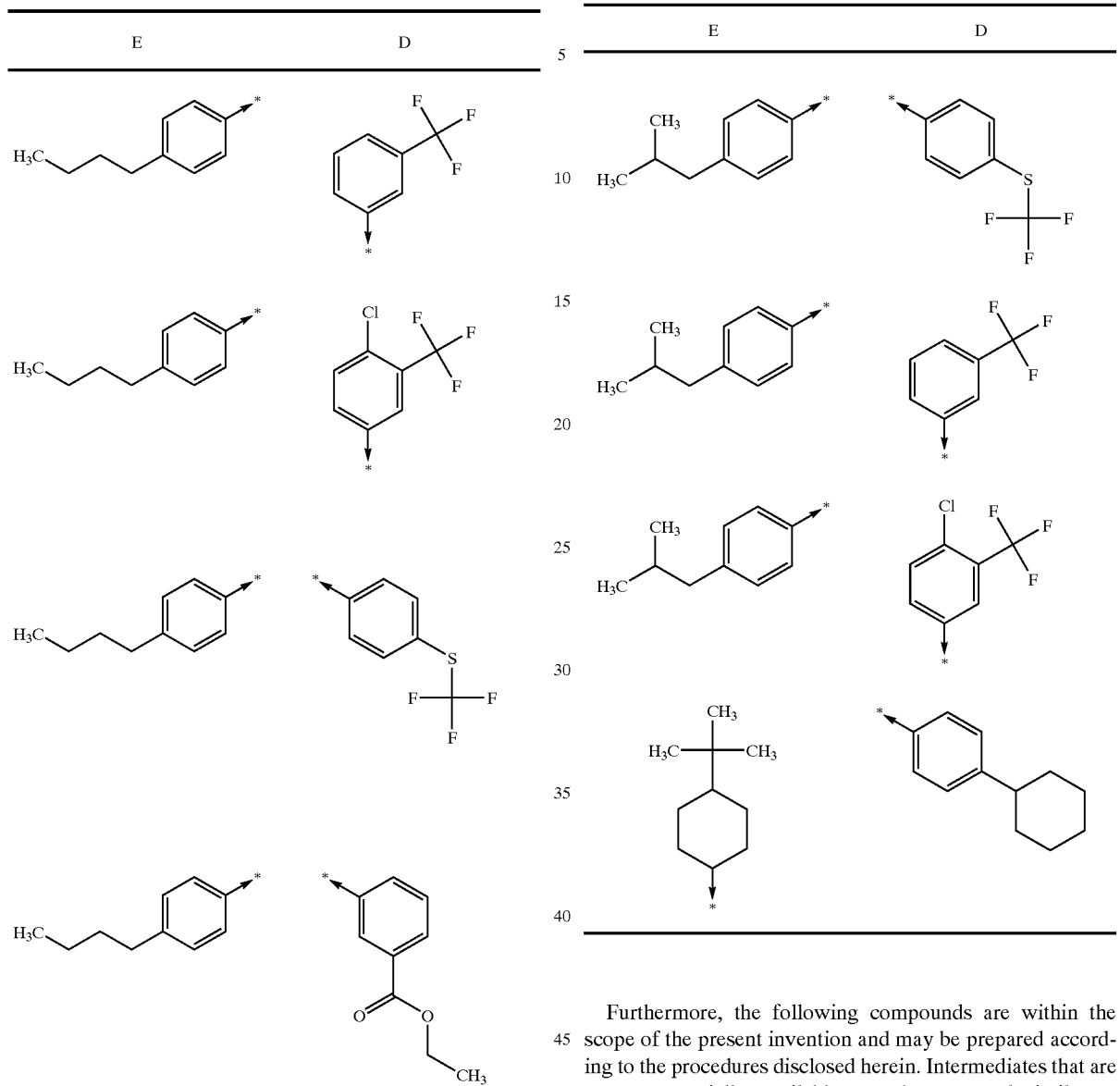
Furthermore, the following compounds are within the scope of the present invention and may be prepared according to the procedures disclosed herein. Intermediates that are not commercially available may be prepared similar to procedures described in WO 00/69810:
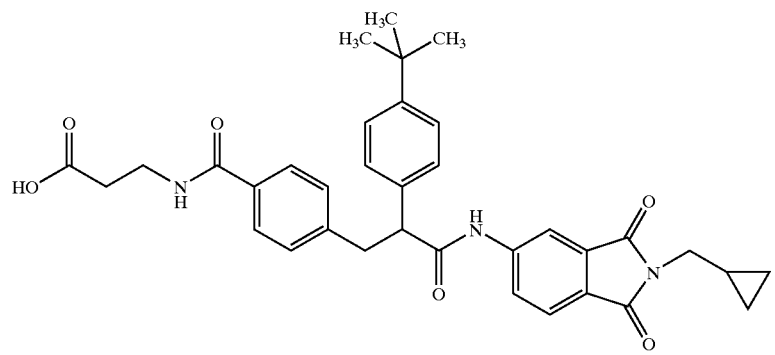

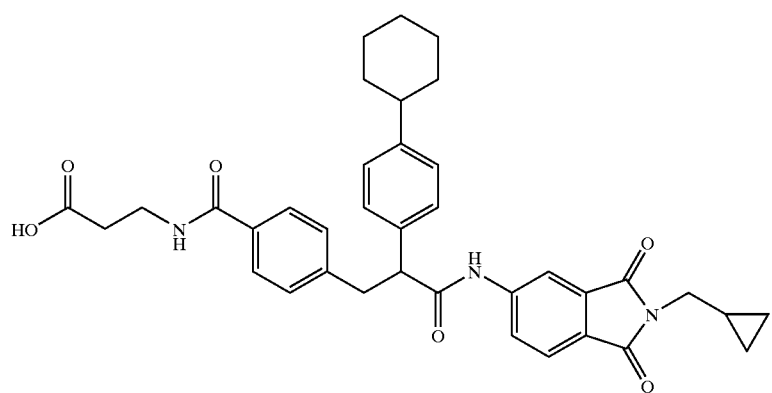
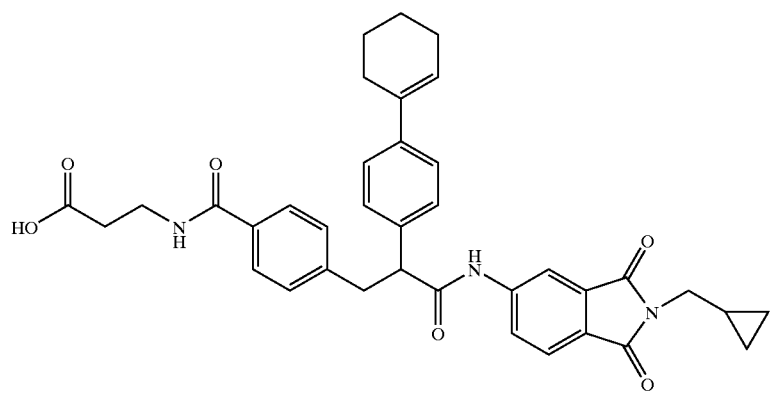
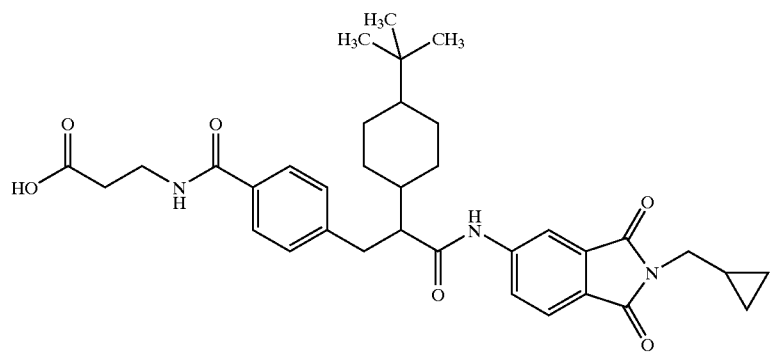
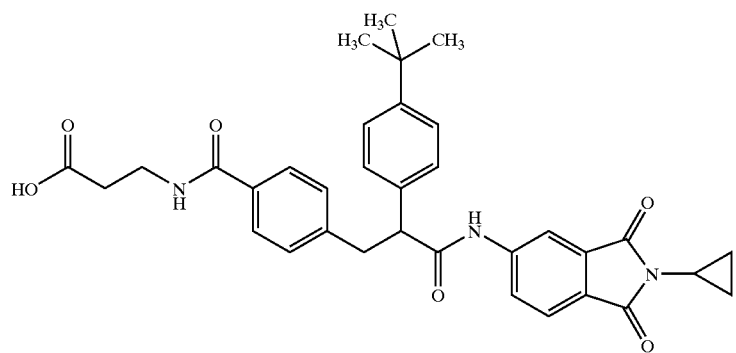

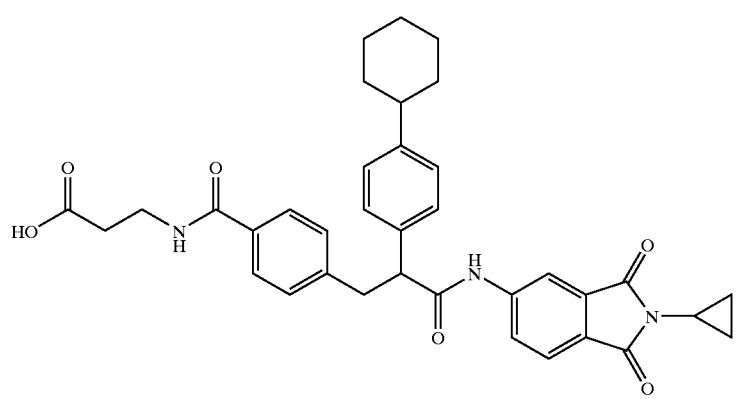
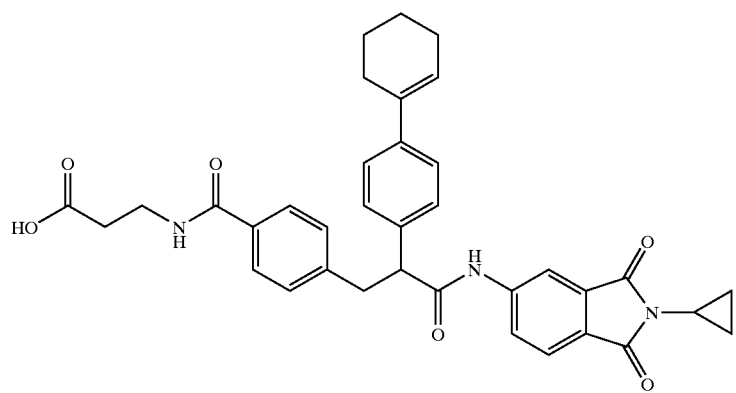
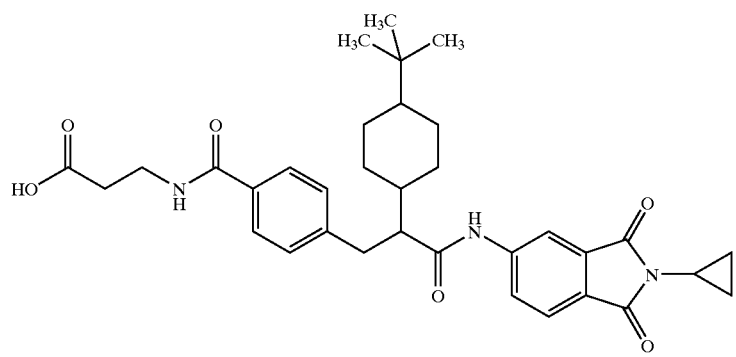
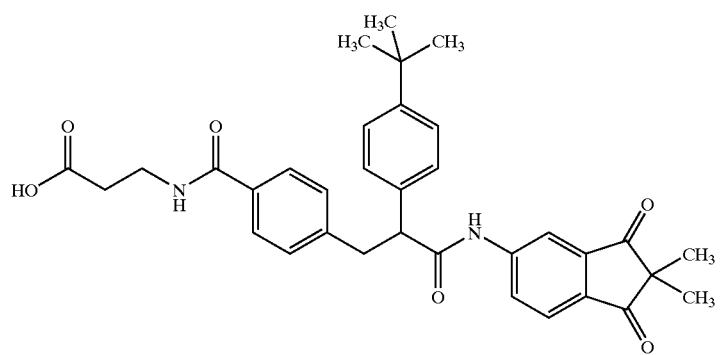

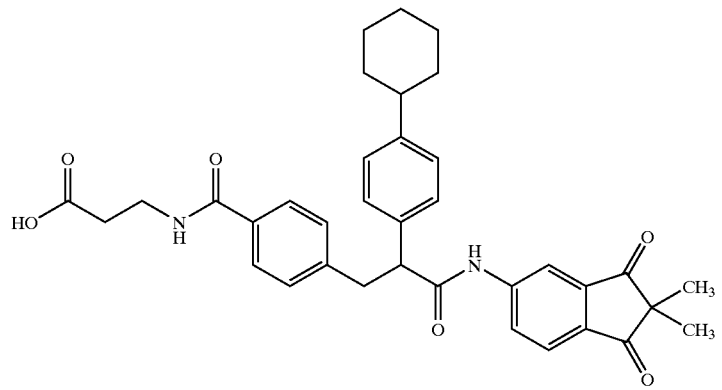
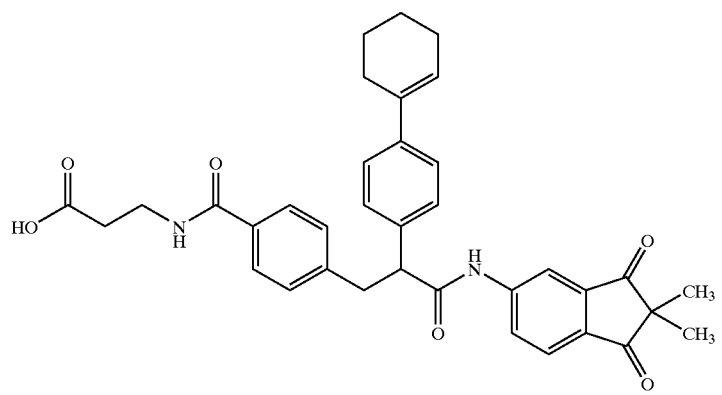
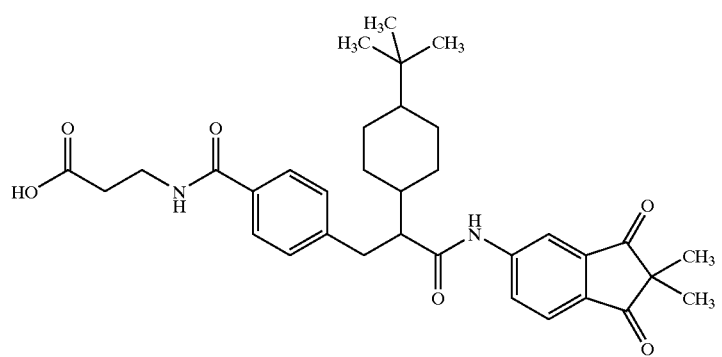
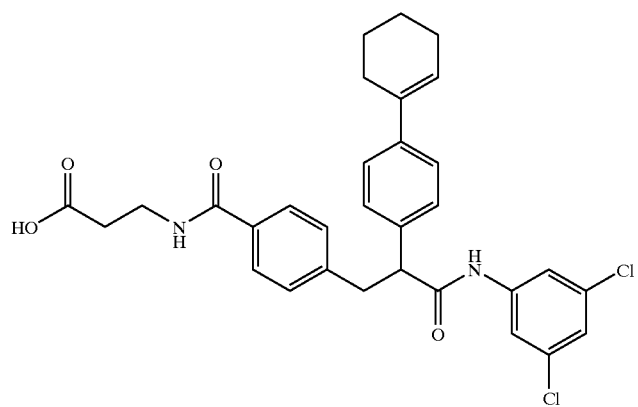

-continued
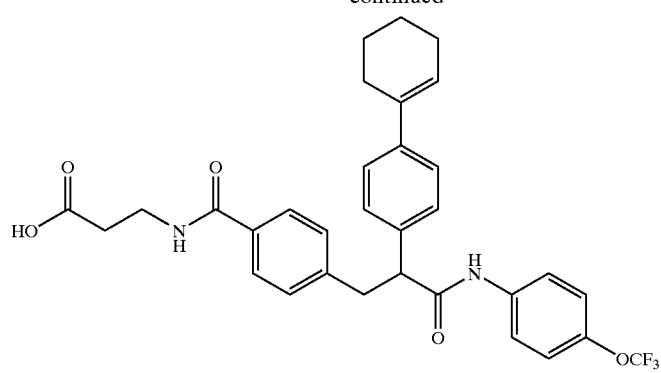
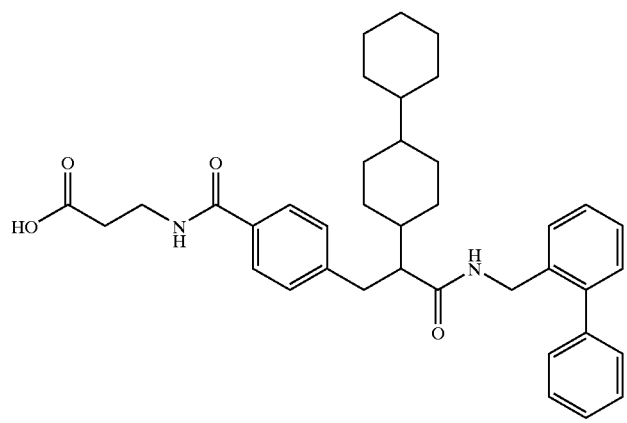
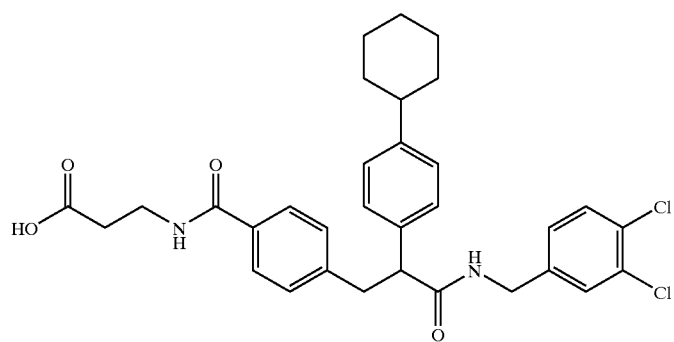
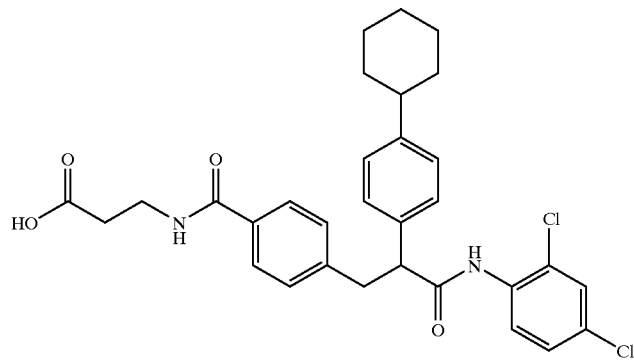

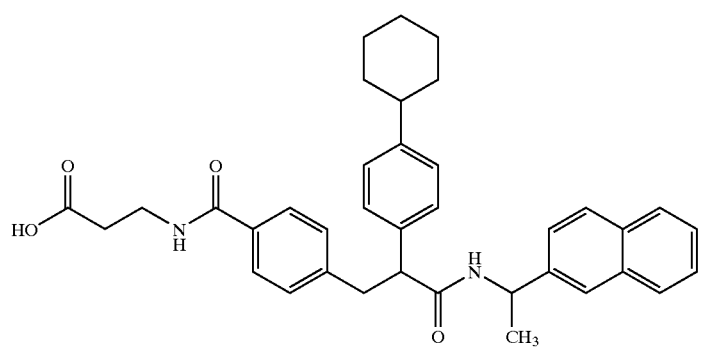
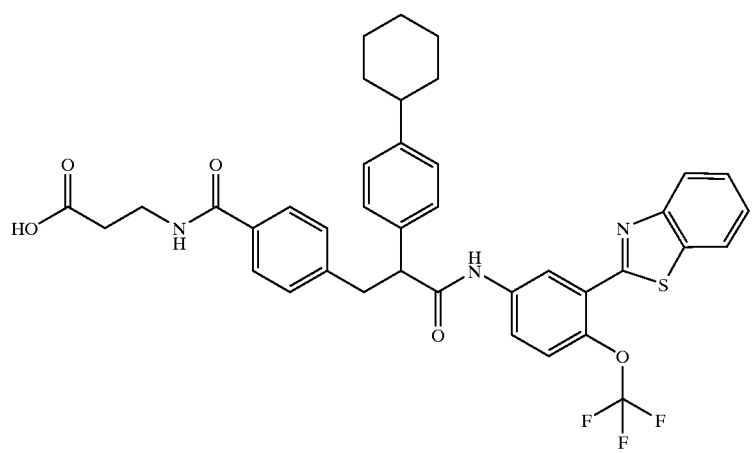
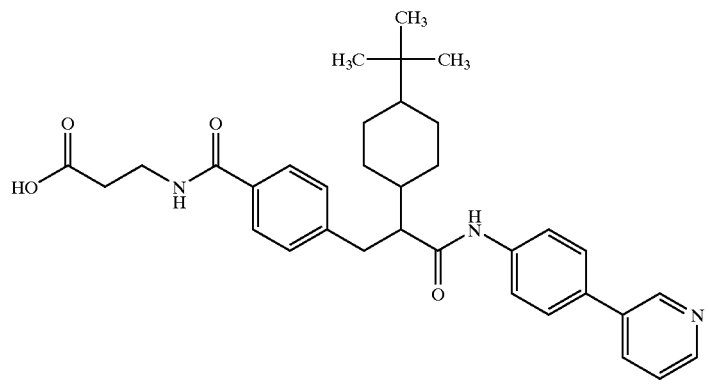
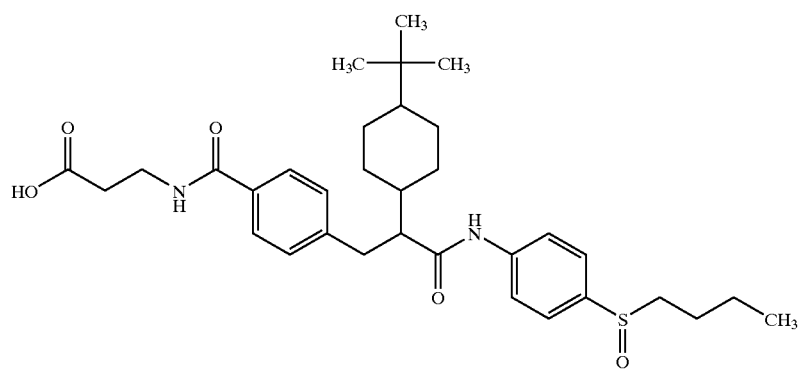

-continued
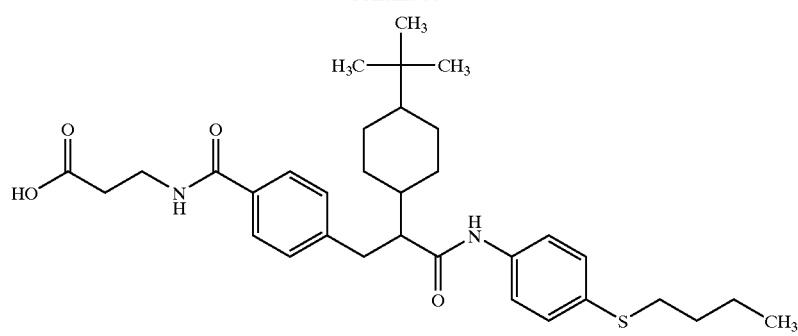
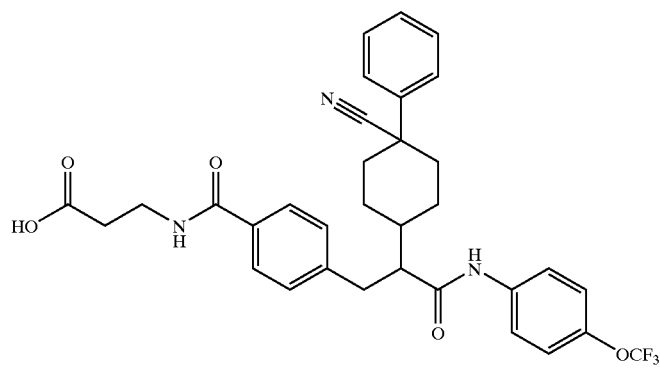
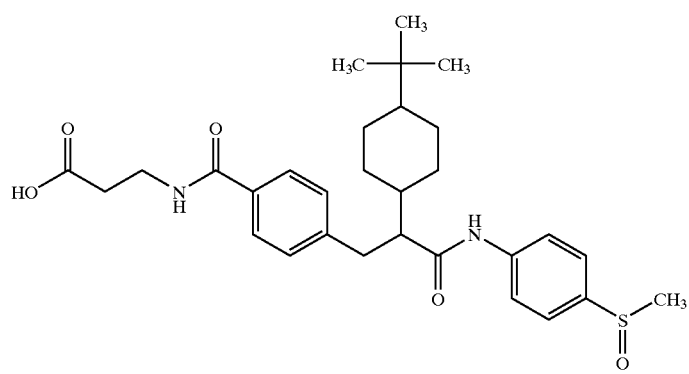
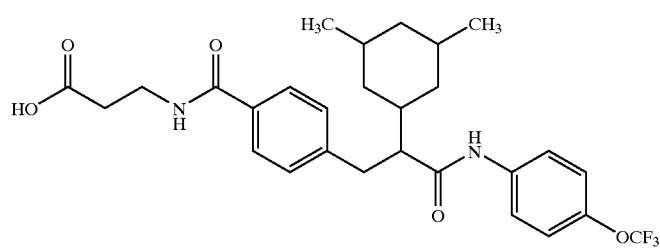
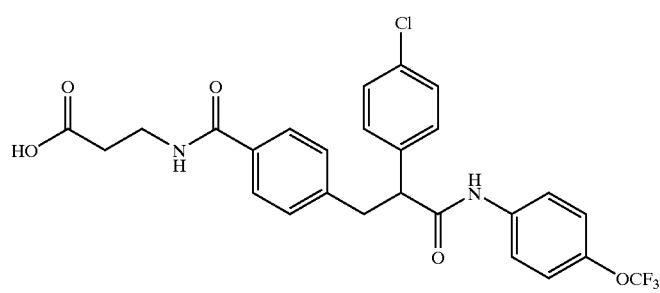

-continued
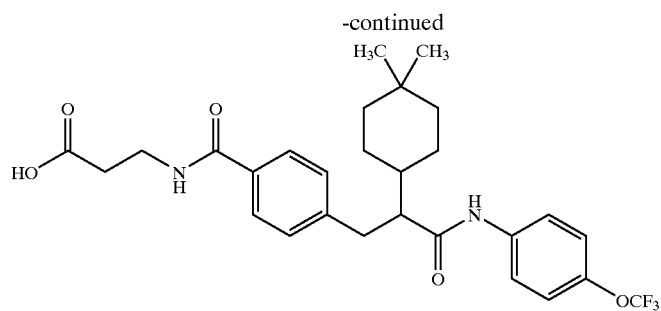
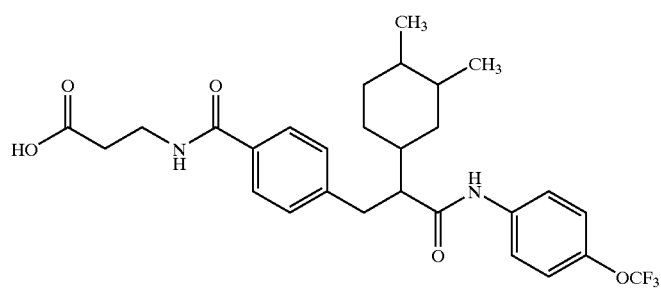
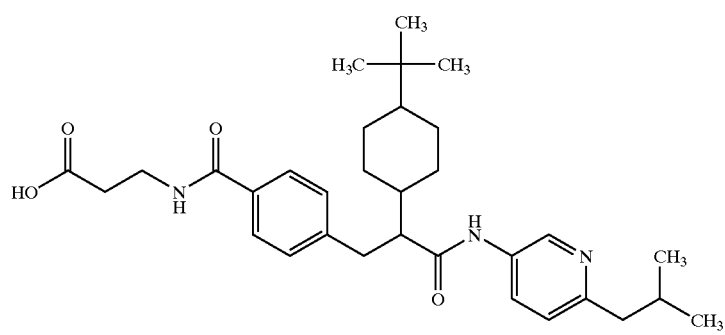
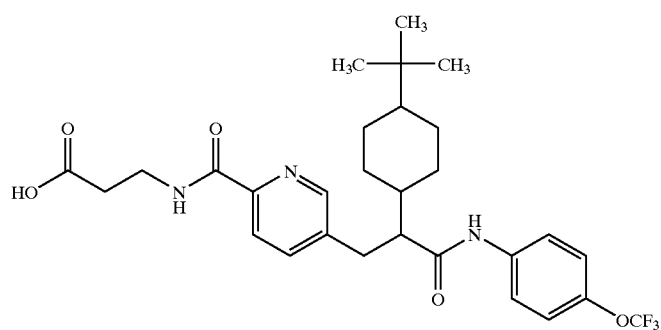
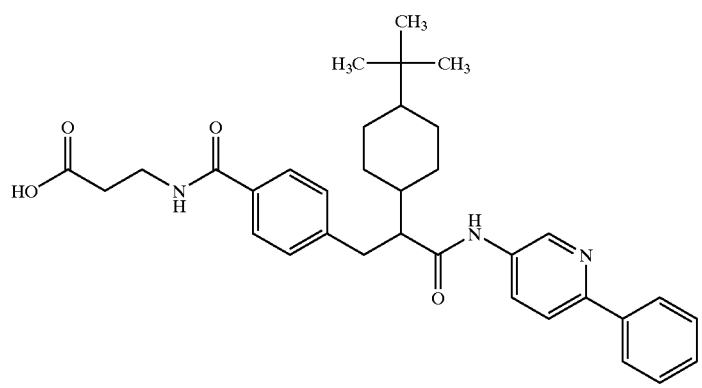

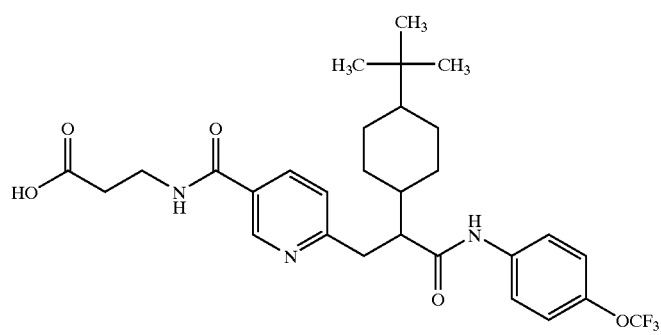
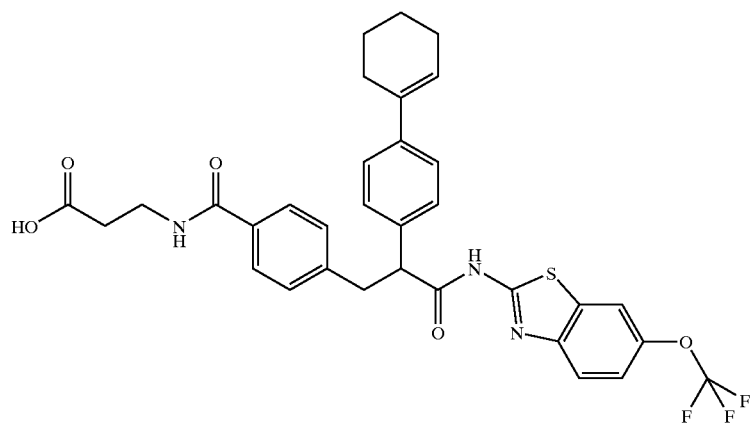
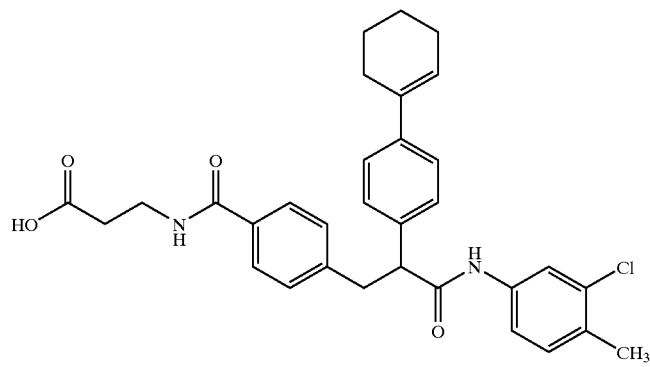
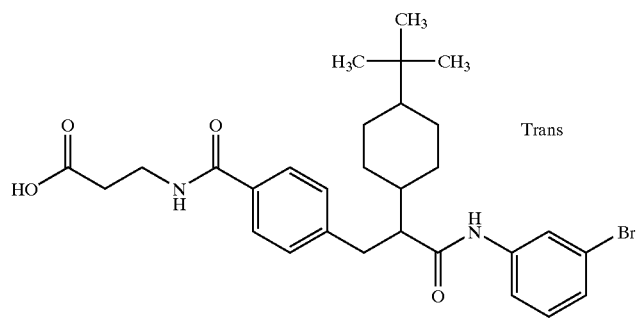

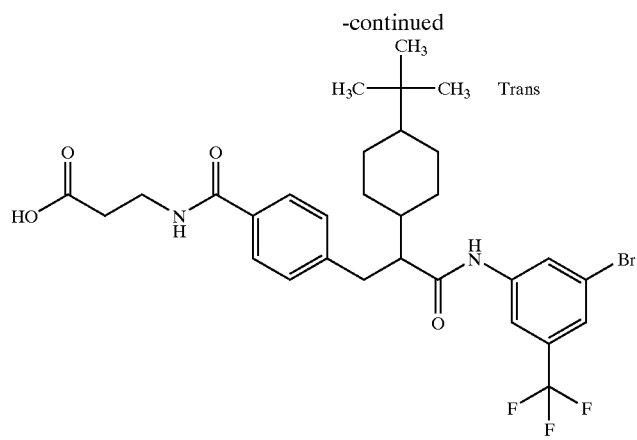
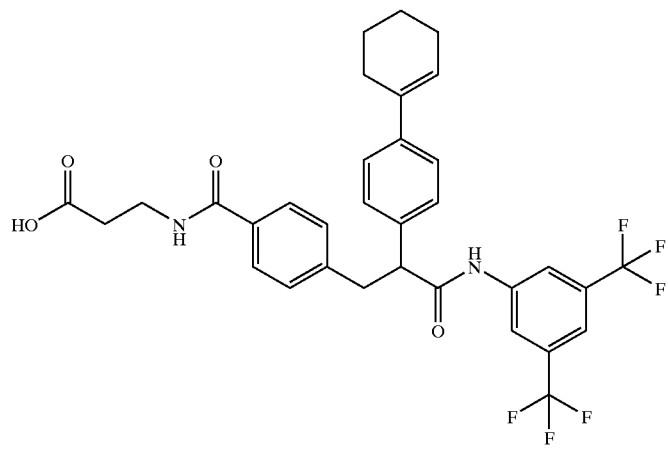
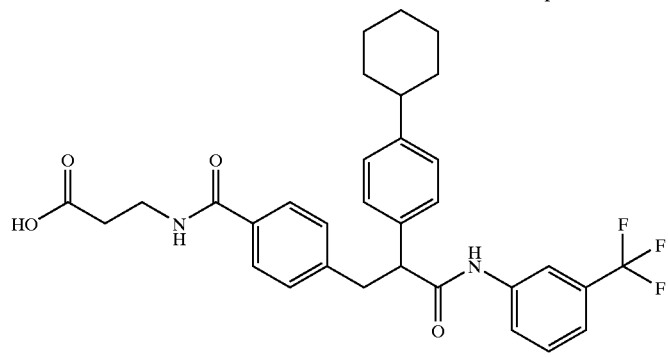
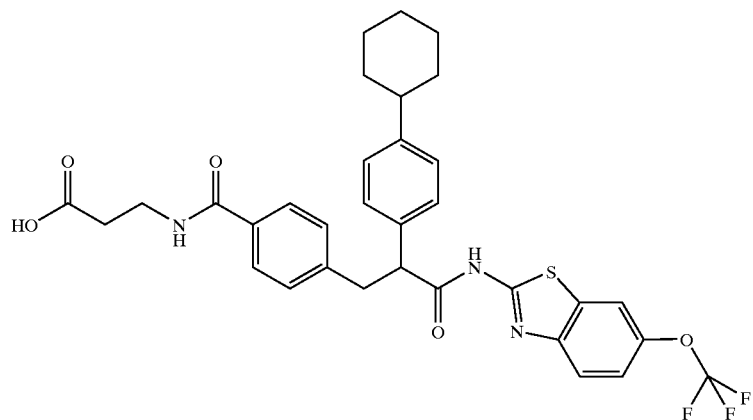

-continued
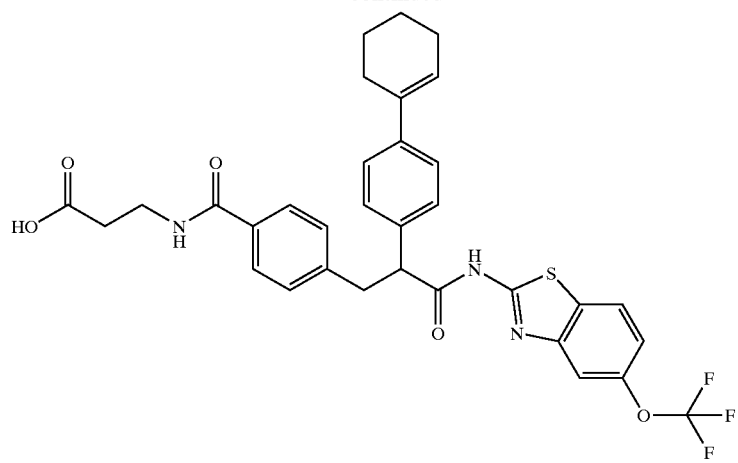
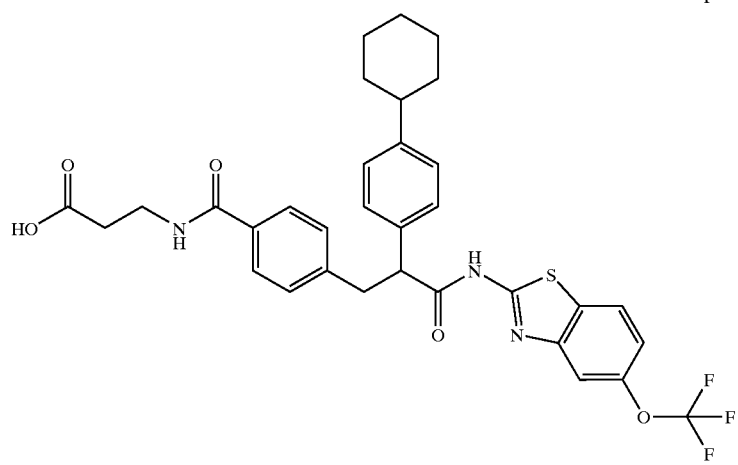
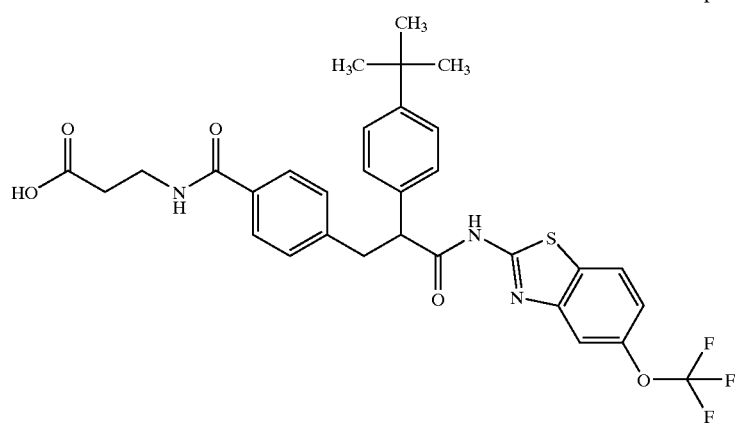
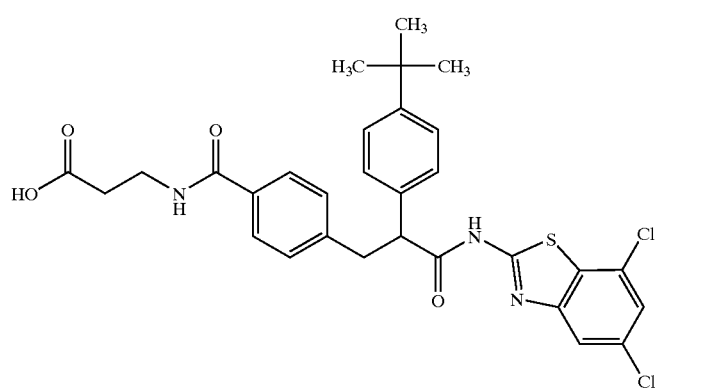

-continued
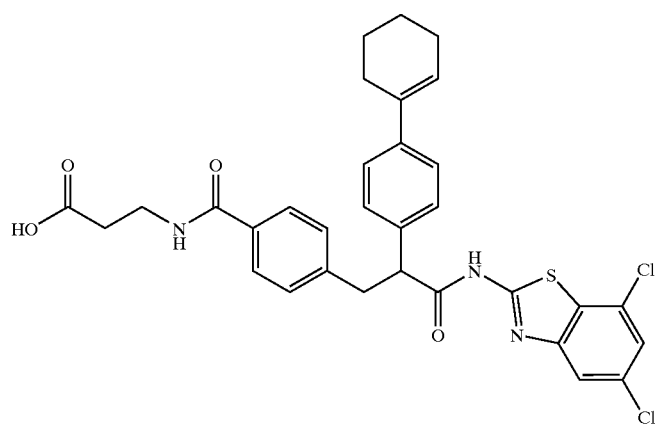
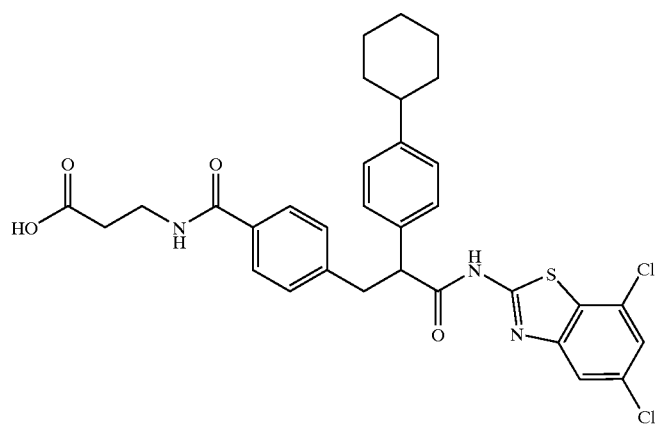
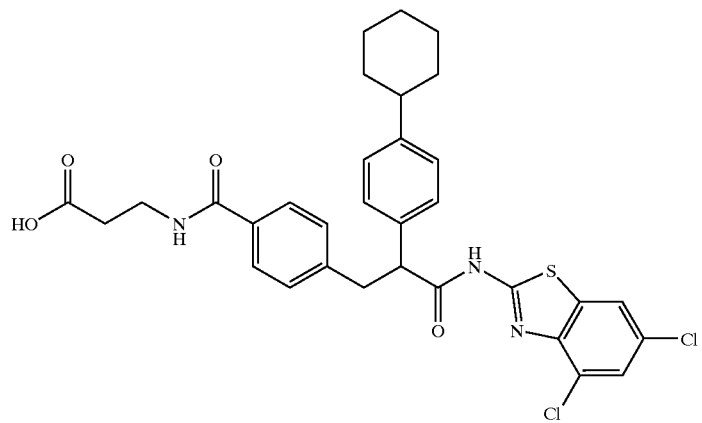
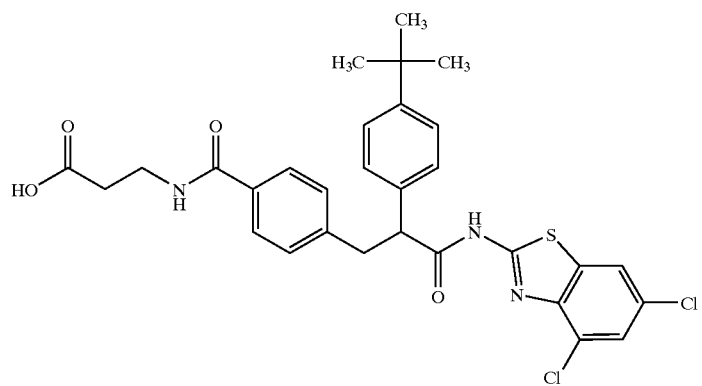

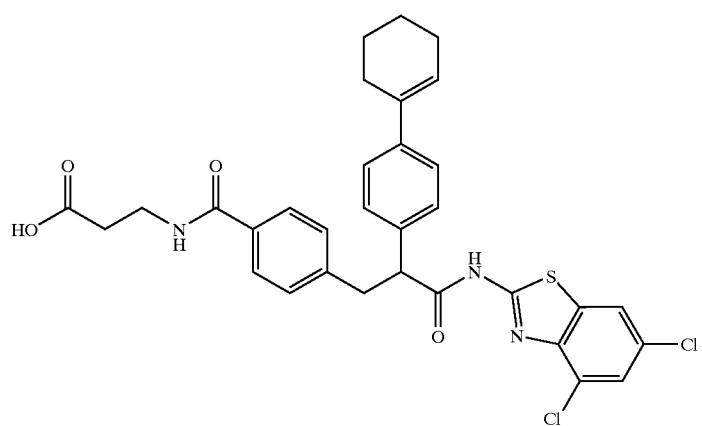
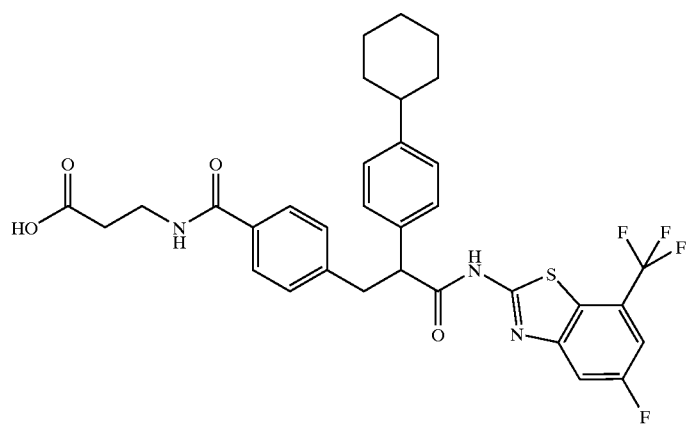
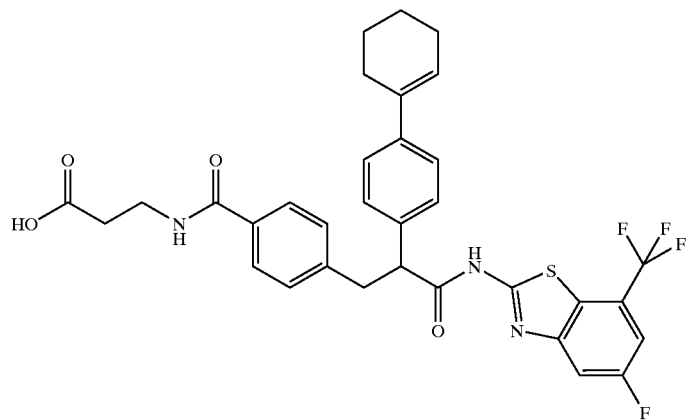
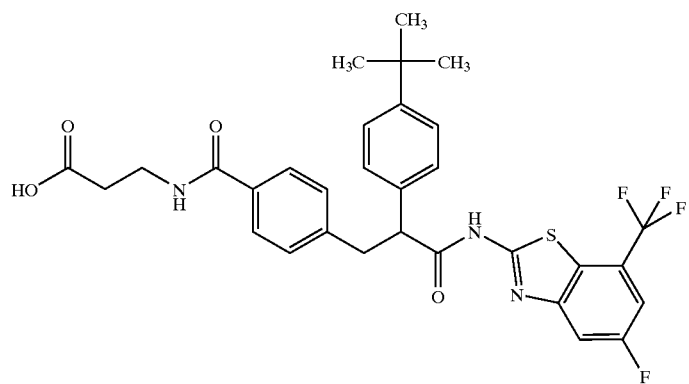

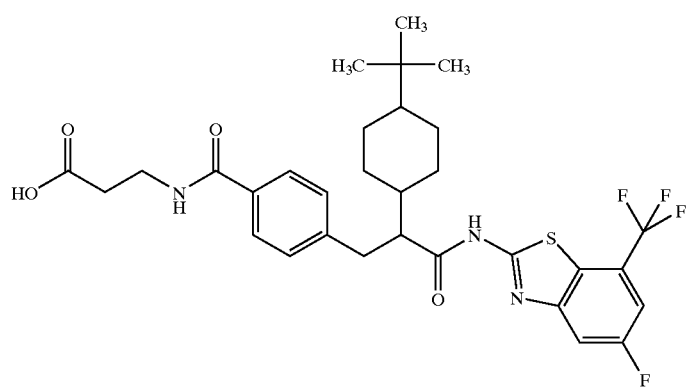
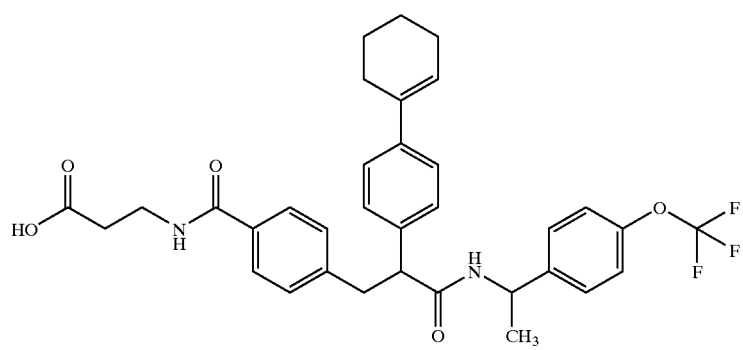
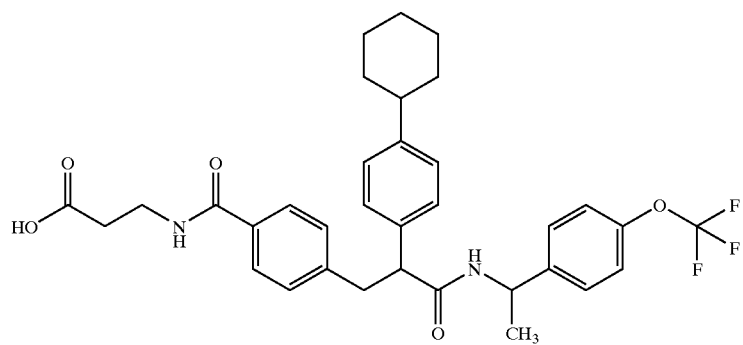
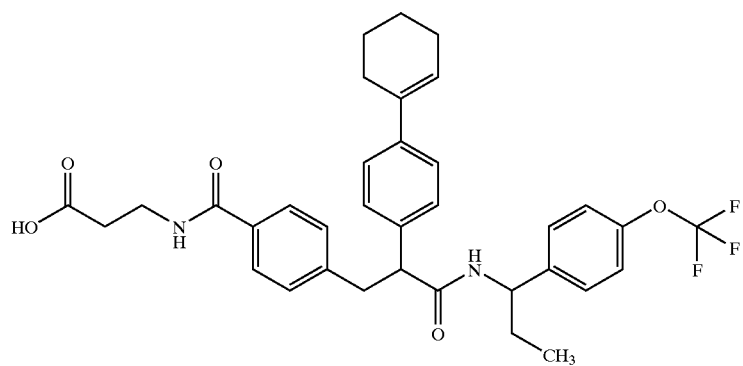

-continued
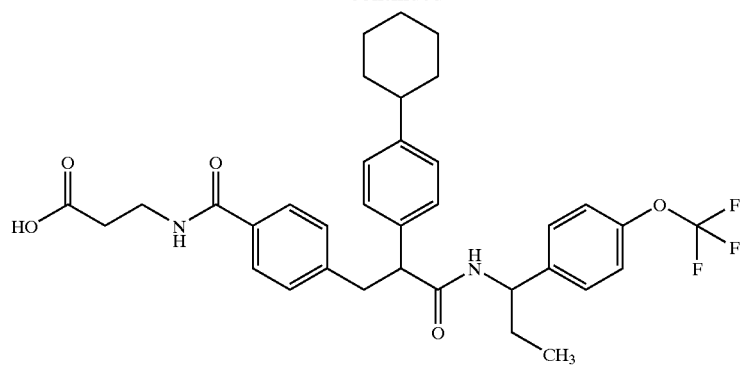
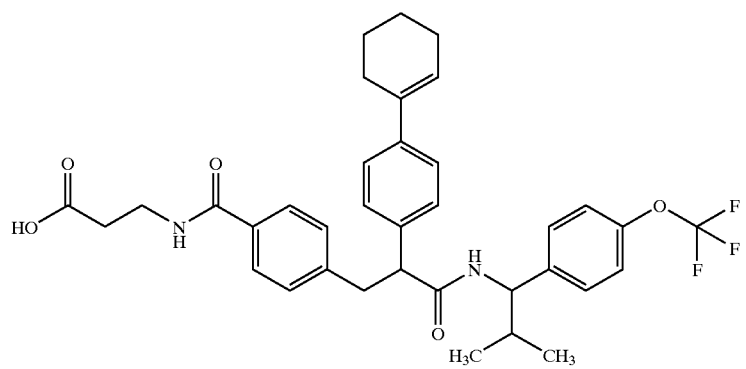
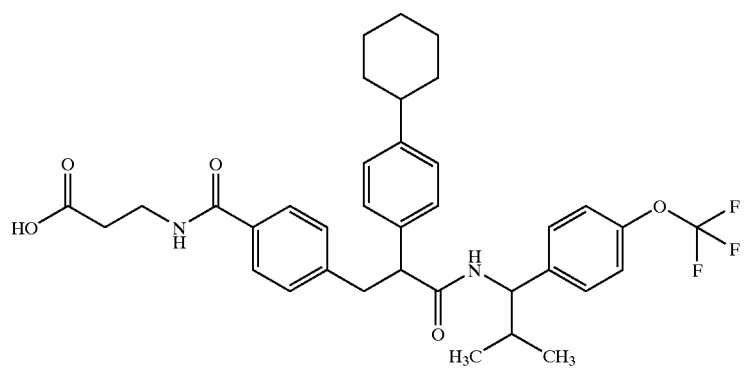
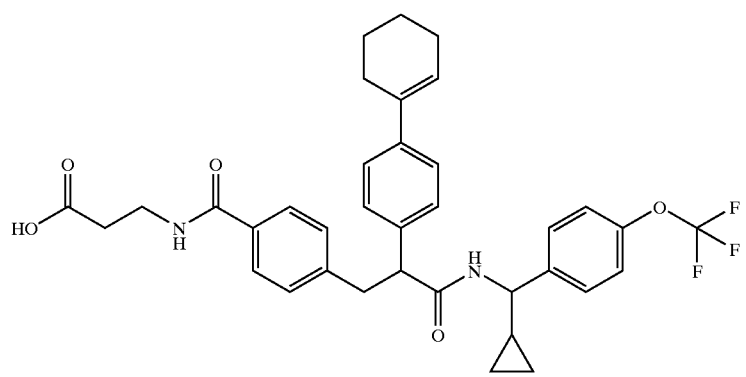

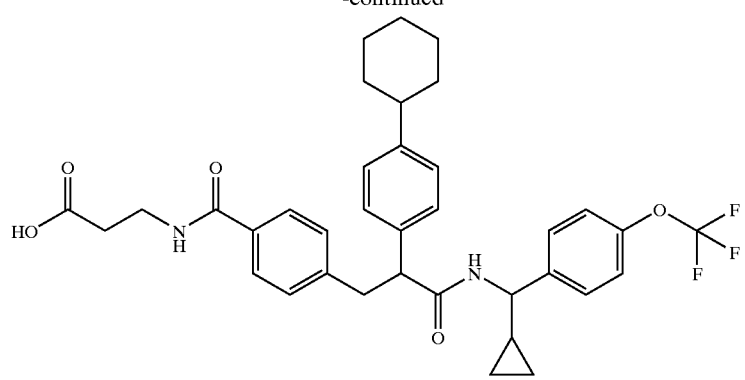
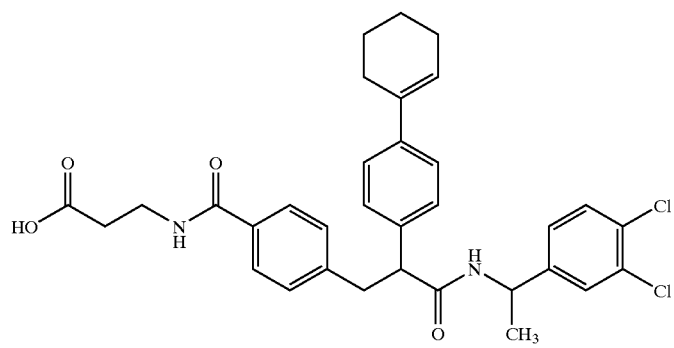
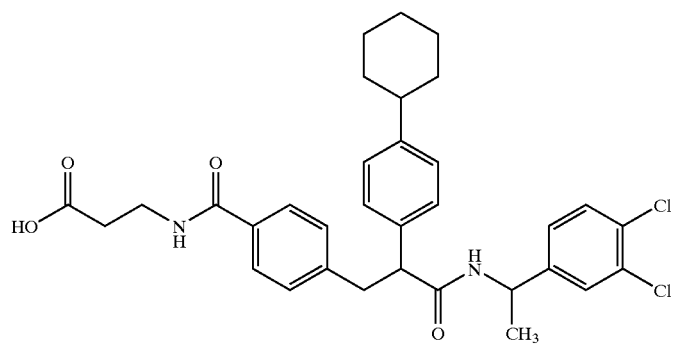
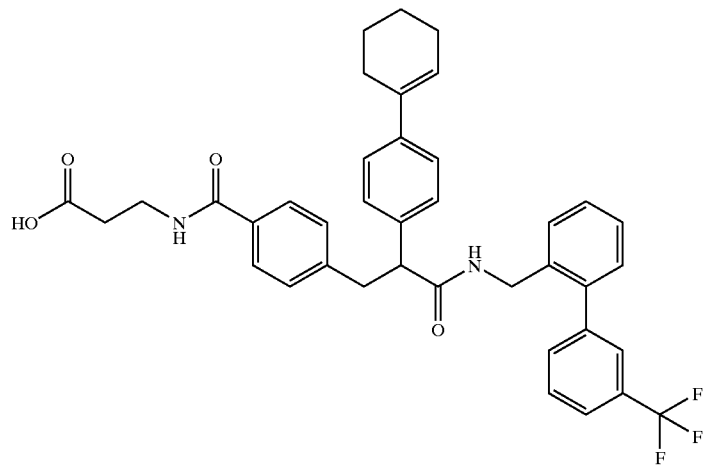

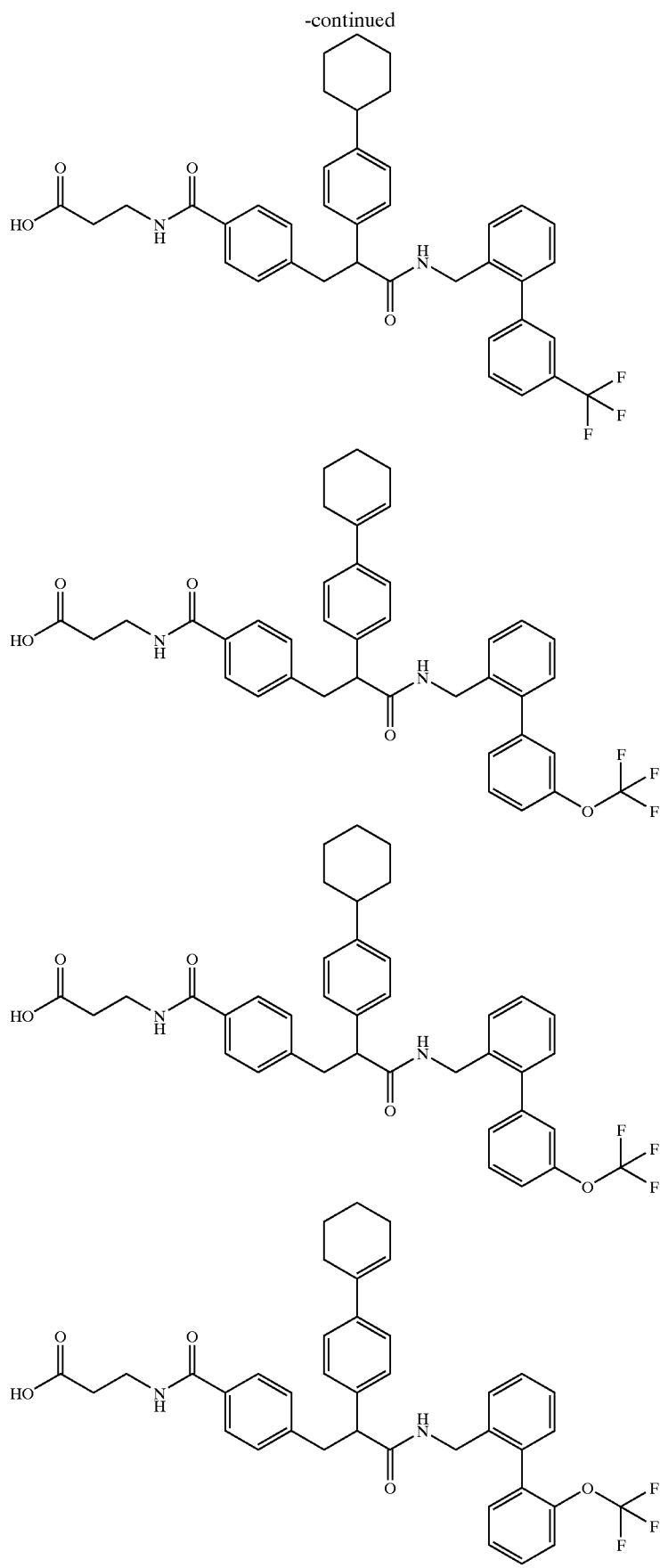

-continued
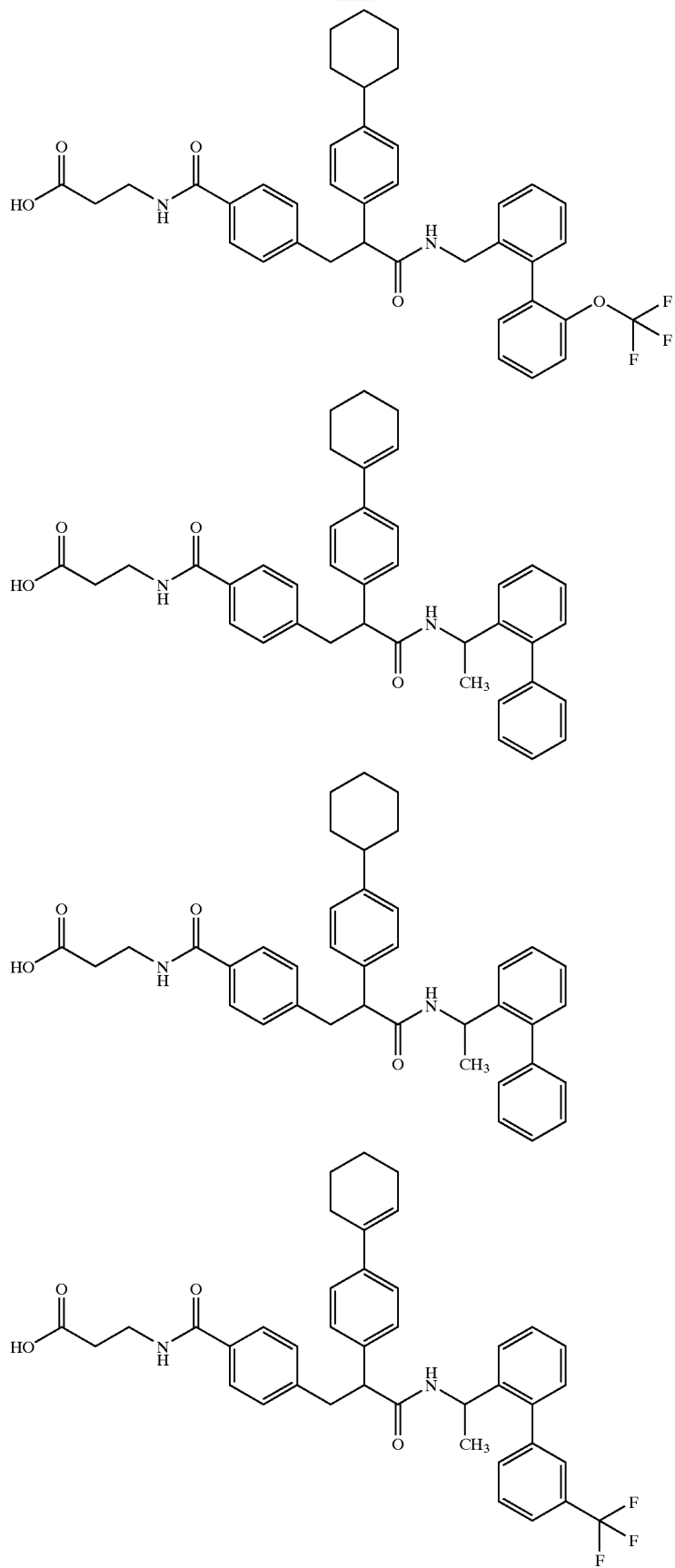

-continued
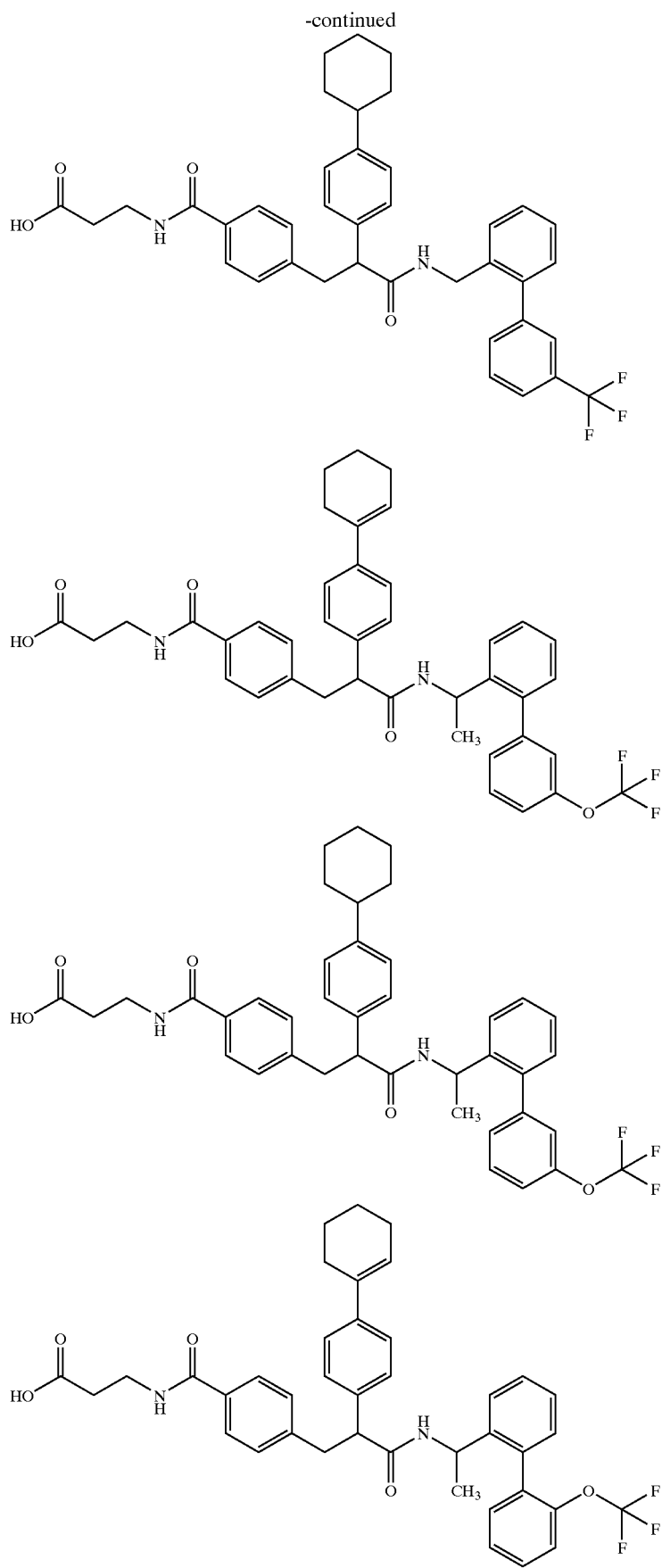

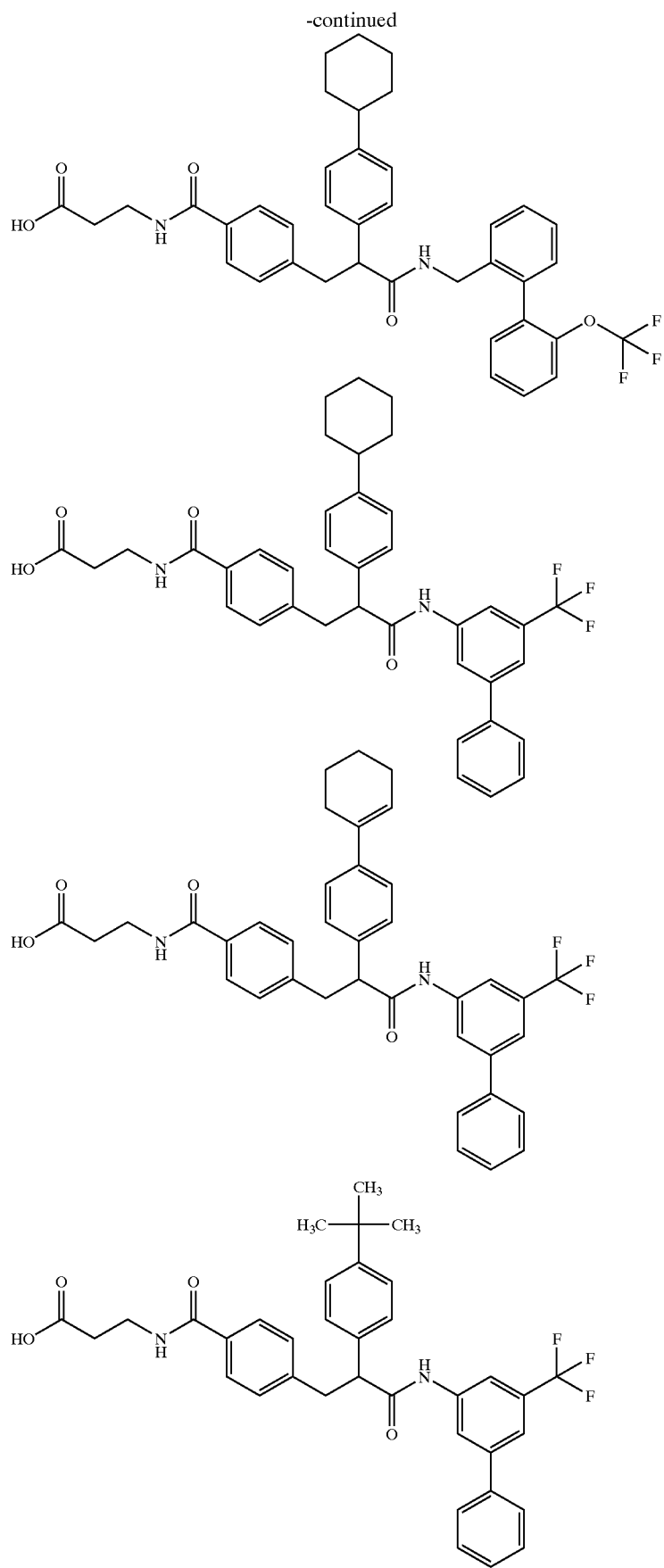

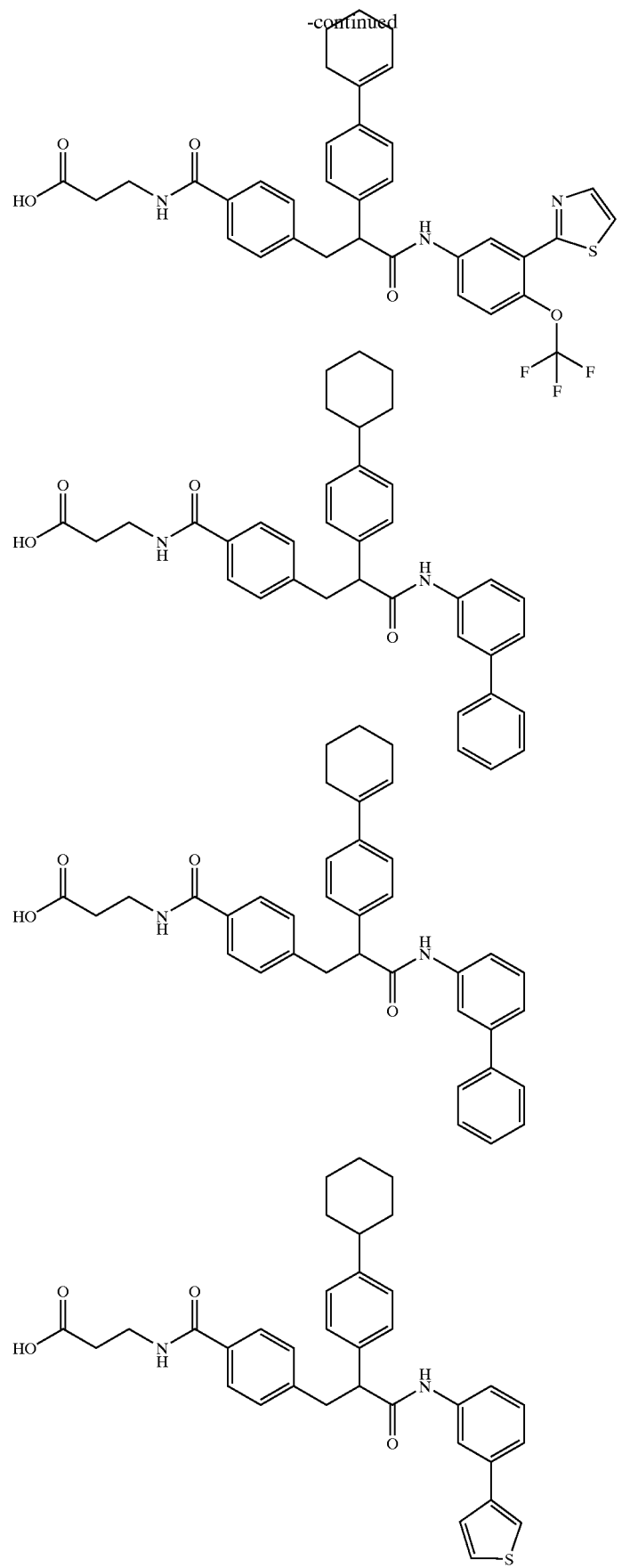

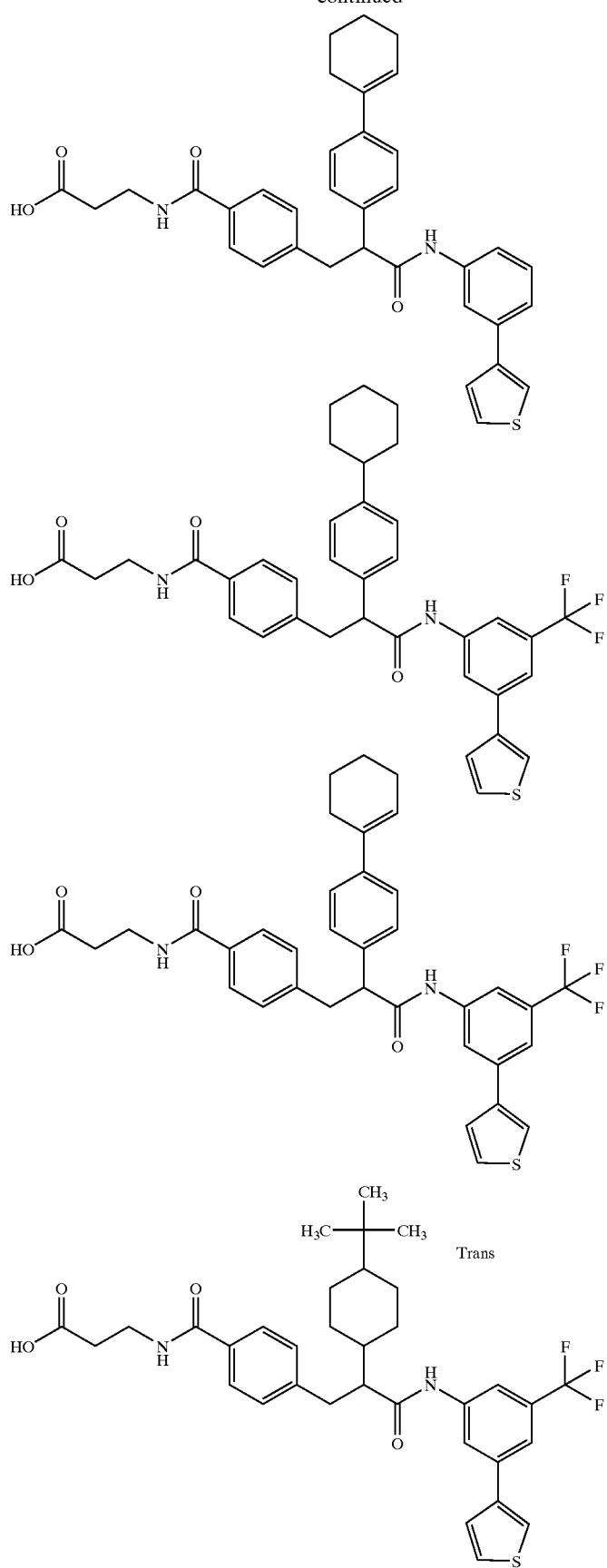

-continued
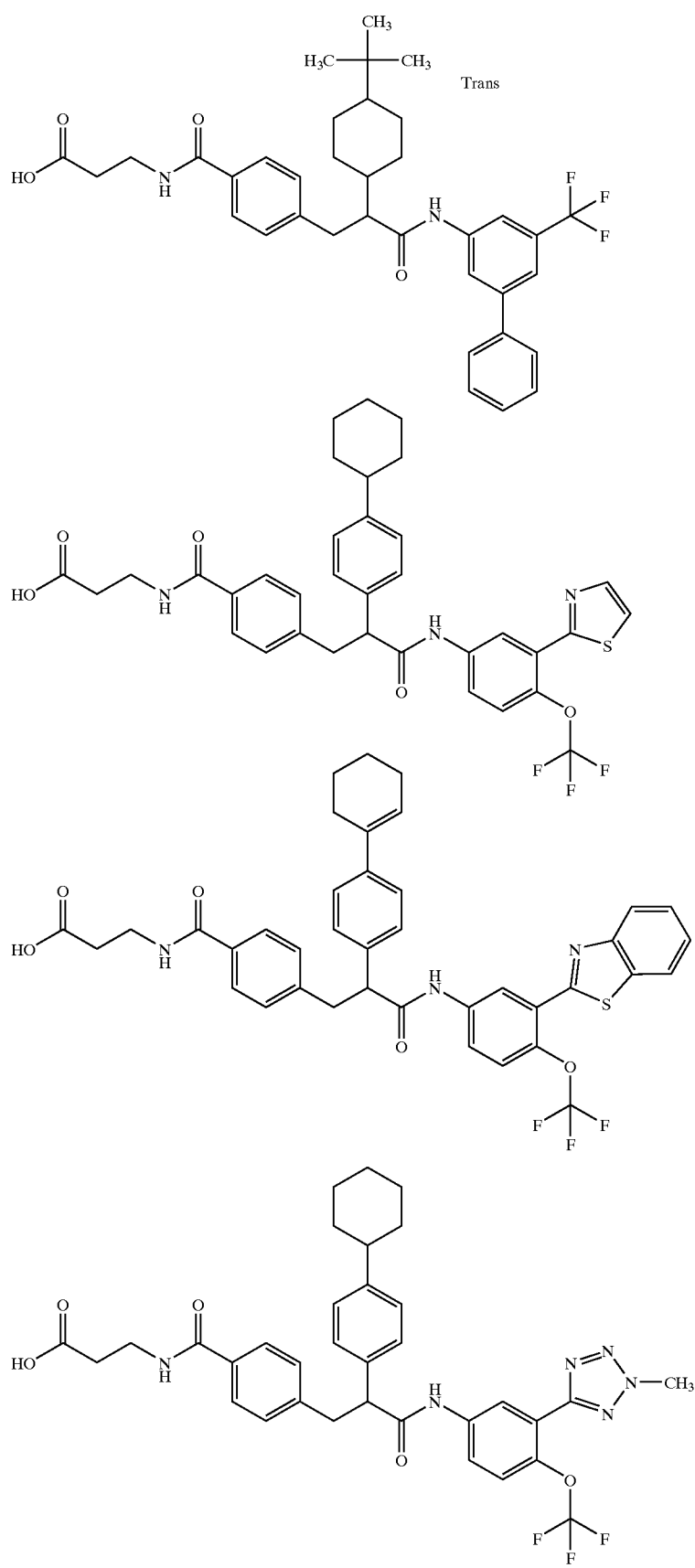

-continued
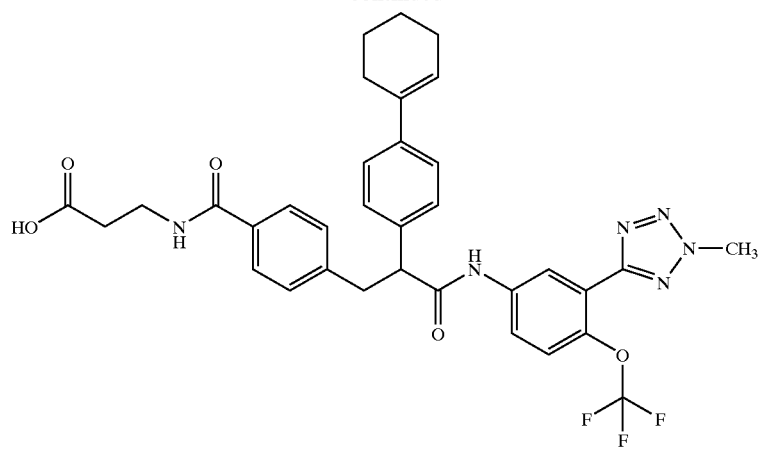
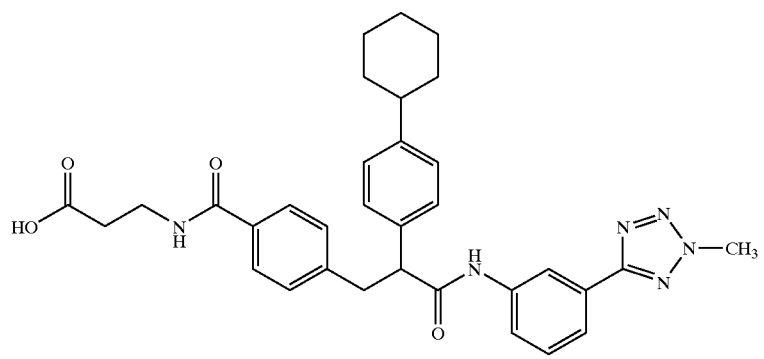
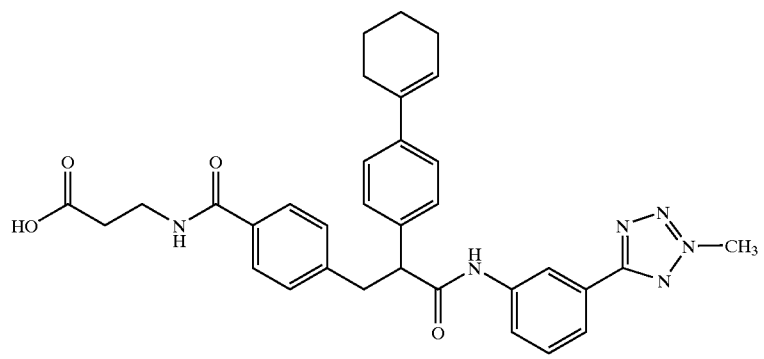
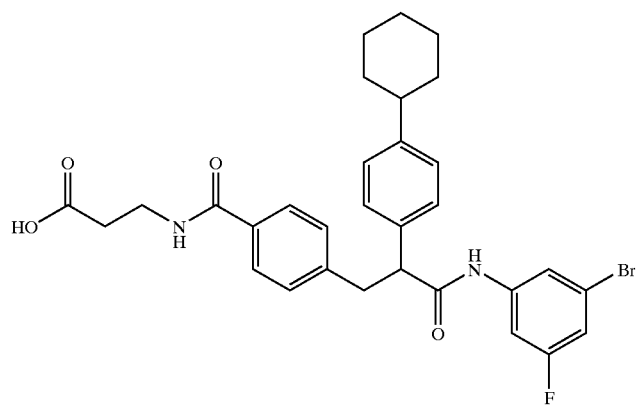

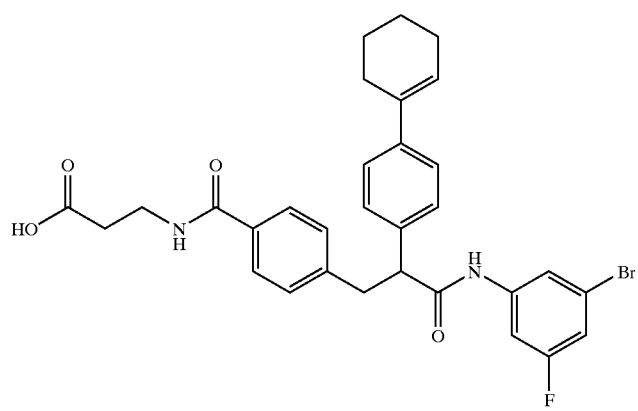
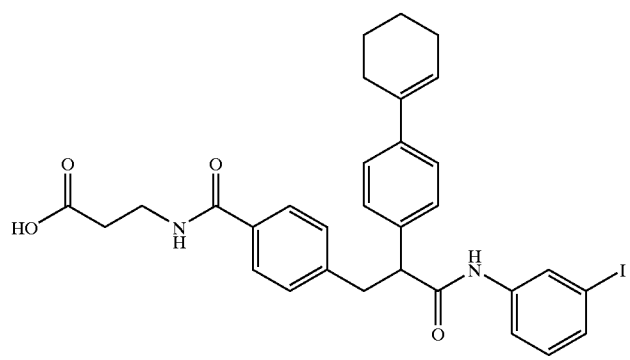
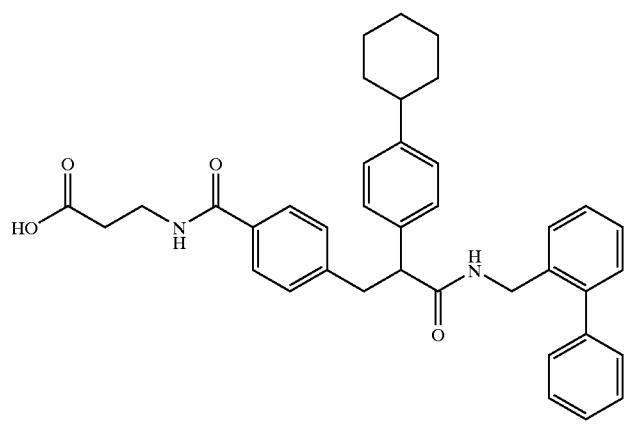
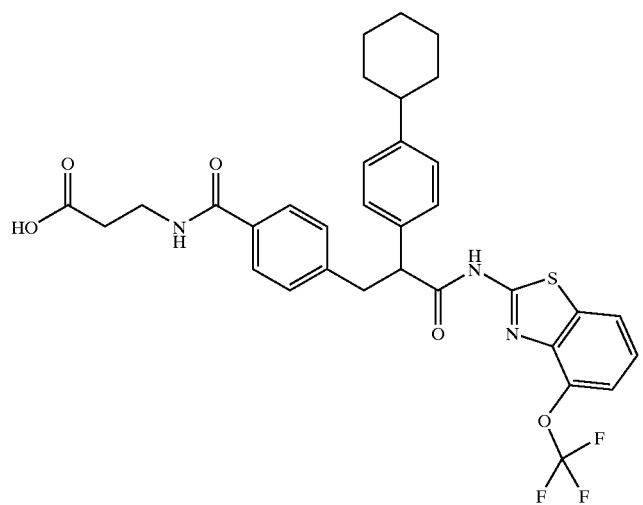

-continued
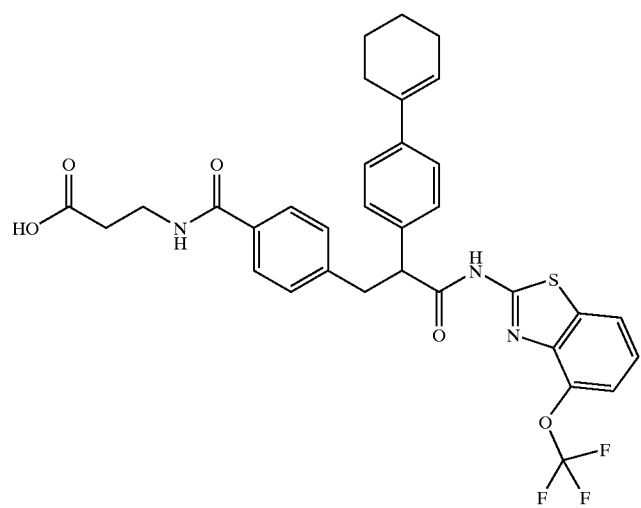
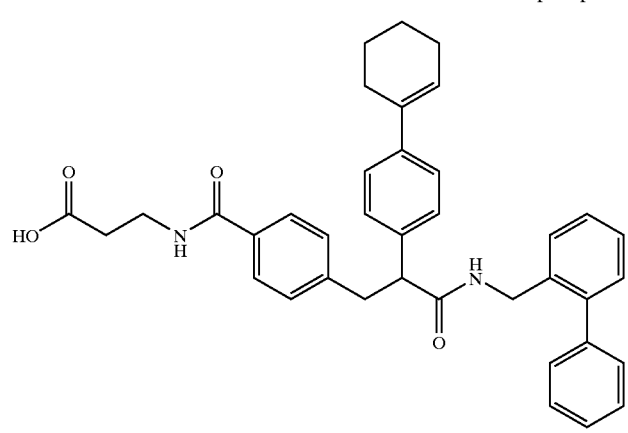
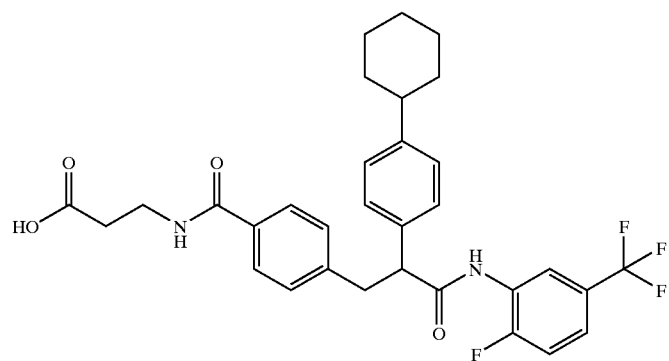
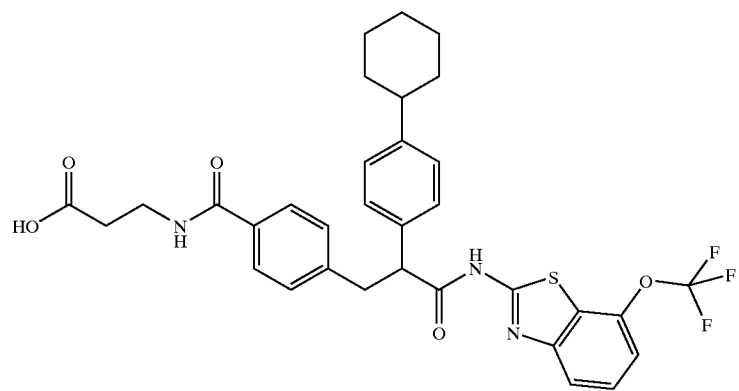

-continued
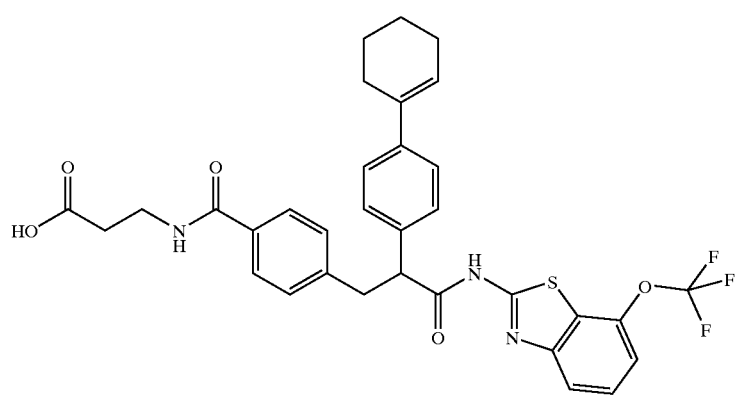
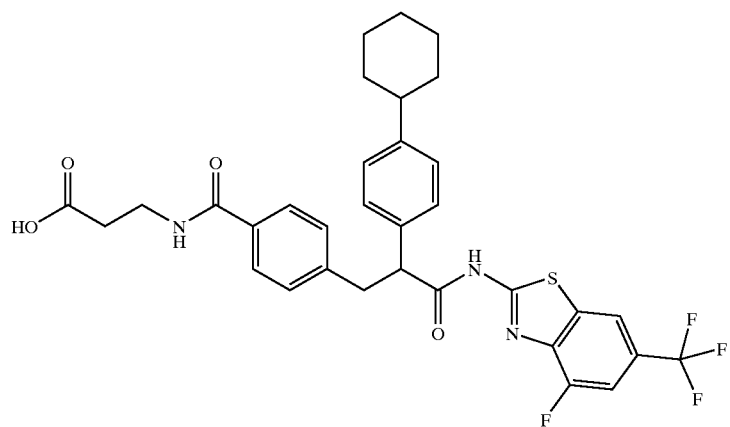
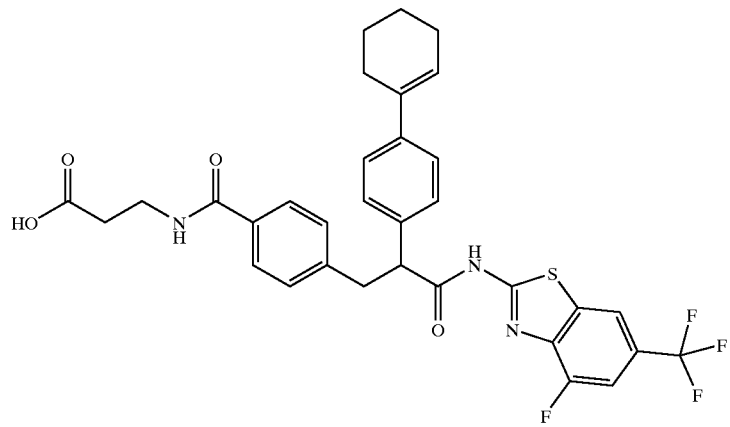
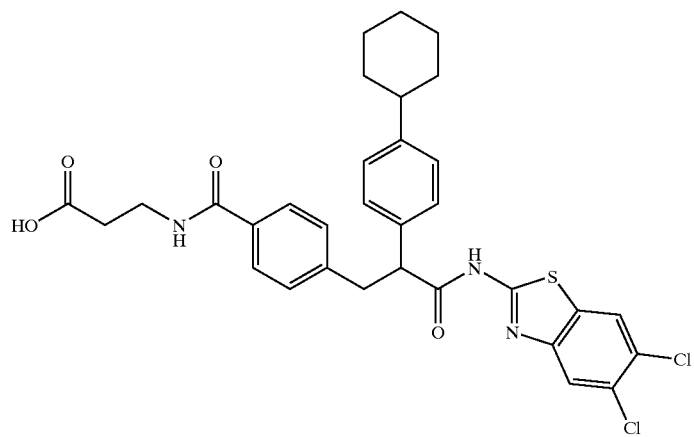

-continued
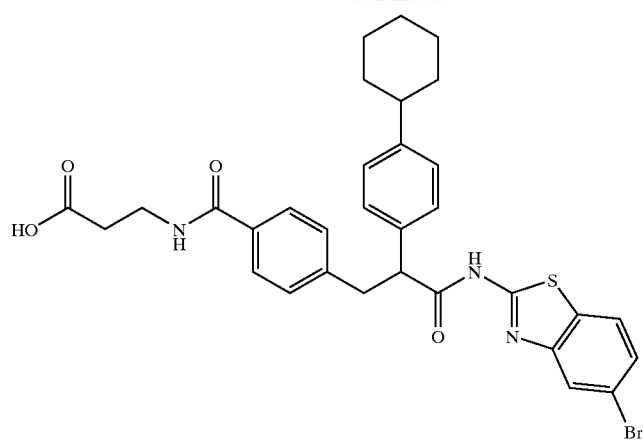
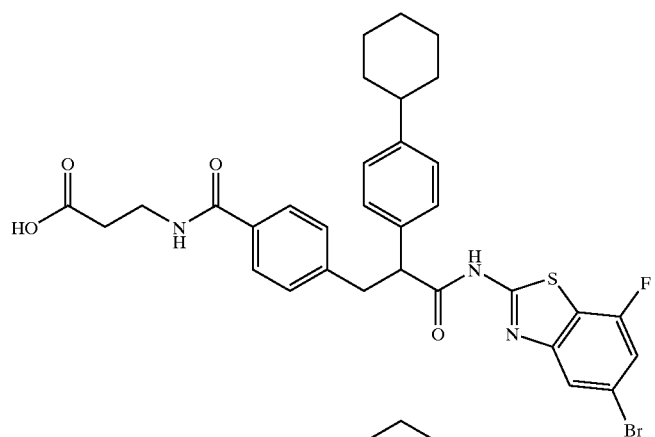
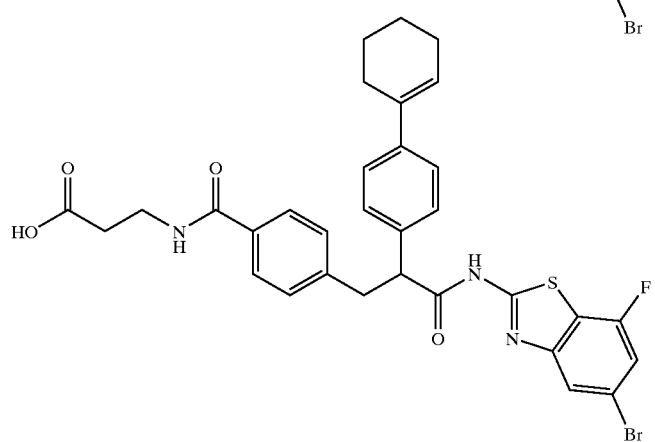
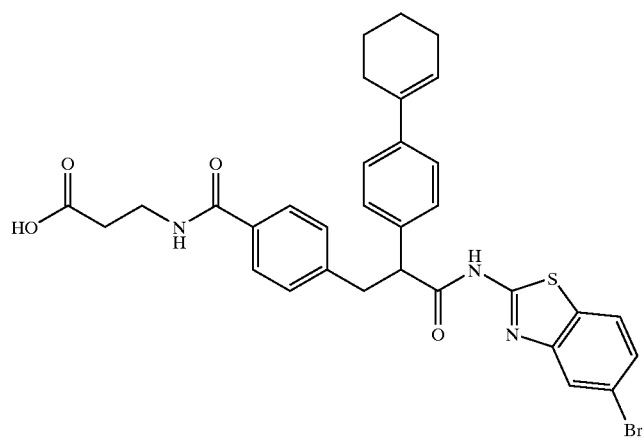

-continued
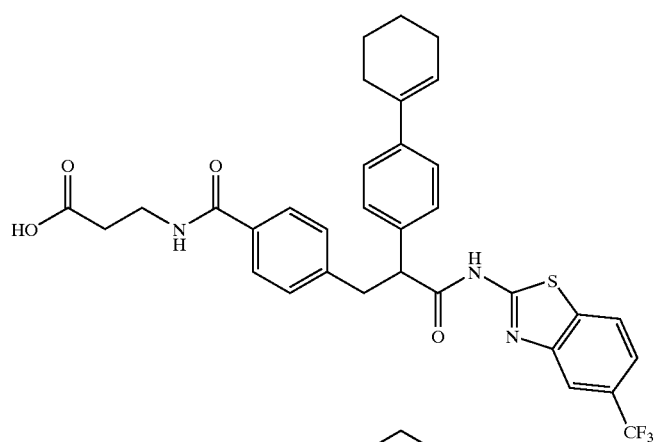
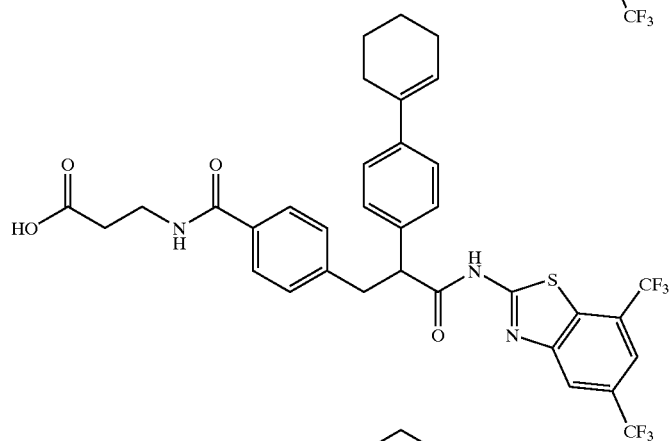
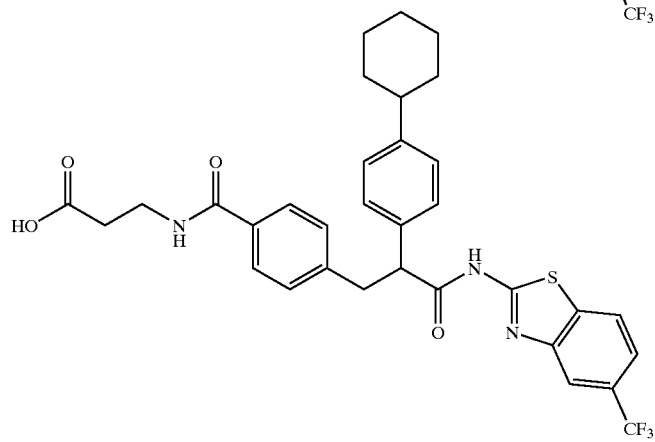
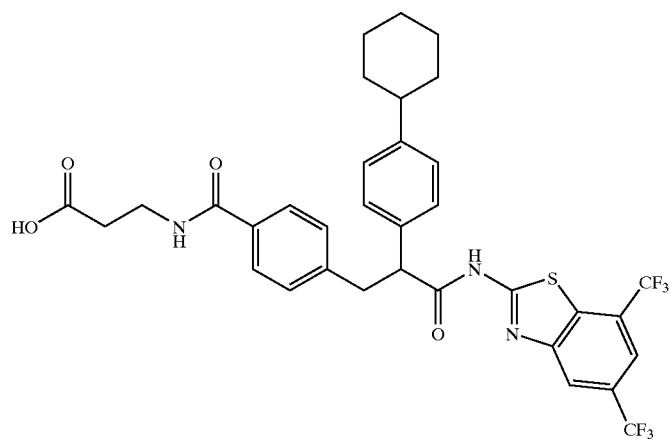

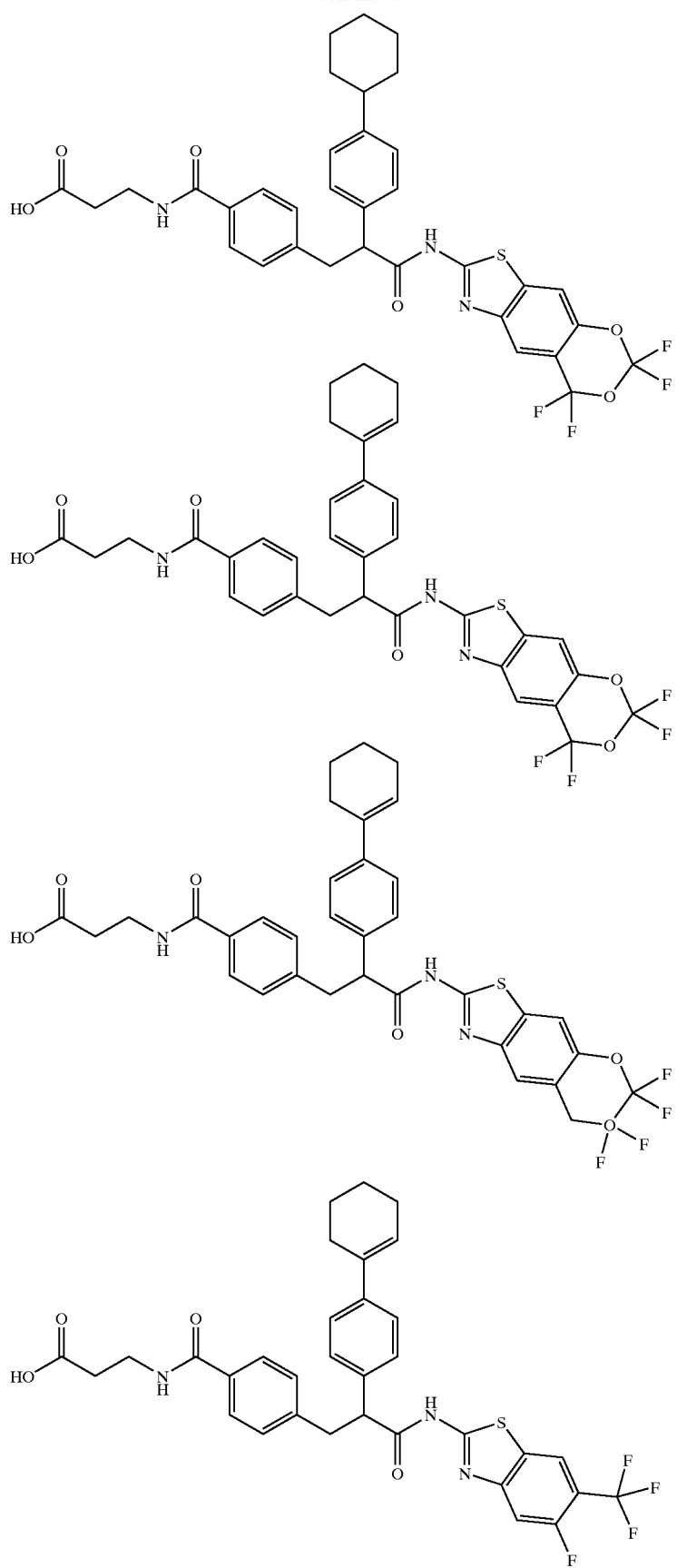

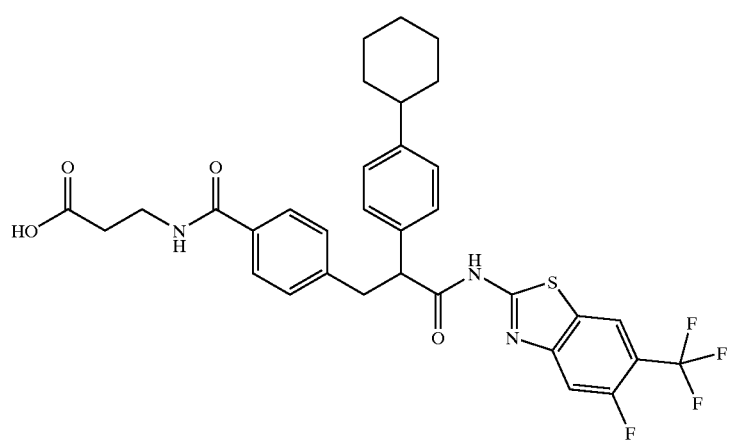
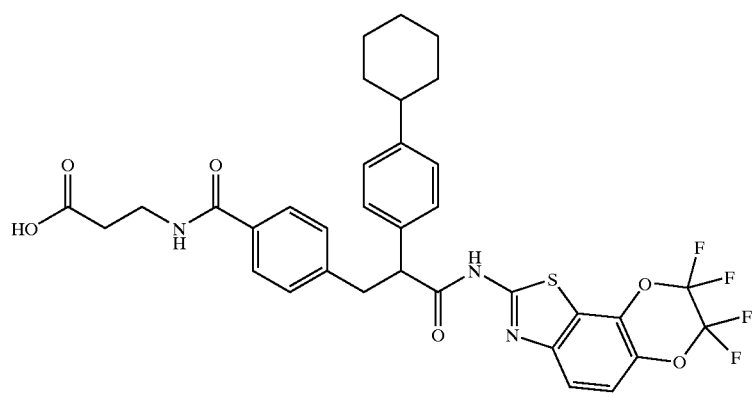
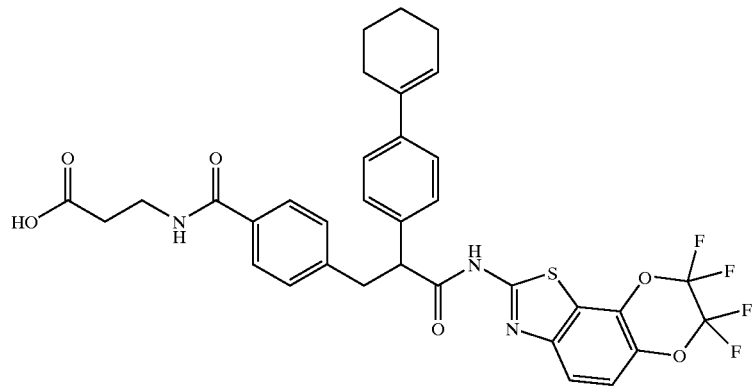
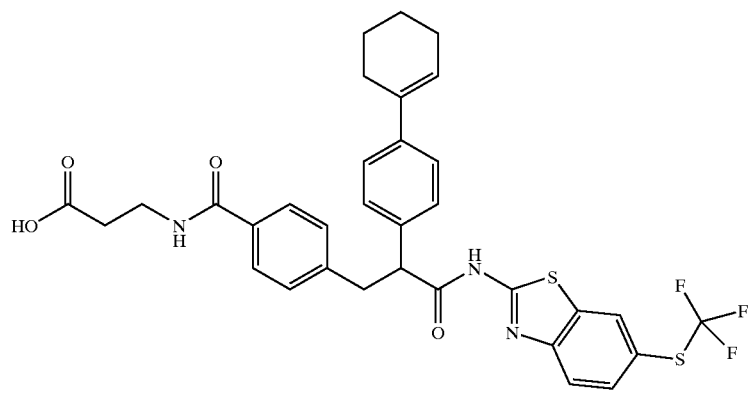

-continued
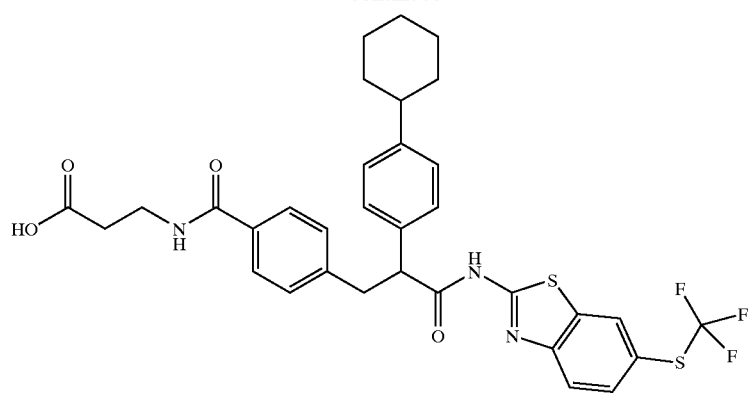
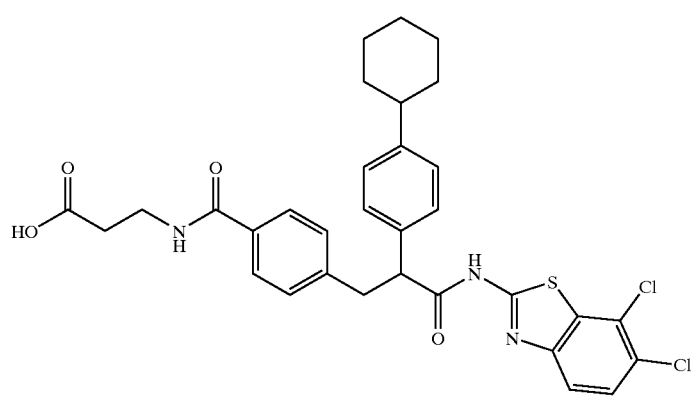
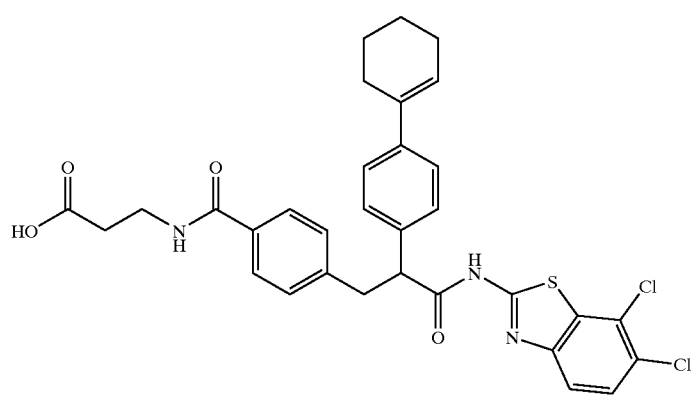
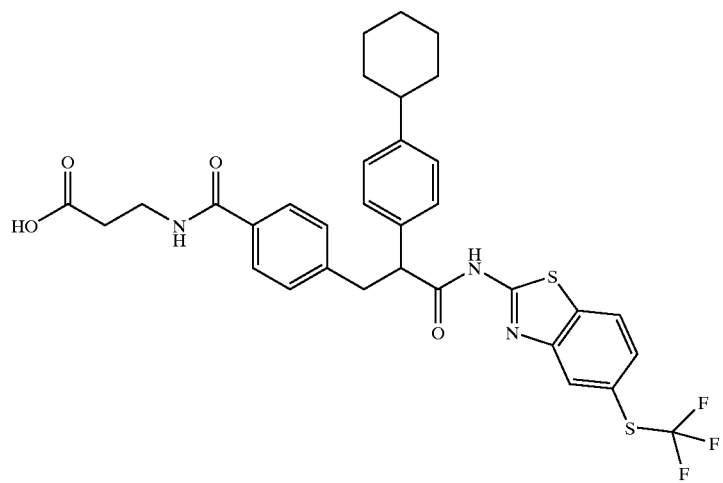

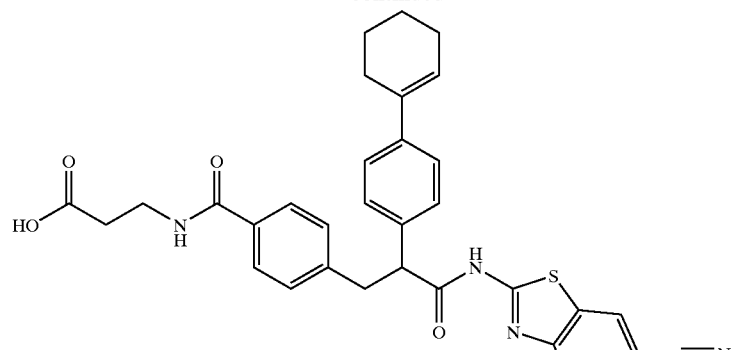
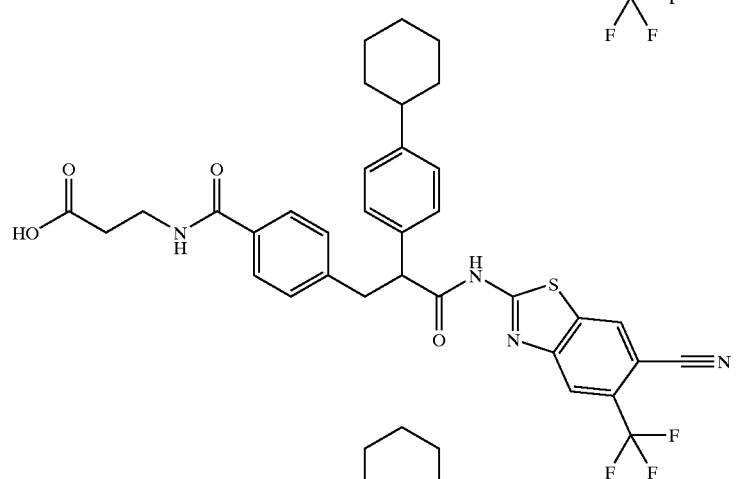
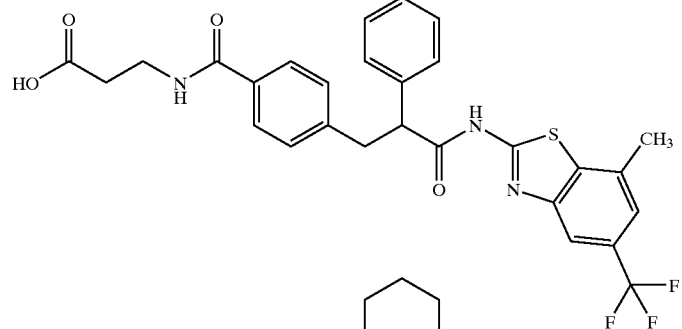
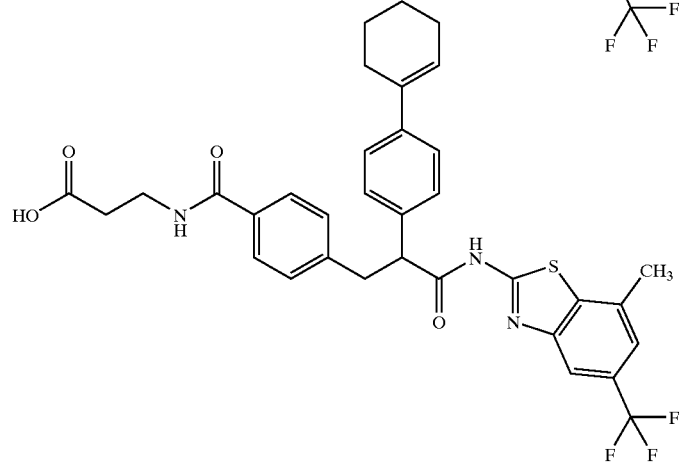

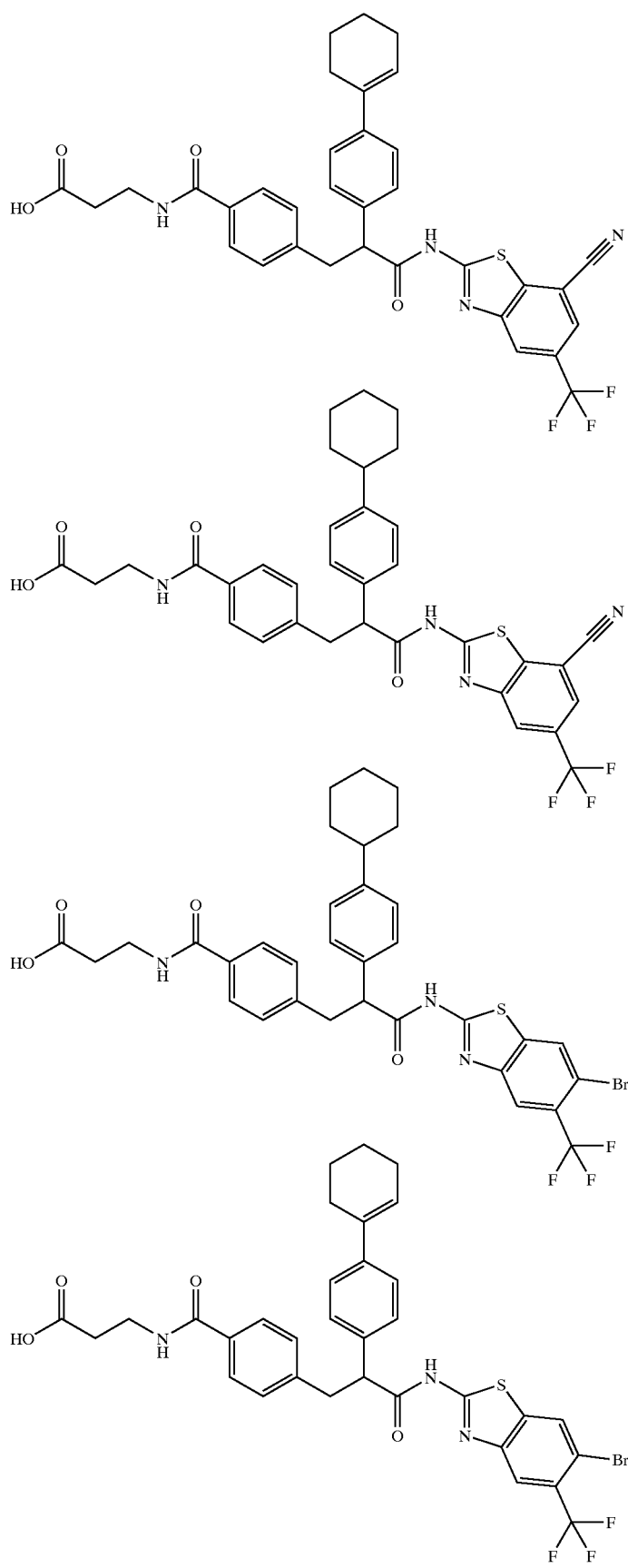

-continued
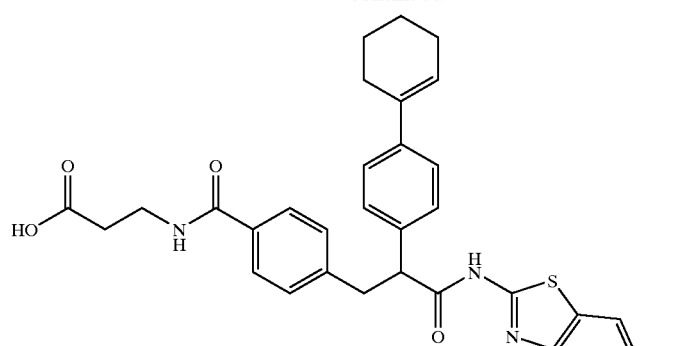
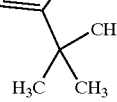
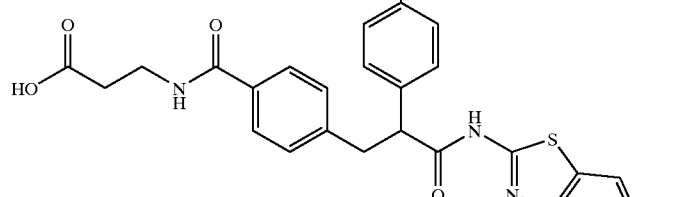
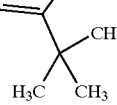
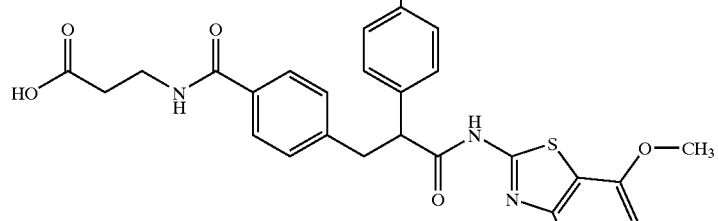
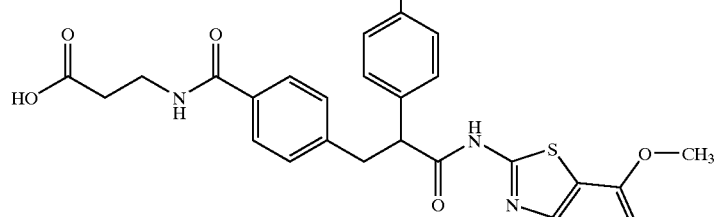

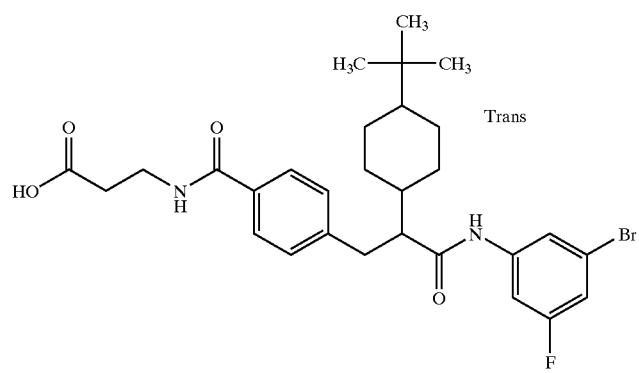
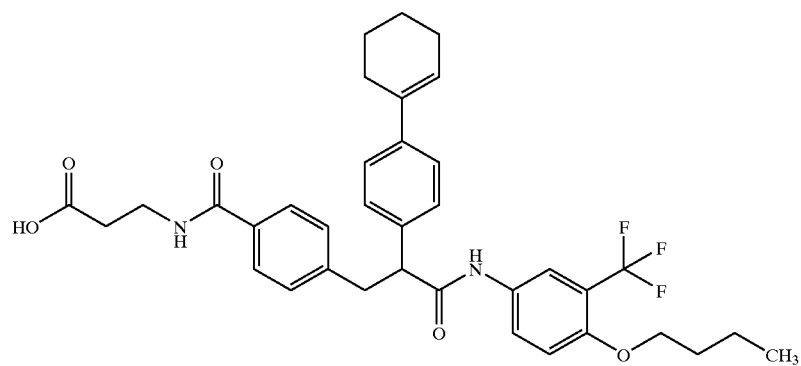
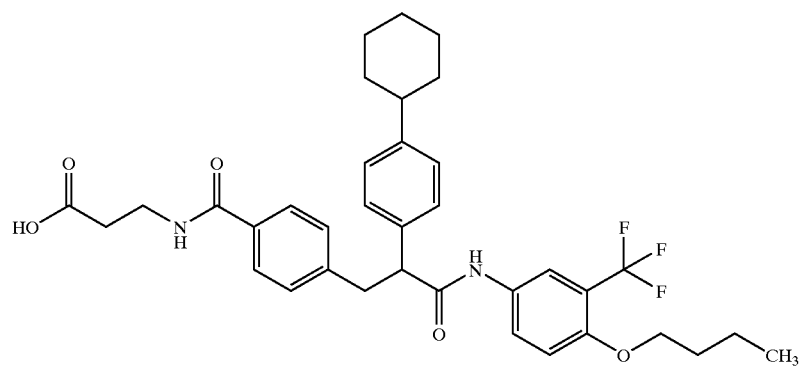
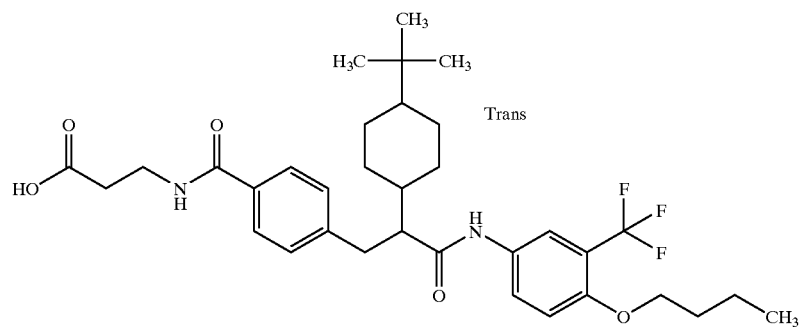

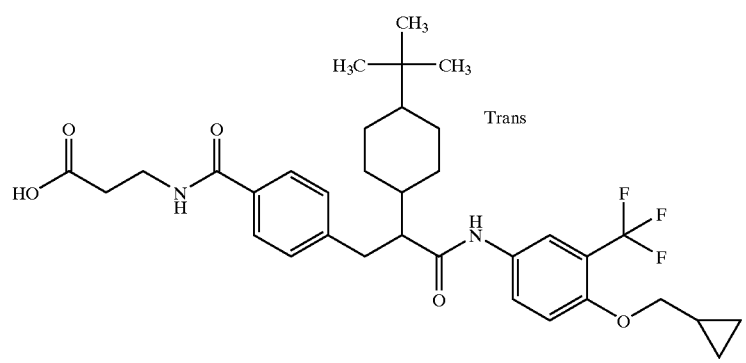
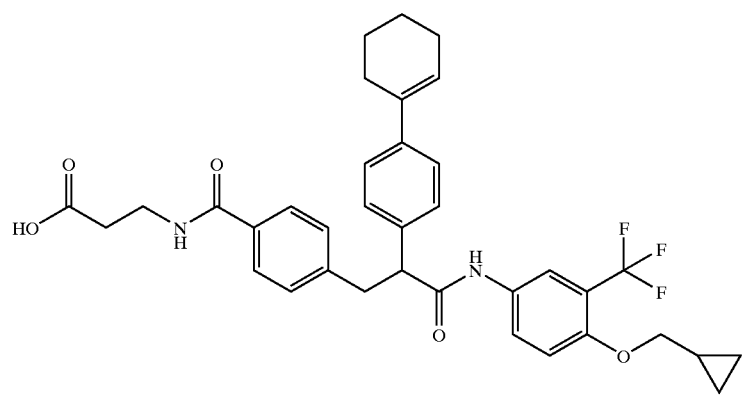
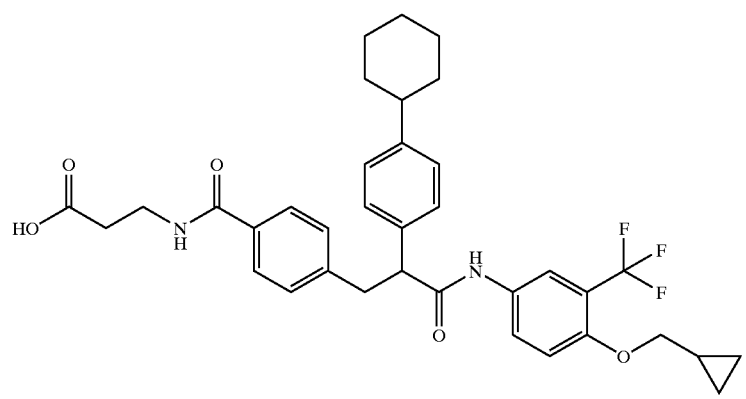
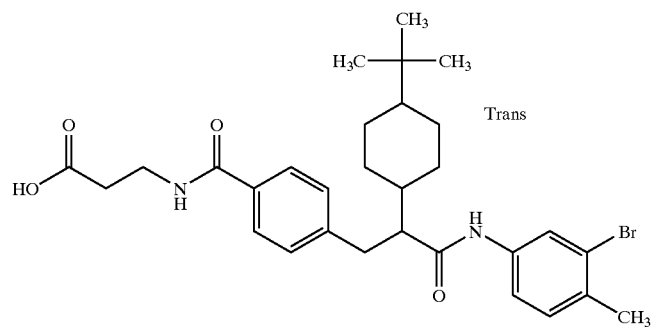

-continued
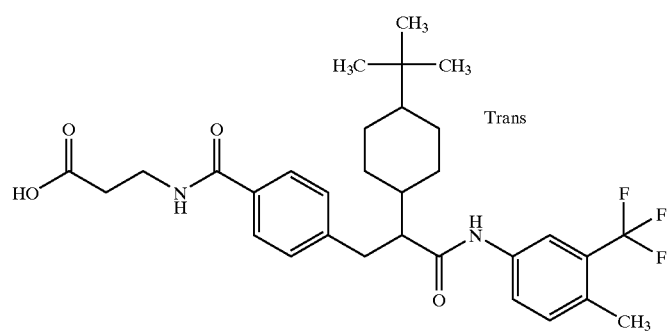
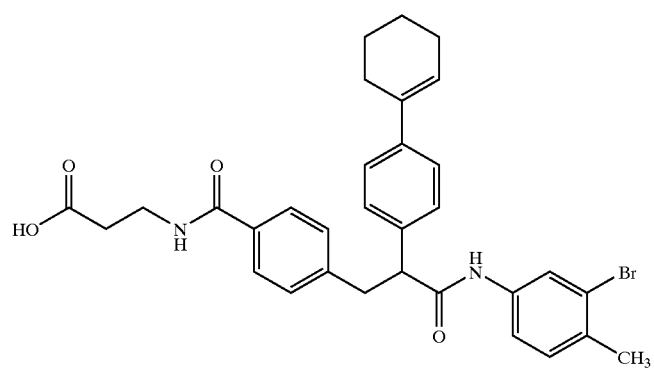
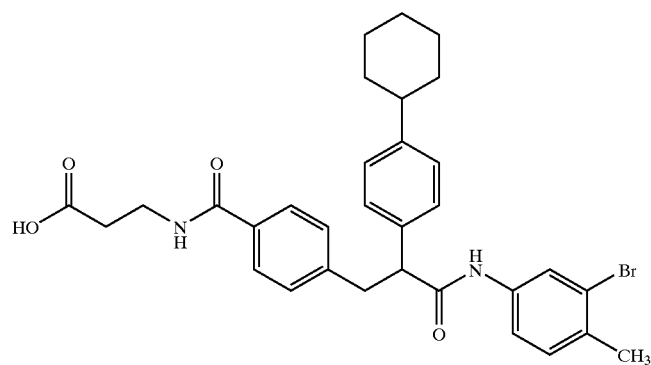
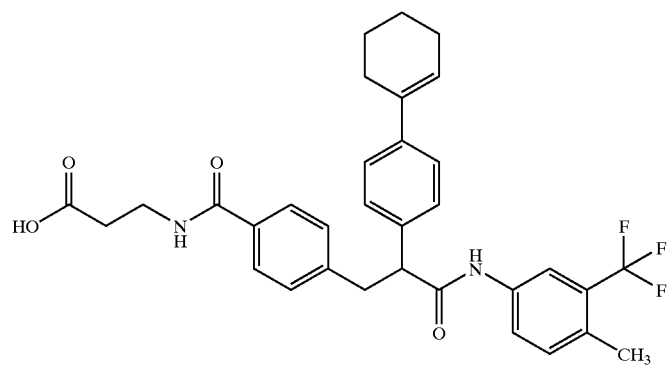

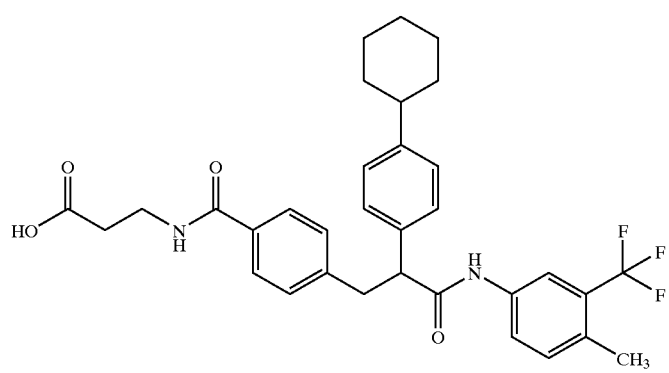
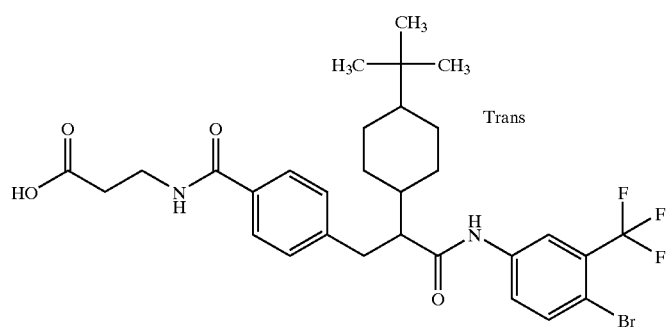
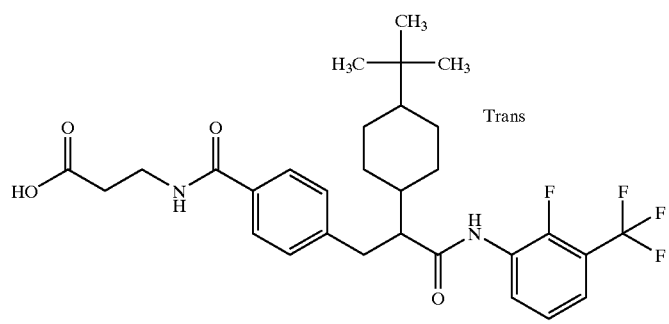
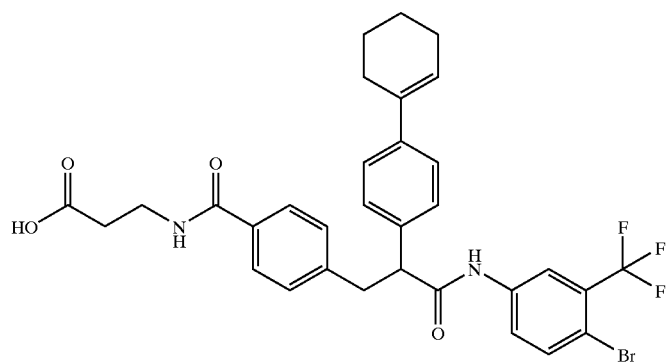

-continued
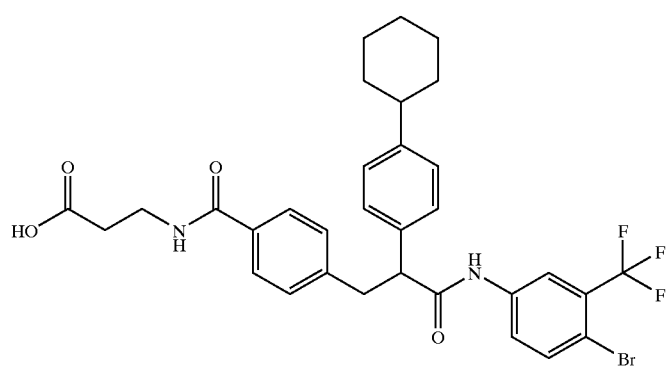
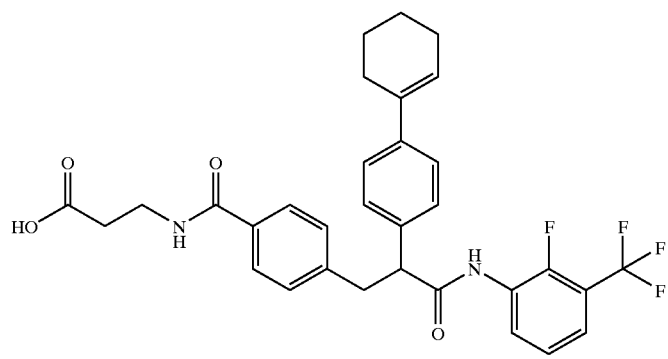
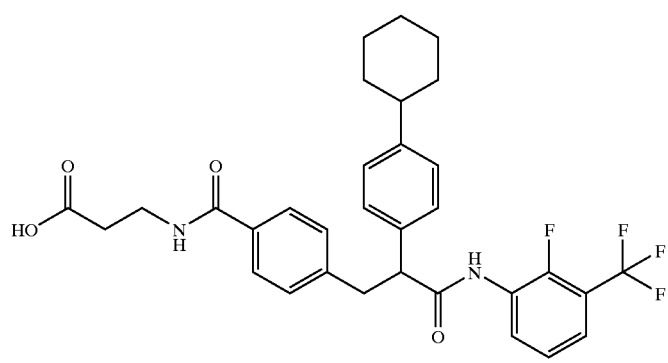
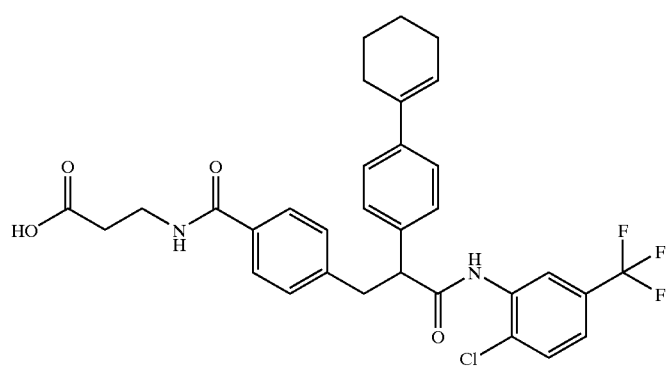

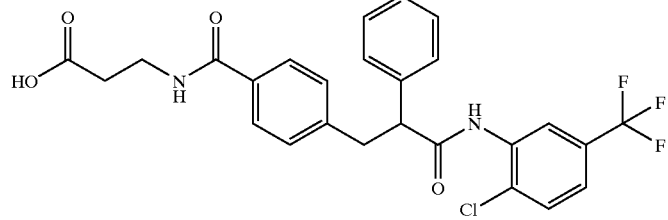
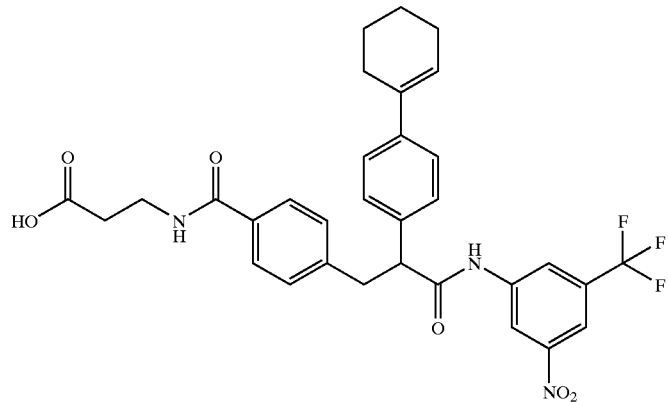
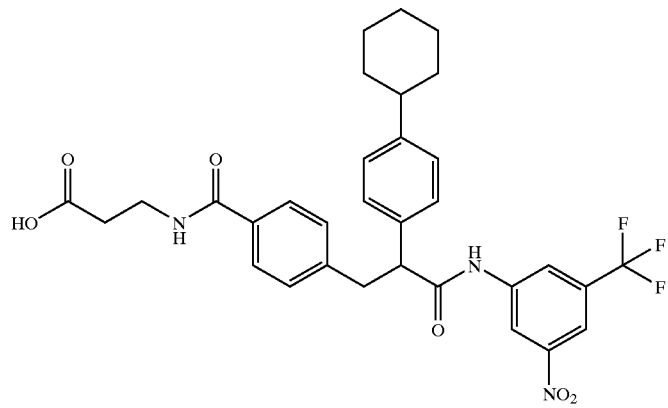
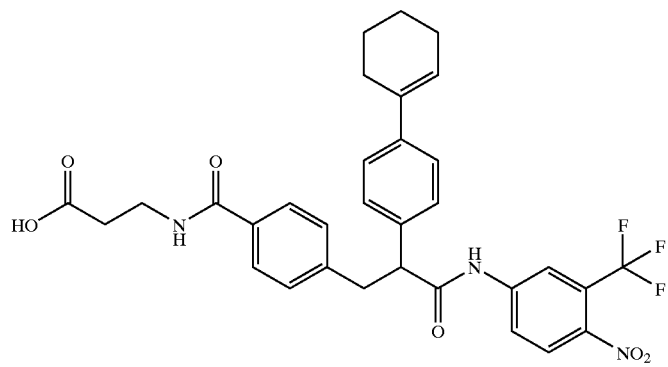

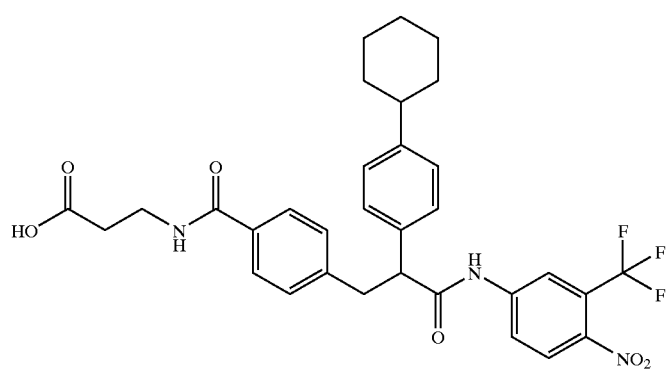
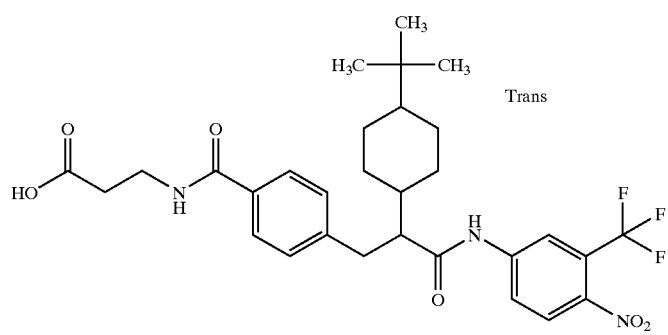
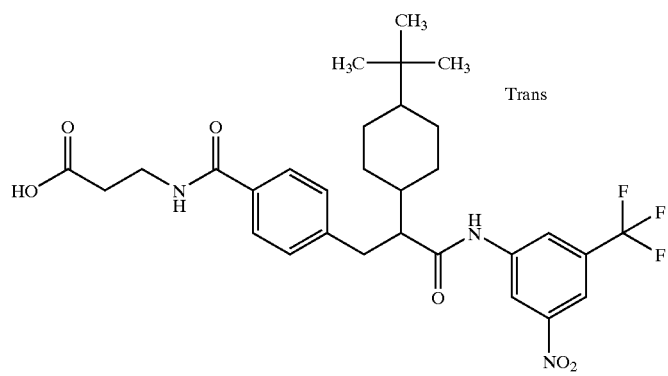
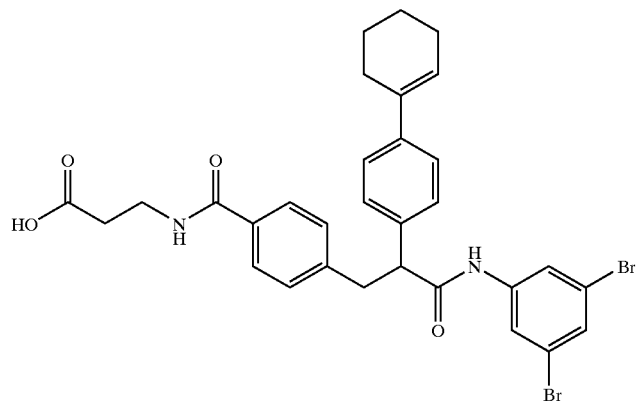

-continued
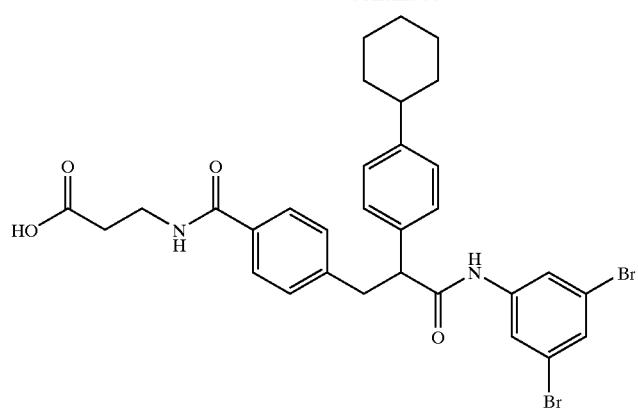
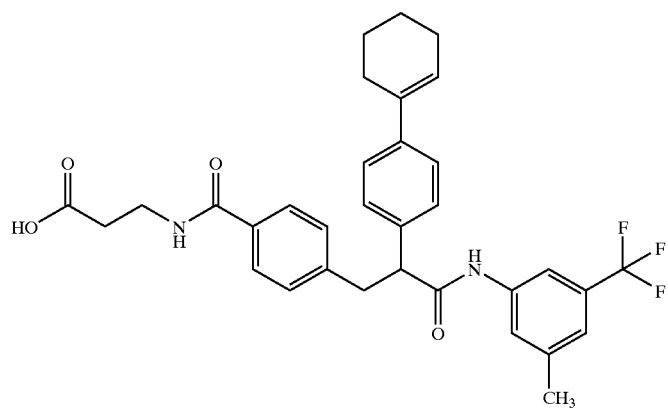
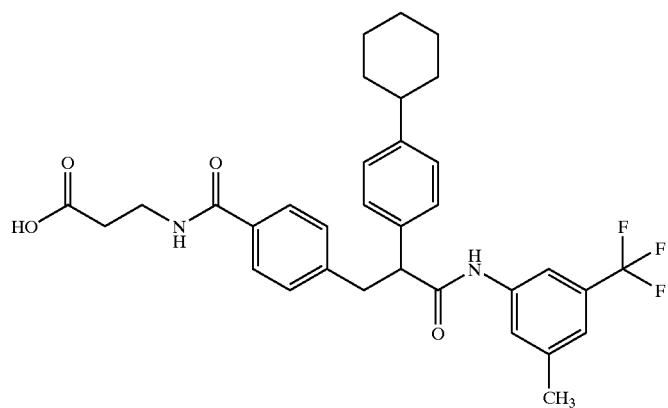
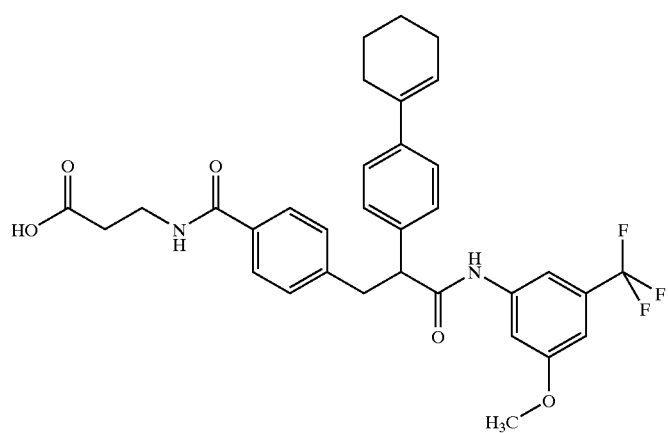

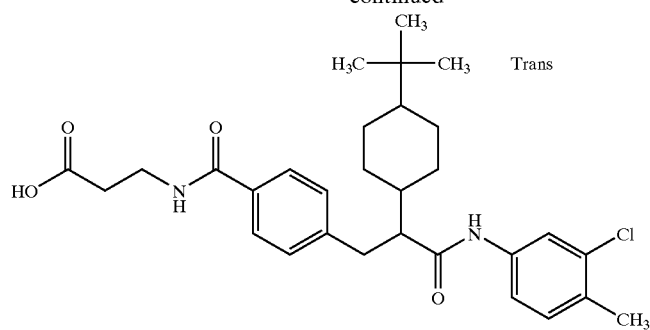
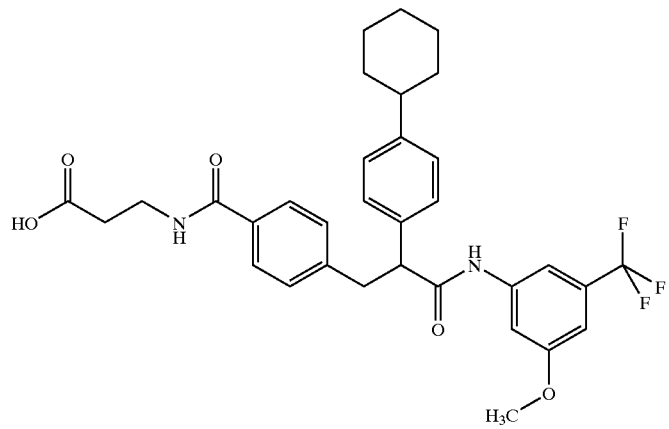
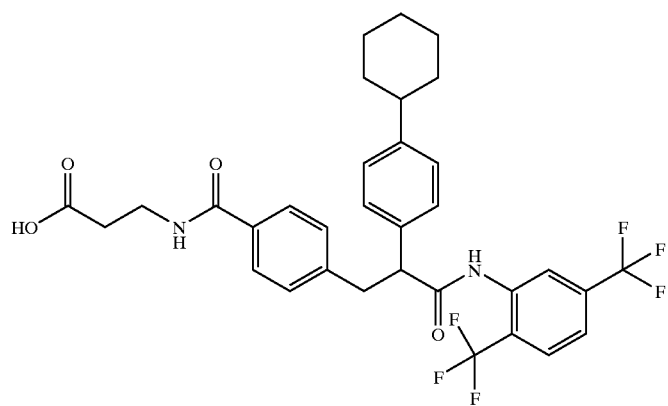
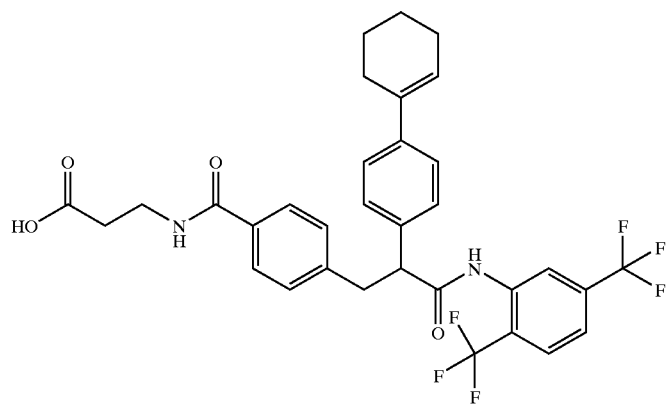

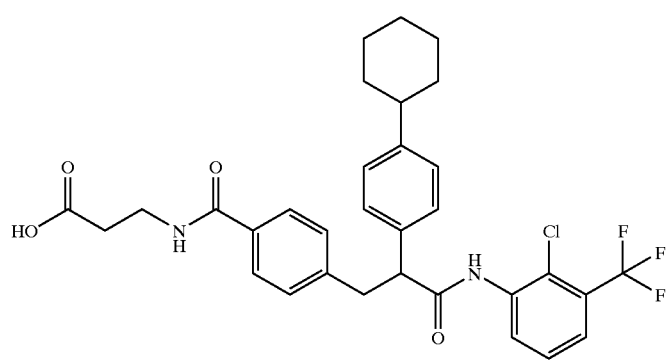
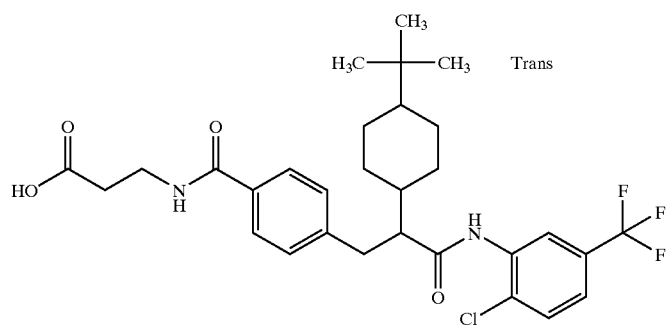
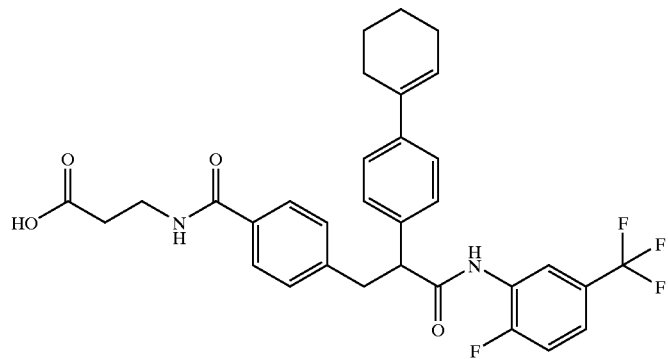
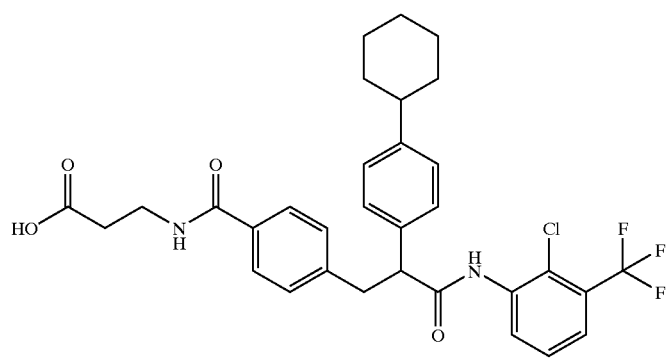

-continued
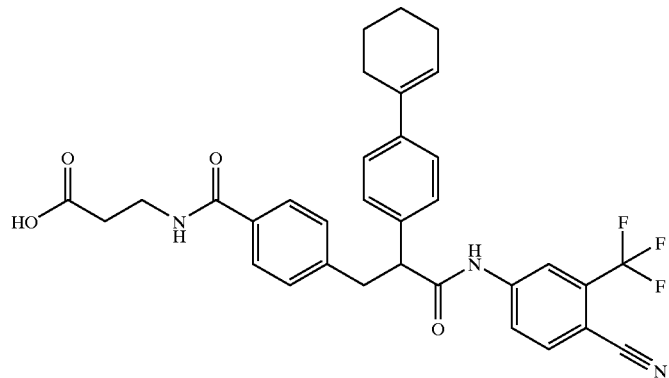
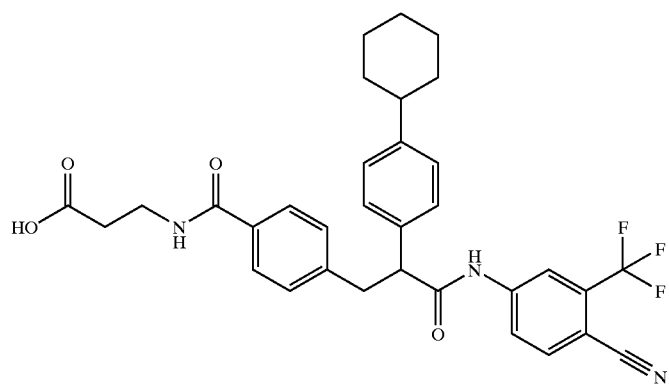
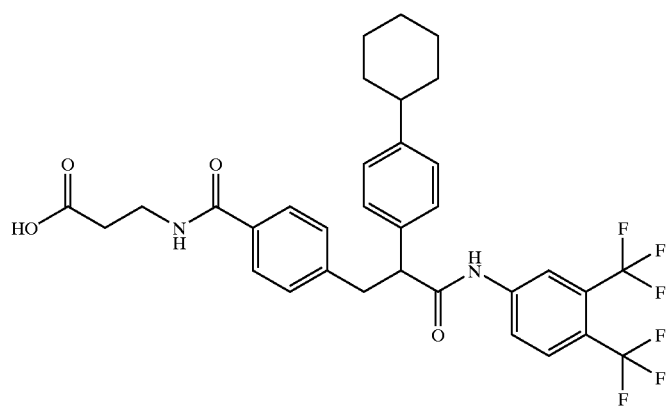
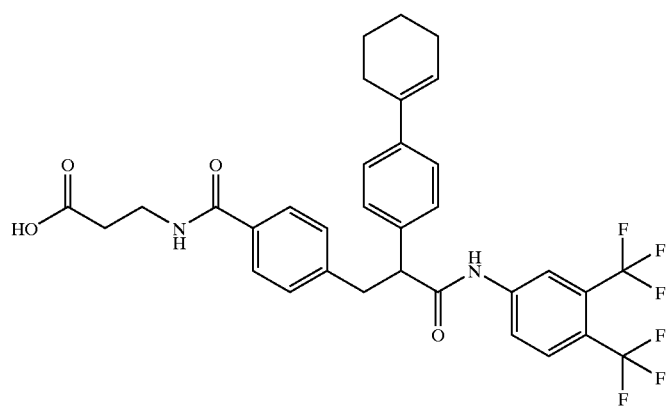

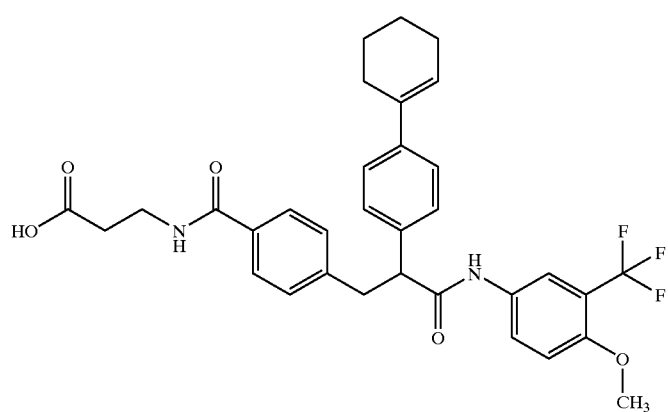
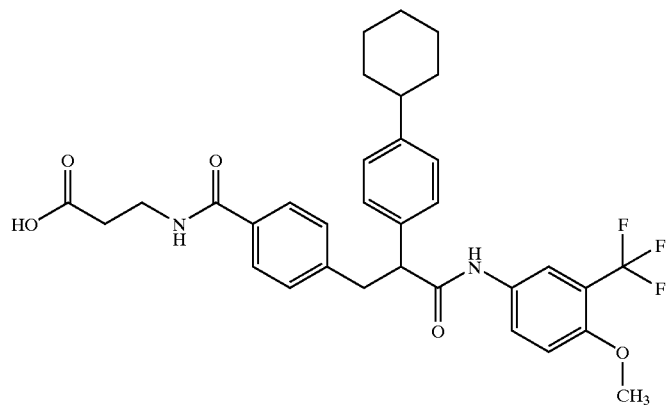
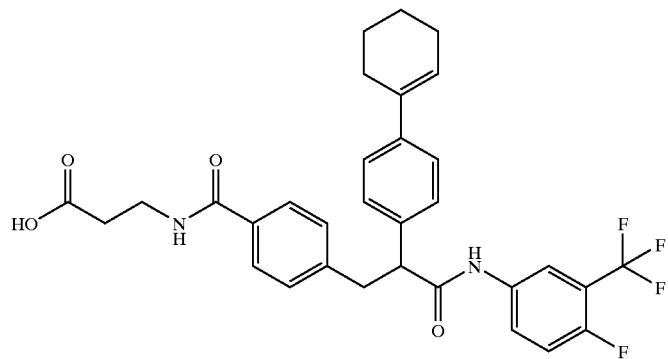
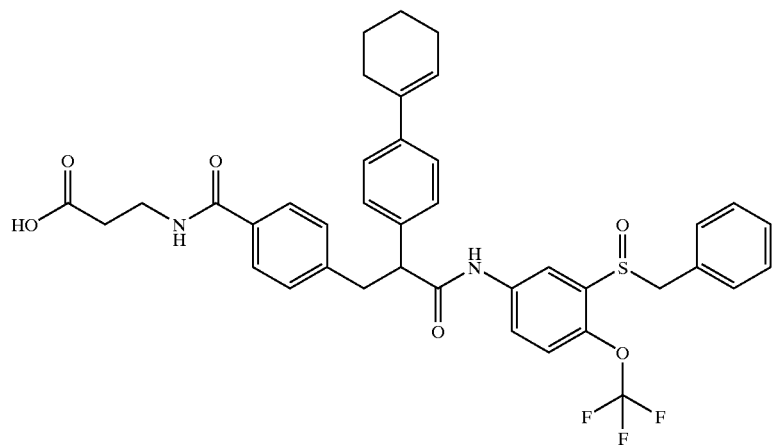

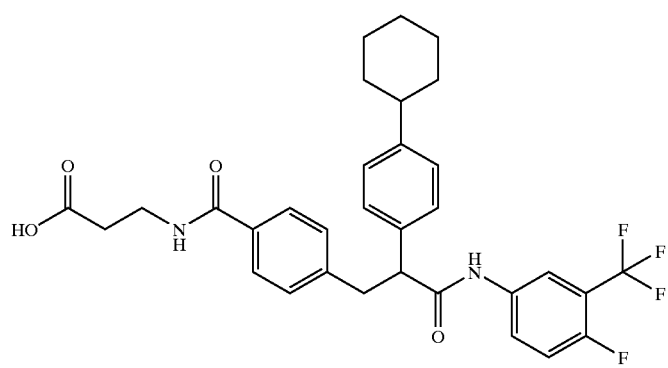
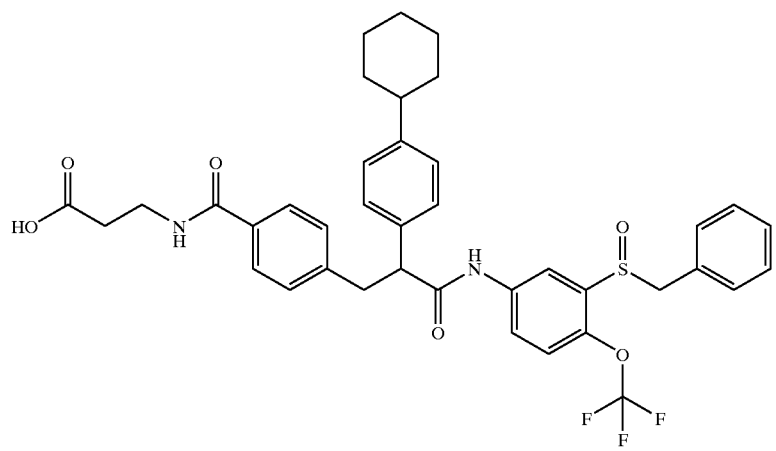
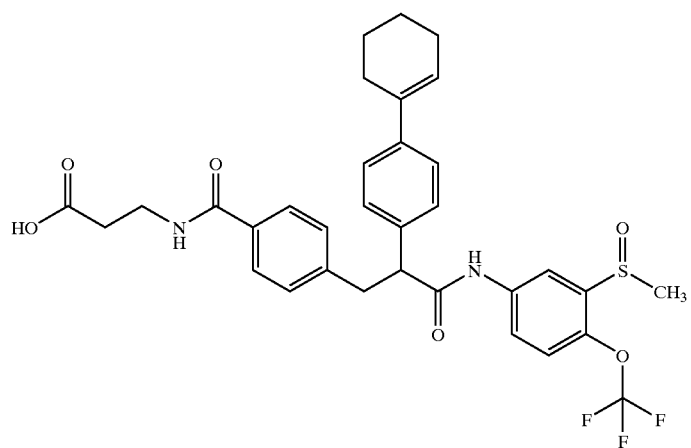
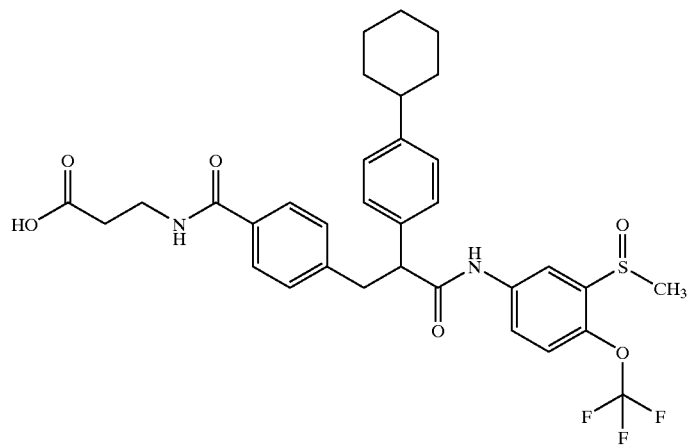

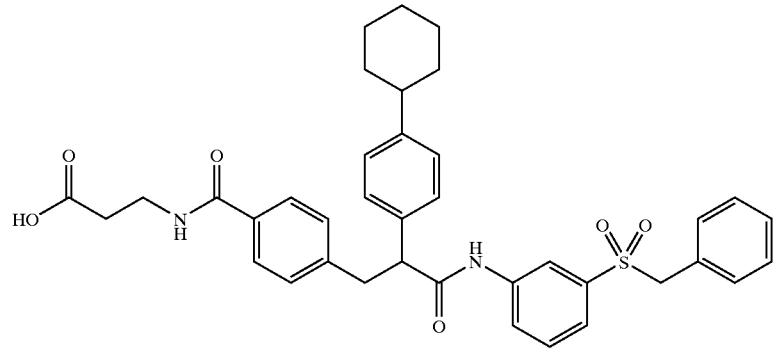
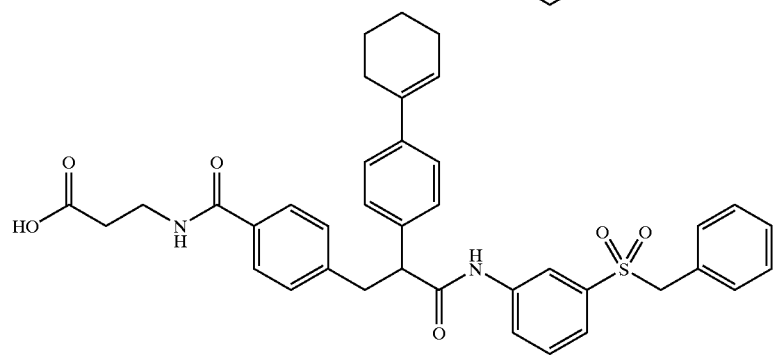
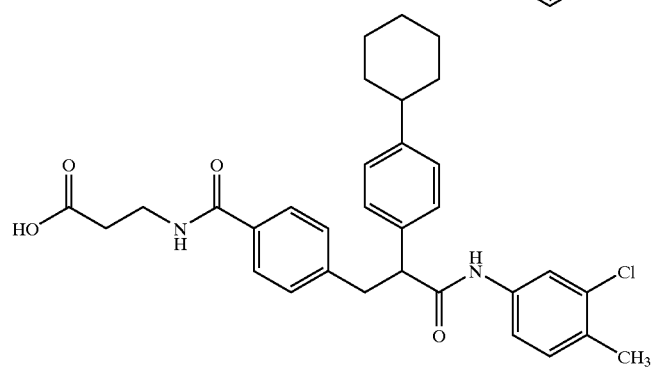
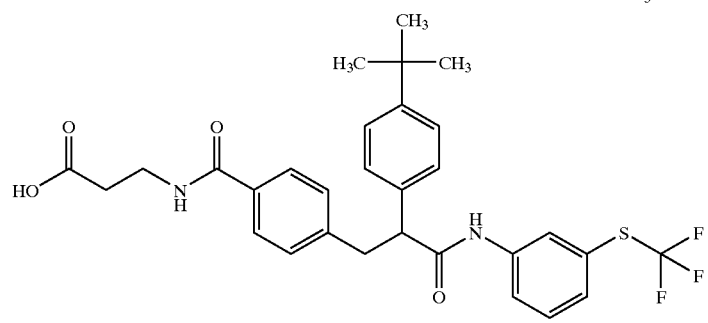
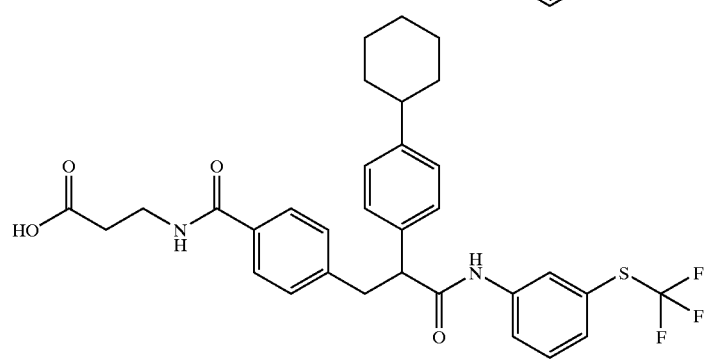

-continued
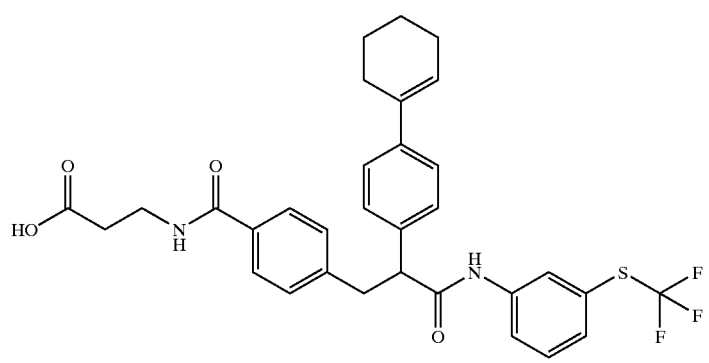
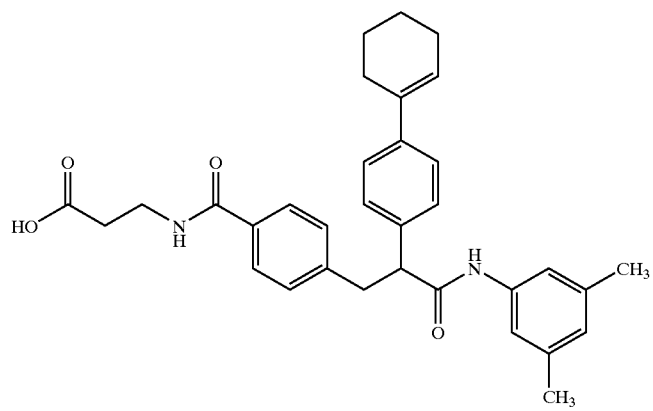
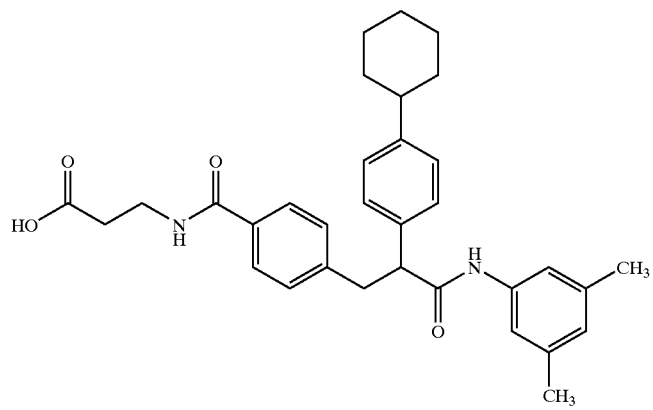
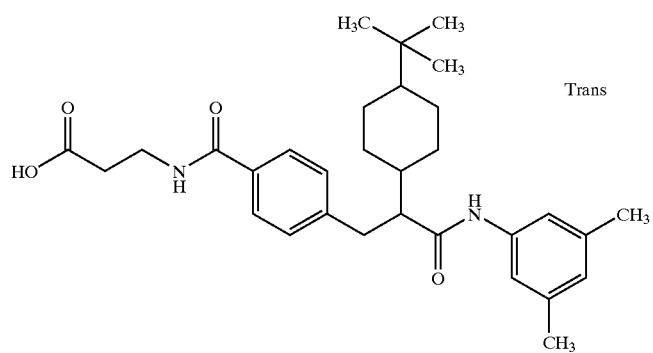

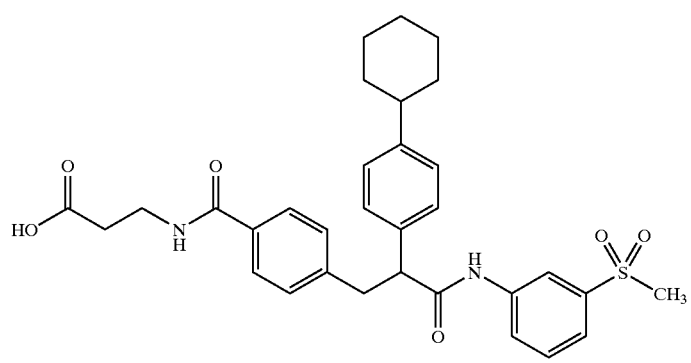
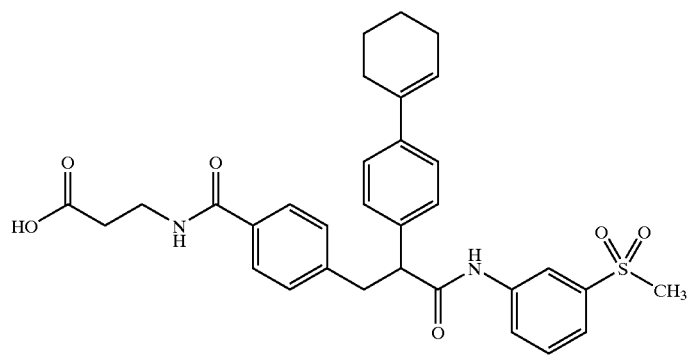
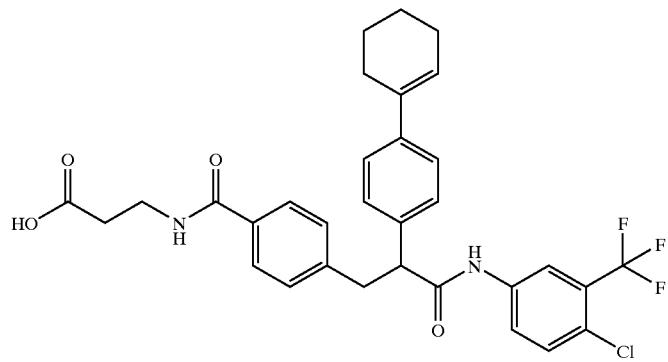
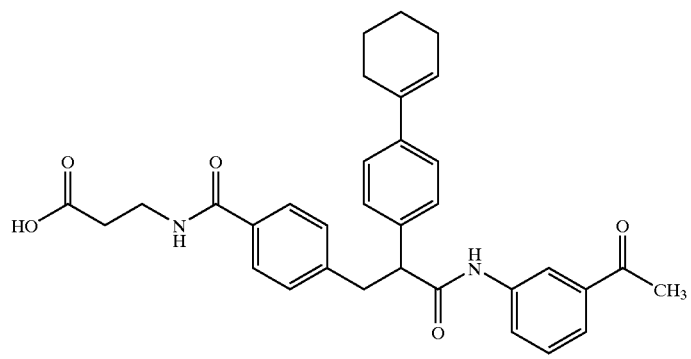

-continued
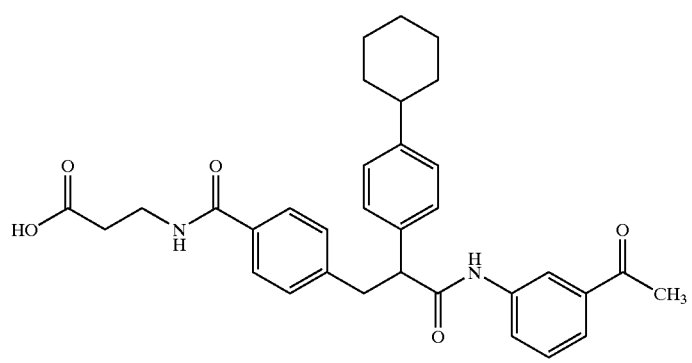
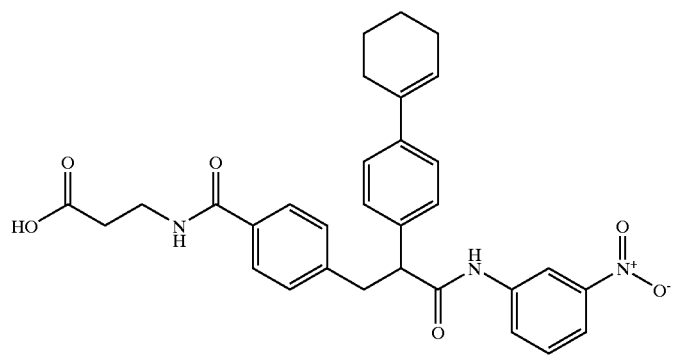
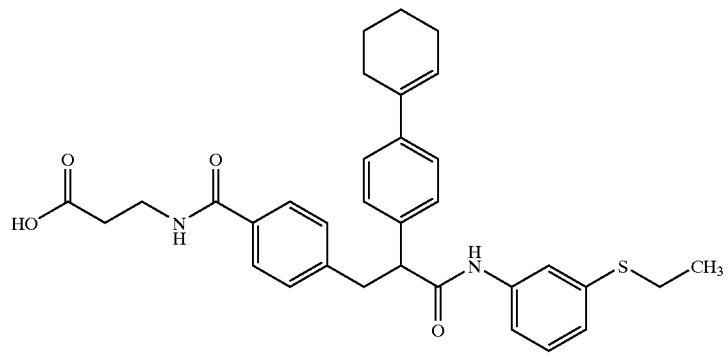
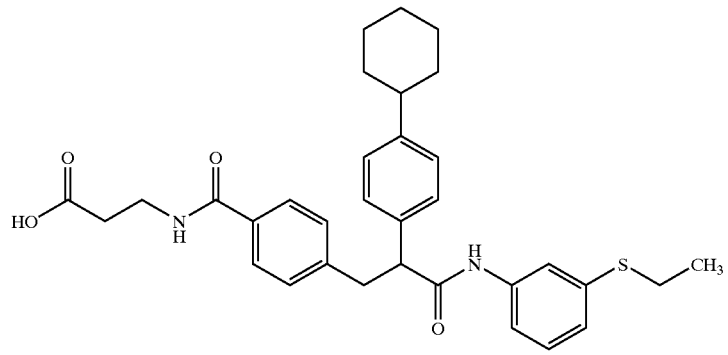

-continued
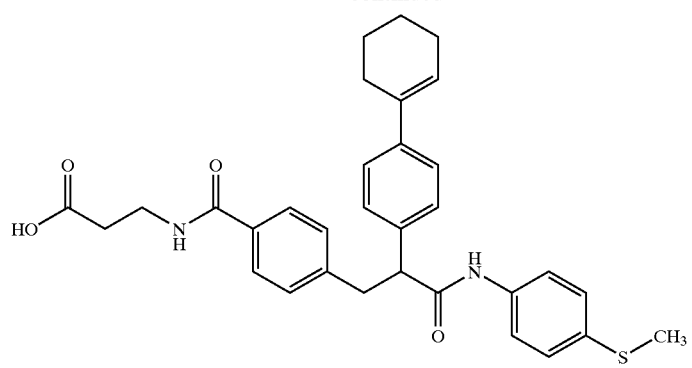
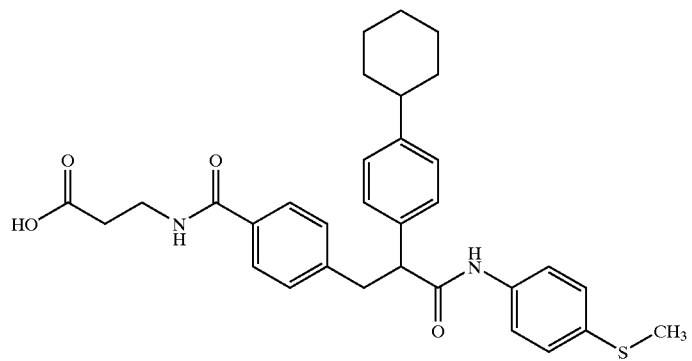
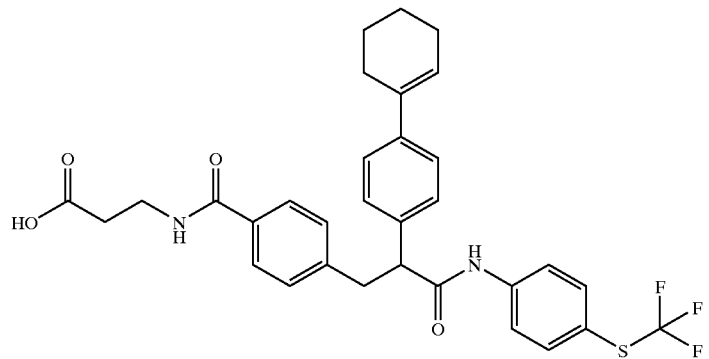
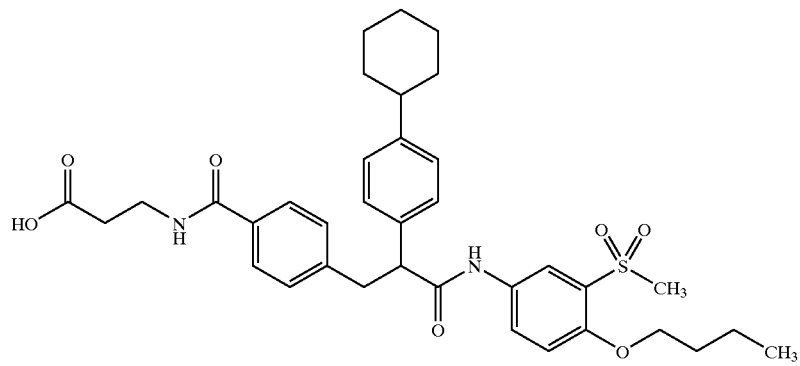

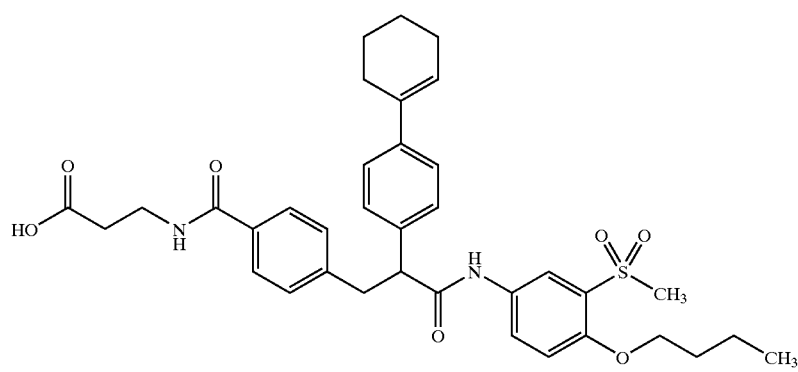
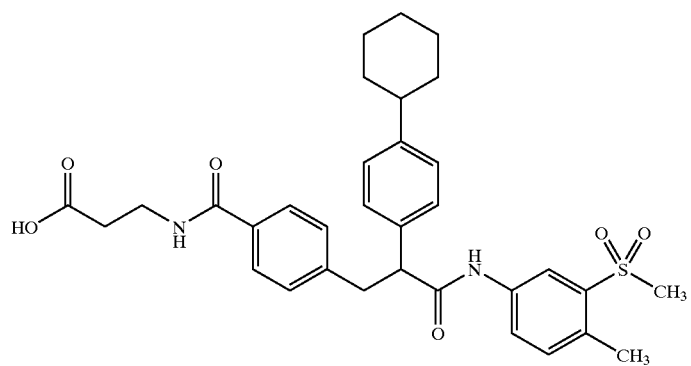
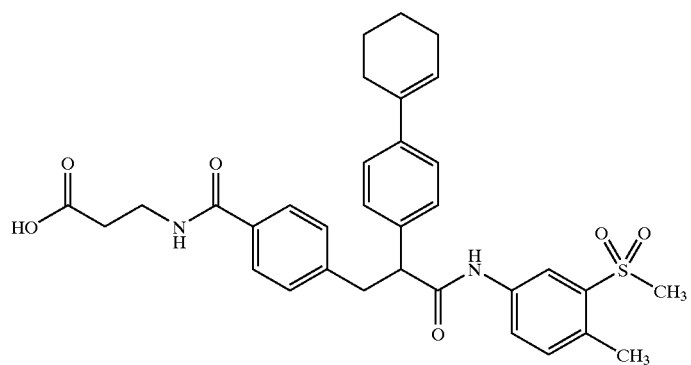
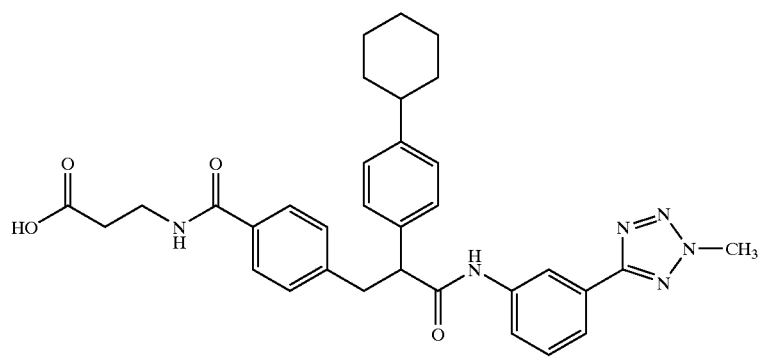

-continued
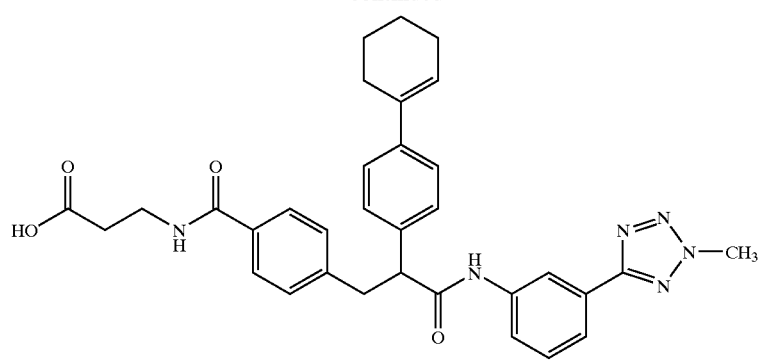
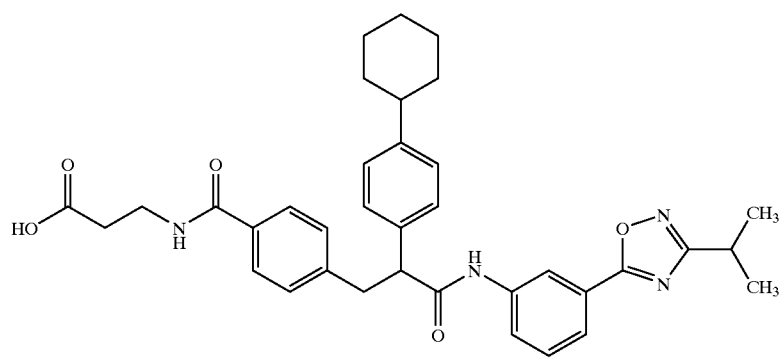
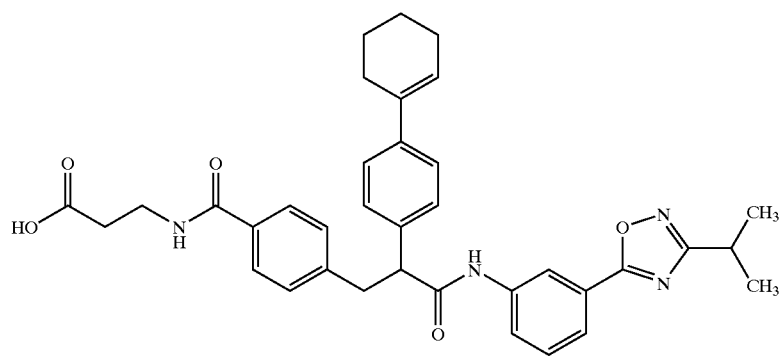
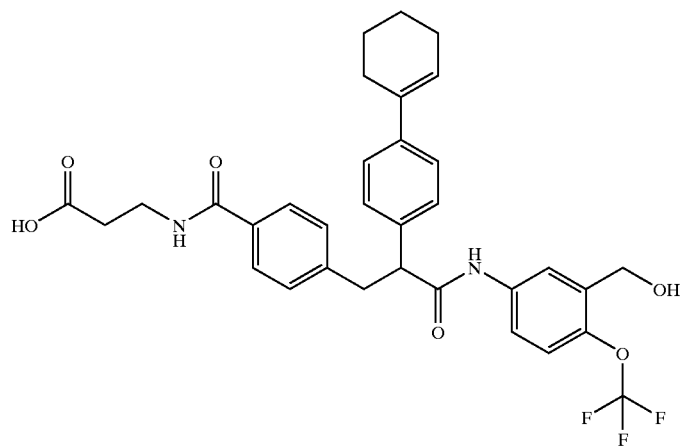

-continued
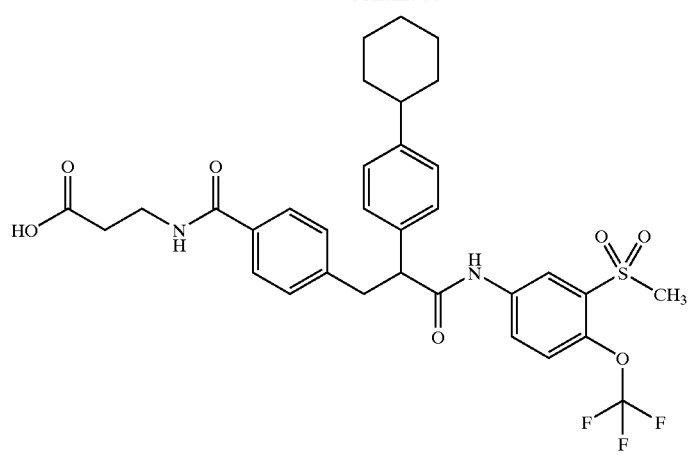
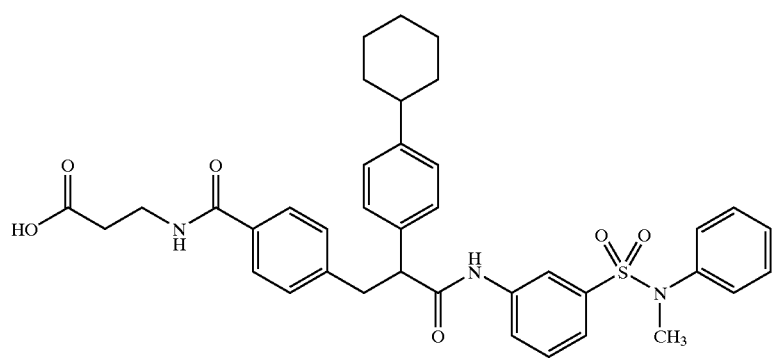
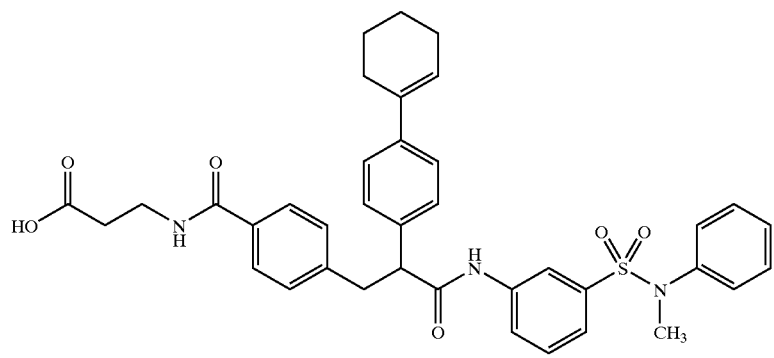
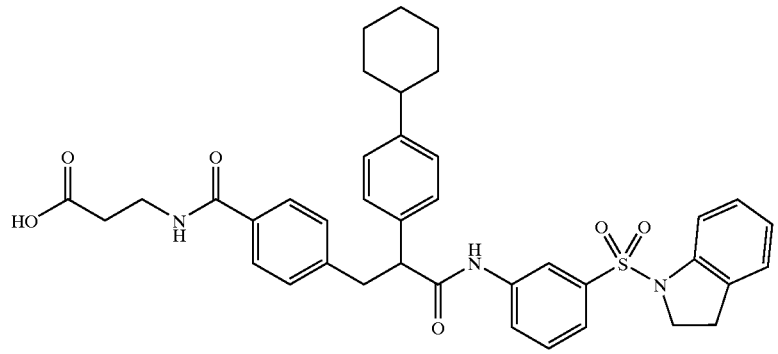

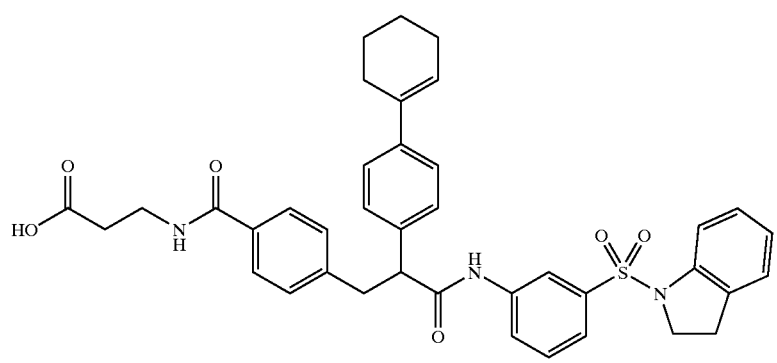
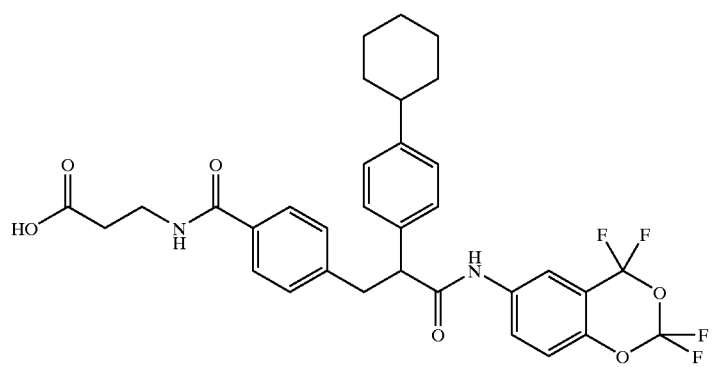
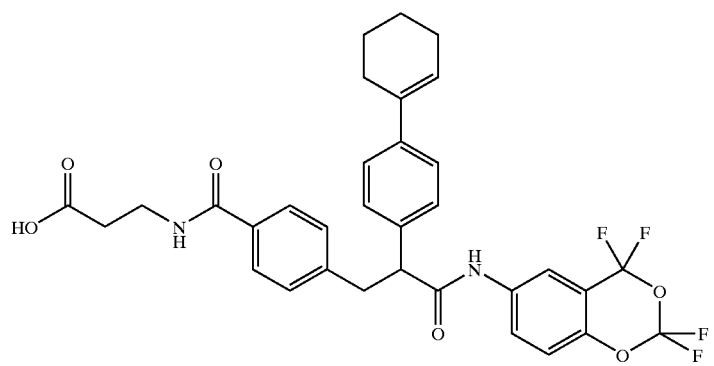
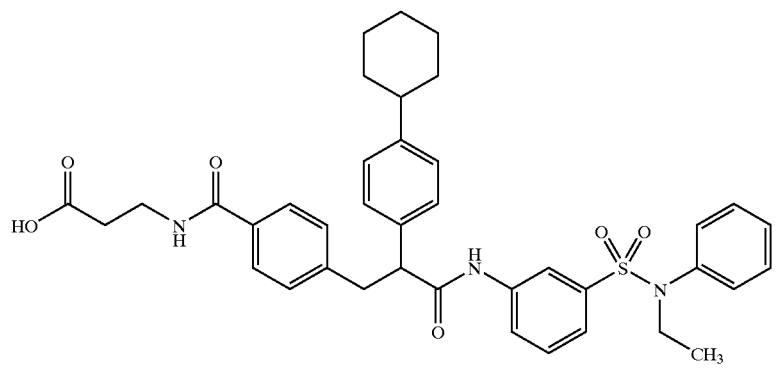

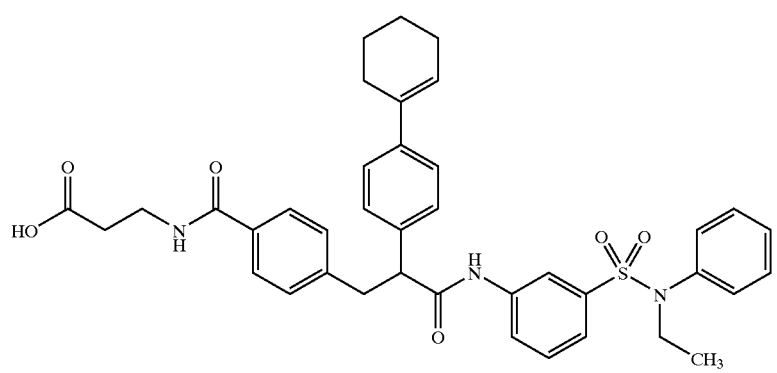
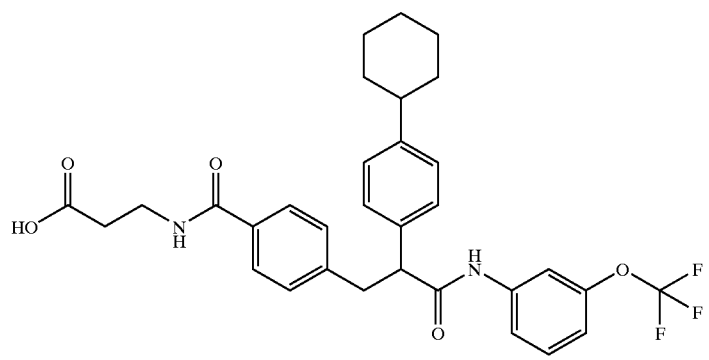
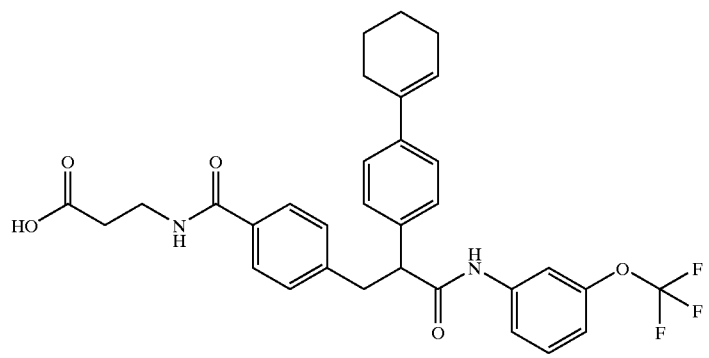
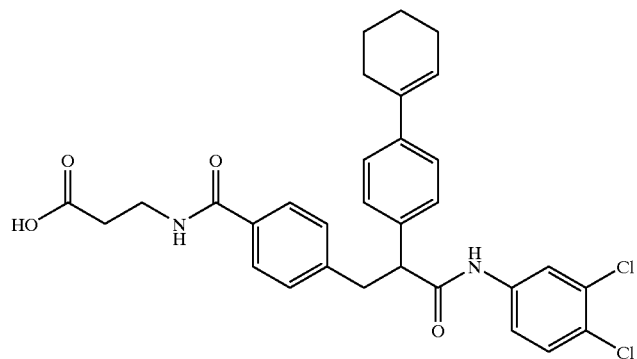

-continued
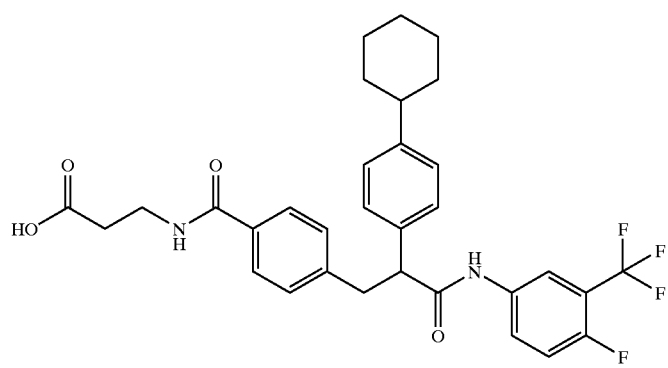
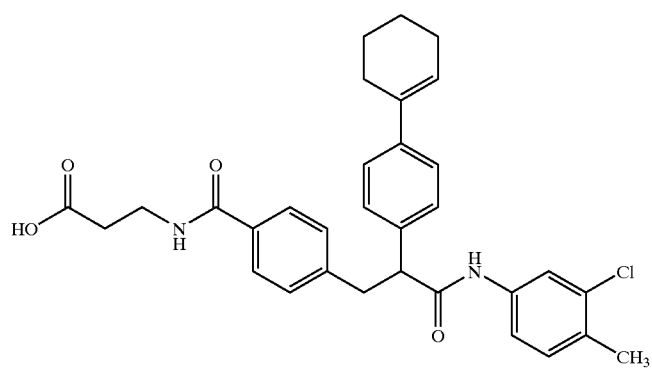
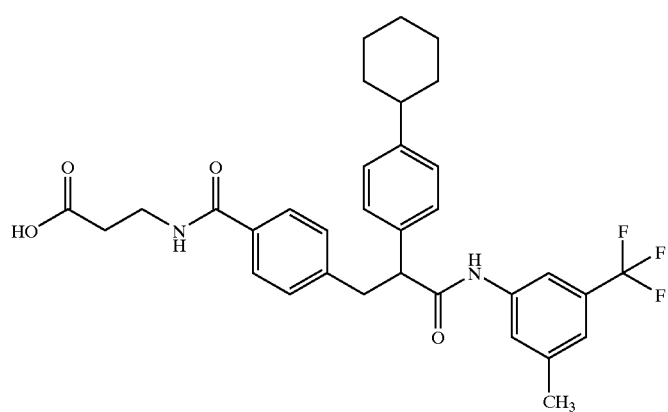
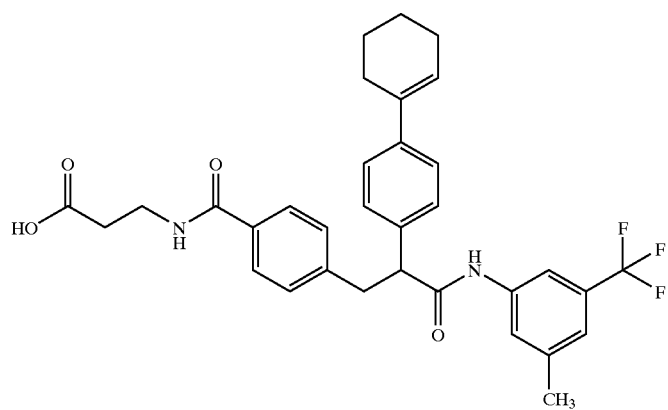

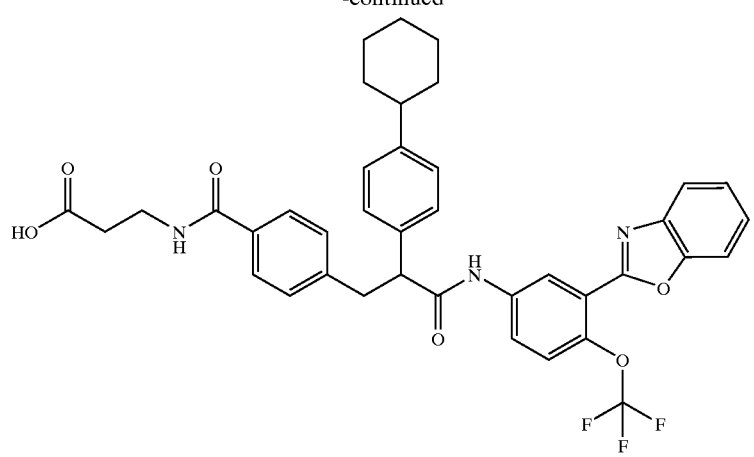
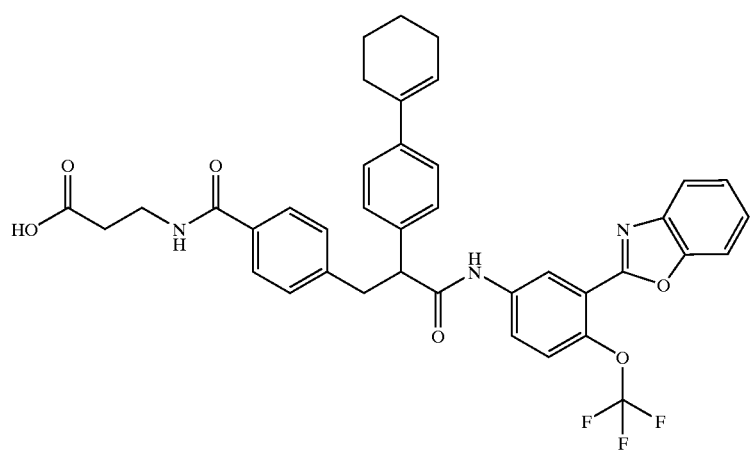
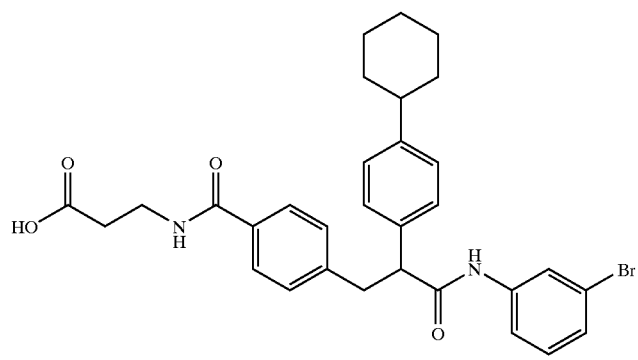
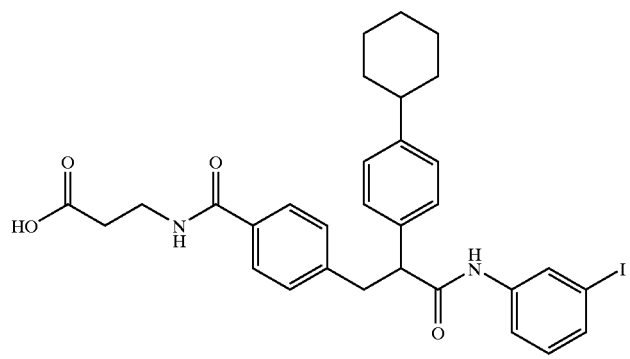

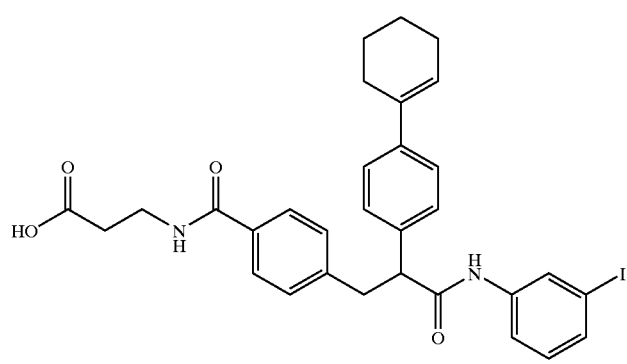
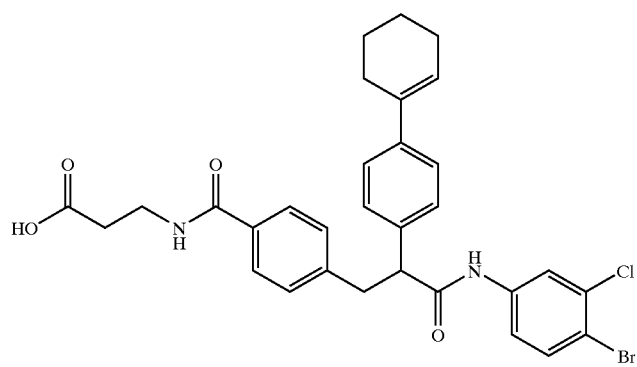
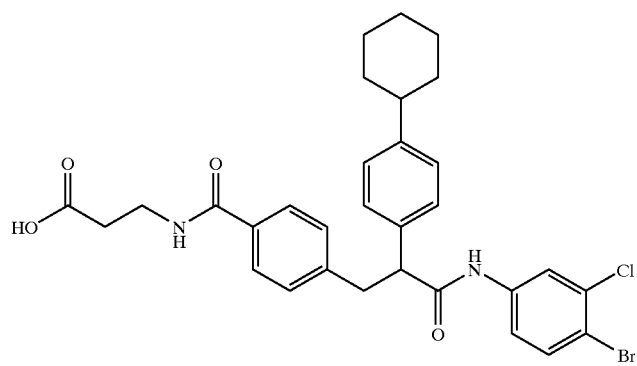
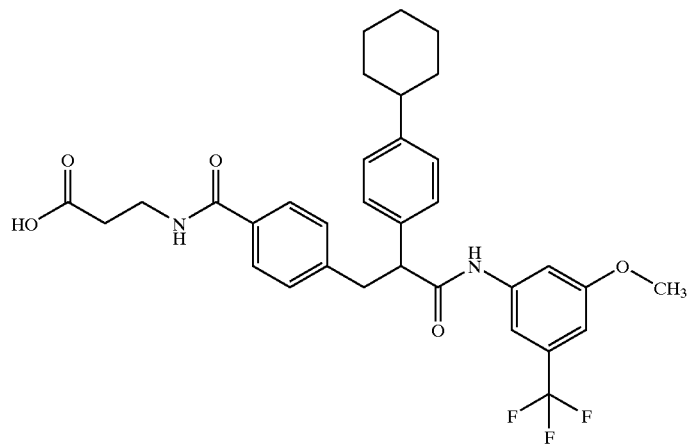

-continued
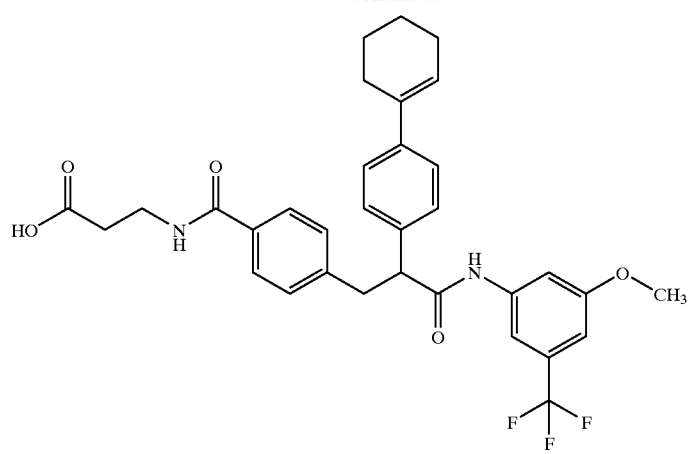
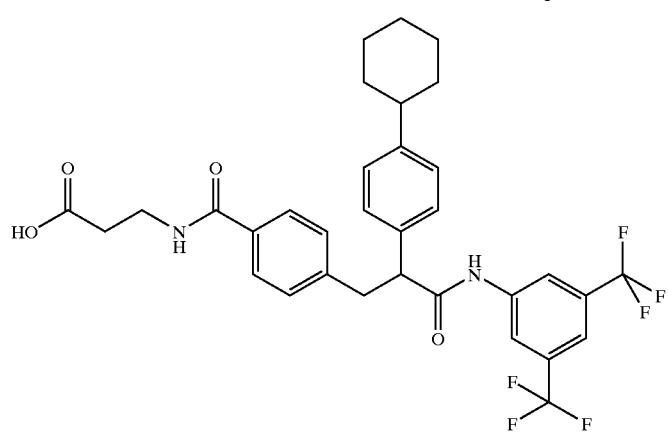
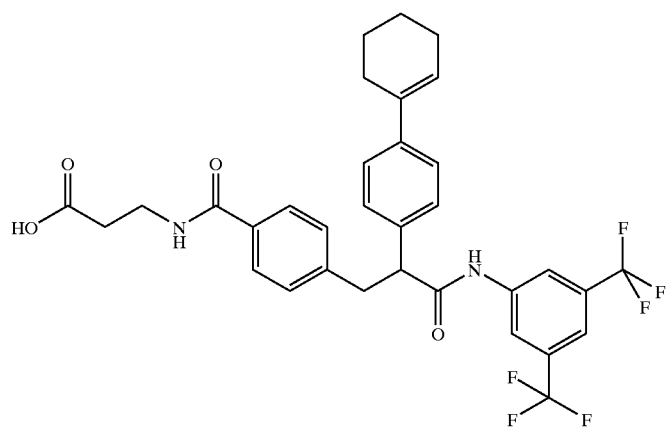
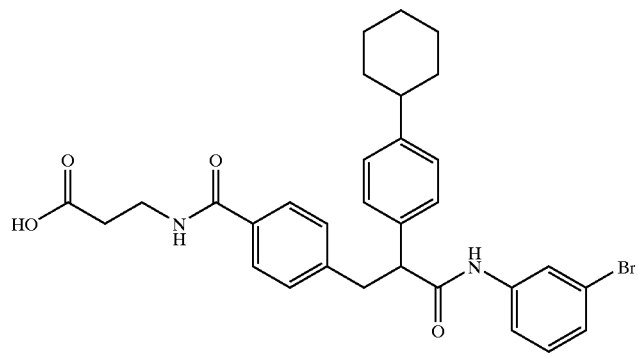

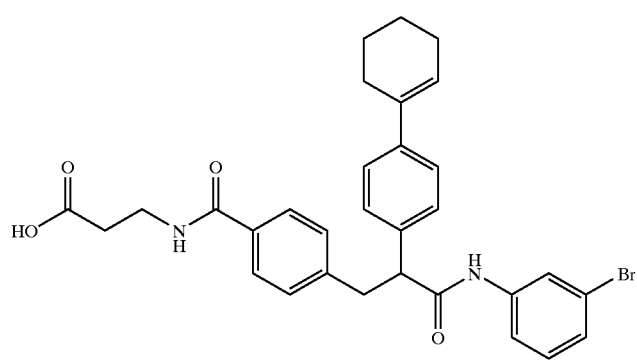
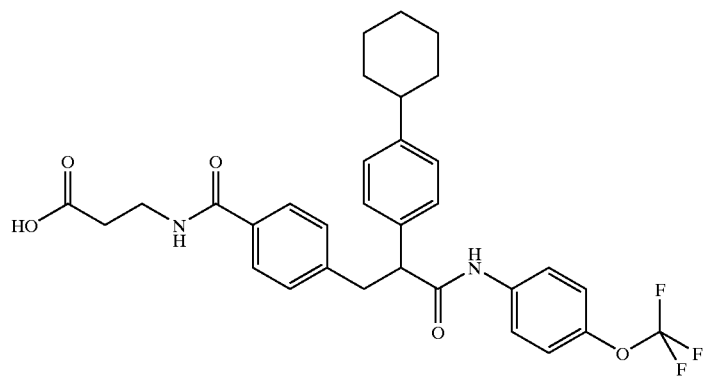
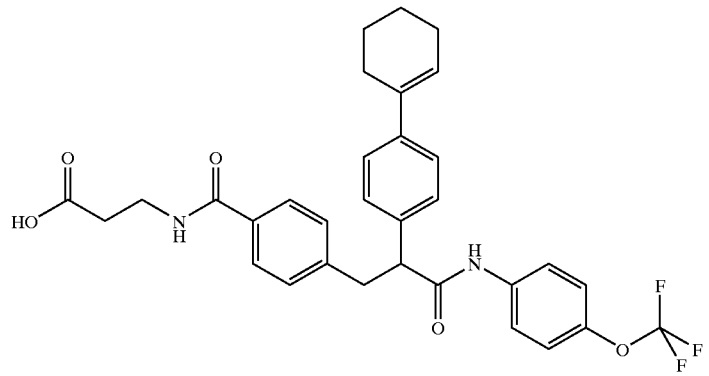
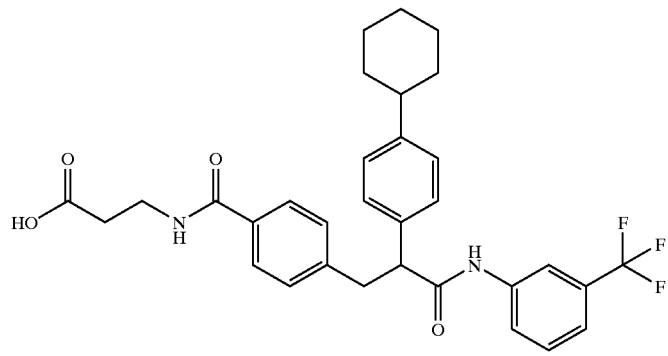

-continued
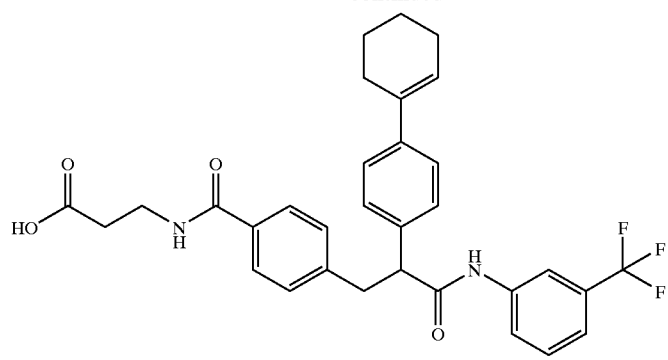
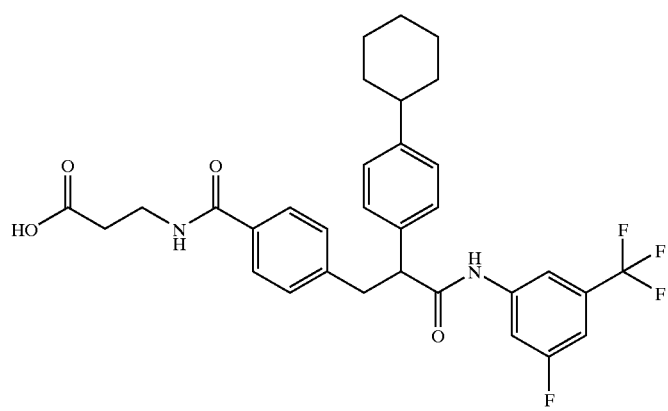
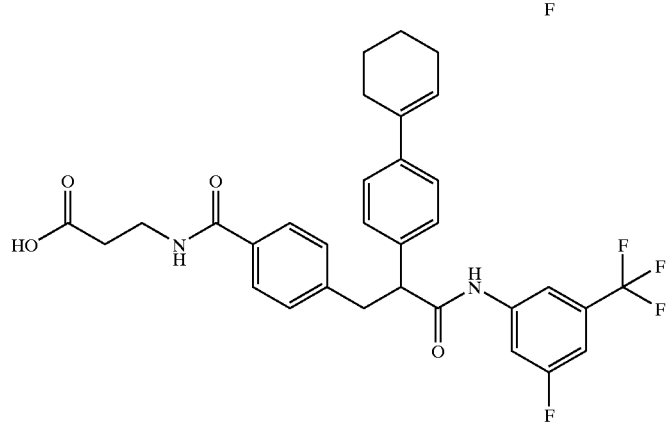
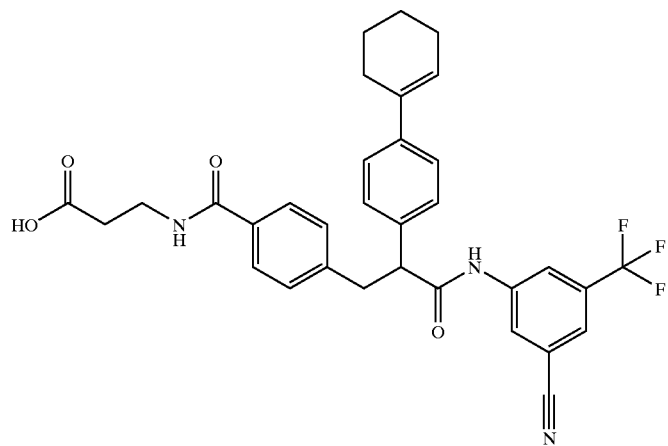

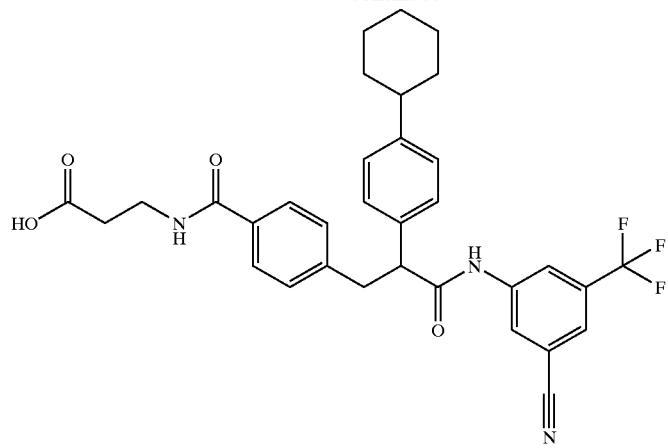
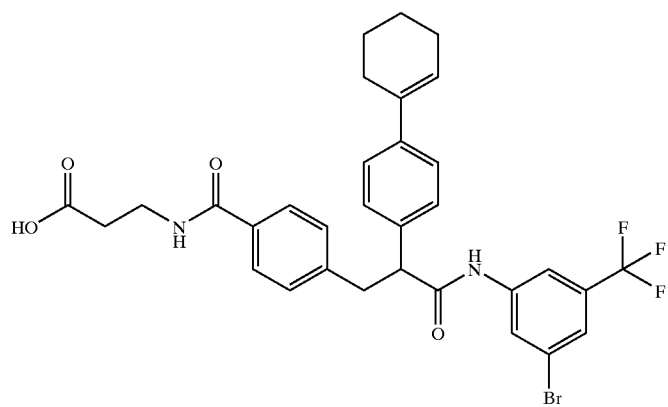
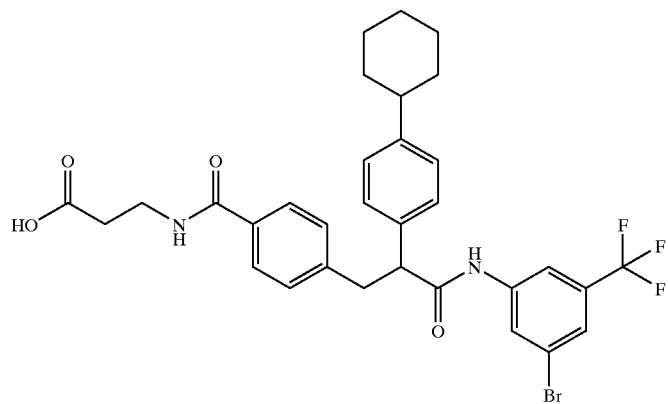
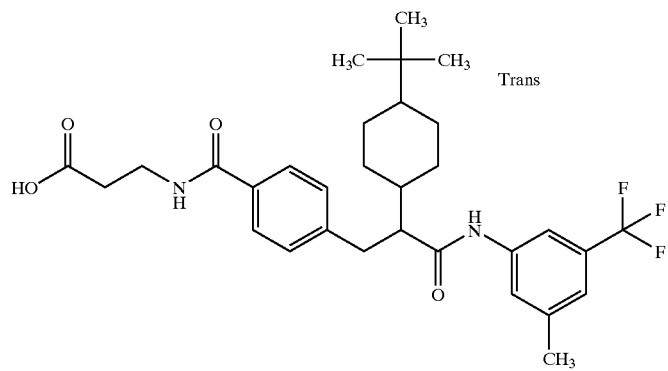

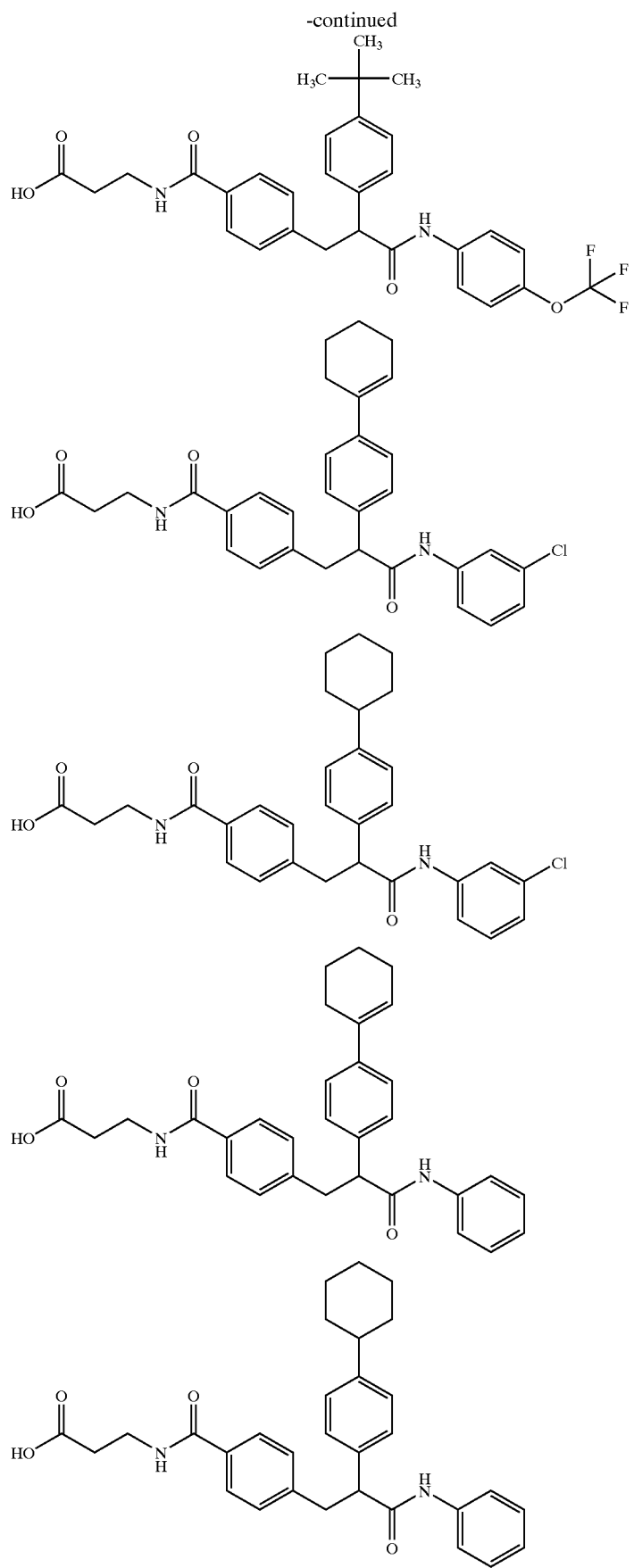

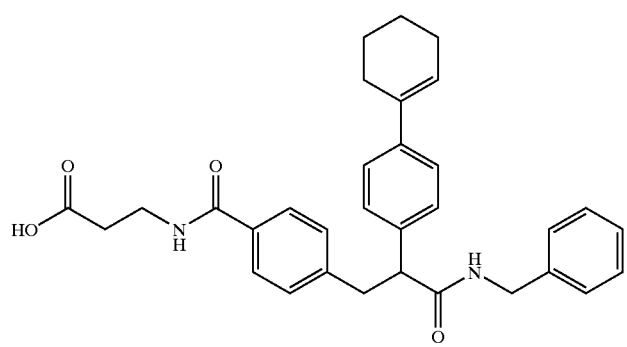
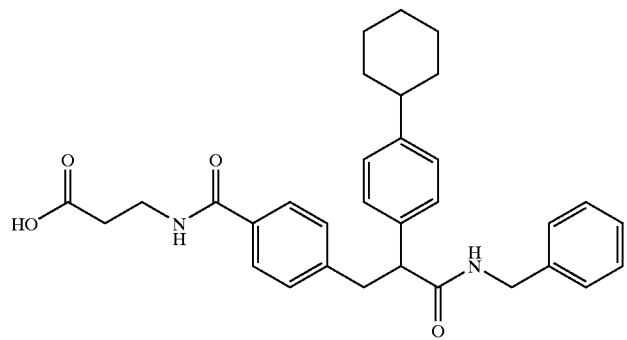
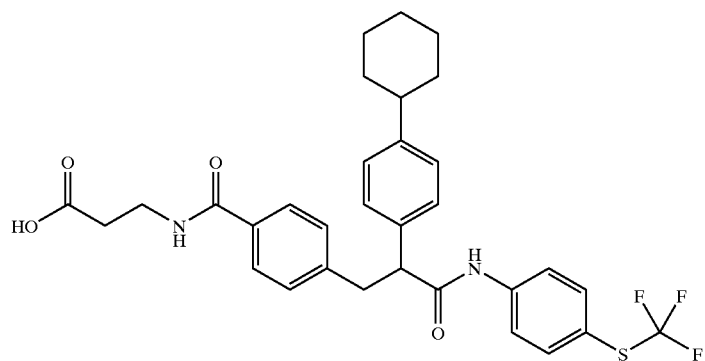
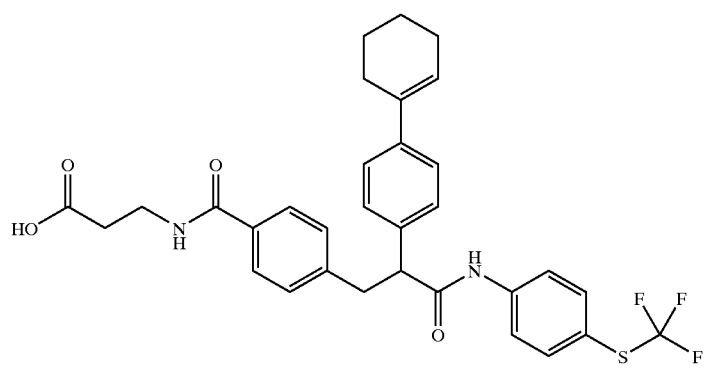

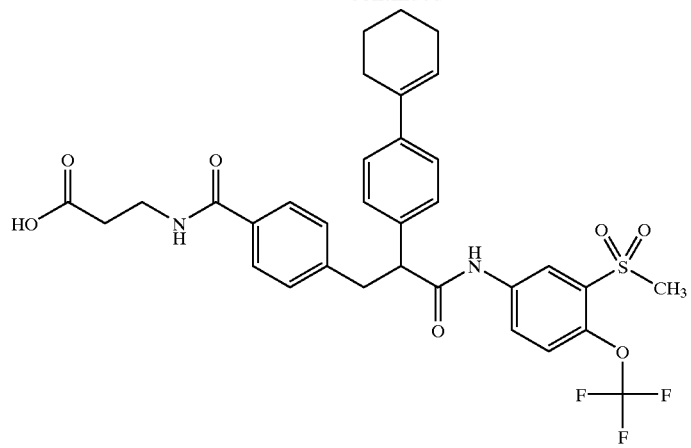
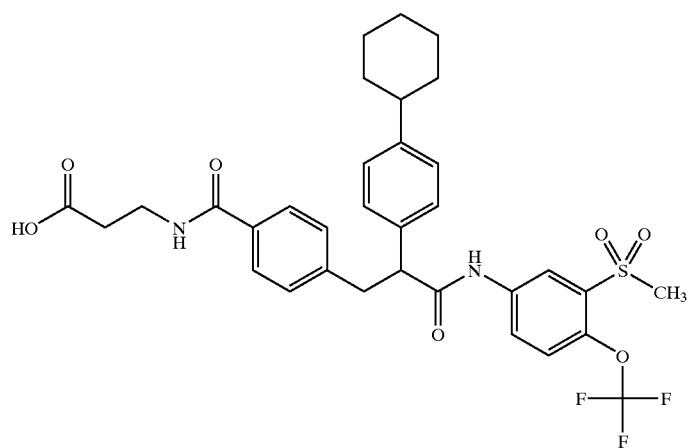
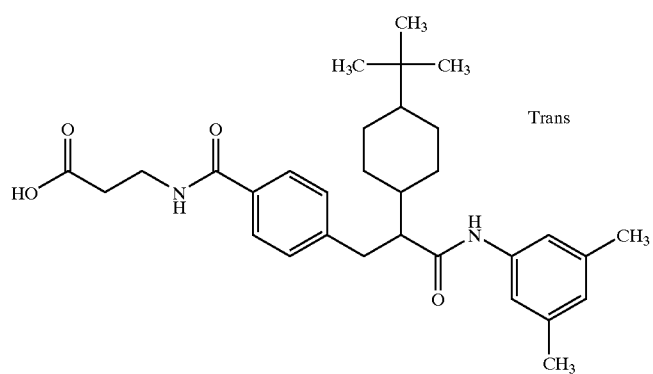
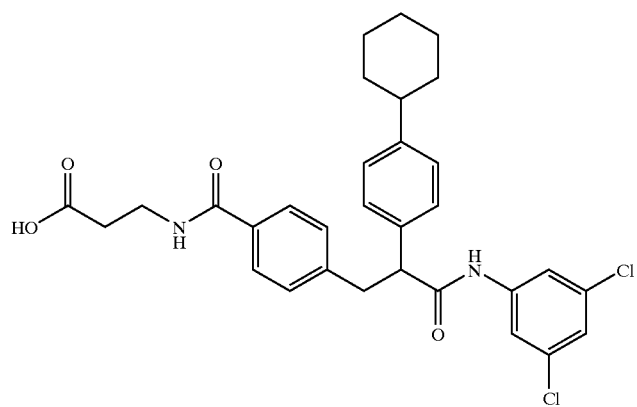

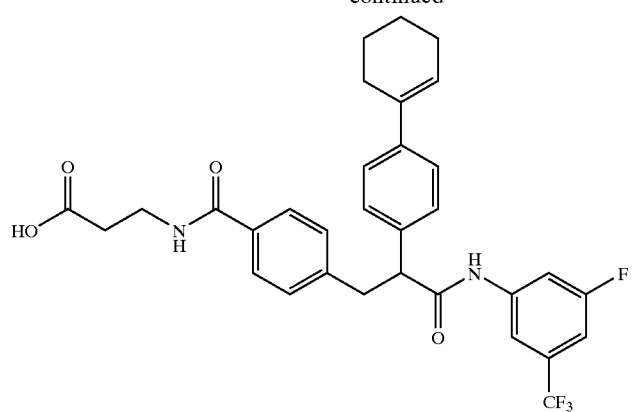
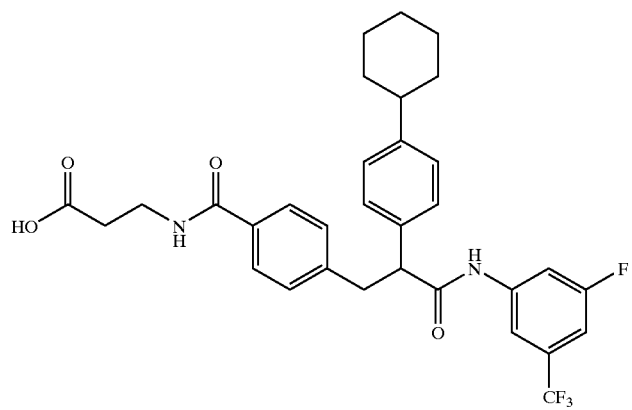
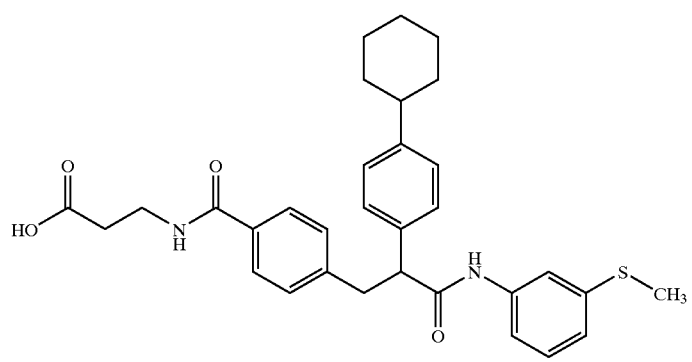
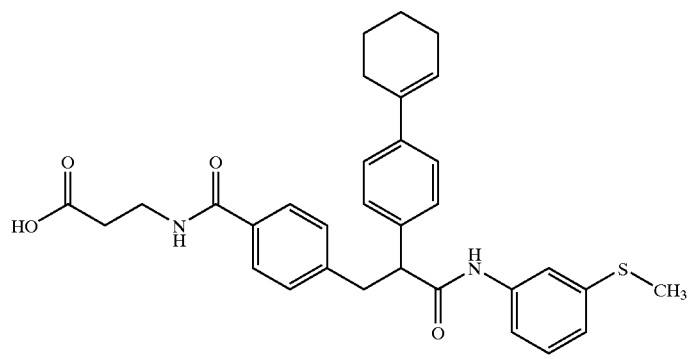

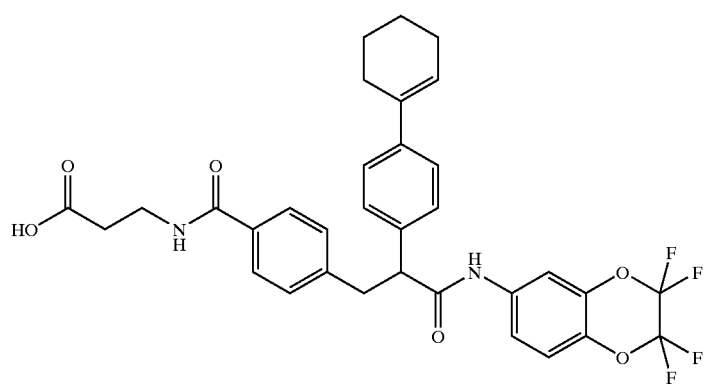
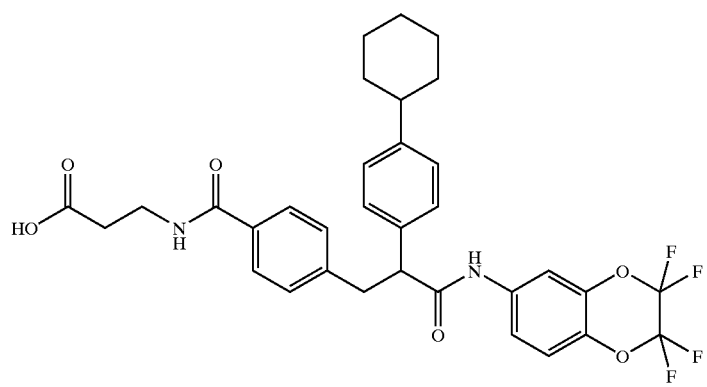
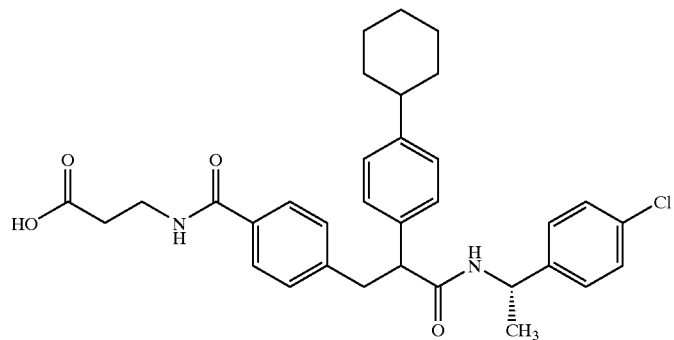
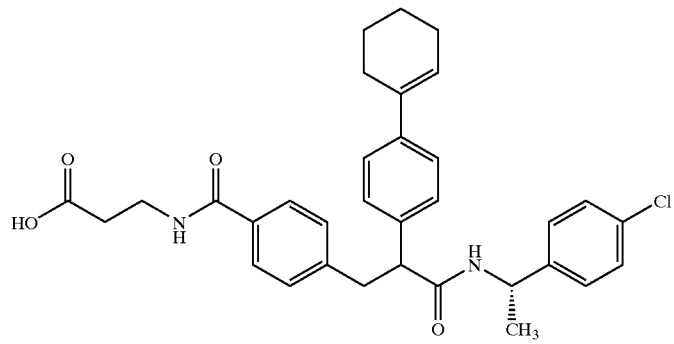

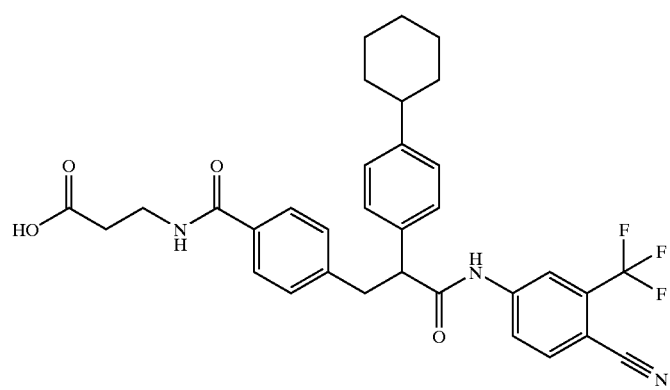
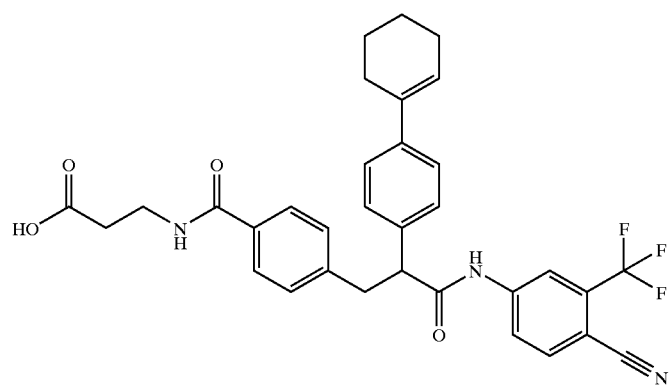
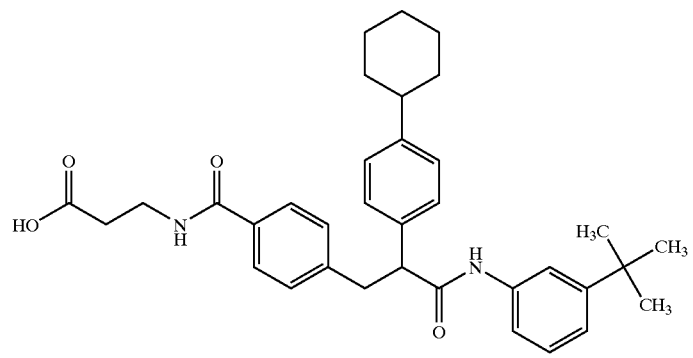
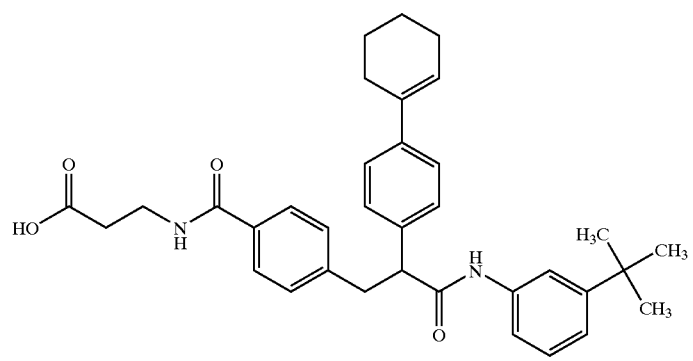

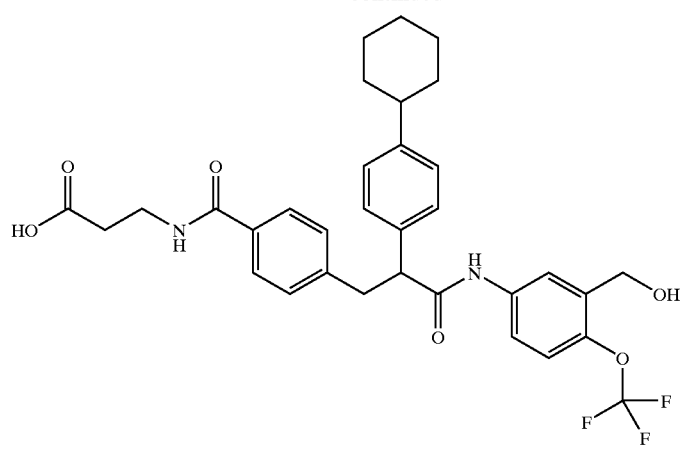
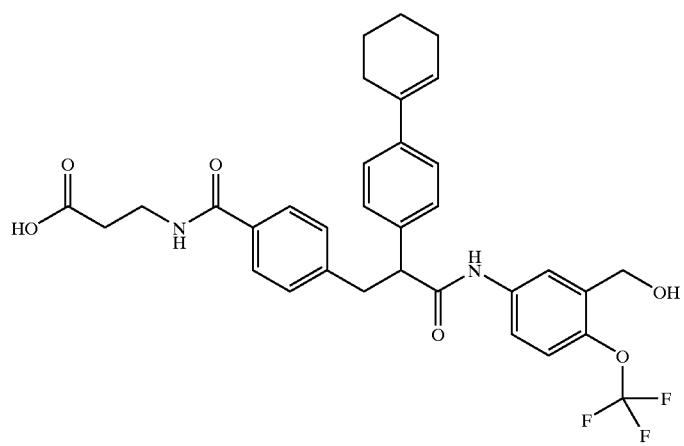
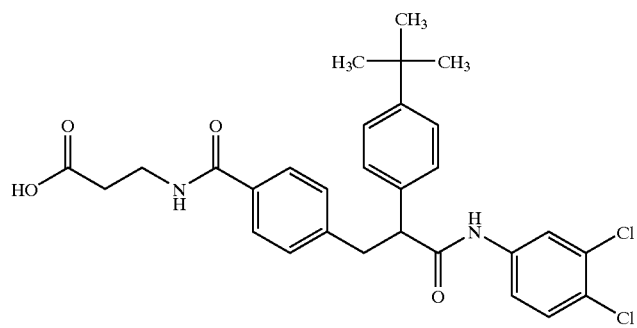
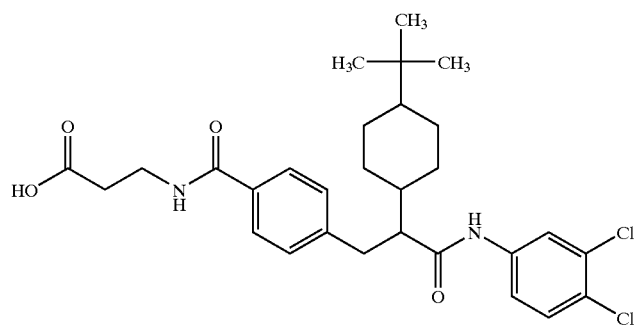

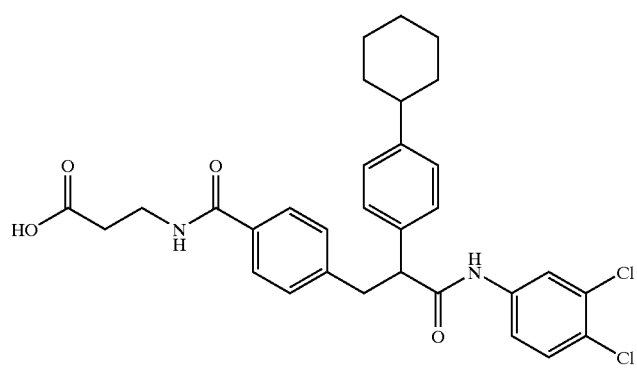
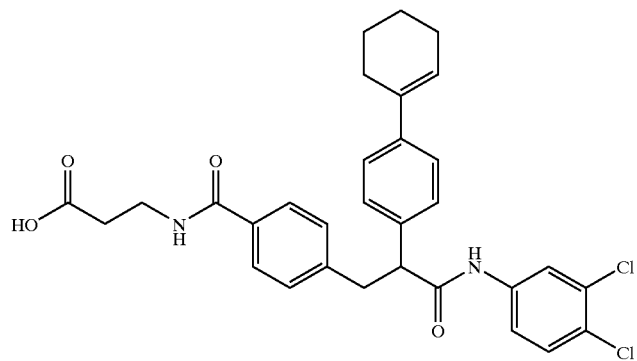
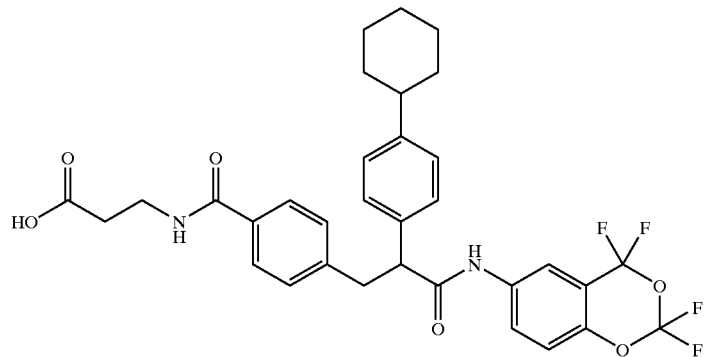
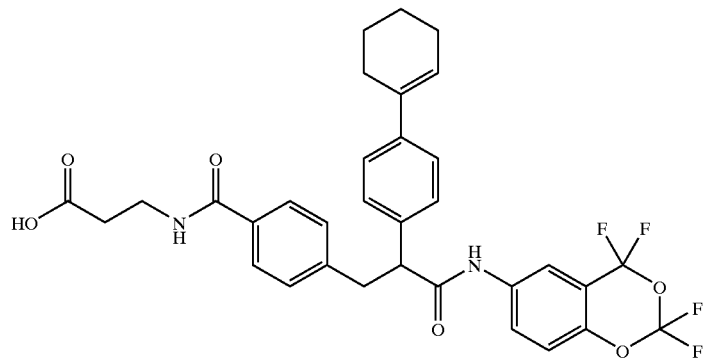

-continued
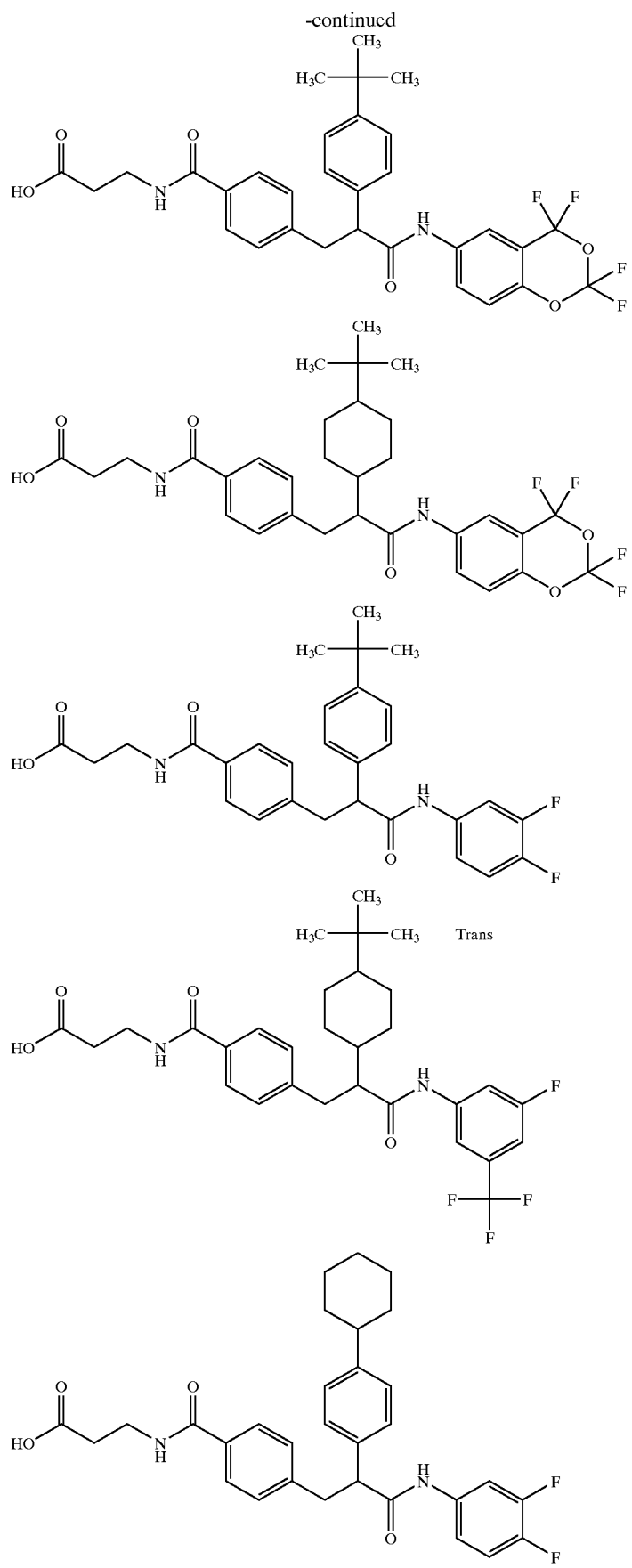

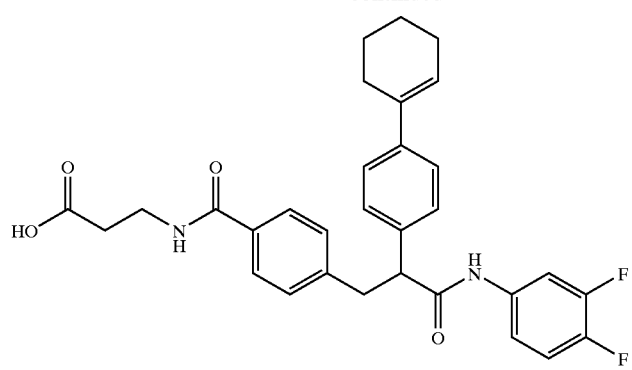
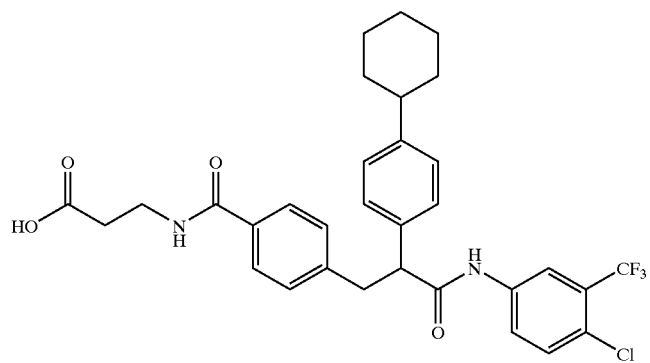
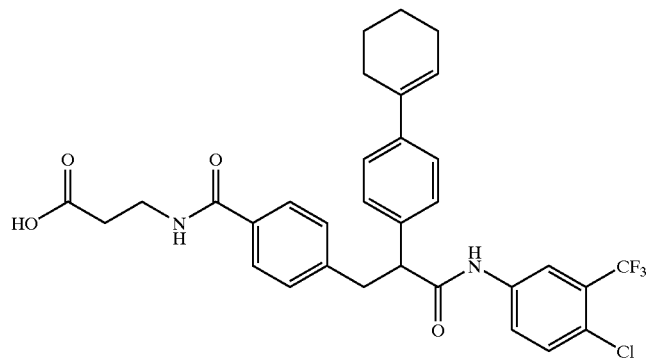
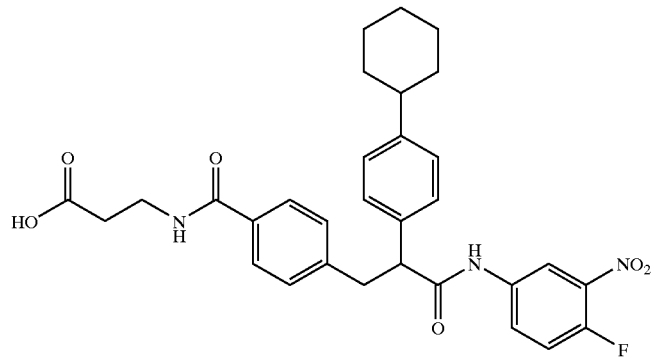

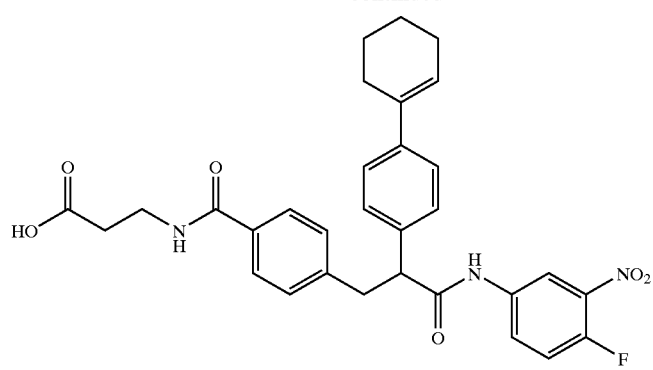
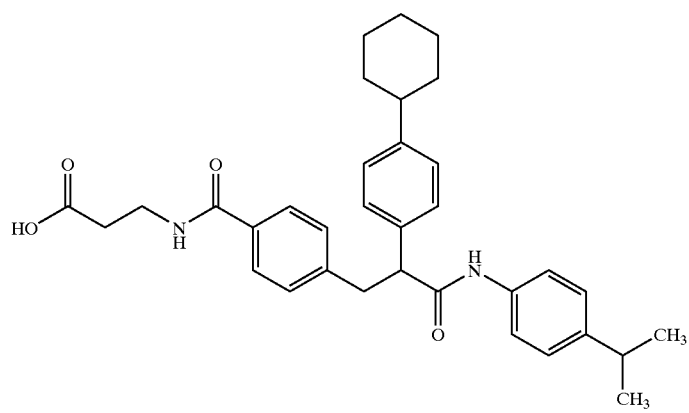
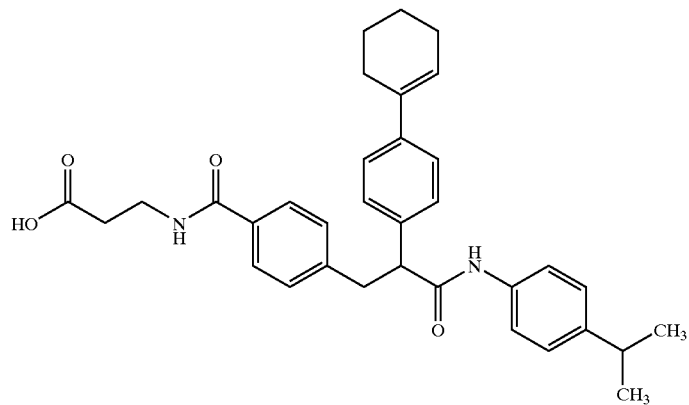
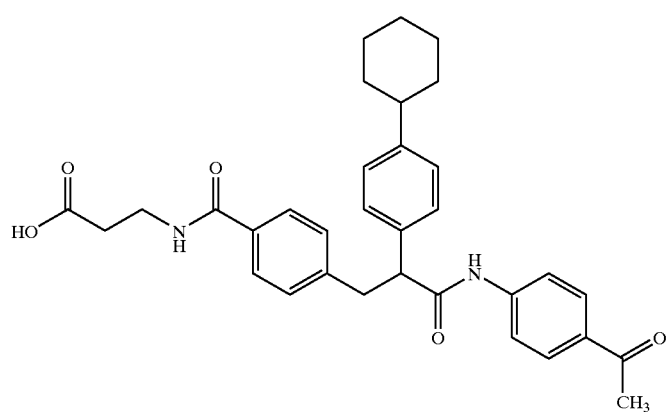

-continued
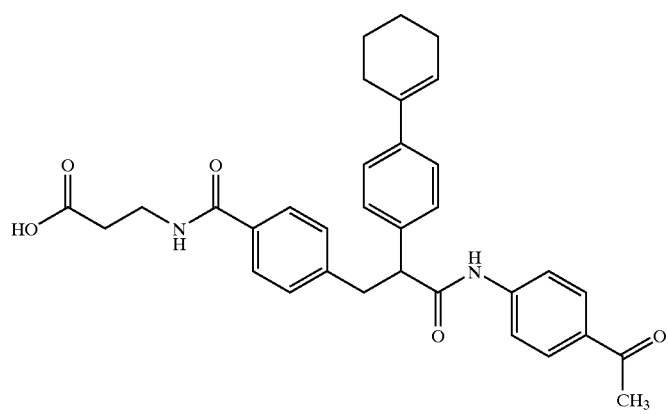
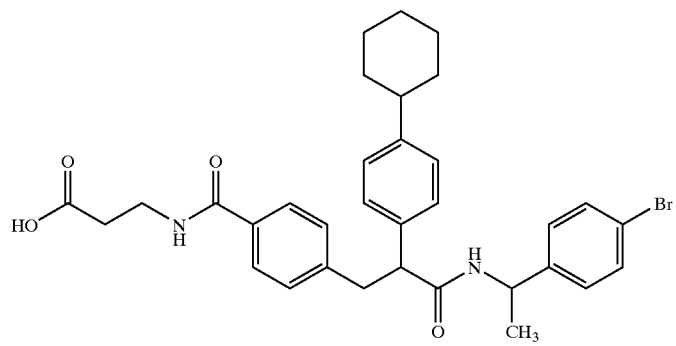
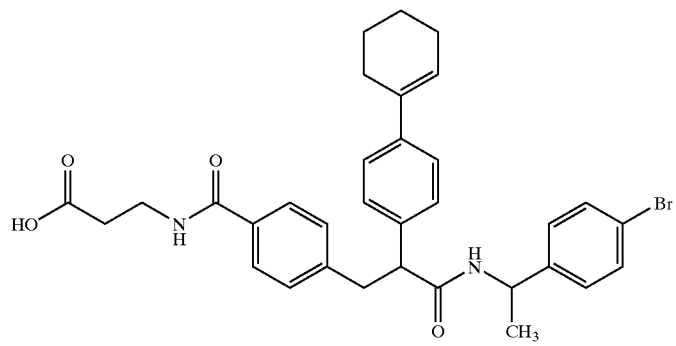
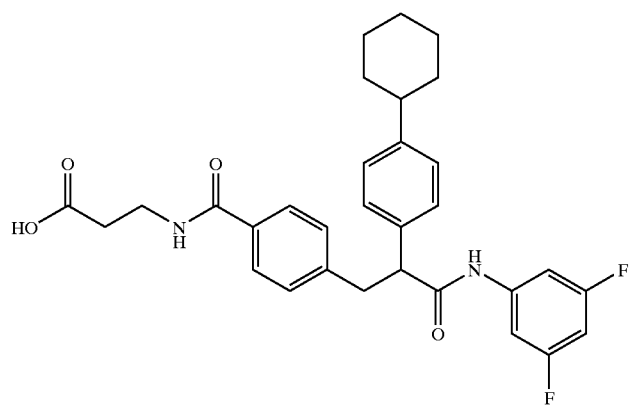

-continued
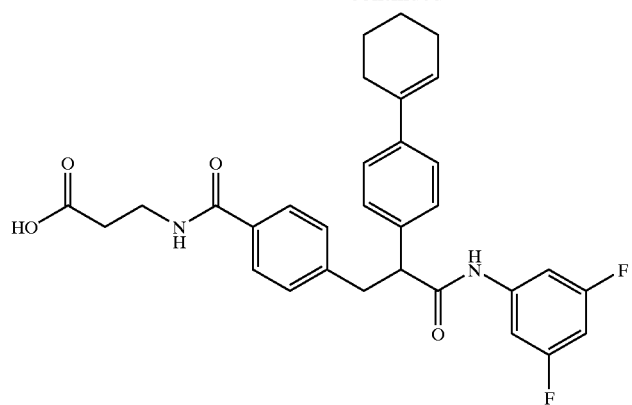
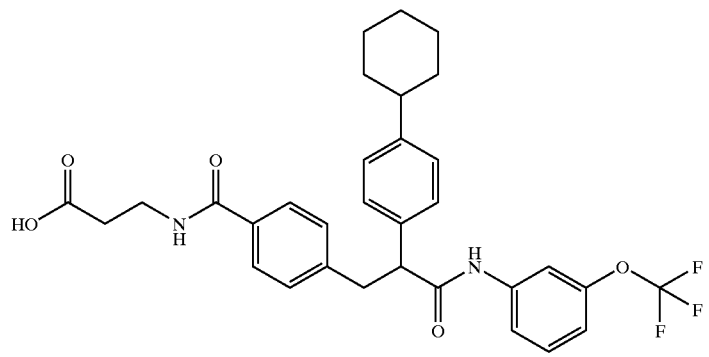
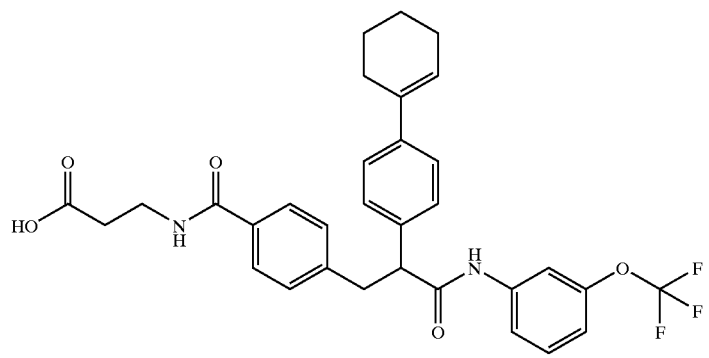
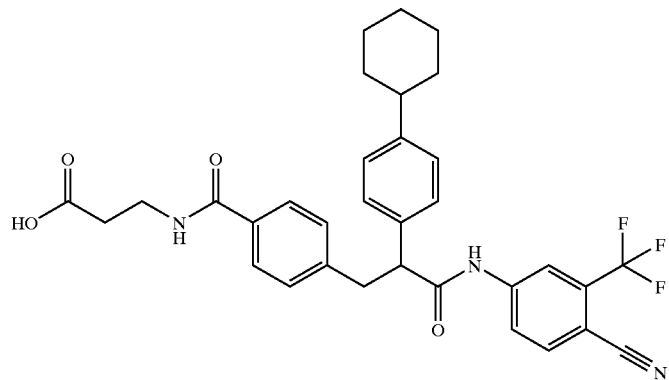

-continued
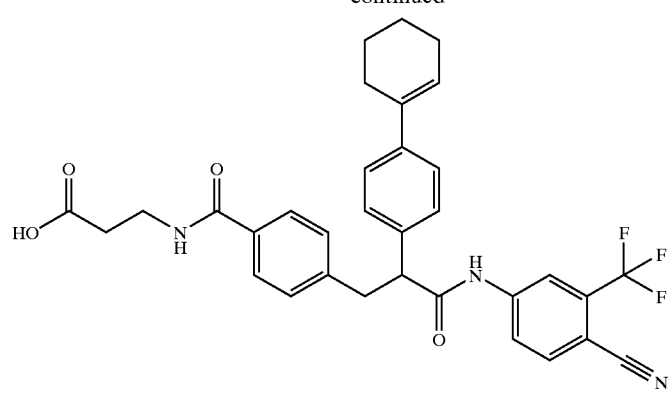
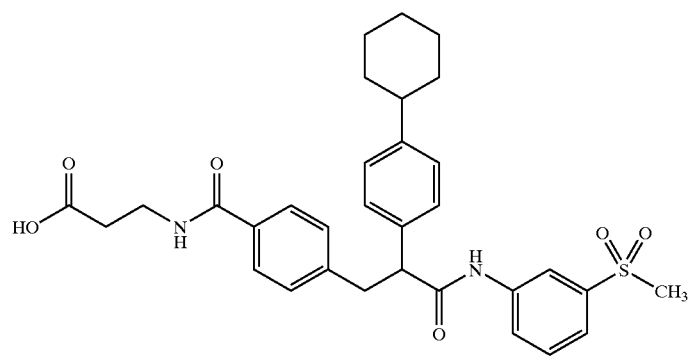
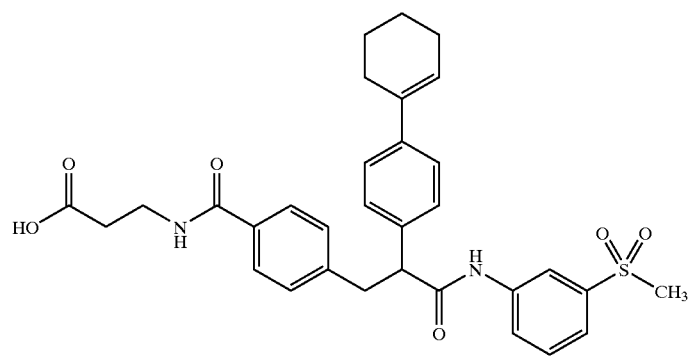
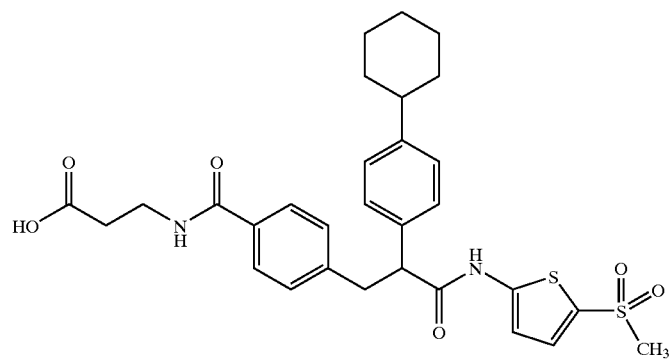

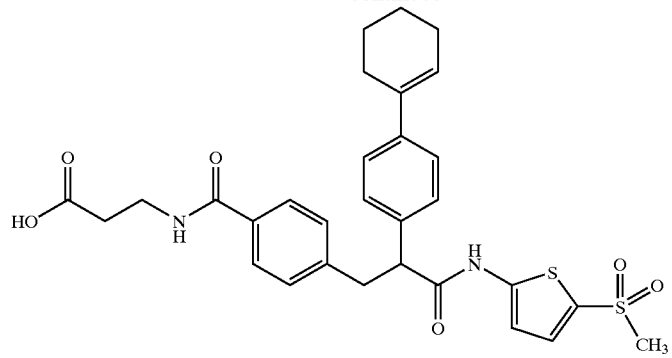

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor.

Antagonism may be determined as the ability of the compounds to inhibit the amount of cAMP formed in the presence of 5 nM glucagon.

Glucagon Binding Assay (I)

Receptor binding are assayed using cloned human receptor (Lok et al., Gene 140, 203–209 (1994)). The receptor inserted in the pLJ6' expression vector using EcoRI/SSt1 restriction sites (Lok et al.) is expressed in a baby hamster kidney cell line (A3 BHK 570–25). Clones are selected in the presence of 0.5 mg/mL G418 and are shown to be stable for more than 40 passages. The $K_d$ is shown to be 0.1 nM.

Plasma membranes are prepared by growing cells to confluence, detaching them from the surface and resuspending the cells in cold buffer (10 mM tris/HCl, pH 7.4 containing 30 mM NaCl, 1 mM dithiothreitol, 5 mg/l leupeptin (Sigma), 5 mg/l pepstatin (Sigma), 100 mg/l bacitracin (Sigma) and 15 mg/l recombinant aprotinin (Novo Nordisk A/S)), homogenization by two 10-s bursts using a Polytron PT 10–35 homogenizer (Kinematica), and centrifugation upon a layer of 41 w/v % sucrose at 95.000×g for 75 min. The white band located between the two layers is diluted in buffer and centrifuged at 40.000×g for 45 min. The precipitate containing the plasma membranes is suspended in buffer and stored at −80° C. until use.

Glucagon is iodinated according to the chloramine T method (Hunter and Greenwood, Nature 194, 495 (1962)) and purified using anion exchange chromatography (Jorgensen et al., Hormone and Metab. Res. 4, 223–224 (1972). The specific activity is 460 $\mu$Ci/$\mu$g on the day of iodination. Tracer is stored at −18° C. in aliquots and used immediately after thawing.

Binding assays are carried out in triplicate in filter microtiter plates (MADV N65, Millipore). The buffer is 50 mM HEPES, 5 mM EGTA, 5 mM $MgCl_2$, 0.005% tween 20, pH 7.4. Glucagon is dissolved in 0.05 M HCl, added an equal amount (w/w) of human serum albumin and freeze-dried. On the day of use, it is dissolved in water and diluted in buffer to the desired concentrations.

Test compounds are dissolved and diluted in DMSO. 140 $\mu$l buffer, 25 $\mu$l glucagon or buffer, and 10 $\mu$l DMSO or test compound are added to each well. Tracer (50.000 cpm) is diluted in buffer and 25 $\mu$l is added to each well. 1–4 $\mu$g freshly thawed plasma membrane protein diluted in buffer is then added in aliquots of 25 $\mu$l to each well. Plates are incubated at 30° C. for 2 hours. Non-specific binding is determined with $10^{-6}$ M of glucagon. Bound tracer and unbound tracer are then separated by vacuum filtration (Millipore vacuum manifold). The plates are washed with 2×100 $\mu$l buffer/well. The plates are air dried for a couple of hours, whereupon the filters are separated from the plates using a Millipore Puncher. The filters are counted in a gamma counter.

Functional Assay (I)

The functional assay is carried out in 96 well microtiter plates (tissue culture plates, Nunc). The resulting buffer concentrations in the assay are 50 mM tris/HCl, 1 mM EGTA, 1.5 mM $MgSO_4$, 1.7 mM ATP, 20 1M GTP, 2 mM IBMX, 0.02% tween-20 and 0.1% human serum albumin. pH was 7.4. Glucagon and proposed antagonist are added in aliquots of 35 $\mu$l diluted in 50 mM tris/HCl, 1 mM EGTA, 1.85 mM $MgSO_4$, 0.0222% tween-20 and 0.111% human serum albumin, pH 7.4. 20 $\mu$l of 50 mM tris/HCl, 1 mM EGTA, 1.5 mM $MgSO_4$, 11.8 mM ATP, 0.14 mM GTP, 14 mM IBMX and 0.1% human serum albumin, pH 7.4 was added. GTP was dissolved immediately before the assay.

50 $\mu$l containing 5 $\mu$g of plasma membrane protein was added in a tris/HCl, EGTA, $MgSO_4$, human serum albumin buffer (the actual concentrations are dependent upon the concentration of protein in the stored plasma membranes).

The total assay volume is 140 $\mu$l. The plates are incubated for 2 hours at 37° C. with continuous shaking. Reaction is terminated by addition of 25 $\mu$l 0.5 N HCl. cAMP is measured by the use of a scintillation proximity kit (Amersham).

Glucagon Binding Assay (II)

BHK (baby hamster kidney cell line) cells are transfected with the human glucagon receptor and a membrane preparation of the cells is prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{125}$I-glucagon.

All steps in the membrane preparation are kept on ice or performed at 4° C. BHK cells are harvested and centrifuged. The pellet is resuspended in homogenisation buffer (25 mM HEPES, pH=7.4, 2.5 mM $CaCl_2$, 1.0 mM $MgCl_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM $CaCl_2$, 1.0 mM $MgCl_2$) and homogenised 2×10 sec. (Polytron). The protein concentration is normally around 1.75 mg/mL. Stabilisation buffer (25 mM HEPES, pH=7.4, 2.5 mM $CaCl_2$, 1.0 mM $MgCl_2$, 1% bovine serum albumin, 500 mg/l bacitracin, 2.5 M sucrose) is added and the membrane preparation is stored at −80° C.

The glucagon binding assay is carried out in opti plates (Polystyrene Microplates, Packard). 50 µl assay buffer (25 mM HEPES, pH=7.5, 2.5 mM $CaCl_2$, 1.0 mM $MgCl_2$, 0.003% Tween-20, 0.005% bacitracin, 0.05% sodium azide) and 5 µl glucagon or test compound (in DMSO) are added to each well. 50 µl tracer ($^{125}$I-porcine glucagon, 50.000 cpm) and 50 µl membranes (7.5 µg) containing the human glucagon receptor are then added to the wells. Finally 50 µl WGA beads containing 1 mg beads are transferred to the well. The opti plates are incubated for 4 hours on a shaker and then settled for 8–48 hours. The opti plates are counted in a Topcounter. Non-specific binding is determined with 500 nM of glucagon.

Most of the compounds according to the examples showed $IC_{50}$ values below 1000 nM when tested in the glucagon binding assay (II).

GIP Binding Assay

BHK (baby hamster kidney cell line) cells are transfected with the human GIP receptor and a membrane preparation of the cells is prepared. Wheat Germ Agglutinin derivatized SPA beads containing a scintillant (WGA beads) (Amersham) bound the membranes. $^{125}$I-GIP bound to human GIP receptor in the membranes and excited the scintillant in the WGA beads to light emission. GIP or samples binding to the receptor competed with $^{125}$I-GIP.

All steps in the membrane preparation are kept on ice or performed at 4° C. BHK cells are harvested and centrifuged. The pellet is resuspended in homogenisation buffer (25 mM HEPES, pH=7.4, 2.5 mM $CaCl_2$, 1.0 mM $MgCl_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM $CaCl_2$, 1.0 mM $MgCl_2$) and homogenised 2×10 sec. (Polytron). The protein concentration is normally around 1.75 mg/mL. Stabilisation buffer (25 mM HEPES, pH=7.4, 2.5 mM $CaCl_2$, 1.0 mM $MgCl_2$, 1% bovine serum albumin, 500 mg/l bacitracin, 2.5 M sucrose) is added and the membrane preparation is stored at −80° C.

The GIP binding assay is carried out in opti plates (Polystyrene Microplates, Packard). 50 µl assay buffer (25 mM HEPES, pH=7.5, 2.5 mM $CaCl_2$, 1.0 mM $MgCl_2$, 0.003% Tween-20, 0.005% bacitracin, 0.05% sodium azide) and 5 µl GIP or test compound (in DMSO) are added to each well. 50 µl tracer ($^{125}$I-porcine GIP, 50.000 cpm) and 50 µl membranes (20 µg) containing the human GIP receptor are then added to the wells. Finally 50 µl WGA beads containing 1 mg beads are transferred to the well. The opti plates are incubated for 3.5 hours on a shaker and then settled for 8–48 hours. The opti plates are counted in a Topcounter. Non-specific binding is determined with 500 nM of GIP.

Generally, the compounds show a higher affinity for the glucagon receptor compared to the GIP receptor.

What is claimed is:

1. A compound of the general formula (I):

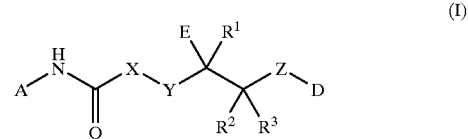

wherein

A is

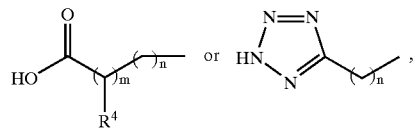

m is 0 or 1, n is 0, 1, 2 or 3, with the proviso that m and n must not both be 0, $R^4$ is hydrogen, halogen or —$(CH_2)_o$—$OR^5$, o is 0 or 1, $R^5$ is hydrogen, $C_{1-6}$-alkyl, $C_{1-6}$-alkanoyl, aryl or aryl-$C_{1-6}$-alkyl, $R^1$ and $R^2$ independently are hydrogen, halogen or $C_{1-6}$-alkyl, or $R^1$ and $R^2$ are combined to form a double bond, $R^3$ is hydrogen, $C_{1-6}$-alkyl or halogen, or $R^3$ and $R^2$ are combined to form a double bond to oxygen, X is arylene or heteroarylene, which may optionally be substituted with one or two groups $R^6$ and $R^7$ selected from halogen, —CN, —$CF_3$, —$OCF_3$, —$OCHF_2$, —$NO_2$, —$OR^8$, —$NR^8R^9$ and $C_{1-6}$-alkyl, $R^8$ and $R^9$ independently are hydrogen or $C_{1-6}$-alkyl, Y is —C(O)—, —O—, —$NR^{10}$—, —S—, —S(O)—, —$S(O)_2$— or —$CR^{11}R^{12}$—, $R^{10}$ is hydrogen or $C_{1-6}$-alkyl, $R^{11}$ and $R^{12}$ independently are hydrogen, $C_{1-6}$-alkyl or hydroxy, or $R^{11}$ is combined with $R^1$ to form a double bond, and $R^{12}$ is hydrogen, $C_{1-6}$-alkyl or hydroxy, Z is —C(O)—$(CR^{13}R^{14})_p$—, —O—$(CR^{13}R^{14})_p$—, —S—$(CR^{13}R^{14})_p$—, —S(O)—$(CR^{13}R^{14})_p$—, —$S(O)_2$—$(CR^{13}R^{14})_p$—, —$NR^{15}$—$(CR^{13}R^{14})_p$— or —$(CR^{13}R^{14})_p$—, p is 0, 1 or 2, $R^{13}$ and $R^{14}$ independently are selected from hydrogen, —$CF_8$, —$OCF_3$, —$OCHF_2$ and $C_{1-6}$-alkyl, $R^{15}$ is hydrogen or $C_{1-6}$-alkyl, D is aryl or heteroaryl, which may optionally be substituted with one or more substituents $R^{16}$, $R^{17}$, $R^{18}$, $R^{19}$, $R^{20}$ and $R^{21}$, wherein $R^{16}$, $R^{17}$, $R^{18}$ and $R^{19}$ independently are hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$SCF_3$, —$NO_2$, —$OR^{22}$, —$NR^{22}R^{23}$, —$SR^{22}$, —$NR^{22}S(O)_2R^{23}$, —$S(O)_2NR^{22}R^{23}$, —$S(O)NR^{22}R^{23}$, —$S(O)R^{22}$, —$S(O)_2R^{22}$, —$C(O)NR^{22}R^{23}$, —$OC(O)NR^{22}R^{23}$, —$NR^{22}C(O)R^{23}$, —$CH_2C(O)NR^{22}R^{23}$, —$OCH_2C(O)NR^{22}R^{23}$, —CH$_2$OR$^{22}$, —CH$_2$NR$^{22}$R$^{23}$, —OC(O)R$^{22}$, —C(O)R$^{22}$ or —C(O)OR$^{22}$, C$_{1-6}$-alkyl, C$_{2-6}$-alkenyl or C$_{2-6}$-alkynyl,
which may optionally be substituted with one or more substituents selected from halogen, —CN, —CF$_3$, —OCHF$_2$, —OCF$_3$, —NO$_2$, —OR$^{22}$, —NR$^{22}$R$^{23}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl,
of which the aromatic and non-aromatic ring systems optionally may be substituted with one or more substituents selected from halogen, —C(O)OR$^{22}$, —CN, —CF$_3$, —OCF$_3$, —OCHF$_2$, —NO$_2$, —OR$^{22}$, —NR$^{22}$R$^{23}$ and C$_{1-6}$-alkyl, R$^{22}$ and R$^{23}$ independently are hydrogen, C$_{1-6}$-alkyl, aryl-C$_{1-6}$-alkyl or aryl, or R$^{22}$ and R$^{23}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{16}$ to R$^{19}$ when placed in adjacent positions together may form a bridge —(CR$^{24}$R$^{25}$)$_a$—O—(CR$^{26}$R$^{27}$)$_c$—O—, a is 0, 1 or 2, c is 1 or 2, R$^{24}$, R$^{25}$, R$^{26}$ and R$^{27}$ independently are hydrogen, C$_{1-6}$-alkyl or fluoro, R$^{20}$ and R$^{21}$ independently are hydrogen, C$_{1-6}$-alkyl, C$_{3-8}$-cycloalkyl or C$_{3-8}$-cycloalkyl-C$_{1-6}$-alkyl, E is C$_{3-8}$-cycloalkyl or C$_{4-8}$-cycloalkenyl, which may optionally be substituted with one or two substituents R$^{28}$ and R$^{29}$, which are independently selected from hydrogen, halogen, —CN, —CF$_3$, —OCF$_3$, —OCHF$_2$, —OR$^{33}$, —NR$^{33}$R$^{34}$, C$_{1-4}$alkyl, C$_{3-8}$-cycloalkyl, C$_{4-8}$-cycloalkenyl, heteroaryl and aryl,
wherein the heteroaryl and aryl groups optionally may be substituted with one or more substituents selected from halogen, —CN, —CF$_3$, —OCF$_3$, —OCHF$_2$, —NO$_2$, —OR$^{33}$, —NR$^{33}$R$^{34}$ and C$_{1-6}$-alkyl, R$^{33}$ and R$^{34}$ independently are hydrogen or C$_{1-6}$-alkyl,
or R$^{33}$ and R$^{34}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, aryl, heteroaryl, aryl-C$_{2-6}$-alkenyl or aryl-C$_{2-6}$-alkynyl, of which the aryl and heteroaryl moieties may optionally be substituted with one or more substituents R$^{28}$, R$^{29}$, R$^{30}$, R$^{31}$ and R$^{32}$,
wherein R$^{28}$ and R$^{29}$ are as defined above, and R$^{30}$, R$^{31}$ and R$^{32}$ are independently selected from hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{35}$, —NR$^{35}$R$^{36}$, —SR$^{35}$, —S(O)R$^{35}$, —S(O)$_2$R$^{35}$, —C(O)NR$^{35}$R$^{36}$, —OC(O)NR$^{36}$R$^{36}$, —NR$^{35}$C(O)R$^{36}$, —OCH$_2$C(O)NR$^{35}$, R$^{36}$, —C(O)R$^{35}$ and —C(O)OR$^{35}$, C$_{1-6}$-alkyl, C$_{2-8}$-alkenyl and C$_{2-6}$-alkynyl,
which may optionally be substituted with one or more substituents selected from halogen, —CN, —CF$_3$, —OCF$_3$, OCHF$_2$, —NO$_2$, —OR$^{35}$, —NR$^{35}$R$^{36}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{2-8}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl and heteroaryl-C$_{2-6}$-alkynyl,
of which the aromatic and non-aromatic ring systems optionally may be substituted with one or more substituents selected from halogen, —CN, —CF$_3$, —OCF$_3$, OCHF$_2$, —NO$_2$, —OR$^{35}$, —NR$^{35}$R$^{36}$ and C$_{1-6}$-alkyl,
wherein R$^{35}$ and R$^{36}$ independently are hydrogen, C$_{1-6}$-alkyl or aryl,
or R$^{35}$ and R$^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the substituents R$^{30}$, R$^{31}$ and R$^{32}$ when attached to the same ring carbon atom or adjacent ring carbon atoms together may form a bridge —O—(CH$_2$)$_t$—CR$^{37}$R$^{38}$—(CH$_2$)$_t$—O—, —(CH$_2$)$_t$—CR$^{37}$R$^{38}$—(CH$_2$)$_t$— or —S—(CH$_2$)$_t$—CR$^{37}$R$^{38}$—(CH$_2$)$_t$—S—, t and l independently are 0, 1, 2, 3, 4 or 5, R$^{37}$ and R$^{38}$ independently are hydrogen or C$_{1-6}$-alkyl, as well as any diastereomer or enantiomer or tautomeric form thereof including mixtures of these or a pharmaceutically acceptable salt thereof.

2. A compound according to claim 1, wherein A is

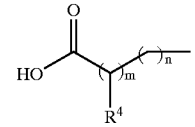

wherein m, n and R$^4$ are as defined in claim 1.

3. A compound according to claim 2, wherein A is

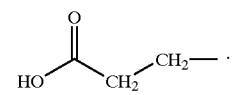

4. A compound according to claim 2, wherein A is

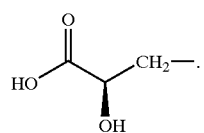

5. A compound according to claim 1, wherein A is

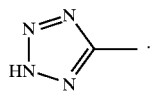

6. A compound according to claim 1, wherein X is monocyclic arylene or heteroarylene, which may optionally be substituted as defined in claim 1.

7. A compound according to claim 1, wherein X is

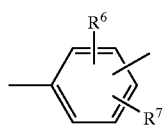

wherein $R^6$ and $R^7$ are as defined in claim 1.

8. A compound according to claim 7, wherein X is

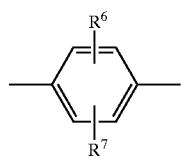

wherein $R^6$ and $R^7$ are as defined in claim 1.

9. A compound according to claim 7, wherein $R^6$ and $R^7$ are both hydrogen.

10. A compound according to claims 1, wherein E is

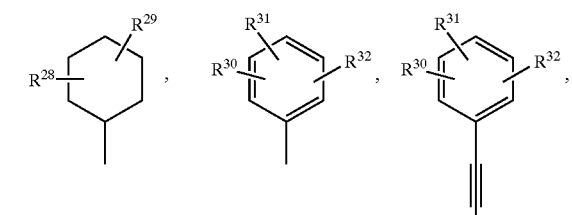

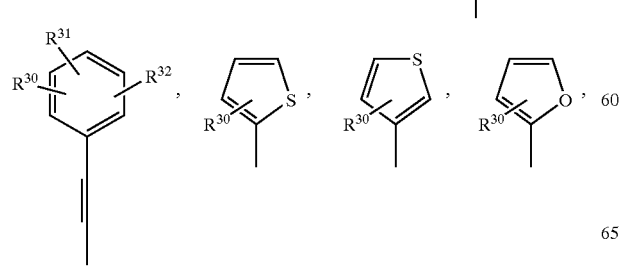

-continued

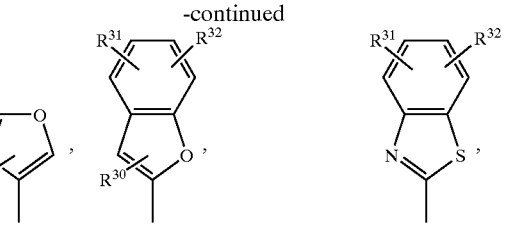

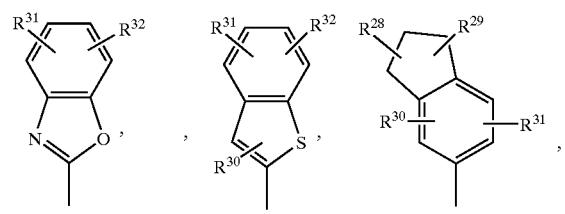

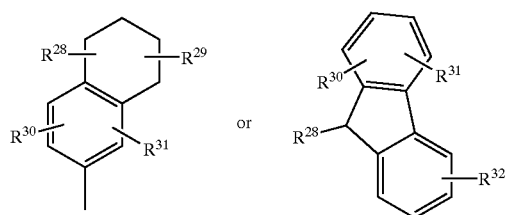

wherein $R^{28}$, $R^{29}$, $R^{30}$, $R^{31}$ and $R^{32}$ are as defined in claim 1.

11. A compound according to claim 10, wherein E is

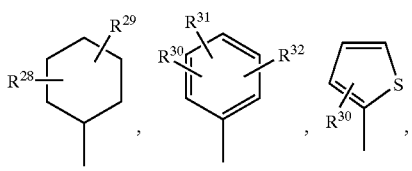

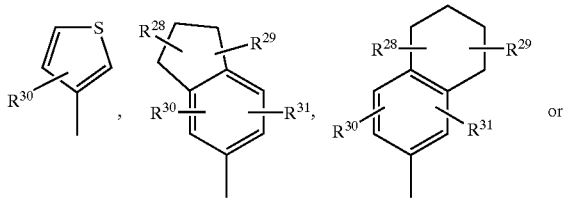

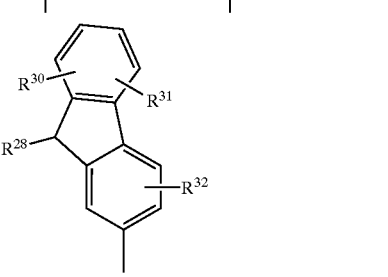

wherein $R^{28}$, $R^{29}$, $R^{30}$, $R^{31}$ and $R^{32}$ are as defined in claim 1.

12. A compound according to claim 11, wherein E is

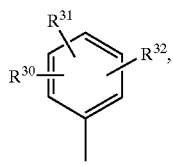

wherein $R^{30}$, $R^{31}$ and $R^{32}$ are as defined in claim 1.

13. A compound according to claim 12, wherein E is

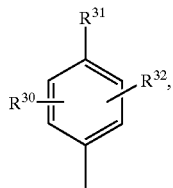

wherein $R^{30}$, $R^{31}$ and $R^{32}$ are as defined in claim 1.

14. A compound according to claim 11, wherein E is

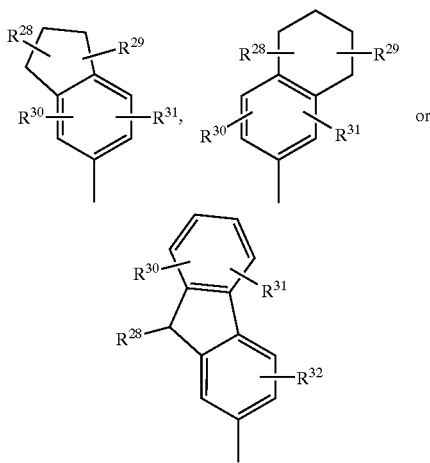

wherein $R^{28}$, $R^{29}$, $R^{30}$, $R^{31}$ and $R^{32}$ are as defined in claim 1.

15. A compound according to claim 10, wherein $R^{30}$, $R^{31}$ and $R^{32}$ independently are hydrogen, halogen, —OCF$_3$, —SCF$_3$, —OCHF$_2$ or —CF$_3$, C$_{1-6}$-alkyl, which may optionally be substituted with one or more substituents selected from fluoro, —CN, —CF$_3$, —OCF$_3$, —OR$^{35}$ and —NR$^{35}$R$^{36}$, C$_{3-8}$-cycloalkyl or C$_{4-8}$-cycloalkenyl, which may optionally be substituted with one or more substituents selected from fluoro, —CN, —CF$_3$, —OCF$_3$, —OR$^{35}$, —NR$^{35}$R$^{36}$ and C$_{1-6}$-alkyl, aryl, aryloxy or aryl-C$_{1-6}$-alkoxy, of which the aryl moieties may optionally be substituted with one or more substituents selected from halogen, —CN, —CF$_3$, —OCF$_3$, —NO$_2$, —R$^{35}$, —NR$^{35}$R$^{36}$ and C$_{1-6}$-alkyl, R$^{35}$ and R$^{36}$ independently are hydrogen, C$_{1-6}$-alkyl or aryl, or R$^{35}$ and R$^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

16. A compound according to claim 15, wherein $R^{30}$, $R^{31}$ and $R^{32}$ independently are hydrogen, halogen, —OCF$_3$, —OCHF$_2$ or —SCF$_3$, C$_{1-6}$-alkyl, which may optionally be substituted with one or more substituents selected from fluoro, —CN, —CF$_3$, —OCF$_3$, —OR$^{35}$ and —NR$^{35}$R$^{36}$, cyclohexyl or cyclohex-1-enyl, which may optionally be substituted with one or more substituents selected from fluoro, —CN, —CF$_3$, —OCF$_3$, —OR$^{35}$, —NR$^{35}$R$^{36}$ and C$_{1-6}$-alkyl, phenyl which may optionally be substituted with one or more substitutents selected from halogen, —CN, —CF$_3$, —OCF$_3$, —NO$_2$, —OR$^{35}$, —NR$^{35}$R$^{36}$ and C$_{1-6}$-alkyl, phenoxy or benzyloxy, of which the phenyl moieties may optionally be substituted with one or more substituents selected from halogen, —CN, —CF$_3$, —OCF$_3$, —NO$_2$, —OR$^{35}$, —NR$^{35}$R$^{36}$ and C$_{1-6}$-alkyl, R$^{35}$ and R$^{36}$ independently are hydrogen or C$_{1-6}$-alkyl.

17. A compound according to claim 10, wherein $R^{30}$ and $R^{32}$ are both hydrogen, and $R^{31}$ is different from hydrogen.

18. A compound according to claim 10, wherein E is

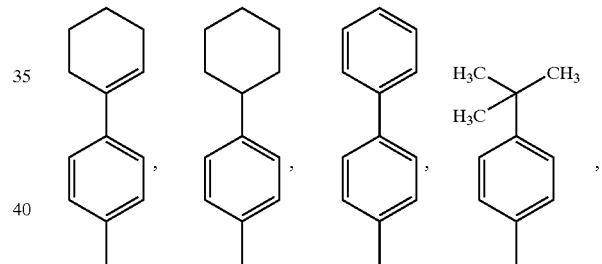

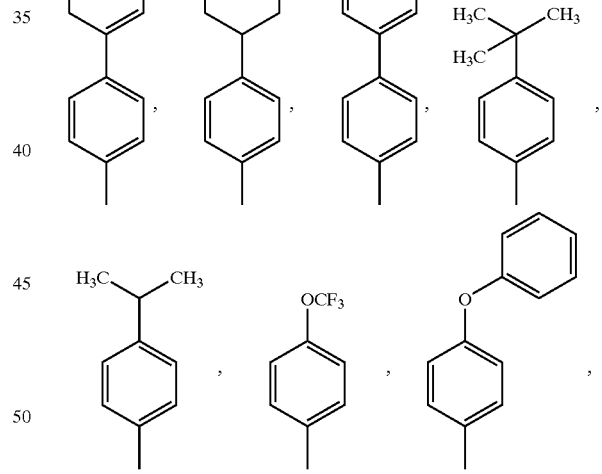

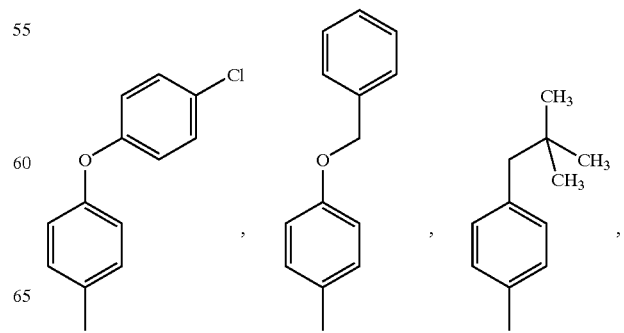

-continued

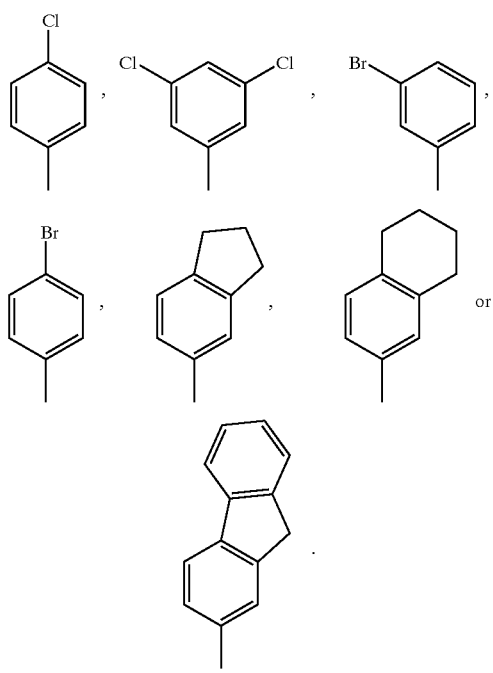

19. A compound according to claim 18, wherein E is

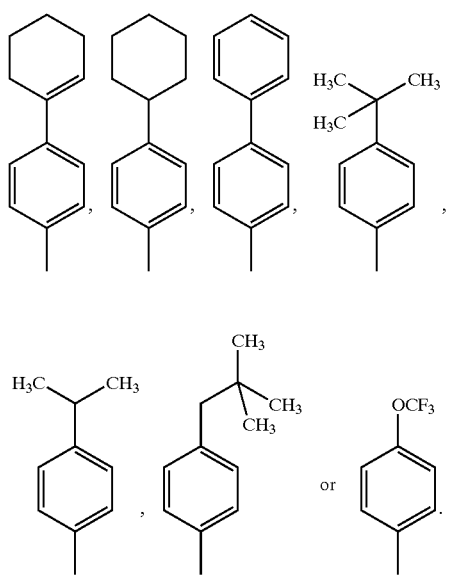

20. A compound according to claim 18 wherein E is

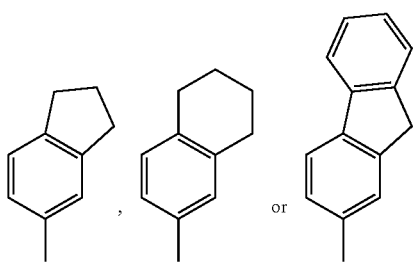

21. A compound according to claim 10, wherein E is

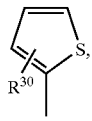

wherein $R^{30}$ is as defined in claim 1.

22. A compound according to claim 21, wherein $R^{30}$ is halogen or heteroaryl, which may optionally be substituted with one or more substituents selected from halogen, —CN, —CF$_3$, —NO$_2$, —OR$^{35}$, —NR$^{35}$R$^{36}$ and C$_{1-6}$-alkyl, R$^{35}$ and R$^{36}$ independently are hydrogen or C$_{1-6}$-alkyl, or R$^{35}$ and R$^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

23. A compound according to claim 22, wherein $R^{30}$ is halogen or thienyl, which may optionally be substituted with one or more substituents selected from halogen, —CN, —CF$_3$, —NO$_2$, —OR$^{35}$, —NR$^{35}$R$^{36}$ and C$_{1-6}$-alkyl, R$^{35}$ and R$^{36}$ independently are hydrogen or C$_{1-6}$-alkyl, or R$^{35}$ and R$^{36}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

24. A compound according to claim 23 wherein E is

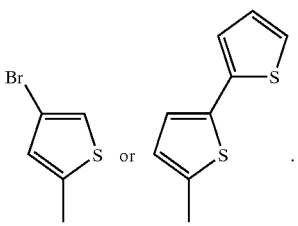

25. A compound according to claim 1, wherein Y is —C(O)—, —O—, —S(O)$_2$—, —NH— or —CH$_2$—.

26. A compound according to claim 1, wherein Y is —CHR$^{11}$—, wherein R$^{11}$ is combined with R$^1$ to form a double bond.

27. A compound according to claim 25, wherein Y is —C(O)—.

28. A compound according to claim 1, wherein R$^1$ and R$^2$ are both hydrogen.

29. A compound according to claim 1, wherein R$^1$ and R$^2$ are combined to form a double bond.

30. A compound according to claim 1, wherein R$^3$ is hydrogen.

31. A compound according to claim 1, wherein Z is —C(O)—(CR$^{13}$R$^{14}$)$_p$—, —O—(CR$^{13}$R$^{14}$)$_p$—, —NR$^{15}$—(CR$^{13}$R$^{14}$)$_p$ or —S(O)$_2$—(CR$^{13}$R$^{14}$)$_p$—, wherein p, R$^{13}$, R$^{14}$ and R$^{15}$ are as defined in claim 1.

32. A compound according to claim 31, wherein Z is —NR$^{15}$—(CR$^{13}$R$^{14}$)$_p$ or —C(O)—(CR$^{13}$R$^{14}$)$_p$—, wherein p is as defined in claim 1, and R$^{13}$ and R$^{14}$ independently are selected from hydrogen, —$CF_3$, —$OCF_3$ and $C_{1-6}$-alkyl and $R^{15}$ is hydrogen.

33. A compound according to claim 32, wherein Z is —$NH(CH_2)_p$— or —$C(O)$—$(CH_2)_p$—, wherein p is as defined in claim 1.

34. A compound according to claim 33, wherein Z is NH or —$C(O)$—.

35. A compound according to claim 34, wherein Z is —$C(O)$—.

36. A compound according to claim 1, wherein D is

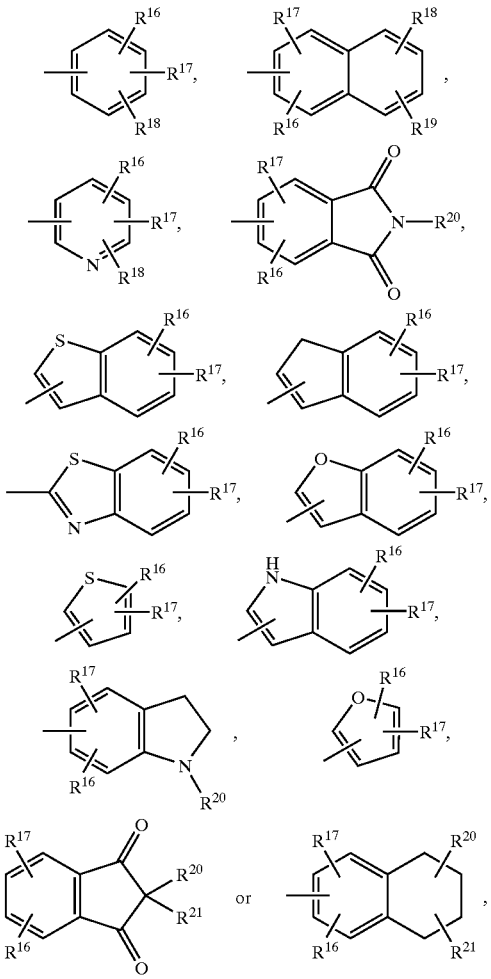

wherein $R^{16}$, $R^{17}$, $R^{18}$, $R^{19}$, $R^{20}$ and $R^{21}$ are as defined in claim 1.

37. A compound according to claim 36, wherein D is

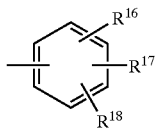

wherein $R^{16}$, $R^{17}$ and $R^{18}$ are as defined in claim 1.

38. A compound according to claim 37, wherein $R^{16}$, $R^{17}$ and $R^{18}$ independently are hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$SCF_3$, —$NO_2$, —$OR^{22}$, —$NR^{22}R^{23}$, —$SR^{22}$, —$NR^{22}S(O)_2R^{23}$, —$S(O)_2NR^{22}R^{23}$, —$S(O)NR^{22}R^{23}$, —$S(O)R^{22}$, —$S(O)_2R^{22}$, —$C(O)NR^{22}R^{23}$, —$OC(O)NR^{22}R^{23}$, —$NR^{22}C(O)R^{23}$, —$CH_2C(O)NR^{22}R^{23}$, —$OCH_2C(O)NR^{22}R^{23}$, —$CH_2OR^{22}$, —$CH_2NR^{22}R^{23}$, —$OC(O)R^{22}$, —$C(O)R^{22}$ or —$C(O)OR^{22}$, $C_{1-6}$-alkyl, which may optionally be substituted with one or more substituents selected from fluoro, —CN, —$CF_3$, —$OCF_3$, —$OR^{22}$ and —$NR^{22}R^{23}$, $C_{3-8}$-cycloalkyl, which may optionally be substituted with one or more substituents selected from fluoro, —$C(O)OR^{24}$, —CN, —$CF_3$, —$OCF_3$, —$OCHF_2$, —$OR^{22}$, —$NR^{22}R^{23}$ and $C_{1-6}$-alkyl, aryl or aryloxy, which may optionally be substituted with one or more substituents selected from halogen, —$C(O)OR^{22}$, —CN, —$CF_3$, —$OCF_3$, —$NO_2$, —$OR^{22}$, —$NR^{22}R^{23}$ and $C_{1-6}$-alkyl, $R^{22}$ and $R^{23}$ independently are hydrogen, $C_{1-6}$-alkyl, aryl-$C_{1-6}$-alkyl or aryl, or $R^{22}$ and $R^{23}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{16}$ to $R^{18}$ when placed in adjacent positions together may form a bridge —$(CR^{24}R^{25})_a$—O—$(CR^{26}R^{27})_c$—O—, a is 0, 1 or 2, c is 1 or 2, $R^{24}$, $R^{25}$, $R^{26}$ and $R^{27}$ independently are hydrogen, $C_{1-6}$-alkyl or fluoro.

39. A compound according to claim 38, wherein $R^{16}$, $R^{17}$ and $R^{18}$ independently are hydrogen, halogen, —$CF_3$, —$OCF_3$, —$SCF_3$, $C_{1-6}$-alkyl, $C_{1-6}$-alkoxy, phenyl, cyclopentyl, cyclohexyl or phenoxy, or two of the groups $R^{16}$ to $R^{18}$ when placed in adjacent positions together may form a bridge —O—$(CF_2)_2$—O—, —$CF_2$—O—$CF_2$—O— or —O—$CH_2$—O—.

40. A compound according to claim 36, wherein $R^{16}$ is hydrogen, and $R^{17}$ and $R^{18}$ are different from hydrogen.

41. A compound according to claim 36, wherein $R^{16}$ and $R^{17}$ are hydrogen, and $R^{18}$ is different from hydrogen.

42. A compound according to claim 1 of the general formula ($I_4$):

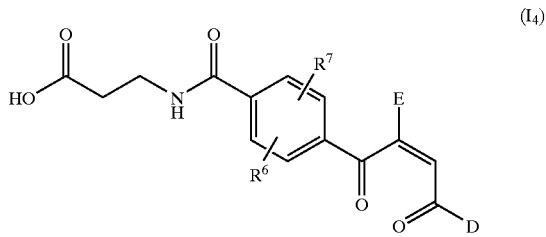

wherein $R^6$, $R^7$, E and D are as defined in claim 1, as any diastereomer or enantiomer or regioisomer or tautomeric form therefore including mixtures of these or a pharmaceutically acceptable salt thereof.

43. A compound according to claim 1 of the general formula ($I_5$):

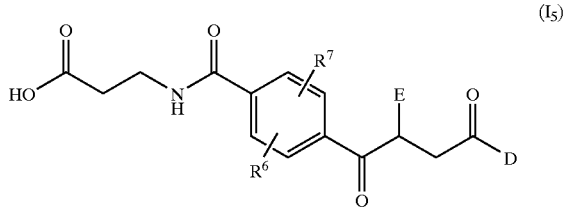

wherein $R^6$, $R^7$, E and D are as defined in claim 1, as well as any diastereomer or enantiomer or regioisomer or tautomeric form thereof including mixtures of these or a pharmaceutically acceptable salt thereof.

44. A compound according to claim 43 represented by the general formula:

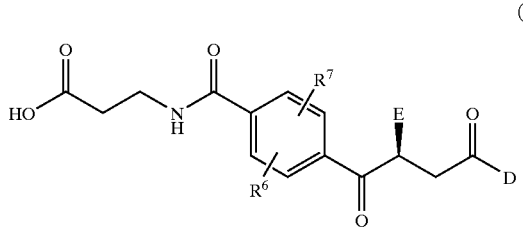

wherein $R^6$, $R^7$, E and D are as defined in claim 1, as well as any diastereomer or enantiomer or regioisomer or tautomeric form thereof including mixtures of these or a pharmaceutically acceptable salt thereof.

45. A compound according to claim 43 represented by the general formula:

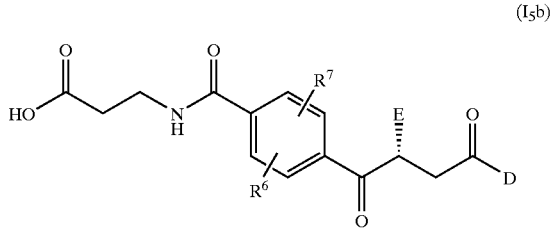

wherein $R^6$, $R^7$, E and D are as defined in claim 1, as well as any diastereomer or enantiomer or regioisomer or tautomeric form thereof including mixtures of these or a pharmaceutically acceptable salt thereof.

46. A compound according to claim 1 of the general formula ($I_6$):

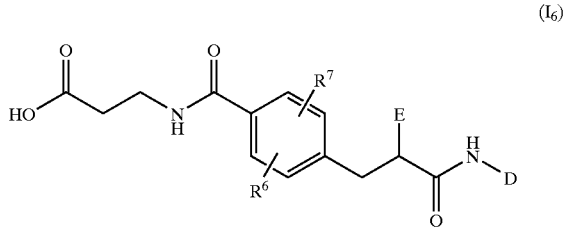

wherein $R^6$, $R^7$, E and D are as defined in claim 1, as well as any diastereomer or enantiomer or regioisomer or tautomeric form thereof including mixtures of these or a pharmaceutically acceptable salt thereof.

47. A compound according to claim 1, which has an $IC_{50}$ value of no greater than 5 µM as determined by the Glucagon Binding Assay (I) or Glucagon Binding Assay (II) disclosed herein.

48. A compound according to claim 47, which has an $IC_{50}$ value of less than 1 µM, preferably of less than 500 nM and even more preferred of less than 100 nM as determined by the Glucagon Binding Assay (I) or Glucagon Binding Assay (II) disclosed herein.

49. A pharmaceutical composition comprising, as an active ingredient, at least one compound according to claim 1 together with one or more pharmaceutically acceptable carriers or excipients.

50. A pharmaceutical composition according to claim 49 in unit dosage form, comprising from about 0.05 mg to about 1000 mg, preferably from about 0.1 mg to about 500 mg and especially preferred from about 0.5 mg to about 200 mg of the compound according to claim 1.

51. A method for the treatment of disorders or diseases, wherein a glucagon antagonistic action is beneficial, the method comprising administering to a subject in need thereof an effective amount of a compound according to claim 1 or a pharmaceutical composition thereof.

52. The method according to claim 51, wherein the effective amount of the compound is in the range of from about 0.05 mg to about 2000 mg, preferably from about 0.1 mg to about 1000 mg and especially preferred from about 0.5 mg to about 500 mg per day.

53. A compound according to claim 8, wherein $R^6$ and $R^7$ are both hydrogen.

54. A method for the treatment of a disease or disorder mediated by glucagon, comprising administering to a subject in need of such treatment: i) a first amount of a compound or pharmaceutical composition according to claim 1; and ii) a second amount of an agent selected from the group: antidiabetic, antiobesity, antihyperlipidemic, and antihypertensive.

55. A method for the treatment of a disease or disorder selected from the group: hyperglycemia, elevated blood glucose, IGT, type II diabetes, type I diabetes, obesity and dyslipidemia, comprising administering to a subject in need of such treatment: i) a first amount of a compound or pharmaceutical composition according to claim 1; and ii) a second amount of an antidiabetic agent.

56. A method for the treatment of a disease or disorder selected from the group: hyperglycemia, elevated blood glucose, IGT, type II diabetes, type I diabetes, obesity and dyslipidemia, comprising administering to a subject in need of such treatment: i) a first amount of a compound or pharmaceutical composition according to claim 1; and ii) a second amount of an antiobesity agent.

57. A method for the treatment of a disease or disorder selected from the group: hyperglycemia, elevated blood glucose, IGT, type II diabetes, type I diabetes, obesity and dyslipidemia, comprising administering to a subject in need of such treatment: i) a first amount of a compound or pharmaceutical composition according to claim 1; and ii) a second amount of an antihyperlipidemic agent.

58. A method for the treatment of a disease or disorder selected from the group: hyperglycemia, elevated blood glucose, IGT, type II diabetes, type I diabetes, obesity and dyslipidemia, comprising administering to a subject in need of such treatment: i) a first amount of a compound or pharmaceutical composition according to claim 1; and ii) a second amount of an antihypertensive agent.

59. A method for the treatment of a disease or disorder selected from the group: hyperglycemia, IGT, type II diabetes, type I diabetes, obesity and dyslipidemia, comprising administering to a subject in need of such treatment a compound according to claim 1, or pharmaceutical composition thereof.

* * * * *

UNITED STATES PATENT AND TRADEMARK OFFICE
CERTIFICATE OF CORRECTION

PATENT NO.       : 6,762,318 B2
APPLICATION NO.  : 10/308528
DATED            : July 13, 2004
INVENTOR(S)      : Kodra et al.

Page 1 of 1

It is certified that error appears in the above-identified patent and that said Letters Patent is hereby corrected as shown below:

Column 319, line 47, claim 1:
"$C_{1-4}$alkyl" should read --$C_{1-6}$alkyl--.

Signed and Sealed this

Seventh Day of August, 2007

JON W. DUDAS
*Director of the United States Patent and Trademark Office*